(12) United States Patent
Diwan et al.

(10) Patent No.: US 9,492,291 B2
(45) Date of Patent: Nov. 15, 2016

(54) SYSTEMS, METHODS AND APPARATUSES FOR FORMATION AND INSERTION OF TISSUE PROSTHESIS

(71) Applicant: SpineCell Private Limited, Kogarah, NSW (AU)

(72) Inventors: Ashish Dhar Diwan, Sydney (AU); Johnathon Choi, Carlingford (AU); Zoran Milijasevic, Bayview Heights (AU)

(73) Assignee: Kunovus Pty Ltd.

( * ) Notice: Subject to any disclaimer, the term of this patent is extended or adjusted under 35 U.S.C. 154(b) by 334 days.

(21) Appl. No.: 14/229,241

(22) Filed: Mar. 28, 2014

(65) Prior Publication Data
US 2014/0257417 A1 Sep. 11, 2014

Related U.S. Application Data

(63) Continuation of application No. 12/920,453, filed as application No. PCT/AU2008/000611 on May 1, 2008, now abandoned.

(51) Int. Cl.
*A61F 2/00* (2006.01)
*A61F 2/46* (2006.01)
(Continued)

(52) U.S. Cl.
CPC ............ *A61F 2/4684* (2013.01); *A61F 2/441* (2013.01); *A61F 2/4611* (2013.01); *A61F 2/4657* (2013.01); *A61F 2002/3008* (2013.01); *A61F 2002/30069* (2013.01); *A61F 2002/30583* (2013.01); *A61F 2002/30586* (2013.01); *A61F 2002/444* (2013.01); *A61F 2002/4635* (2013.01); *A61F 2002/4663* (2013.01); *A61F 2002/4685* (2013.01); *A61F 2210/0085* (2013.01); *A61F 2250/0098* (2013.01)

(58) Field of Classification Search
CPC .......... A61F 2/4684; A61B 17/8802; A61M 5/145; A61M 5/19; A61M 5/178
USPC ........................................... 606/93
See application file for complete search history.

(56) References Cited

U.S. PATENT DOCUMENTS

| | | | |
|---|---|---|---|
| 3,030,951 A | 4/1962 | Mandarino |
| 3,223,083 A | 12/1965 | Cobey |
| 3,320,131 A | 5/1967 | Smith |

(Continued)

FOREIGN PATENT DOCUMENTS

| | | |
|---|---|---|
| AU | WO2006092015 | 9/2006 |
| AU | WO2007019631 | 2/2007 |

(Continued)

*Primary Examiner* — Ellen C Hammond
*Assistant Examiner* — Stuart S Bray
(74) *Attorney, Agent, or Firm* — Jerry R. Potts; James R. McDaniel

(57) ABSTRACT

A tissue prosthesis insertion system includes a first assembly comprising a plurality of nested tubes, one of the tubes being a carrier tube which, in use, receives a component of a tissue prosthesis at a distal end of the carrier tube. A magnetic mount is carried at a proximal end of the first assembly. A second assembly is removably attachable to the first assembly. An attachment device is carried at a distal end of the second assembly, the attachment device being responsive to the magnetic mount of the first assembly, the magnetic mount and the attachment device carrying complementary engaging formations to facilitate hermetic sealing between the magnetic mount and the attachment device.

15 Claims, 42 Drawing Sheets

(51) Int. Cl.
*A61F 2/44* (2006.01)
*A61F 2/30* (2006.01)

(56) References Cited

U.S. PATENT DOCUMENTS

| | | | |
|---|---|---|---|
| 3,805,767 A | 4/1974 | Erb | |
| 3,875,595 A | 4/1975 | Froning | |
| 3,879,767 A | 4/1975 | Stubstab | |
| RE29,345 E | 8/1977 | Erb | |
| 4,052,753 A | 10/1977 | Dedo | |
| 4,085,466 A | 4/1978 | Goodfellow et al. | |
| 4,098,626 A | 7/1978 | Graham et al. | |
| 4,203,444 A | 5/1980 | Bonnell et al. | |
| 4,245,623 A | 1/1981 | Erb | |
| 4,274,414 A | 6/1981 | Johnson et al. | |
| 4,292,972 A | 10/1981 | Pawelchak et al. | |
| 4,368,040 A | 1/1983 | Weissman | |
| 4,385,404 A | 5/1983 | Sully et al. | |
| 4,446,578 A | 5/1984 | Perkins et al. | |
| 4,456,745 A | 6/1984 | Rajan | |
| 4,463,141 A | 7/1984 | Robinson | |
| 4,476,293 A | 10/1984 | Robinson | |
| 4,477,604 A | 10/1984 | Oechsle, III | |
| 4,570,270 A | 2/1986 | Oechsle, III | |
| 4,594,380 A | 6/1986 | Chapin et al. | |
| 4,647,643 A | 3/1987 | Zdrahala et al. | |
| 4,651,736 A | 3/1987 | Sanders | |
| 4,705,038 A | 11/1987 | Sjostrom et al. | |
| 4,722,948 A | 2/1988 | Sanderson | |
| 4,734,097 A | 3/1988 | Tanabe et al. | |
| 4,743,632 A | 5/1988 | Marinovic | |
| 4,759,766 A | 7/1988 | Buettner-Janz et al. | |
| 4,772,287 A | 9/1988 | Ray et al. | |
| 4,808,691 A | 2/1989 | Konig et al. | |
| 4,834,729 A | 5/1989 | Sjostrom | |
| 4,834,757 A | 5/1989 | Brantigan | |
| 4,842,578 A | 6/1989 | Johnson et al. | |
| 4,863,477 A | 9/1989 | Monson | |
| 4,873,308 A | 10/1989 | Coury et al. | |
| 4,880,610 A | 11/1989 | Constantz | |
| 4,904,260 A | 2/1990 | Ray et al. | |
| 4,913,701 A | 4/1990 | Tower | |
| 4,932,969 A | 6/1990 | Frey et al. | |
| 4,969,888 A | 11/1990 | Scholten et al. | |
| 4,983,179 A | 1/1991 | Sjostrom | |
| 5,002,576 A | 3/1991 | Fuhrmann et al. | |
| 5,007,940 A | 4/1991 | Berg | |
| 5,047,055 A | 9/1991 | Bao et al. | |
| 5,059,193 A | 10/1991 | Kuslich | |
| 5,064,426 A | 11/1991 | Huebsch | |
| 5,067,964 A | 11/1991 | Richmond et al. | |
| 5,071,437 A | 12/1991 | Steffee | |
| 5,078,720 A | 1/1992 | Burton et al. | |
| 5,082,803 A | 1/1992 | Sumita | |
| 5,108,404 A | 4/1992 | Scholten et al. | |
| 5,109,077 A | 4/1992 | Wick | |
| 5,130,347 A | 7/1992 | Mitra | |
| 5,143,942 A | 9/1992 | Brown | |
| 5,156,777 A | 10/1992 | Kaye | |
| 5,163,949 A | 11/1992 | Bonutti | |
| 5,166,115 A | 11/1992 | Brown | |
| 5,171,244 A | 12/1992 | Caspari et al. | |
| 5,171,280 A | 12/1992 | Baumgartner | |
| 5,192,326 A | 3/1993 | Bao et al. | |
| 5,228,459 A | 7/1993 | Caspari et al. | |
| 5,254,662 A | 10/1993 | Szycher et al. | |
| 5,258,028 A | 11/1993 | Ersek et al. | |
| 5,263,498 A | 11/1993 | Caspari et al. | |
| 5,278,201 A | 1/1994 | Dunn | |
| 5,288,797 A | 2/1994 | Khalil et al. | |
| 5,290,306 A | 3/1994 | Trotta et al. | |
| 5,295,994 A | 3/1994 | Bonutti | |
| 5,304,181 A | 4/1994 | Caspari et al. | |
| 5,314,477 A | 5/1994 | Marnay | |
| 5,314,478 A | 5/1994 | Oka et al. | |
| 5,320,611 A | 6/1994 | Bonutti et al. | |
| 5,334,201 A | 8/1994 | Cowan | |
| 5,342,305 A | 8/1994 | Shonk | |
| 5,344,444 A | 9/1994 | Glastra | |
| 5,344,456 A | 9/1994 | Nonami et al. | |
| 5,344,459 A | 9/1994 | Swartz | |
| 5,376,064 A | 12/1994 | Cerny | |
| 5,385,469 A | 1/1995 | Weissman | |
| 5,395,376 A | 3/1995 | Caspari et al. | |
| 5,411,477 A | 5/1995 | Saab | |
| 5,425,772 A | 6/1995 | Brantigan | |
| 5,447,497 A | 9/1995 | Sogard et al. | |
| 5,458,638 A | 10/1995 | Kuslich et al. | |
| 5,458,642 A | 10/1995 | Beer et al. | |
| 5,458,643 A | 10/1995 | Oka et al. | |
| 5,470,314 A | 11/1995 | Walinsky | |
| 5,489,256 A * | 2/1996 | Adair | A61B 1/00073 600/123 |
| 5,489,308 A | 2/1996 | Kuslich et al. | |
| 5,492,538 A * | 2/1996 | Johlin, Jr. | A61M 25/0068 128/899 |
| 5,514,153 A | 5/1996 | Bonutti | |
| 5,529,653 A | 6/1996 | Glastra | |
| 5,534,028 A | 7/1996 | Bao et al. | |
| 5,545,229 A | 8/1996 | Parsons et al. | |
| 5,549,679 A | 8/1996 | Kuslich | |
| 5,556,429 A | 9/1996 | Felt | |
| 5,562,736 A | 10/1996 | Ray et al. | |
| 5,571,189 A | 11/1996 | Kuslich | |
| 5,573,517 A | 11/1996 | Bonutti et al. | |
| 5,587,125 A | 12/1996 | Roychowdhury | |
| 5,589,563 A | 12/1996 | Ward et al. | |
| 5,591,199 A | 1/1997 | Porter et al. | |
| 5,591,235 A | 1/1997 | Kuslich | |
| 5,601,590 A | 2/1997 | Bonutti et al. | |
| 5,620,649 A | 4/1997 | Trotta | |
| 5,624,463 A | 4/1997 | Stone et al. | |
| 5,632,275 A | 5/1997 | Browne et al. | |
| 5,643,175 A * | 7/1997 | Adair | A61B 1/00073 600/123 |
| 5,645,597 A | 7/1997 | Krapiva | |
| 5,674,295 A | 10/1997 | Ray et al. | |
| 5,674,296 A | 10/1997 | Bryan et al. | |
| 5,769,817 A | 6/1998 | Burgmeier | |
| 5,797,877 A | 8/1998 | Hamilton et al. | |
| 5,800,549 A | 9/1998 | Bao et al. | |
| 5,824,093 A | 10/1998 | Ray et al. | |
| 5,827,289 A | 10/1998 | Reiley et al. | |
| 5,827,318 A | 10/1998 | Bonutti | |
| 5,830,125 A | 11/1998 | Scribner et al. | |
| 5,834,011 A | 11/1998 | Rose et al. | |
| 5,860,997 A | 1/1999 | Bonutti | |
| 5,888,220 A | 3/1999 | Felt et al. | |
| 5,895,427 A | 4/1999 | Kuslich et al. | |
| 5,895,428 A | 4/1999 | Berry | |
| 5,954,739 A | 9/1999 | Bonutti | |
| 5,972,015 A | 10/1999 | Scribner et al. | |
| 5,989,256 A | 11/1999 | Kuslich et al. | |
| 6,001,130 A | 12/1999 | Bryan et al. | |
| 6,017,305 A | 1/2000 | Bonutti | |
| 6,019,760 A | 2/2000 | Metz-Stavenhagen et al. | |
| 6,022,376 A | 2/2000 | Assell et al. | |
| 6,030,415 A * | 2/2000 | Chuter | A61F 2/07 604/191 |
| 6,048,346 A | 4/2000 | Reiley et al. | |
| 6,053,904 A | 4/2000 | Scribner et al. | |
| 6,056,749 A | 5/2000 | Kuslich | |
| 6,059,719 A * | 5/2000 | Yamamoto | A61B 1/00059 600/104 |
| 6,065,371 A * | 5/2000 | Yacowitz | A61M 37/0076 30/362 |
| 6,066,154 A | 5/2000 | Reiley et al. | |
| 6,074,391 A | 6/2000 | Metz-Stavenhagen et al. | |
| 6,079,868 A * | 6/2000 | Rydell | A61B 17/00234 222/145.6 |
| 6,086,589 A | 7/2000 | Kuslich et al. | |
| 6,090,110 A | 7/2000 | Metz-Stavenhagen | |
| 6,096,039 A | 8/2000 | Stoltenberg et al. | |
| 6,102,928 A | 8/2000 | Bonutti | |

(56) References Cited

U.S. PATENT DOCUMENTS

| | | |
|---|---|---|
| 6,106,557 A | 8/2000 | Robioneck et al. |
| 6,110,210 A | 8/2000 | Norton et al. |
| 6,113,639 A | 9/2000 | Ray et al. |
| 6,127,597 A | 10/2000 | Beyar et al. |
| 6,132,465 A | 10/2000 | Ray et al. |
| 6,139,550 A | 10/2000 | Michelson |
| 6,139,551 A | 10/2000 | Michelson et al. |
| 6,140,452 A | 10/2000 | Felt et al. |
| 6,149,686 A | 11/2000 | Kuslich et al. |
| RE37,005 E | 12/2000 | Michelson et al. |
| 6,156,067 A | 12/2000 | Bryan et al. |
| 6,171,236 B1 | 1/2001 | Bonutti |
| 6,171,299 B1 | 1/2001 | Bonutti |
| 6,183,518 B1 | 2/2001 | Ross et al. |
| 6,187,023 B1 | 2/2001 | Bonutti |
| 6,187,048 B1 | 2/2001 | Milner et al. |
| 6,193,721 B1 | 2/2001 | Michelson |
| 6,193,755 B1 | 2/2001 | Metz-Stavenhagen et al. |
| 6,214,006 B1 | 4/2001 | Metz-Stavenhagen |
| RE37,161 E | 5/2001 | Michelson et al. |
| 6,224,630 B1 | 5/2001 | Bao et al. |
| 6,235,043 B1 | 5/2001 | Reiley et al. |
| 6,241,734 B1 | 6/2001 | Scribner et al. |
| 6,241,770 B1 | 6/2001 | Michelson |
| 6,245,107 B1 | 6/2001 | Ferree |
| 6,248,110 B1 | 6/2001 | Reiley et al. |
| 6,248,131 B1 | 6/2001 | Felt et al. |
| 6,264,695 B1 | 7/2001 | Stoy |
| 6,277,136 B1 | 8/2001 | Bonutti |
| 6,280,456 B1 | 8/2001 | Scribner et al. |
| 6,280,475 B1 | 8/2001 | Bao et al. |
| 6,287,343 B1 | 9/2001 | Kuslich et al. |
| 6,306,170 B2 | 10/2001 | Ray |
| 6,306,177 B1 | 10/2001 | Felt et al. |
| RE37,479 E | 12/2001 | Kuslich |
| 6,350,283 B1 | 2/2002 | Michelson |
| 6,358,266 B1 | 3/2002 | Bonutti |
| 6,364,880 B1 | 4/2002 | Michelson |
| 6,371,990 B1 | 4/2002 | Feree |
| 6,391,058 B1 | 5/2002 | Kuslich et al. |
| 6,395,034 B1 | 5/2002 | Suddaby |
| 6,425,919 B1 | 7/2002 | Lambrecht |
| 6,428,576 B1 | 8/2002 | Haldimann |
| 6,443,988 B2 | 9/2002 | Felt et al. |
| 6,458,889 B1 | 10/2002 | Trollsas et al. |
| 6,482,235 B1 | 11/2002 | Lambrecht et al. |
| 6,508,839 B1 | 1/2003 | Lambrecht et al. |
| 6,534,591 B2 | 3/2003 | Rhee et al. |
| 6,558,390 B2 | 5/2003 | Cragg |
| 6,592,625 B2 | 7/2003 | Cauthen |
| 6,613,054 B2 | 9/2003 | Scribner et al. |
| 6,623,505 B2 | 9/2003 | Scribner et al. |
| 6,705,756 B2 * | 3/2004 | Botrie ............... B01F 5/0613 222/136 |
| 6,969,404 B2 | 11/2005 | Ferree |
| 7,001,431 B2 | 2/2006 | Bao et al. |
| 7,025,771 B2 | 4/2006 | Kuslich et al. |
| 7,077,339 B2 * | 7/2006 | Leach ............ A61B 17/00491 222/137 |
| 7,077,865 B2 | 7/2006 | Bao et al. |
| 7,316,704 B2 * | 1/2008 | Bagaoisan ......... A61B 17/0057 606/213 |
| 7,713,301 B2 | 5/2010 | Bao et al. |
| 7,766,965 B2 | 8/2010 | Bao et al. |
| 7,960,935 B2 * | 6/2011 | Farritor ............ A61B 1/00156 318/568.11 |
| 2001/0004710 A1 * | 6/2001 | Felt ................... A61B 17/7097 623/17.12 |
| 2001/0011174 A1 | 8/2001 | Reiley et al. |
| 2001/0034553 A1 | 10/2001 | Michelson |
| 2001/0041896 A1 | 11/2001 | Reiley et al. |
| 2001/0047207 A1 | 11/2001 | Michelson |
| 2001/0047208 A1 | 11/2001 | Michelson |
| 2002/0004683 A1 | 1/2002 | Michelson |
| 2002/0010511 A1 | 1/2002 | Michelson |
| 2002/0013624 A1 | 1/2002 | Michelson |
| 2002/0016583 A1 | 2/2002 | Cragg |
| 2002/0016595 A1 | 2/2002 | Michelson |
| 2002/0022843 A1 | 2/2002 | Michelson |
| 2002/0026195 A1 | 2/2002 | Layne et al. |
| 2003/0018390 A1 * | 1/2003 | Husson ............. A61B 17/3201 623/17.16 |
| 2003/0033017 A1 | 2/2003 | Lotz et al. |
| 2003/0069641 A1 | 4/2003 | Reuter et al. |
| 2004/0024465 A1 * | 2/2004 | Lambrecht ........... A61B 5/1076 623/17.16 |
| 2004/0044412 A1 * | 3/2004 | Lambrecht ........... A61B 5/1076 623/17.16 |
| 2005/0043806 A1 * | 2/2005 | Cook .................. A61B 17/15 623/20.12 |
| 2006/0004326 A1 * | 1/2006 | Collins ............. A61B 17/8811 604/57 |
| 2006/0084983 A1 * | 4/2006 | Kim .................. A61B 17/7065 606/914 |
| 2006/0247776 A1 * | 11/2006 | Kim ....................... A61F 2/442 623/17.12 |
| 2006/0265077 A1 * | 11/2006 | Zwirkoski .......... A61B 17/7094 623/17.16 |
| 2006/0270781 A1 * | 11/2006 | Ruberti .................. A61F 2/442 524/503 |
| 2006/0276802 A1 * | 12/2006 | Vresilovic ............. A61F 2/4611 606/102 |
| 2006/0287726 A1 * | 12/2006 | Segal ...................... A61F 2/441 623/17.12 |
| 2006/0287727 A1 * | 12/2006 | Segal ...................... A61F 2/441 623/17.12 |
| 2006/0287729 A1 * | 12/2006 | Segal ...................... A61F 2/441 623/17.16 |
| 2006/0287730 A1 * | 12/2006 | Segal ...................... A61F 2/441 623/17.16 |
| 2006/0293750 A1 * | 12/2006 | Sherman ................. A61F 2/44 623/17.12 |
| 2007/0123986 A1 * | 5/2007 | Schaller ................. A61B 17/70 623/17.11 |
| 2007/0162135 A1 * | 7/2007 | Segal ...................... A61F 2/441 623/17.11 |
| 2007/0185513 A1 * | 8/2007 | Woolfson ............. A61F 2/2427 606/108 |
| 2009/0012621 A1 * | 1/2009 | James ..................... A61F 2/442 623/17.16 |
| 2009/0240341 A1 * | 9/2009 | Diwan ................... A61F 2/4611 623/23.72 |
| 2009/0276048 A1 * | 11/2009 | Chirico ................ A61B 17/025 623/17.11 |
| 2009/0281538 A1 * | 11/2009 | Chong ................. A61B 18/1492 606/41 |
| 2009/0292323 A1 * | 11/2009 | Chirico ............... A61B 17/8858 606/86 R |
| 2010/0036392 A1 * | 2/2010 | Milijasevic ....... A61M 25/0043 606/129 |
| 2010/0145454 A1 * | 6/2010 | Hoffman ................ A61F 2/447 623/17.12 |
| 2010/0168859 A1 * | 7/2010 | Wardlaw ................ A61F 2/441 623/17.12 |
| 2011/0125158 A1 * | 5/2011 | Diwan .................... A61F 2/441 606/93 |
| 2011/0153021 A1 * | 6/2011 | Diwan ................... A61F 1/0125 623/17.16 |
| 2011/0208308 A1 * | 8/2011 | Choi ....................... A61F 2/441 623/17.16 |
| 2015/0066429 A1 * | 3/2015 | Nielsen ............... G06F 19/345 702/177 |
| 2016/0030663 A1 * | 2/2016 | Adaniya ................ A61M 5/20 604/28 |

FOREIGN PATENT DOCUMENTS

| | | |
|---|---|---|
| GB | WO9902108 | 1/1999 |
| WO | WO9530388 | 11/1995 |
| WO | WO9531946 | 11/1995 |
| WO | WO9531948 | 11/1995 |
| WO | WO9726847 | 7/1997 |
| WO | WO9820929 | 5/1998 |
| WO | WO9944509 | 9/1999 |

(56) References Cited

FOREIGN PATENT DOCUMENTS

| WO | WO9956800 | 11/1999 |
| WO | WO9961084 | 12/1999 |
| WO | WO0002613 | 1/2000 |
| WO | WO0004851 | 2/2000 |
| WO | WO0013020 | 3/2000 |
| WO | WO0013619 | 3/2000 |
| WO | WO0059412 | 10/2000 |
| WO | WO0061037 | 10/2000 |
| WO | WO0064385 | 11/2000 |
| WO | WO0066044 | 11/2000 |
| WO | WO0069374 | 11/2000 |
| WO | WO0074606 | 12/2000 |
| WO | WO0110316 | 2/2001 |
| WO | WO0112107 | 2/2001 |
| WO | PCT/US2001/041906 | 8/2001 |
| WO | WO0160234 | 8/2001 |
| WO | WO0160270 | 8/2001 |
| WO | WO0189428 | 11/2001 |
| WO | WO0193784 | 12/2001 |
| WO | WO0195837 | 12/2001 |
| WO | WO0213731 | 2/2002 |
| WO | WO0217824 | 3/2002 |
| WO | WO0217825 | 3/2002 |
| WO | WO2004073563 | 2/2004 |
| WO | WO2006132858 | 12/2006 |

* cited by examiner

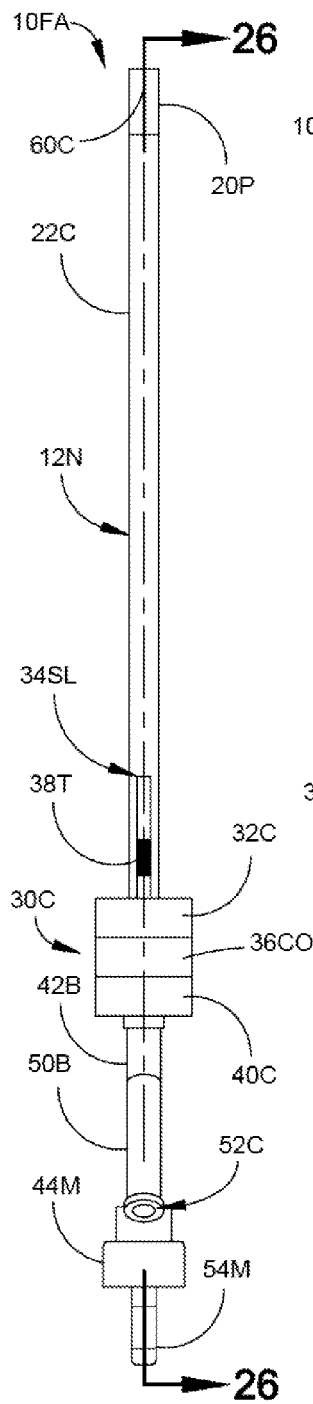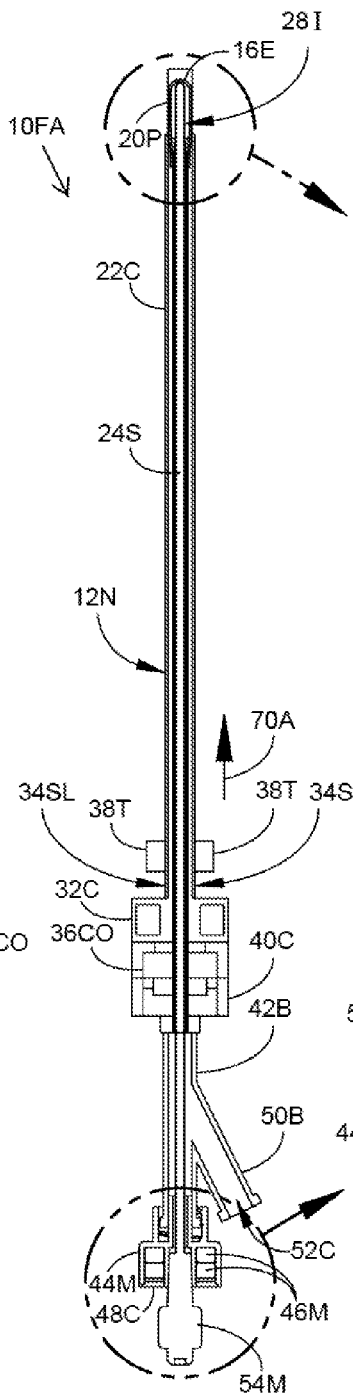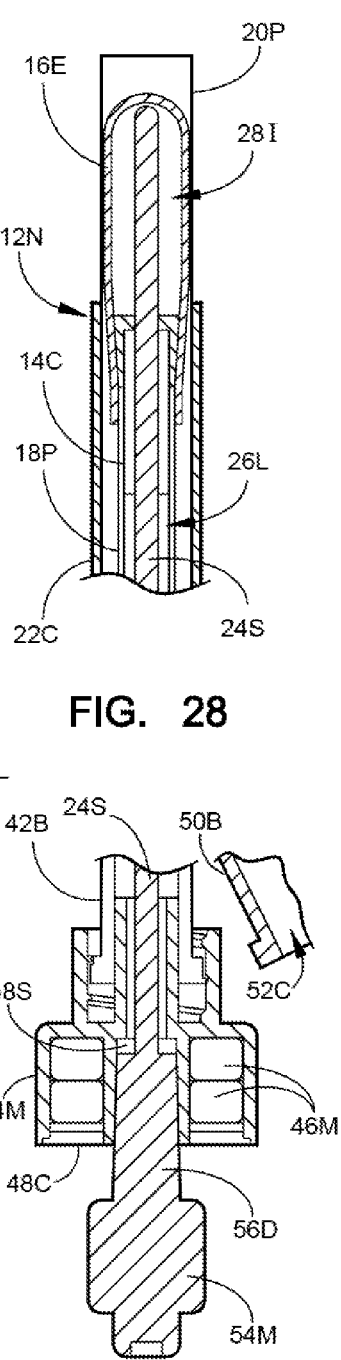
FIG. 25   FIG. 26   FIG. 27
FIG. 28

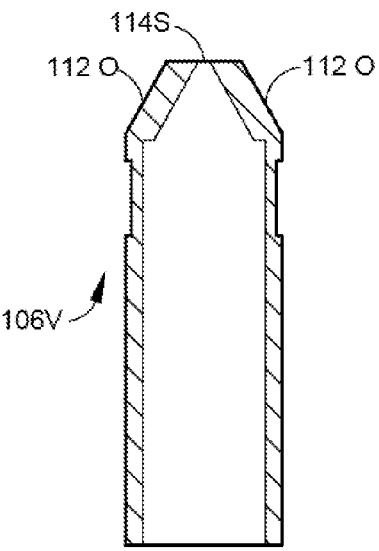
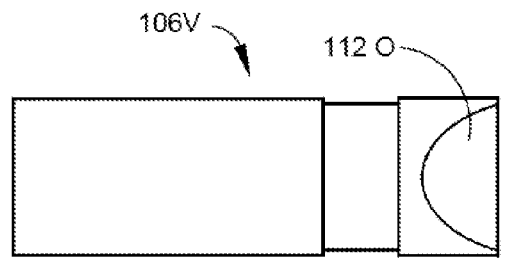
FIG. 33
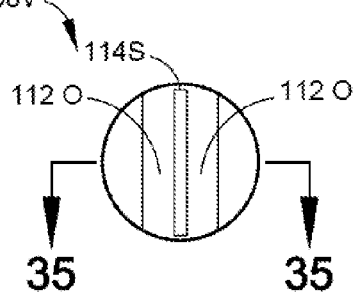
FIG. 34
FIG. 35
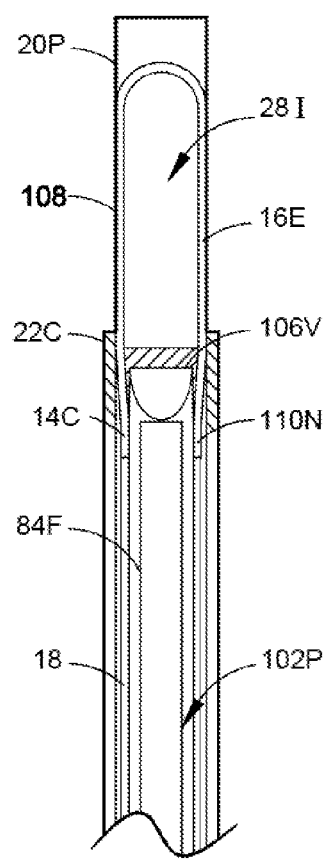
FIG. 32
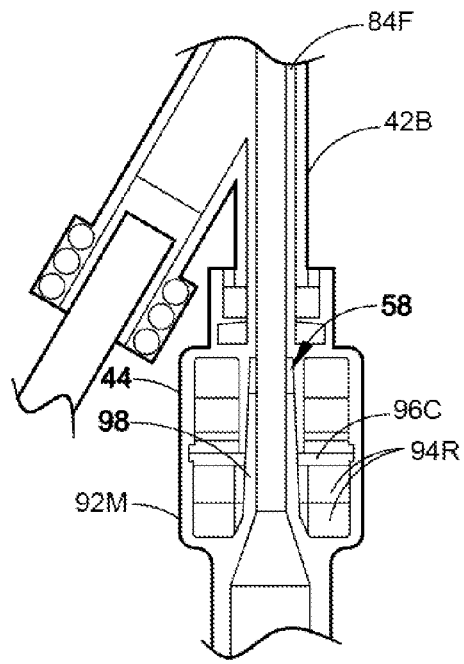
FIG. 31

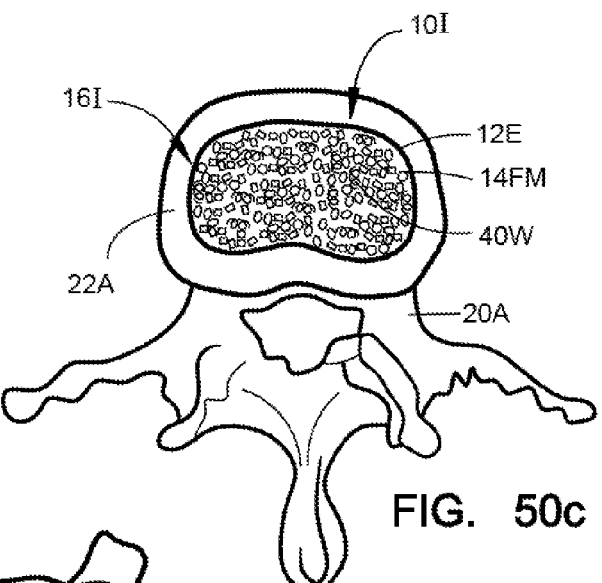
FIG. 50c
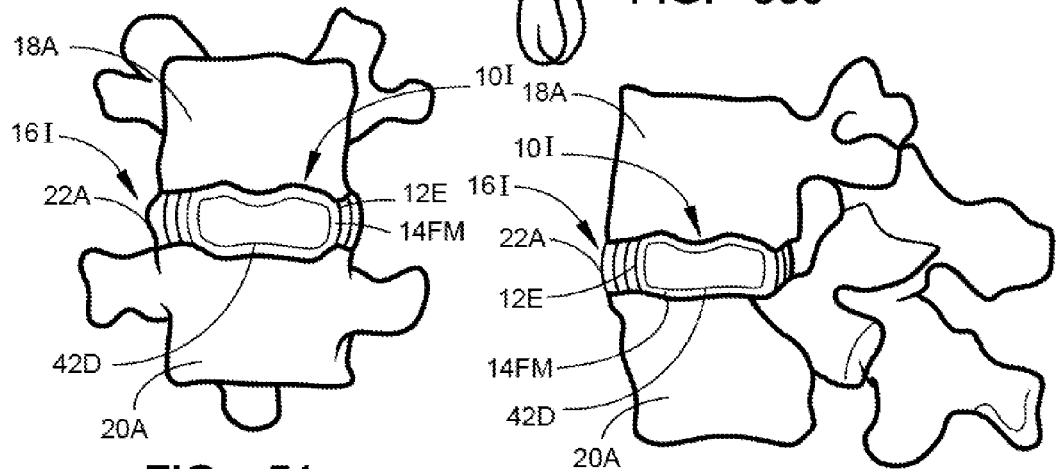
FIG. 51a
FIG. 51b
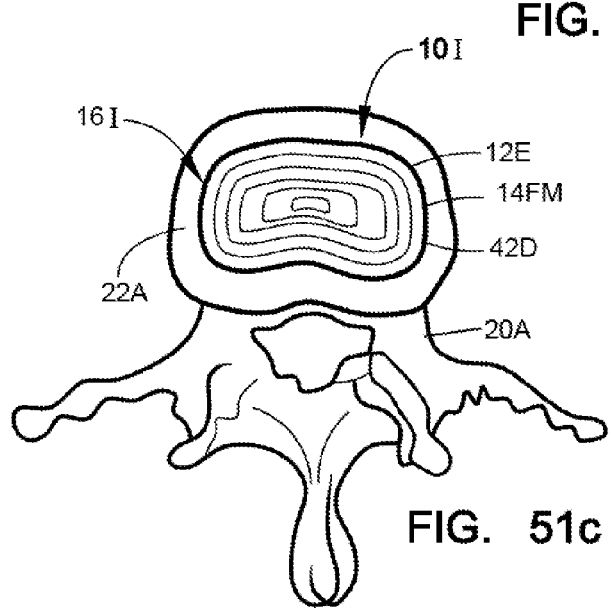
FIG. 51c

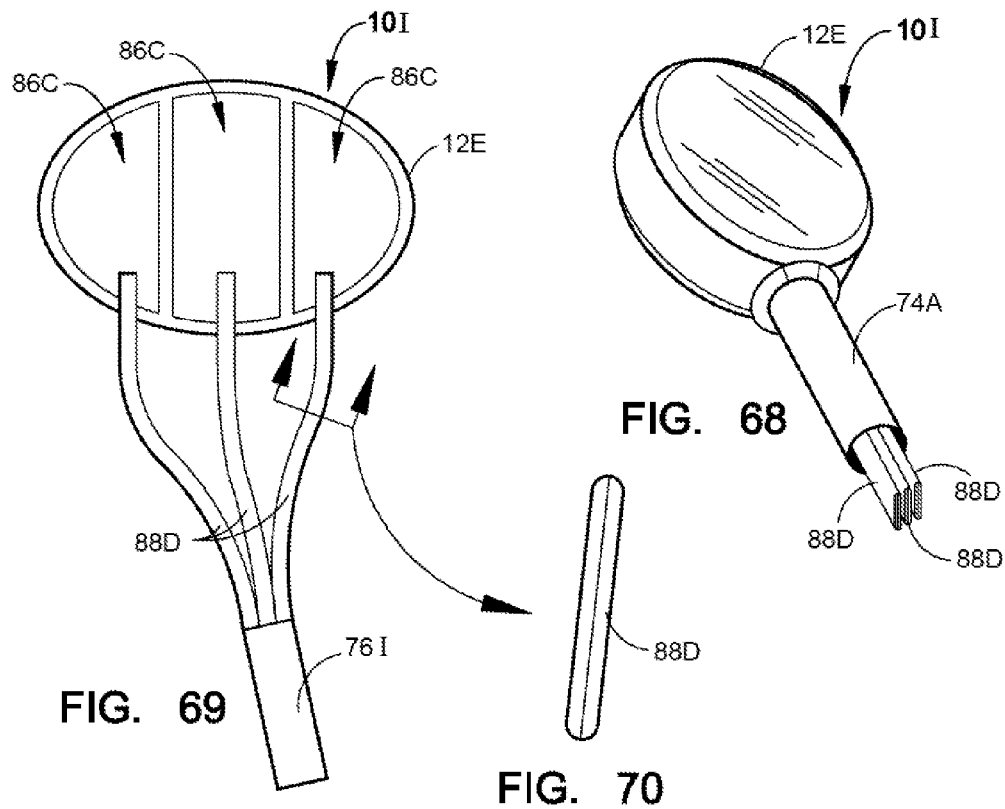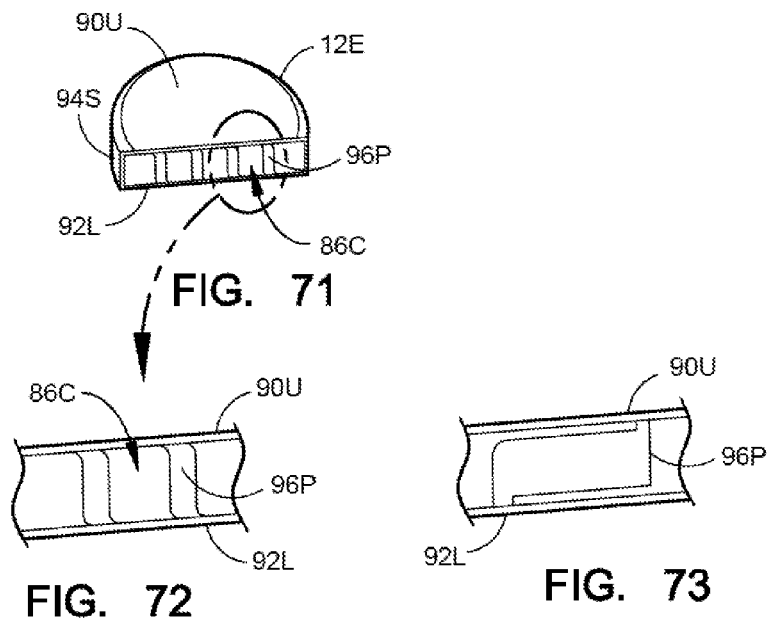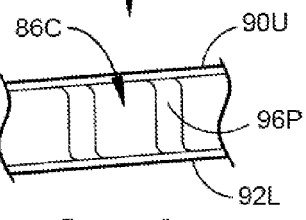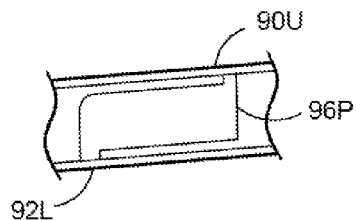

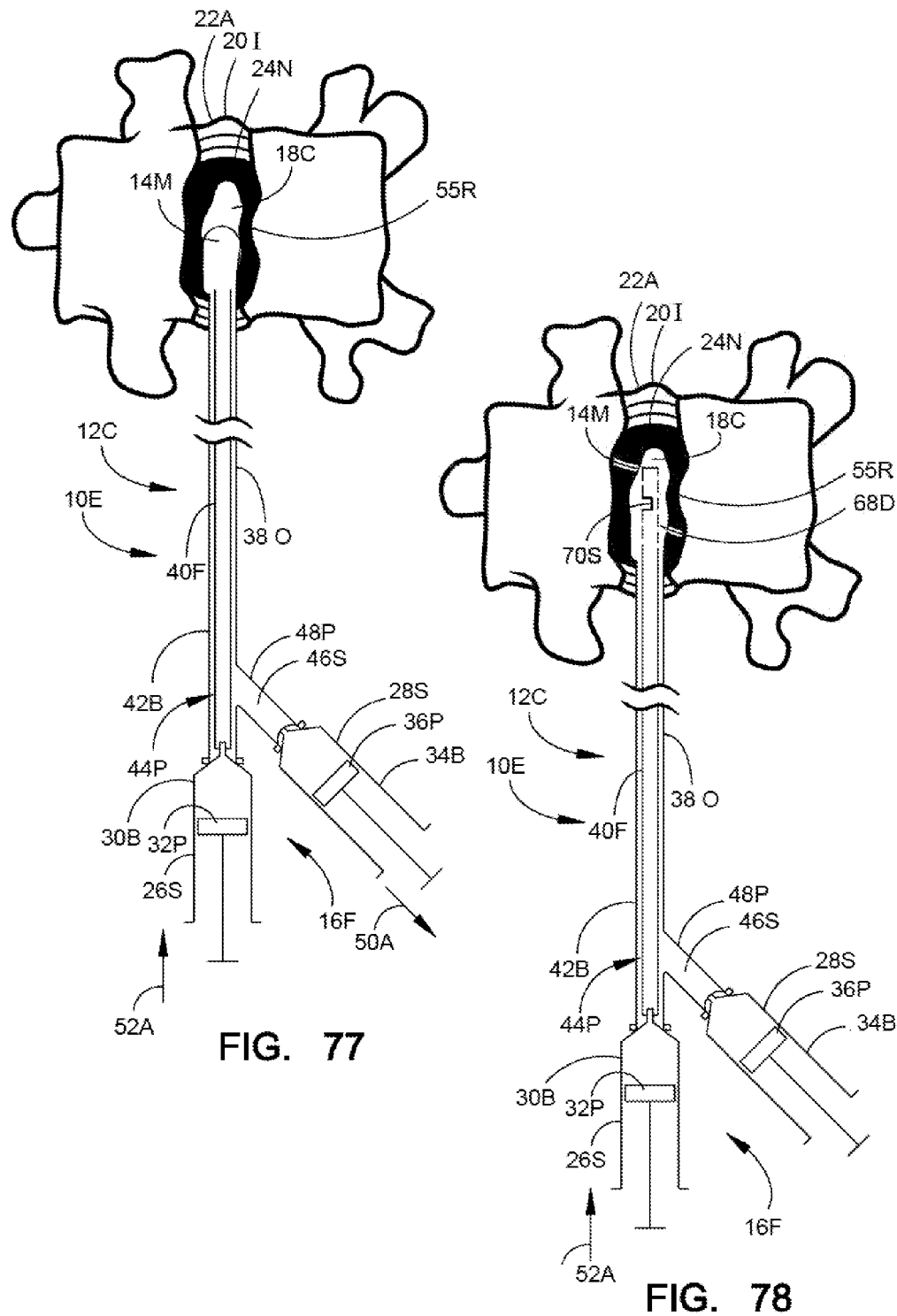

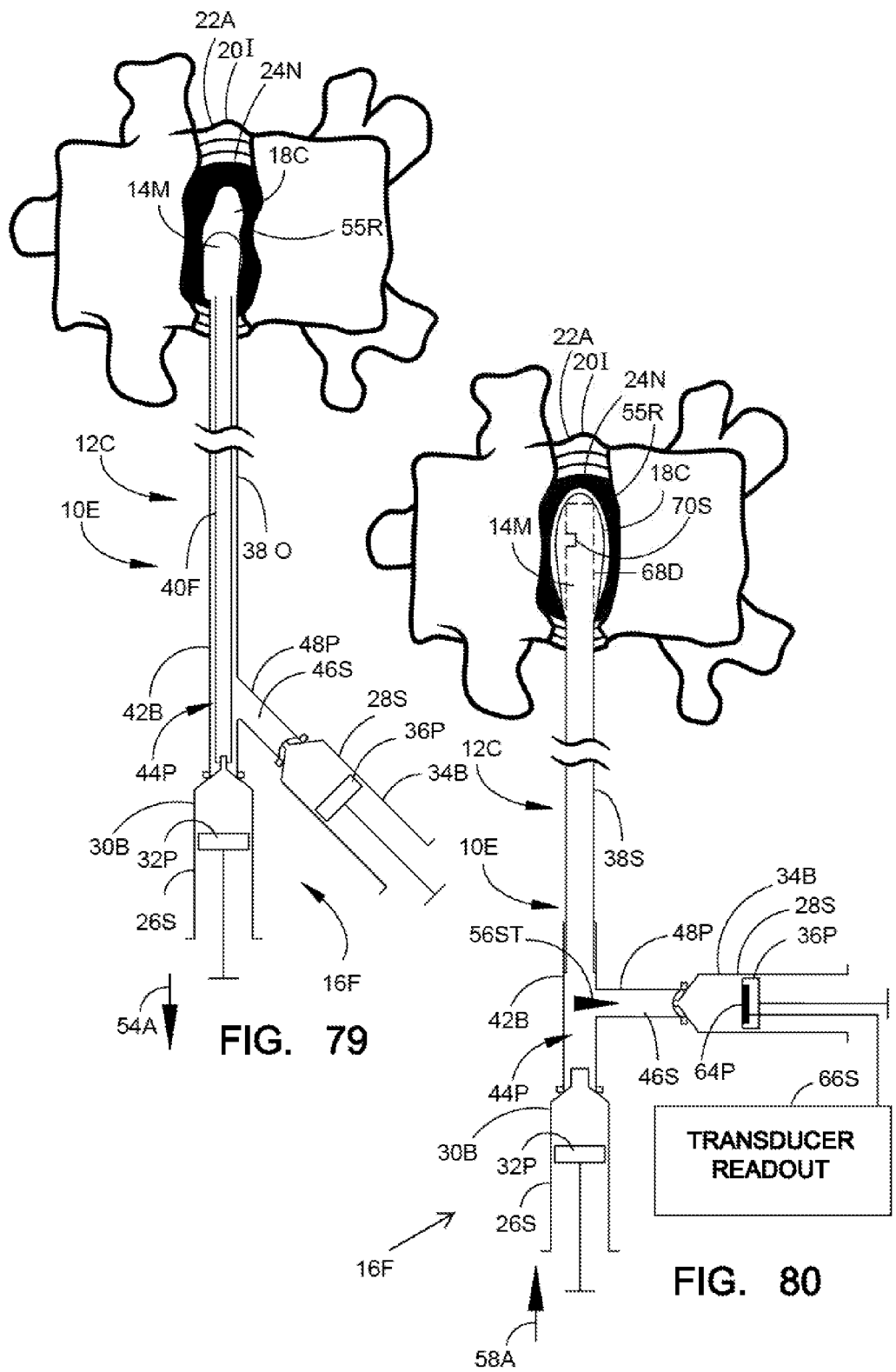

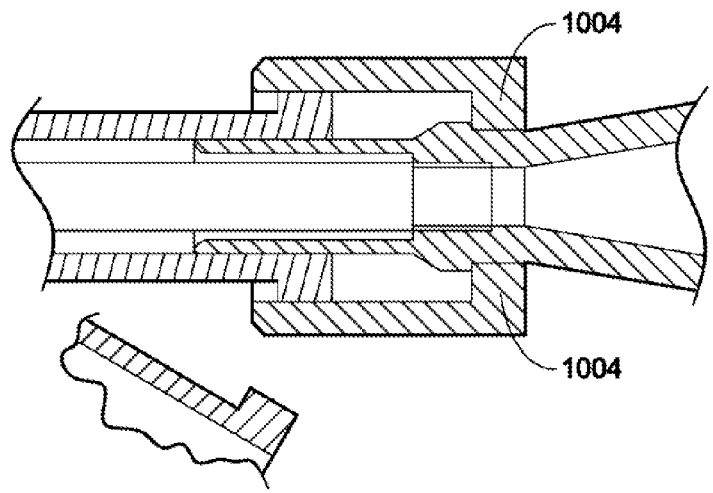
FIG. 93
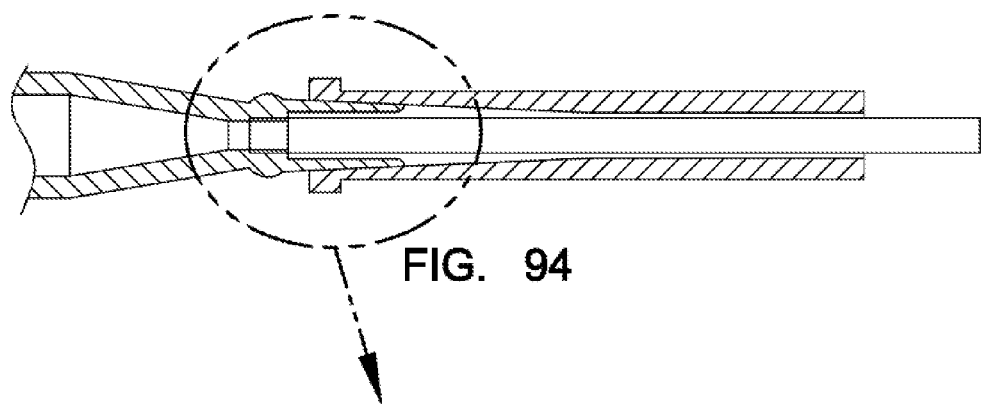
FIG. 94
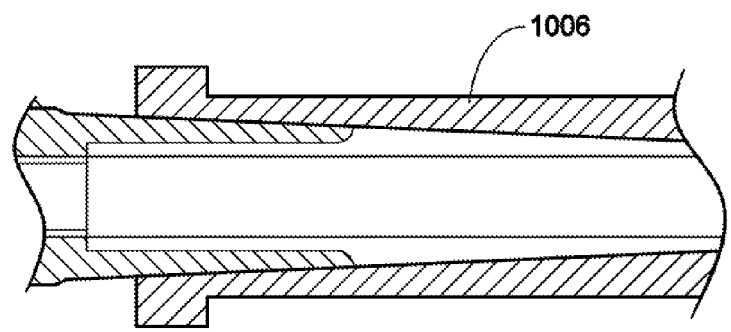

SYSTEMS, METHODS AND APPARATUSES FOR FORMATION AND INSERTION OF TISSUE PROSTHESIS

CROSS REFERENCE TO RELATED APPLICATIONS

This application claims priority to U.S. Provisional Application No. 60/915,410, filed on May 1, 2007.

Additionally, each of the following applications are herein incorporated by reference, in its entirety:

International Application No. PCT/AU2003/001289, filed on Sep. 30, 2003;
Australian Provisional Application No. 2002951762, filed on Oct. 1, 2002;
International Application No. PCT/AU2006/000267, filed on Mar. 1, 2006;
Australian Provisional Application No. 2005900952, filed on Mar. 1, 2005;
International Application No. PCT/AU2006/001176, filed on Aug. 15, 2006;
U.S. Provisional Application No. 60/708,687, filed on Aug. 15, 2005;
International Application No. PCT/AU2007/00001601 filed on Oct. 22, 2007;
U.S. Provisional Application No. 60/867,574, filed on Nov. 28, 2006;
International Application No. PCT/AU2007/001657, filed on Oct. 31, 2007;
U.S. Provisional Application No. 60/915,410, filed on May 1, 2007; and
U.S. Provisional Application No. 60/971,633 filed on Sep. 12, 2007.

FIELD OF THE DISCLOSURE

The present disclosure generally relates to tissue prostheses and more particularly, the present disclosure relates to systems, methods, and apparatuses for formation and insertion of tissue prostheses.

BACKGROUND INFORMATION

Joints of the musculoskeletal system of the human or animal body rely on the presence of healthy cartilaginous tissue for proper operation. Cartilaginous tissue can degenerate due to a number of causes, e.g., age or injury. Degradation of the tissue can reach a point where movement can cause severe discomfort and pain.

Degradation of tissue can occur in the spinal column. The spinal column comprises a series of 26 mobile vertebral bones, or vertebrae, connected by 75 stable articulations that control motion. The vertebrae are generally divided into posterior and anterior elements by thick pillows of bone called pedicles. The anterior element of the vertebra is a kidney shaped prism of bone with a concavity directed posteriorly and has flat superior and inferior surfaces called end plates. An intervertebral disc is sandwiched between adjacent pairs of vertebrae forming a joint between the adjacent pair of vertebrae. These discs are viscoelastic structures comprising a layer of strong, deformable, soft tissue. The intervertebral discs are subjected to a considerable variety of forces and moments resulting from the movements and loads of the spinal column. Each intervertebral disc has two components, being the annulus fibrosis surrounding a nucleus pulposus. The intervertebral disc cooperates with end plates of the vertebrae between which it is sandwiched.

The primary function of the nucleus pulposus of the disc is to give the disc its elasticity and compressibility characteristics to assist in sustaining and transmitting weight. The annulus fibrosis contains and limits the expansion of the nucleus pulposus during compression and also holds together successive vertebrae, resisting tension and torsion in the spine. The end plates of the vertebrae are responsible for the influx of nutrients into the disc and the efflux of waste products from within the disc.

With age or injury, a degenerative process of the disc may occur whereby its structures undergo morphological and biological changes affecting the efficiency with which the disc operates. Thus, the nucleus pulposus may reduce in volume and dehydrate resulting in a load reduction on the nucleus pulposus, a loss in intradiscal pressure and, hence, additional loading on the annulus fibrosis. In a normally functioning disc, the intradiscal pressure generated results in deformation of the end plates of the adjacent vertebrae generating the natural pumping action which assists in the influx of the nutrients and the efflux of waste products as stated above. A drop in intradiscal pressure therefore results in less end plate deformation. The nutrients supplied to the discal tissue are reduced and metabolic wastes are not removed with the same efficiency. This contributes to a degenerative cascade.

Radial and circumferential tears, cracks and fissures may begin to appear within the annulus fibrosis. If these defects do not heal, some of the nuclear material may begin to migrate into the defects in the annulus fibrosis. Migration of the nuclear material into the annulus fibrosis may cause stretching and delamination of layers of the annulus fibrosis resulting in back pain due to stimulation of the sinu-vertebral nerve. An intervertebral disc without a competent nucleus is unable to function properly. Further, since the spine is a cooperative system of elements, altering the structure and mechanics at one location of the spinal column may significantly increase stresses experienced at adjacent locations thereby further contributing to the degenerative cascade.

In the past, operative intervention has occurred to relieve lower back pain arising from intervertebral disc degeneration. Most of this operative intervention has been by way of a discectomy where leaking nuclear material is removed or, alternatively, fusion. The primary purpose of a discectomy is to excise any disc material that is impinging on the spinal nerve causing pain or sensory changes. Fusion means eliminating a motion segment between two vertebrae by use of a bone graft and sometimes internal fixation. Biomechanical studies show that fusion alters the biomechanics of the spine and causes increased stresses to be experienced at the junction between the fused and unfused segments. This promotes degeneration and begins the degenerative cycle anew. Clearly, being an invasive operative procedure, fusion is a risky procedure with no guarantee of success.

Due to the minimal success rate of these previous procedures, as well as their inability to restore complete function to the spinal column, alternative treatments have been sought in the form of artificial disc replacements. Theoretical advantages of artificial disc replacement over a fusion procedure include preservation or restoration of segmental motion in the spine, restoration of intervertebral architecture and foraminal height, sparing of adjacent segments of the spine from abnormal stresses and restoration of normal biomechanics across the lumbar spine. The established artificial disc replacement procedure consists of techniques that require a surgical incision on the abdomen, retraction of large blood vessels, a total excision of the anterior longitudinal ligament, anterior and posterior annulus along with the nucleus and near total removal of the lateral annulus and implantation of an articulated prosthesis. This is a major spinal column reconstruction operation carried out by a very invasive technique.

Accordingly, the present inventors have observed that there is a need for surgical procedures, methods, and/or systems which, as far as possible, restore the biomechanics of joints such as those between adjacent vertebrae of the spine by the provision of a tissue prosthesis mimicking natural, healthy cartilaginous tissue as well as a means of carrying out the surgical procedure in a minimally invasive manner and/or percutaneous manner.

BRIEF DESCRIPTION OF THE DRAWINGS

FIG. 25 shows a plan view of a first assembly of a tissue prosthesis insertion system in accordance with certain exemplary embodiments disclosed herein;

FIG. 26 shows a sectional side view of the first assembly of the system of FIG. 25 taken along line 26-26 in FIG. 25 in accordance with certain exemplary embodiments disclosed herein;

FIG. 27 shows a sectional side view, on an enlarged scale, of the part of the first assembly surrounded by circle "27" in FIG. 26 in accordance with certain exemplary embodiments disclosed herein;

FIG. 28 shows a sectional side view, on an enlarged scale, of the part of the first assembly surrounded by circle "28" in FIG. 26 in accordance with certain exemplary embodiments disclosed herein;

FIG. 31 shows a sectional side view, on an enlarged scale, of the part of the assembly surrounded by circle "31" in FIG. 30 in accordance with certain exemplary embodiments disclosed herein;

FIG. 32 shows a sectional side view, on an enlarged scale, of the part of the assembly surrounded by circle "32" in FIG. 30 in accordance with certain exemplary embodiments disclosed herein;

FIG. 33 shows a plan view of a valve member forming part of a tissue prosthesis of the system in accordance with certain exemplary embodiments disclosed herein;

FIG. 34 shows an end view of the valve member in accordance with certain exemplary embodiments disclosed herein;

FIG. 35 shows a sectional side view of the valve member taken along line 35-35 in FIG. 34 in accordance with certain exemplary embodiments disclosed herein;

FIGS. 50a, 50b and 50c show, respectively, front, side and plan views of an intervertebral disc implant, in accordance with certain exemplary embodiments disclosed herein:

FIGS. 51a, 51b and 51c show, respectively, front, side and plan views of an intervertebral disc implant, in accordance with certain exemplary embodiments disclosed herein;

FIG. 68 shows a schematic three dimensional view of an intervertebral disc implant, in accordance with certain exemplary embodiments disclosed herein;

FIG. 69 shows a schematic, sectional plan view of an intervertebral disc implant, in accordance with certain exemplary embodiments disclosed herein;

FIG. 70 shows sectional end view taken along line 70-70 in FIG. 69 in accordance with certain exemplary embodiments disclosed herein;

FIG. 71 shows a schematic, sectional three dimensional view of an intervertebral disc implant, in accordance with certain exemplary embodiments disclosed herein;

FIG. 72 shows embodiments disclosed herein; on an enlarged scale, the detail encircled by "72" in FIG. 71 in accordance with certain exemplary FIG. 73 shows the detail of FIG. 72 in a collapsed configuration in accordance with certain exemplary embodiments disclosed herein:

FIGS. 77-79 illustrate, schematically, various stages of the use of an embodiment of equipment, in accordance with certain exemplary embodiments disclosed herein, for preparing a site for the implantation of a tissue prosthesis;

FIGS. 80-85 illustrate, schematically, various stages of the use of another exemplary embodiment of equipment, in accordance with certain exemplary embodiments disclosed herein, for preparing a site for the implantation of a tissue prosthesis;

FIG. 93 illustrates a means of sealing through a luer lock in accordance with certain exemplary embodiments disclosed herein:

FIG. 94 illustrates a means of sealing through a luer slip or luer fitting (taper fit) in accordance with certain exemplary embodiments disclosed herein;

DETAILED DESCRIPTION

Figure 1:
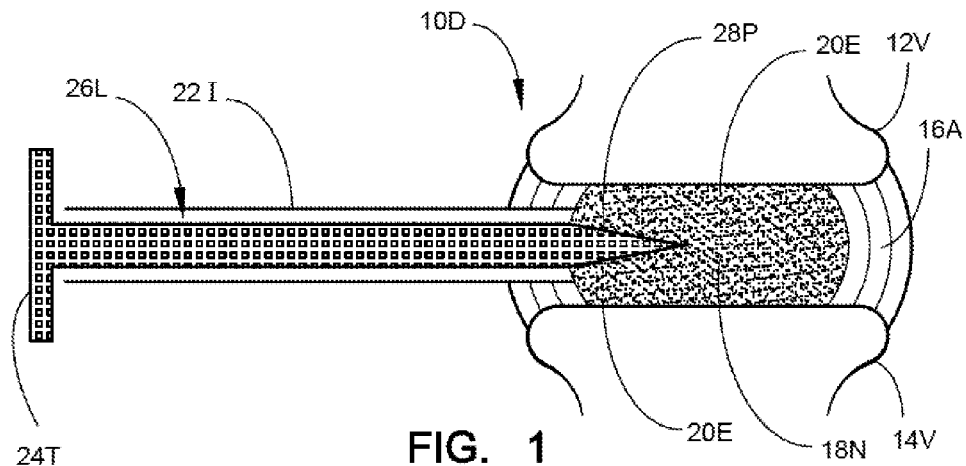
FIGS. 1-8 show schematic illustrations of various steps of a method, in accordance with certain exemplary embodiments disclosed herein, for forming a tissue prosthesis in situ at a site in a patient's body.

In certain exemplary embodiments disclosed herein, there may be provided methods of forming a tissue prosthesis in situ at a site in a patient's body, that comprise accessing the site in the patients body; if necessary, removing tissue from the site to form a cavity; inserting an envelope of a biologically inert, elastically deformable material into the cavity; charging a filler material, in a fluent state, into the envelope to cause the envelope to expand and, if necessary, stretch and conform to the shape of the cavity, and allowing the filler material to cure, the filler material being of the same class of material as the envelope so that, when the filler material has cured, a unified prosthesis is formed. In some aspects, these methods may be carried out using minimally invasive techniques. In some aspects, these methods may be carried out using percutaneous techniques. In some aspects, these methods may be carried out using a combination of minimally invasive and percutaneous techniques.

In certain exemplary embodiments disclosed herein, there may be provided methods of forming a tissue prosthesis in situ at a site in a patient's body, that comprise means for accessing the site in the patient's body; if necessary, means for removing tissue from the site to form a cavity; means for inserting an envelope of a biologically inert, elastically deformable material into the cavity; means for charging a filler material, in a fluent state, into the envelope to cause the envelope to expand and or stretch, if necessary and conform to the shape of the cavity; and means for allowing the filler material to cure, the filler material being of the same class of material as the envelope so that, when the filler material has cured, a unified prosthesis is formed. In some aspects, these methods may be carried out using minimally invasive techniques. In some aspects, these methods may be carried out using percutaneous techniques. In some aspects, these methods may be carried out using a combination of minimally invasive and percutaneous techniques.

In certain exemplary embodiments disclosed herein, the methods may include accessing the site percutaneously in a surgical procedure that is less invasive than conventional procedures. Hence, the method may be used to perform less invasive intervertebral disc nucleus replacement and the method may comprise forming an aperture in an annulus fibrosis of the disc percutaneously; extracting a nucleus pulposus of the disc to form a disc cavity bounded by the annulus fibrosis of the disc and end plates of vertebrae between which the disc is located; inserting the envelope, in a first state, into the cavity through the aperture; charging the filler material into the envelope to cause the envelope to expand and conform to the shape of the disc cavity; allowing the filler material to cure to form, together with the envelope, the substantially unified prosthesis; and occluding the aperture.

In certain exemplary embodiments disclosed herein, there may be provided methods of preparing a first assembly of a tissue prosthesis system for insertion into a patient's body, the methods comprising providing a first assembly which comprises a plurality of nested tubes, one of the tubes being a carrier tube; mounting a component of the prosthesis on a distal end of the carrier tube, the component being of an elastically deformable material; inserting a stiffening member into the first assembly so that the stiffening member extends into an interior of the component and causing a proximal end of the stiffening member to engage a proximal end of the first assembly; attaching a withdrawing device to the first assembly so that the withdrawing device is in fluid communication, at least with the interior of the component; and operating the withdrawing device to reduce the pressure, at least in the interior of the component to cause the component to collapse about the stiffening member.

In certain embodiments disclosed herein, there may be provided methods of preparing a first assembly of a tissue prosthesis system for insertion into a patient's body, the methods comprising means for providing a first assembly which comprises a plurality of nested tubes, one of the tubes being a carrier tube; means for mounting a component of the prosthesis on a distal end of the carrier tube, the component being of an elastically deformable material; means for inserting a stiffening member into the first assembly so that the stiffening member extends into an interior of the component and causing a proximal end of the stiffening member to engage a proximal end of the first assembly; means for attaching a withdrawing device to the first assembly so that the withdrawing device is in fluid communication with the interior of the component; and means for operating the withdrawing device to reduce the pressure in the interior of the component to cause the component to collapse about the stiffening member.

In certain exemplary embodiments of the disclosed herein, there may be provided methods of forming a tissue prosthesis at a site in a patient's body, the methods comprising providing a first assembly comprising a plurality of nested tubes, one of the tubes being a carrier tube with a component of the prosthesis carried at a distal end of the carrier tube; inserting the first assembly into a cannula placed in the patient's body, whereby the working cannula or cannula provides percutaneous access to the disc; engaging (e.g. magnetically attaching) a second assembly to a proximal end of the first assembly; and charging a filler material from the second assembly into the component and allowing the filler material to set.

In certain exemplary embodiments disclosed herein, there may be provided methods of implanting an intervertebral disc implant into an intervertebral disc, the methods comprising percutaneously performing a nucleotomy on the disc to remove a at least a portion of the nucleus pulposus of the disc to create a volume, inserting an envelope of the implant into the volume; charging an interior of the envelope with filler material in a manner to allow the envelope to expand to conform substantially to the volume, and causing the interior of the envelope to be closed off to retain the filler material within the envelope. The filler material may be selected to mimic, enhance or at least restore as much as possible the natural biomechanical characteristics of the nucleus pulposus of the disc. In certain embodiments, the filler material (e.g., the implant) may cooperate with the annulus to restore at least a portion of the natural biomechanical characteristics of the disc.

In certain embodiments, the various methods of implanting an intervertebral disc implant described throughout the specification may be performed in less time than prior art methods. For example, in certain embodiments, the method may be performed in less than 30 minutes, or less than 20 minutes, or less than 15 minutes, or less than 10 minutes. In certain embodiments, the method, excluding the charging of the interior of the envelope, may be performed in less than 30 minutes, or less than 20 minutes, or less than 15 minutes, or less than 10 minutes. In certain embodiments, the method, excluding the nucleotomy procedure may be performed in less than 30 minutes, or less than 20 minutes, or less than 15 minutes, or less than 10 minutes.

In certain exemplary embodiments disclosed herein, there may be provided methods of implanting an intervertebral disc implant into an intervertebral disc, the methods comprising means for accessing the disc percutaneously using for example a working cannula; means for percutaneously performing a nucleotomy on the disc to remove at least a portion of the nucleus pulposus of the disc to create a volume; means for inserting an envelope of the implant into the volume; means for charging an interior of the envelope with filler material in a manner to allow the envelope to expand to conform substantially to the volume; and means for causing the interior of the envelope to be closed off to retain the filler material within the envelope, the filler material being selected to mimic natural biomechanical characteristics of the nucleus pulposus of the disc.

In certain exemplary embodiments disclosed herein, there is provided methods of implanting an intervertebral disc implant into an intervertebral disc, the methods including a method of accessing the disc percutaneously using for example a working cannula, a method for removing at least a portion of the nucleus pulposus of the disc to create a volume; inserting at least one envelope into the volume; charging an interior of the at least one envelope with material in a manner to allow the at least one envelope to expand to substantially fill the volume, or partially fill the volume; and causing the interior of the envelope to be closed off to retain the material, the filler material being selected to at least partially mimic characteristics of the nucleus pulposus of the disc.

In certain exemplary embodiments disclosed herein, there is provided methods of implanting an intervertebral disc implant into an intervertebral disc, the methods including means for performing a nucleotomy on the disc to remove a nucleus pulposus of the disc to create a volume; means for inserting an envelope of the implant into the volume; means for charging an interior of the envelope with filler material in a manner to allow the envelope to expand to conform substantially to the volume; and means for causing the interior of the envelope to be closed off to retain the filler material within the envelope, the filler material being selected to mimic natural biomechanical characteristics of the nucleus pulposus of the disc.

In certain exemplary embodiments disclosed herein, there is provided methods of implanting an intervertebral disc implant into an intervertebral disc, the methods including percutaneously performing a nucleotomy on the disc to remove a nucleus pulposus of the disc to create a volume; inserting an introducer into an opening formed in an annulus of the disc; and introducing into the volume, via the introducer, at least one element which changes from a first configuration, in which the at least one element is able to be inserted into the introducer, to a second configuration in which the at least one element conforms substantially to the volume.

In certain exemplary embodiments disclosed herein, devices may be provided for forming a tissue prosthesis in situ at a site in a patient's body, the devices may comprise a delivery device displaceably receivable in a lumen of an introducer, the delivery device defining a passageway; an envelope carried at a distal end of the delivery device, the envelope being of a biologically inert, elastically deformable material capable of being expanded to conform to an interior surface of a cavity formed at the site; and a supply of a filler material chargeable in a fluent state into the envelope through the passageway of the delivery device, the filler material being of the same class of material as the envelope to form, when cured, together with the envelope, a unified prosthesis.

In certain exemplary embodiments disclosed herein, devices may be provided for forming a tissue prosthesis in situ at a site in a patient's body, the devices may comprise a tubular delivery device, the delivery device defining a passageway, an envelope of the prosthesis being mountable to a distal end of the delivery device to be received in a cavity at the site; a filler member receivable in the passageway of the delivery device, the filler member being receivable with clearance in the passageway to define a gap to enable fluid to be manipulated, or displaced at least from the envelope; and a removal mechanism carried by the delivery device for enabling the envelope to be removed from the delivery device after the envelope has been charged with filler material via the filler member.

In certain exemplary embodiments disclosed herein, devices may be provided for forming a tissue prosthesis in situ at a site in a patient's body, the devices may comprise a means for tubular delivery device, the delivery device defining a passageway, an envelope of the prosthesis being mountable to a distal end of the delivery device to be received in a cavity at the site; a filler member receivable in the passageway of the delivery device, the filler member being receivable with clearance in the passageway to define a gap to enable fluid to be manipulated at least from the envelope; and a means for a removal mechanism carried by the delivery device for enabling the envelope to be removed from the delivery device after the envelope has been charged with filler material via the filler member.

In certain exemplary embodiment disclosed herein, devices may be provided for forming a tissue prosthesis in situ at a site in a patient's body, the devices may comprise a tubular delivery device, the delivery device defining a passageway, an envelope of the prosthesis being mountable to a distal end of the delivery device to be received in a cavity at the site; a stiffening element arranged, or means for providing a stiffening element, to project from a distal end of the delivery device with the envelope, in use, being received over the stiffening element to be supported by the stiffening element; and a removal mechanism carried by the delivery device for enabling the envelope to be removed from the delivery device after the envelope has been charged with filler material via the filler member.

In certain exemplary embodiment disclosed herein, tissue prosthesis insertion systems may be provided which include a first assembly comprising a plurality of nested tubes, one of the tubes being a carrier tube which, in use, receives a component of a tissue prosthesis at a distal end of the carrier tube; a magnetic mount carried at a proximal end of the first assembly; a second assembly removably attachable to the first assembly; and an attachment device carried at a distal end of the second assembly, the attachment device being responsive to the magnetic mount of the first assembly, the magnetic mount and the attachment device carrying complementary engaging formations to facilitate sealing between the magnetic mount and the attachment device. In certain embodiments, the second assembly may have the magnetic mount where the first assembly has the engaging member which is sealingly responsive to the magnetic mount of the second assembly.

In certain exemplary embodiment disclosed herein, tissue prosthesis insertion systems may be provided which include an assembly comprising a plurality of nested tubes, one of which is a carrier tube for carrying a component of a tissue prosthesis at its distal end and another of which is a filler tube received with clearance in the carrier tube to define a passage between the filler tube and the carrier tube, the proximal end of the filler tube and the proximal end of the carrier tube being in sealing engagement; and a withdrawing device attachable to the assembly so that, when the withdrawing device and material dispenser is attached and the component of the tissue prosthesis is mounted on the distal end of the carrier tube, a closed system is formed which allows the withdrawing device to be used to increase the volume of the closed system to form a low pressure region at least in the component.

In certain exemplary embodiment disclosed herein, tissue prosthesis insertion systems may be provided which include a working cannula for accessing a site in a patient's body percutaneously, in a less invasive manner for carrying out a tissue prosthesis insertion procedure at the site; and an obturating device receivable in the cannula for tamping a part of a tissue prosthesis into position after formation of the tissue prosthesis.

The obturating device may comprise a blunt-ended rod slidably receivable in the working cannula.

In certain exemplary embodiment disclosed herein, tissue prosthesis components may be provided which include an envelope of an elastically deformable material, the envelope defining an access opening; and a flow control member arranged in the access opening, the flow control member being configured to permit withdrawal of fluid from an interior of the envelope prior to filling the envelope with a filler material.

In certain exemplary embodiment disclosed herein, prosthesis delivery systems may be provide which includes a plurality of nested tubes, an outermost tube of which functions as a cannula in which the remaining tubes are received, the remaining tubes forming part of a prosthesis delivery apparatus, a wall portion of at least one of the tubes having a change in diameter along its length to mate with a corresponding part of a dispensing arrangement for use with the prosthesis delivery apparatus.

In certain exemplary embodiments disclosed herein, systems are provided which include a plurality of tubes, wherein an outermost tube functions as a cannula in which the remaining tubes are received, the remaining tubes forming part of a prosthesis delivery apparatus, a wall portion of at least one of the tubes having a change in diameter along its length to mate with a corresponding part of a dispensing arrangement for use with the prosthesis delivery apparatus.

In some exemplary embodiments, the prosthesis delivery devices may include at least one carry tube which may carry at least one component of the prosthesis on its distal end and at least one filler tube receivable in the carrier tube for charging a filler material into the component when the component is located at the desired location. The prosthesis delivery apparatus may include a connector for connection to a withdrawal device to enable fluid (e.g., air or gas) to be manipulated (e.g., withdrawn) from the component during formation of the prosthesis in situ, the connector being arranged, in use, at a proximal end of the prosthesis delivery apparatus.

In some exemplary embodiments, the prosthesis delivery apparatus may include a displacement device for displacing the component of the prosthesis after it has been charged with the filler material. The displacement device may be a further tube mounted about the carrier tube.

In some exemplary embodiments, the prosthesis delivery apparatus may include at least one cover tube to cover the component of the prosthesis, the at least one cover tube fitting over the at least one carrier tube. The at least one cover tube may include a resiliently flexible distal portion to accommodate the component of the prosthesis. In certain embodiments, the at least one cover tube may be received over the displacement device/tube which is mounted about the carrier tube.

In some exemplary embodiments, a wall portion of each of the tubes has a change in diameter along its length. In some exemplary embodiments, the change in diameter along the length of each tube may be provided by a flared wall portion of each tube.

In some exemplary embodiments, the systems may include a manipulating arrangement for effecting manipulation of the tubes located within the cannula. The manipulating arrangement may include a rupturing mechanism for rupturing the cannula for removal. The rupturing mechanism may comprise a plurality of spaced zones of weakness in a wall of the tube of the cannula and a gripping device arranged at a proximal end of the tube of the cannula. The gripping device may comprise a plurality of outwardly extending tabs which are pulled outwardly to cause rupturing of the zones of weakness of the cannula to facilitate withdrawal of the cannula after placement and positioning of the component of the prosthesis in the cavity or after formation and/or setting of the prosthesis.

In some exemplary embodiments, the systems may include the dispensing mechanism, the dispensing mechanism including a tubular element having a distal end which corresponds with and mates with that part of the wall portion of the at least one tube having the change in diameter. The nested tubes may be configured to extend proximally of the distal end of the element to overlie the element. With this arrangement, the length of the unsupported ends of the tubes is shortened thereby improving the rigidity of the tubes and the stability of the system. In addition, the balance of the system is improved rendering it easier for the clinician to control the system. This overall reduction in the length of the delivery system may also result in a reduction in the pressure required to deliver the filler material to the envelope component of the prosthesis.

The dispensing mechanism may include a dispenser to which the element is attachable. The element may be a static mixer.

In certain exemplary embodiment disclosed herein, prosthesis delivery systems are provided which include a plurality of nested tubes, one tube being a carrier tube which carries at least a component of a prosthesis at its distal end and another tube constituting a delivery tube for delivering the nested tubes to a site at a patient's body; and a cover tube forming part of the nested tubes, the cover tube being arranged outwardly of the carrier tube to cover the component when the carrier tube is inserted into the delivery tube to protect the component.

In certain exemplary embodiments disclosed herein, there is provided an introducer for introducing an intervertebral disc implant into a disc that has undergone a nucleotomy, the introducer including at least two sleeves arranged telescopically with respect to each other; and a displacement mechanism arranged on an operatively inner surface of an innermost one of the sleeves for assisting in displacing filler material along the sleeves into an interior of the disc, in use.

The displacement mechanism may comprise a ratchet arrangement for urging the filler material along the sleeve.

In certain embodiments disclosed herein, equipment may be provided for preparing a site for the implantation of tissue prosthesis. The equipment may include, for example a conduit assembly; an elastically stretchable and/or an inflatable member receivable on a distal end of the conduit assembly, the inflatable member being positioned, in use, at a site in a patient's body at which a tissue prosthesis is to be implanted; and a plurality of fluid dispensers connectable to the conduit assembly to communicate with the inflatable member, operation of the fluid dispensers manipulating the inflatable member to facilitate formation of the tissue prosthesis at the site.

Manipulating the inflatable member may comprise priming the inflatable member to receive a volume of fluid (e.g., a liquid or gas) to determine a size of the site. Still further, manipulating the inflatable member may comprise cyclically inflating and deflating the inflatable member to condition tissue surrounding the site.

The equipment may include a monitoring mechanism for monitoring a volume of fluid dispensed by a selected one or more of the fluid dispensers into the inflatable member to determine a size of a cavity at the site to be filled by the tissue prosthesis. In this manner, the inflatable member may act as a mock implant and may also determine the relative position of the implant as well. In certain exemplary embodiments, the monitoring device may be a pressure transducer. It will, however, be appreciated that other transducers such as force transducers, strain gauges, or the like could be employed to function as an end-point monitor. Alternatively, in embodiments where at least the volume of nucleus removed, or the volume created by the nucleotomy procedure, is replaced. Accordingly, the device may allow the volume to be measured which allows the surgeon to gauge the required volume of biomaterial to be dispensed into the envelope component of the implant.

In certain embodiments, the conduit assembly may comprise at least one tube on which the inflatable member is mountable with a branched connector being carried at a proximal end of the at least one tube, one of the fluid dispensers being connectable to each branch of the connector. The branched connector may be for example, a Y connector or a T connector.

In certain exemplary embodiments, the conduit assembly may comprise a pair (e.g., at least 2, 3, 4, 5, 6, 7, 8, etc.) of nested tubes, an outer tube being a carrier tube on which the inflatable member is carried and an inner tube being a fluid delivery tube for dispensing a volume of fluid from one of the dispensers into the interior of the tube. In certain embodiments, at least one of the tubes may extend, in use, to a distal end of the inflatable member and the tube may have an aperture defined in it which facilitates fluid communication between an interior of the inflatable member and an interior of the tube or tubes. The at least one tube extending into the inflatable member may, in certain embodiments, serve to allow the inflatable member to be collapsible about the tube and more easily introduced percutaneously or minimally invasively through the working cannula.

In another exemplary embodiment, the conduit assembly may comprise a single tube on a distal end of which the inflatable member is carried. A flow control member may be received in communication with an interior of the tube for placing a selected one of the fluid dispensers in fluid communication with the interior of the tube and hence the interior of the inflatable member as desired. Similar to other exemplary embodiments, the tube may extend, in use, to a distal end of the inflatable member and have an aperture defined in it which facilitates fluid communication between an interior of the inflatable member and an interior of the tube.

In certain embodiments, the flow control member may be a device which controls the direction and flow of fluid. This can be, for example, a 3-way stopcock, or it can be a valve which opens up when the fluid dispenser is engaged, and shuts off when the fluid dispenser is disengaged (e.g., a duck bill valve). For example, with a duck bill valve, when the fluid dispenser is engaged, the tip of the fluid dispenser pushes open the leaflets of the valve, placing the interior of the tubes and inflatable component in fluid communication with the fluid dispenser. When the fluid dispenser is disengaged, the leaflets of the valve. Such an apparatus using this form of valve system can omit the need for the dual syringe system because a single syringe can be used to prime the system and any air or gas or other unwanted fluids which are displaced from within the system and into the syringe can be purged by removing the syringe from the rest of the apparatus and purged by manipulating the piston of the syringe. In the meantime, the fluid within the system is maintained within the system because of the valve which has closed off to substantially seal in the fluid which has been used to displace the unwanted air, gas or other fluid which was originally within the system.

At least one of the fluid dispensers may be a reciprocally operable device such as for example, a syringe.

In certain exemplary embodiments disclosed herein, there may be provided methods of preparing a site for the implantation of tissue prosthesis. The methods may include inserting a member into a cavity at a tissue site to be prepared; priming the member; and inflating the member at least once with a volume of fluid to determine a size of the cavity.

In certain exemplary embodiments disclosed herein, there may be provided methods of preparing a site for the implantation of tissue prosthesis. The methods may include means for inserting an inflatable member into a cavity at a tissue site to be prepared, means for priming the inflatable member; and means for inflating the inflatable member at least once with a volume of fluid to determine a size and/or position of the cavity.

The method may include priming the inflatable member prior to inserting into the cavity which may entail priming the inflatable member prior to inserting the inflatable member into the patient's body. In certain exemplary embodiments, the method may include inflating and deflating the inflatable member a number of times to condition tissue surrounding the cavity. In certain exemplary embodiment, the method may include monitoring a predetermined parameter to determine the quantity of fluid dispensed into the inflatable member to fill the cavity.

The method may include means for priming the inflatable member prior to inserting into the cavity which may entail priming the inflatable member prior to inserting the inflatable member into the patient's body. In certain exemplary embodiments, the method may include means for inflating and deflating the inflatable member a number of times to condition tissue surrounding the cavity. In certain exemplary embodiments the method may include means for monitoring a predetermined parameter to determine the quantity of fluid dispensed into the inflatable member to fill the cavity.

In certain exemplary embodiments disclosed herein, tissue prostheses are provided which comprise at least one envelope of a biologically inert, elastically deformable material capable of being expanded to conform to an interior surface of a cavity formed at a site in a patient's body; and a filler material received in a fluent state in the at least one envelope, the filler material being of the same class of material as the at least one envelope to form, when cured, together with the envelope, a unified, or substantially unified, structure.

In certain exemplary embodiments disclosed herein, tissue prostheses are provided which comprise an envelope of a foraminous, chemically inert material shaped to conform to an interior surface of a cavity formed at a site in a patient's body in which the envelope is to be placed, and a filler material received in a fluent state in the envelope, the filler material being of an elastomeric material which, prior to being cured, is urged into foramens of the envelope to form an integrated structure which inhibits relative movement between the envelope and the filler material, in use, and once the filler material has cured.

In certain exemplary embodiments, there is provided an intervertebral disc implants which includes an envelope constructed of at least one stretchable and/or elastically deformable elastomeric material, the envelope including an attaching formation for attachment to an introducer to enable the envelope, in a first state, to be introduced into a volume of an intervertebral disc that has undergone a nucleotomy; and a filler material receivable in the envelope via the introducer to cause the envelope to expand elastically to conform substantially to the volume in which the envelope is received, in use.

According to certain exemplary embodiments, there is provided an intervertebral disc implant which includes a first object constructed of at least one stretchable and/or elastically deformable elastomeric material, the first object being in communication with second object for attachment to a third object to enable the first object, in a first state, to be introduced into a volume of an intervertebral disc that has undergone a nucleotomy; and a material receivable in the first object via the second object which results in expansion, or partial expansion of the first object such that the first object substantially conforms to the volume in which the first object is received, in use.

According to certain exemplary embodiments, there is provided an intervertebral disc implant which includes an envelope constructed of at least one stretchable and/or elastically deformable elastomeric material, the envelope including means for attaching an introducer to enable the envelope, in a collapsed state, to be introduced into a volume of an intervertebral disc that has undergone a nucleotomy; and means for introducing a filler material into the envelope via the introducer to cause the envelope to expand elastically to conform substantially to the volume in which the envelope is received, in use.

In certain exemplary embodiments, there is provided an intervertebral disc implant which includes an envelope, the envelope including an attaching formation for attachment to an introducer to enable the envelope, in a collapsed state, to be introduced into a volume of an intervertebral disc that has undergone a nucleotomy; and a filler material receivable in the envelope after placement of the envelope in the volume of the disc, in use, to cause expansion of the envelope to conform to the volume, the filler material comprising a plurality of discrete, elongate elements introducible, via the introducer, into an interior of the envelope.

In certain exemplary embodiments, there is provided an intervertebral disc implant which comprises an envelope receivable in a volume of an intervertebral disc that has undergone a nucleotomy, the envelope defining a plurality of chambers, the chambers being configured so that, when at least certain of the chambers contain a filler material, the envelope conforms substantially to the volume of the disc; a filler material receivable in the at least certain of the chambers; and at least one of the chambers having a filler mechanism associated with it.

One advantage of certain disclosed methods and equipment are that they facilitate minimally invasive formation of tissue prosthesis in situ. Another advantage of certain disclosed methods and equipment are that they facilitate percutaneous formation of tissue prosthesis in situ. In addition, tissue prosthesis is provided which are resistant to delamination. In particular, in the case where the tissue prosthesis has an envelope and filler material of the same class of material, a substantially unified, integrated structure may be provided which is resistant to delamination and relative movement between the envelope and the filler material. The unified structure and the fact that the envelope is elastically deformed and is retained under tension also renders the envelope resistant to creasing increasing the operational efficiency of the prosthesis by being better able to distribute forces to the annulus fibrosis of the disc.

In addition, the use of a silicone rubber envelope in certain embodiments is particularly advantageous due to the fact that, when a nucleotomy has been performed, residue remains behind which is irregular in shape. It is beneficial to have a prosthesis which expands and conforms as closely as possible to the shape (micro and macrostructure) of the cavity in order that compressive, tensile, bending and torsional forces can be accommodated by the disc. In addition, the provision of a tissue prosthesis expanding and closely conforming to the shape of the cavity results in an improvement in stimulation and deformation of the end plates of the vertebrae and thereby aiding in restoration of the natural pumping action which assists in the influx of nutrients and the efflux of waste products from within the disc.

It is yet a further advantage of certain embodiments that the tissue prosthesis can be formed in situ in a minimally invasive manner. The need for invasive surgical procedures is therefore obviated and there is the added advantage of more rapid post-operative recovery and the reduced need for a prolonged period in hospital.

In certain embodiments, the equipment further provides an efficient, easy to use manner of forming the tissue prosthesis. By having the tubes etc. nested, a clinician is more easily able to manipulate the equipment to place and form the tissue prosthesis. With the added use of a working cannula, the access to the disc and hence the nucleus pulposus need only to be established once. All the remaining tubular apparatus for positioning and forming the tissue prosthesis are slidably receivable within the protected confines of the working cannula. Therefore, there is no repeated movement of having to go in and out of the tissue which could increase the risk of damage to muscle, subcutaneous tissue and particularly nerves. Further, the use of a barreled dispensing device connected to a static mixer and tube which delivers the mixed biomaterial directly into the envelope avoids the use of complex systems (for example, ones with pressure feedback etc.) for injecting the material which may be used to overcome the changes in pressures while injecting into confined tissue spaces.

It is yet a further advantage that the procedure is not restricted to large hospitals requiring costly operating tools in the hand of professionals like spinal surgeons, neurosurgeons and orthopedic surgeons: but can be performed by numerous physician including pain physicians, radiologists, anesthesiologists, sports physicians and any other professional confident of using a fluoroscope imaging device and placing needles into intervertebral discs. The larger community and societal benefit of such superiority of the present inventions are great as it improves access and affordability to a large population of chronic back pain sufferers. Other advantages include at non-heat generating catalytic interaction (or in certain embodiments, the reaction may be slightly endothermic or slightly exothermic) for polymerization of the flowable material, obviating the risk of thermal damage to adjacent tissues. More advantages include, prevention of leakage of flowable material into undesirable confines in the event the prepared tissues walls have fissures and or breaches that communicate to areas where there may be organs at risk.

While the inventions described herein are described with reference to certain exemplary embodiments related to intervertebral disc nucleus replacement, it will readily be appreciated by persons of ordinary skill in the art, in view of this disclosure, that the inventions disclosed herein are not limited to such embodiments and that the inventions described herein are more generally related to tissue prostheses.

In certain exemplary embodiments, the filler material may be any natural, synthetic or biological polymer. The materials may be polymers or copolymers. The material should preferably present with biocompatible characteristics. The material may at least closely mimic and or at least closely restore the function of the joint or tissue it is replacing. In the case of the intervertebral disc, the material may restore the biomechanics of the joint by restoring the intradiscal pressure and hence the hoop stresses to the annulus fibrosis. Should it be required, the material may also be able to supply sufficient pressure to the disc to restore any loss in disc height or at least maintain the disc height. The material may also have some load bearing capabilities. Patients undergoing nucleus prosthesis treatment may have a mildly compromised annulus fibrosis (small tears and or fissures), hence the prosthesis may bear some of the axial load, whilst still sharing and distributing some of the incident load to the annulus to keep it in tension (i.e., be both load bearing and load sharing). Also, the material should preferably not inhibit the flow of nutrients and other such fluids through the disc, as the residual (remaining) nucleus and annulus still requires hydration and nutrients to at least slow down or halt the degeneration of the disc. The material may also possess resilience, viscoelasticity and fatigue resistance (as the disc is loaded cyclically during everyday activities, the disc needs to be able to retain or at least restore its height under cyclic fatigue). The class of materials which suits these features are elastomers, in particular silicones. Silicones have an established history of use. They are extremely stable (mechanically and biologically) in its cured form and even when they are cured in situ, the catalysts used to cure the material are not harmful to the surrounding tissue and the curing process is harmless to the surrounding tissue. Silicones are resilient, elastic and have excellent shock absorbing capabilities.

Although the range of hardness for the silicones (or elastomer in general) which are suitable for this application are between about 5-90 A (e.g., 5-15 A, 15-20 A, 20-40 A, 40-50 A, 50-70 A, 70-90 A, etc.), the preferred hardness range is about 20-40 A and more specifically about 30 A (e.g.; about 27, 28, 29, 30, 31, 32, 33, etc.). Since silicones deform elastically under a given load, it spreads the load evenly across the endplates and minimizes stress concentration and or stress shielding which could all lead to subsidence of the implant into the endplate.

Additionally, the filler material may have varying degrees of porosity (such as silicone foams). Porosity may allow for tissue to grow into it, it may not affect the flow of nutrients across the disc, and by adjusting the porosity, the mechanical characteristics of the material may also be varied (such as deformation under load, creep, fatigue properties etc.).

The filler material may be selected to at least partially mimic natural biomechanical characteristics of the nucleus pulposus of the disc.

The at least one envelope may be made from an elastomeric material, preferably a silicone, which is biologically inert and which can elastically deform up to 3, 5, 7, 10, 30, 50, 80, 100, 120, or 150 times the size of the at least one envelope in its relaxed state. In some embodiments, the at least one envelope may be made from the silicone rubber material which is substantially biologically inert and which can elastically deform in the ranges of 3 to 5, 5 to 7, 7 to 10, 10 to 50, 10 to 100, 20 to 150, 30 to 100, 20 to 120, 70 to 100, or 50 to 150 times the size of the at least one envelope in its relaxed state. In other embodiments, the envelope may be compliant (e.g., with or without be elastic) which may allow the envelope to conform or substantially conform to the cavity.

The at least one envelope may also be made of other materials. For example, the at least one envelope made from less expansible material such as a biological or a synthetic polymeric material. A suitable synthetic polymeric material may, for example, be polyester such as polyethylene terephthalate (PET). The at least one envelope may also be constructed of a knitted PET material so that, when the filler material is charged into the at least one envelope, the filler material fills foramens or interstices in the at least one envelope to form an integrated structure which resists relative movement between the filler material and the at least one envelope. Alternatively, the knitted PET material may be coated with silicone allowing the filler material to integrate with the coating.

The materials which the envelope may be made from may be any natural, synthetic or biological polymer or copolymer which possesses biocompatibility. The envelope may be a porous material which allows for the surrounding tissue to grow into the implant and anchor or stabilize the implant within the disc space for in general at the tissue site which it is being implanted into). The porosity may also allow for the filler material to seep through the envelope and bond to the envelope to form a substantially fled structure. Should the envelope be made of a non-porous material, the advantage is that it prevents filler material from seeping into unwanted fissures, cracks and tears in the annulus. Even if the envelope is non porous, having filler and envelope of the same class of materials can also achieve the same substantial unification. Having a unified structure means that there is no relative movement between the filler and envelope, thus reducing the wear and hence the wear particles being produced. An advantage of having an envelope of an elastic, resilient material such as silicone is that the envelope may be capable of expanding and conforming to the macro and micro structures of the interior of the disc. This also increases the contact area of the implant across the endplates reducing stress concentrations and thus reducing the chances of implant subsidence.

As used in the specification the performance of a nucleotomy on the disc involves the removal of a certain amount of the nuclear tissue constituting the nucleus pulposus. The methods, devices, and/or systems disclosed herein often refer to the removal of the nuclear tissue. The amount of nuclear material removed may vary from procedure to procedure and this will be understood by those skilled in the art in view of the present disclosure. Using the devices, methods, and/or systems disclosed herein, it may be desirable to completely remove the nuclear tissue, in other instances it may be sufficient to substantially remove the nuclear tissue, or in other instances it may be sufficient to partially remove the nuclear tissue.

Depending on the degree of nucleus pulposus removal, the prosthesis may be classed as a total nucleus replacement or a partial nucleus replacement. Regardless of the degree of tissue removal, the one or more implants may completely or at least partially fill the cavity which remains. Completely filling the cavity will allow the transfer of load onto the annulus and restore the hoop stresses which are necessary to minimise the shear stresses on the annular layers and hence, at least slow further degeneration of the disc. If the implant were to partially fill the space, it allows the implant to reposition itself in a manner which prevents further migration and minimise the chances of extrusion. It may also reposition itself to a position which is of least resistance and hence minimise the stresses on the implant and surrounding tissue. The kangaroo data detailed later demonstrates the restoration of the kinematics of the spine even after the partial filling of the nucleus cavity.

One of the advantages of the implant is that multiple units can be implanted from various directions to achieve a partial, near complete or complete filling of the nuclear space. For example, one device can be implanted on the right side from the right posterolateral corner or the right lateral corner or anteriorly. The other one can be implanted from the opposite side as well.

In certain embodiments, a percutaneous approach as opposed to open or minimally invasive surgery may be used. With a percutaneous approach, a needle is usually used for intravenous injections, intramuscular injections or intradiscal injections. For minimally invasive surgery, some operations have been described and defined as requiring 1. visualization; which may be magnified by using optical loops, endoscopic cameras, microscopes etc. 2. illumination which is obtained either via cold light sources, optical cables or other means 3. retraction; retraction of tissues is an important components of minimally invasive surgery as a lot of resources and effort have gone into developing this third and final component of minimally invasive surgery. It is understandable that a small incision may be required for minimally invasive surgery (e.g., about 5 cm, about 6 cm, about 7 cm, etc.) and such incisions can be multiple in nature. The present inventors propose the percutaneous surgery which is carried out without the aid of optical visualization, illumination, or the use of any specialized retractors as is required for minimally invasive surgery. In certain embodiments the method may be performed as a micro-invasive surgery. For example, in certain embodiments, the opening used may be less than 4 cm. For example, the opening (e.g., the incision, puncture, or other means of accessing the body) may be up to 200 microns, or up to 400 microns, or up to 800 microns (e.g., about 200, 250, 300, 350, 400, 450, 500, 550, 600, 650, 700, 750, or 800) or alternatively of the order of about 2 cm to about 4 cm (e.g., about 2, 2.5, 3, 3.5, 4) or alternatively, of the order of up to 1 cm.

The methods and apparatus defined for formation and insertion of tissue prosthesis can be used in many clinical scenarios in varying fashions. In the area of degenerative disc of the spine, advanced stage disc diseases require the application of posterior spinal fusion with or without decompression with the fusion either being static or dynamic. In situations where the fusion is dynamic and performed with the use of pedicle screws there is a risk that the lordosis of the motion segment may be compromised. In static fusions, the lordosis is recreated by use of an interbody cage or interbody fusion device and the operation is called posterior interbody lumbar fusion. In dynamic fusions, the CPDRD can be implanted in an interbody manner within the nucleus to recreate the hunbar lordosis, to share load bearing anteriorly and thereby prevent loosening of the pedicle screws. This method may be a preferable method of performing posterior dynamic fusion of the spine, using existing systems like Dynesis, N-Flexrod (Spine next).

Further, in more advanced disc disease, the clinical condition of spinal stenosis exists where the gap between the spinous processes decreases. In these patients, the classical older operation has been laminectomy, foraminolaminectomy, posterior spinal decompression. More modern operations include implantation of the Wallis device. X-Stop, or In Space, Diam. However, these interspinous distraction devices have numerous disadvantages including incisions to expose the area (minimally invasive spinal surgery), and/or being hard and not allowing for shock absorption. The device disclosed herein can be implanted in the interspinous area in a percutaneous manner after clearing the interspinous area with the patient in a flexed position. The distraction of the interspinous area leads to effective improvement in the spinal stenosis. The same interspinous implant can be used after discectomies performed for herniated nucleus pulposus fragments either by small incision or endoscopically.

In certain embodiments, an apparatus for forming a tissue prosthesis (e.g. a disk prosthesis) in situ in a patient's body may be provided. The apparatus may comprise, an inflatable component and a delivery mechanism for delivering a filler material into the inflatable component so that when the filler material is cured, a unified prosthesis is formed. In certain embodiments, the delivery mechanism may comprise at least one priming mechanism a hole, valve, or opening) proximate to the area where the inflatable component is coupled to the delivery mechanism (see, for example, FIG. 386 for an example of a hole 1010 on either side of the delivery mechanism and proximate to an end of the delivery mechanism). The at least one hole may be large enough for gas to pass through but small enough so that the filler material cannot pass through. In this manner, it may be possible to prime the apparatus to remove a substantial amount of the gas from within the system so that the gas does not need to be purged when the delivery system is in the body.

Certain embodiments may provide a method system or apparatus that comprises any of the details disclosed throughout this specification exclusive of for example, a bone grafting, stabilization, or fastening and/or holding devices such as screws (e.g., facet screws, and/or pedicle screws), staples, etc. For example, in certain embodiments, a method may be provided that consists only of accessing the site in the body of a patient (e.g., a vertebral disk), removing tissue from the site to form a cavity, if necessary, inserting an inflatable component into the cavity, and delivering, via a delivery mechanism, a filler material into the inflatable component so that when the filler material is cured, a unified prosthesis is formed. The exemplary method may optionally include some of the additional steps disclosed throughout the specification. In certain embodiments, a method for completing the implantation of a tissue prosthesis in situ in a patient's body may be provided and the method may consist exclusively of accessing the site in the body of a patient; optionally, removing tissue from the site to form a cavity; optionally, priming a delivery mechanism with filler material to remove gas from within the delivery system; optionally, sizing the cavity; inserting an inflatable component into the cavity; delivering a filler material into the inflatable component so that when the filler material is cured, a unified prosthesis is formed; and completing the procedure by removing the delivery mechanism from the site in the patient's body and optionally, applying a bandage to the site. In certain embodiments, the method may not require a bandage but may merely be completed without the use of any mechanical closing means such as for example, sutchers or stitches.

Certain embodiments may provide a method for forming a tissue prosthesis in situ in a patient's body. The method may comprise accessing the site in the body of a patient (e.g., a vertebral disk), removing tissue from the site to form a cavity, if necessary, and priming a delivery mechanism with filler material to remove gas from within the delivery system. The method may further comprise inserting an inflatable component into the cavity, and delivering, via a delivery mechanism, a filler material into the inflatable component so that when the filler material is cured, a unified prosthesis is formed.

In certain embodiments, the delivery mechanism may be configured to be primed prior to forming the tissue prosthesis and the inflatable component may be deflated during the priming so that after the delivery mechanism is primed, there is an acceptable amount of gas (e.g., substantially no gas or a minimal amount of gas) in the inflatable component, thereby further eliminating the need for a gas removal system during delivery of the filler material (e.g., a two lumen system such as discussed elsewhere herein). In certain embodiments, the opening discussed above may be used to remove the gas. In particular, as the filler material fills the delivery mechanism, the gas within the system may be pushed out through the hole. In this manner, only a desirable amount of gas may remain in the delivery mechanism. In certain embodiments, the inflatable component may be at least partially primed with filler material. Partially priming the inflatable component may include partially filling the inflatable component in a manner such that the inflatable component remains in a relaxed state or alternatively in a state where it may still be inserted into the site of the body without substantially more difficulty than if the inflatable component was not primed (e.g., readily inserted into the working cannula after priming).

In certain embodiments, delivery mechanism and inflatable component may form a closed system or in certain embodiments, the delivery mechanism and inflatable component may form an open system. An open system is one where matter and or energy can flow into and or out of the system. A system that receives inputs of energy and or matter and then outputs material into surrounding environments is termed an open system. In contrast, a closed system is where energy can enter or leave but matter may not. A system that is shut off from the surrounding environment and is self-contained is termed a closed system. More specifically, a closed system may be enclosed by barriers which prevent the influx of material and also efflux of material. The volume, pressure and or temperature are still able to change, but, fluid and or other matter are not in direct fluid communication with the surrounds external to the bounds of the closed system.

In certain embodiments, the site within the body of the patient may be accessed in a minimally invasive manner, percutaneously, or in a micro-invasive manner. Additionally, the diameter of the access point for accessing the site within the patient's body may less than 6 cm, less than 5 cm, less than 4 cm or less than 3 cm, less than 2 cm less than 1 cm, less than 0.75 cm, less than 0.6 cm, less than 0.5 cm, or less than 0.4 cm. In certain embodiments, the access point through the skin for accessing the site within the patient's body may be sufficiently small so as not to require anything more than a bandage. In certain embodiments, the access point may be sufficiently small so as not to require any closing device such as for example, stitches, sutures, or a fastening bandage upon termination of the surgical procedure.

In certain embodiments, the filler material may have a shore hardness of less than about 10 A, between 10 to 20 A, between 20 to 30 A, between 30 to 50 A, between 50 to 70 A or greater than 70 A, but preferably about 30 A. In certain embodiments the filler material may be CSM-2186-14, manufactured by Nusil Technologies or MED5-4230, manufactured by Nusil Teclhnologies. In certain embodiments, the inflatable component may be made from liquid silicone rubbers. Examples include, but are not limited to, MED-4805, MED-4810, MED-4820, MED-4830, MED-4840 manufactured by Nusil Technologies. In certain embodiments, the inflatable component may be made from high consistency elastomers. Examples include, but are not limited to MED-2174, MED4-4515, MED-4520, MED-4535 manufactured by Nusil Technologies. In certain embodiments, the inflatable component may be made from dispersions. Examples include, but are not limited to MED-2214, MED-6400, MED-6600, MED1-6604, MED-6605 manufactured by Nusil Technologies.

Certain embodiments may provide a tissue prosthesis comprising: an inflatable component; and a filler material received in a fluent state in the inflatable component, the filler material being of an elastomeric material with a shore hardness of less than 90 A and preferably about 30 A. In certain embodiments the filler material may be CSM-2186-14, manufactured by Nusil Technologies or MED5-4230, manufactured by Nusil Technologies. In certain embodiments, the inflatable component may be MED-4830, manufactured by Nusil Technologies.

The filler material is a two-part pourable silicone elastomer that cures at room temperature. It contains about 5% $BaSO_4$ (e.g., about 3%, 4%, 5%, 6%, or 7%) in both parts and mixes at about a ratio of 3:1 to 1:3 (e.g. 0.5:1 to 1.5:1, 1:1). The viscosity of part A may be about 105,000 cP (e.g., about 100,000 cp, 101,000 cp, 102,000 cp, 103,000 cp, 104,000 cp, 105,000 cp, 106,000 cp, 107,000 cp, 108,000 cp, 109,000 cp, or 110,000 cp) while the viscosity of part B may be about 71,000 cp (e.g., about 65,000 cp, 67,000 cp, 69,000 cp, 71,000 cp, 73000 cp, or 75,000 cp). Additionally, the filler material may have a durometer of about 22-35 D2240 (e.g., about 22, 23, 24, 25, 26, 27, 28, 29, 30, 31, 32, 33 or 34), a tensile strength of between 850 to 1200 psi (e.g., about 900 psi, 950 psi, 1000 psi, 1050 psi, or 1100 psi), an elongation of between 500%-1200% (e.g., about 500%, 550%, 600%, 650%, 700%, 750%, 800%, 850%, 900,% or 1000%), and a tear strength of between 80-120 (e.g., about 90 ppi, 95 ppi, 100 ppi, 105 ppi, or 110 ppi). The filler material may typically be filled with inorganic material for example silica, titanium dioxide, fly ash or other bio-acceptable fillers (e.g. amorphous silica). These fillers can optionally be surface treated with hydrophilic agents and/or hydrophobic agents. The inorganic fill material may be present in the filler material in amounts between 5 and 50 wt. %, (e.g., 10-40 wt. % including 15 wt. %, 20 wt. % up to 30 wt. %, 35 wt. %, 40 wt. %). The inorganic fill material may be present in either part A or B or both A and B.

The envelope material may typically be a two-part translucent silicone system that cures rapidly with no required post-cure. It mixes at about a 3:1 to 1:3 ratio (e.g., 0.5:1 to 1.5:1 and 1:1). The composition may have a durometer of about 25-35 D2240 (e.g., about 26, 27, 28, 29, 30, 31, 32, 33, or 34), a tensile strength of between 1100 and 1500 psi (e.g., about 1250 psi, 1300 psi, 1350 psi, 1400 psi, or 1450 psi), an elongation of between 500% and 1100% (e.g., about 550% 600%, 650%, 700%, 750%, 800%, 8505, 900%, 950% or 1000%), a tear strength of between 140 175 ppi (e.g., about 140 ppi, 145 ppi, 150 ppi, 155 ppi, or 160 ppi), and a stress at 200% strain of between 150 and 200 psi (e.g., about 160 psi, 165 psi, 170 psi, 175 psi, 180 psi, 185 psi, or 190 psi).

The silicone used for the filler material or envelope material may include any one of a variety of silicones generally referred to bio-compatible elastomers formed from polysiloxanes or polyorganosiloxanes which are polymers having the general chemical formula [R.sub.2SiO].sub.n, where R is any suitable organic group and n is any integer. Such polysiloxanes suitable for these purposes may also include a broad family of more complex synthetic polymers containing a repeating silicon-oxygen backbone with organic side groups attached via carbon-silicon bonds. Such complex silicones, or polymeric siloxanes, may be linear, branched or cross-linked, and can be represented by the formula [R.sub.p SiO.sub.4−p/2)].sub.m, where p is 1-3, m<1, and R is any suitable organic group such as alkyl, alkenyl, fluoroalkyl, phenyl, vinyl, hydroxyl, alkoxy, amino or alkylamino or combination of one or more of these organic groups, e.g., -phenylvinyl. The term silicone as used herein is also meant to include elastomers that are hetero- or copolymers of the above-described polysiloxanes. The polysiloxanes suitable for the present invention may also have their terminal ends such as alkyl, alkenyl, fluoroalkyl, phenyl, hydride, vinyl, hydroxyl, alkoxy, amino or alkylamino group or combinations of one or more of these organic groups, e.g., -alkylvinyl (this could be part A of a two-part system). The polysiloxanes suitable for example as a counter-part polysiloxane (e.g., part B) can be modified to include functional, active or inactive organic groups for various purposes, such as to promote crosslinking (for example hydrides or other terminal groups functional groups suitable for treating with ethylenically unsaturated functional groups) or for copolymerization or other reactions. The two groups undergoing an addition reaction during curing. Such addition reaction can be aided by a Group VIII metal (e.g., platinum, rhodium, or palladium).

Non-limiting examples of some polysiloxanes include: polydiorganosiloxanes, polyaklysiloxanes, polydialkylsiloxanes, polydimethylsiloxanes, polyaminoalyklisiloxanes, polyaminoalklsiloxanes, polyethyleneglycol-polydimethyl siloxane co-polymers, silicone polyesters, polysiloxane-polylactone copolymers, polydimethyldiphenylsiloxane, polyalkylsiloxane-polyurethane copolymers with one or more terminal groups such as alkyl, alkenyl, fluoroalkyl, phenyl, vinyl hydroxyl, alkoxy, amino or alkylamino group or combination of two, three or more of these groups (e.g., -alkylvinyl).

Figure 95:
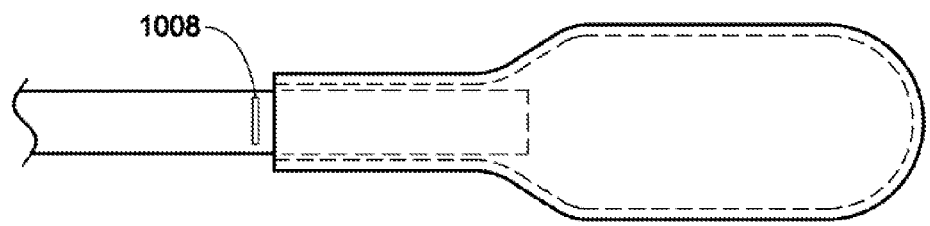
FIG. 95 illustrates an exemplary priming means in which air is vented through a slit as the biomaterial primes the tube in accordance with certain exemplary embodiments disclosed herein.

In certain embodiments, the priming may occur after the inflatable component is inserted into the cavity. In either of these cases, the priming may be achieved by having a small opening or several small perforations at some point near the distal end of the delivery mechanism, preferably just proximal to the inflatable member. This opening may allow for gases or certain fluids within the delivery mechanism to escape through the opening, but will substantially limit the flow of the filler material through this opening. The opening may allow less viscous fluids to pass through the opening easily, but substantially limit more viscous fluids from passing through this opening. Therefore, as the filler material primes the delivery mechanism, the gases or certain fluids within the delivery mechanism may be pushed out through this opening and limit the entrapment of gas or certain fluids within the inflatable member. The opening may be a slit or a hole (see, for example, FIG. 95 for an example of a slit 1008 on a side of the delivery mechanism and proximate to an end of the delivery mechanism). In the case of a slit, the width of the slit may be less than 0.1 mm, between 0.1 to 0.5 mm, between 0.5 to 1 mm, between 1 to 5 mm or greater than 5 mm. In the case of a hole, the diameter may be less than 0.1 mm, between 0.1 to 0.5 mm, between 0.5 to 1 mm, between 1 to 5 mm or greater than 5 mm. In certain embodiments, the inflatable component is deflated during the priming and preferably maintained deflated until at least the delivery mechanism is substantially primed. In either of these situations, after priming, there may be substantially minimal quantities of gas or certain fluids in the inflatable component, thereby eliminating the need for a gas removal system (e.g., a second lumen) during delivery of the filler material. Additionally, in certain embodiments, the inflatable component may be primed during the priming.

In certain embodiments, the body of the patient may be accessed in a minimally invasive manner, percutaneously, or in a micro-invasive manner. Additionally, the diameter of the incision for accessing the patient's body may less than 6 cm, less than 5 cm, less than 3 cm or less than 2 cm. In some embodiments, the incision may be less than 1 cm. In certain embodiments, no external stitches would be required to close the incision or puncture created when the site is accessed.

In certain embodiments, the delivery apparatus may comprise a carrier tube for carrying a component of the prosthesis at its distal end. There is also a filler tube which is slidably receivable within the lumen of the carrier tube with clearance. At some point near the distal end of the carrier tube is at least one slit or several small perforations which may allow for gases or certain fluids within the delivery mechanism to escape through the opening, but will substantially limit the flow of the filler material through this opening. The opening may allow less viscous fluids to pass through the opening easily, but substantially limit more viscous fluids, such as the biomaterial, from passing through this opening. The method of forming the implant in situ may comprise positioning the carrier tube at the desired location within the patient's body. Then the filler tube (which may be attached to a material dispenser apparatus) is primed substantially with the biomaterial prior to being inserted into the carrier tube. As the filler tube is inserted into the carrier tube, the volume of gas, or air, or other fluids within the delivery apparatus, are displaced by the volume occupied by the introduction of the filler tube. This gas is displaced through the perforations at the distal end of the carrier tube. The gas within the delivery apparatus may preferably be displaced through the perforations at the distal end of the carrier tube than the annular space between the carrier tube and filler tube for a couple of reasons. First, the biomaterial may have overflowed from the distal tip of the filler tube (substantially enough), to form a plug at the tip of the filler tube as it is introduced through the carrier tube, thereby not allowing gas to flow around and between the carrier tube and filler tube. Second, the resistance to the flow of gas or air is significantly less through the perforations than through the annular space between the filler tube and carrier tube.

Whatever the case may be, substantial volumes of the gas, air or certain fluids within the delivery apparatus would have been displaced and only a small quantity of air entrapment is likely to occur within the implant. Additionally, if the component of the implant were to be maintained collapsed (either through a clamping mechanism, or the sheath) throughout the procedure whilst the filler tube is being introduced, then removal of the sheath or clamping mechanism from around the component of the implant would result in an even further reduction of air entrapment into the component.

Using the apparatus described in above, a similar method may be used to form the tissue prosthesis. If the filler tube were to terminate proximally to the perforation within the carrier tube, when nested and assembled as it would be in use, the filler tube may not need to be primed before being introduced into the lumen of the carrier tube. If the resistance to the flow of gas or air at the perforations is significantly less than that of the annular space between the carrier tube and the filler tube, then as the filler material is charged through the filler tube, the air or gas may be displaced through the perforations, minimizing air entrapment into the envelope.

In certain embodiments, the means for maintaining the envelope collapsed may be a sheath which has built in weaknesses in its walls at its distal end. Rather than having to retract the sheath, by delivering the biomaterial into the envelope, causes a rise in the internal pressure, breaking the sheath open (in the form of e.g., an orange peel opening) and filling the envelope can commence with minimal introduction of air or gases into the envelope. This form of a sheath may be used to allow for easy delivery of the envelope through the introducer (working cannula) and rather than having to retract the sheath, any form of pressure (such as that by inflating the envelope with air) will break the sheath open, thereby exposing the envelope within the disc cavity. Preferably however, the sheath will be maintained over the envelope until such time the biomaterial has reached the envelope and as the pressure builds up within the envelope, the sheath breaks open and the expansion and filling of the envelope can commence (with minimal air entrapment). This apparatus may be applicable in combination with the apparatus and method disclosed elsewhere herein.

The preferred number of mixing elements for the static mixer, to achieve an optimal mix and hence an optimal cure characteristics of the biomaterial, are 12. However, the mixing elements may range up to about 5, 10, 15, 20, 25, 30, 35.

Exemplary elements of percutaneous surgery is the development of a series of nested tubes that may or may not interlock with each other by various means which enables the device in its preformed or fully formed stage to be delivered to the tissue site being treated to achieve an implantable status. A component of these nested tubes is a working cannula which has the advantages of docking and can have elements which lock the other tubes or the unlocking and unsheathing of a component of the prosthesis.

Advantages of the system may include: (1) that it is capable of achieving compactness with the system and fit lots of components and elements into a small confinement; (2) the compactness of the system provides the means for conducting percutaneous, minimally invasive procedures; and the working cannula is docked relative to the patient and the tubes which go through the working cannula are locked or lockable or reversibly lockable to the working cannula. This means that during the implant positioning, deployment or filling process, the procedure can be performed in a stable manner and there is no unnecessary or unintentional relative movement during the implantation which can damage the tissue and the tissue prosthesis. Additionally, this may help avoid repeated trauma to tissue as instruments go in and out—preventing the crowding of muscles into the path and isolating structures like nerves etc—thereby not only protects outer structures—but internally protects our device. It may also maintain the deployment of a disc device or prosthesis) in the desired position. Additionally, in certain embodiments, the device and or components of the device may be substantially frictionless. If more force is required ratchets can be built into the wall to crawl the progress of the device and or components of the device and or components of the system.

Implant detachment means may include, screw in and screw off of the implant, chemically dissolve the interface which holds the implant, vibrational detachment, RF (Radiofrequency) or infrared cutter. Other means of implant removal include, sliding the implant off the carrier tube by utilization of slideably displaceable nested tubes. These can be tubular structures. Also, external or internal cutting mechanism on the tubes which can sever the implant from the delivery apparatus. Also, means of twisting and or crimping the neck of the implant. This can both seal and detach the implant. Also if the means in which the envelope is held onto the carrier tube is purely an interference fit or friction fit, or just tight fit, then pulling on the carrier tube can result in detachment of the envelope. Also, the tube can be rotated to detach. Also, another means for detachment of the implant can include lubrication of the interface which holds the implant. There may be a preformed opening or multiple preformed perforations at the distal end of the carrier tube and or filler tube. The perforations on the carrier tube may be at or near the implant interface. Once the implant has been substantially filled to capacity, the pressure of filling forces the filler material to seep through these perforations and lubricate the interface of the implant allowing it to be removed easily. Other suitable, biocompatible lubricating media may be used in this way or similar way to lubricate the interface which holds the implant.

In certain embodiments, a pressure generating apparatus may prevent outer bulging of the barrels, counterbalances the thrust force. Alternatively, the barrel may be integrated into the base of the pressure generating apparatus.

Referring to FIG. 1, an intervertebral disc 10D is generally arranged between adjacent vertebrae 12V and 14V. The disc 10D comprises an annulus fibrosis 16A made up of concentric layers of fibrous tissue. The annulus fibrosis 16A circumscribes a nucleus pulposus 18N of the disc 10D, the nucleus pulposus 18N being of soft tissue. The disc 10D is sandwiched between end plates 20E of the vertebrae 12V and 14V. Relative movement between the vertebrae 12V and 14V causes compression of the nucleus pulposus 18N by the end plates 20E. This serves to assist in the influx of nutrients into the disc 10D and the efflux of waste products from within the disc 10D.

Certain exemplary embodiments disclosed herein provide methods for implanting an intervertebral disc implant into an intervertebral disk by percutaneously performing a nucleotomy on the disc, if necessary, to remove a nucleus pulposus of the disc to create a volume. Once the volume is created, at least one envelope of the implant is inserted into the volume and an interior of the envelope is charged with at least one filler material in a manner to allow the at least one envelope to expand to conform substantially, or partially to the volume. Additionally, the interior of the at least one envelope is closed oft or substantially close off, to retain the at least one filler material within the envelope. As discussed herein, the filler material may be selected to at least partially mimic natural biomechanical characteristics of the nucleus pulposus of the disc.

As will be discussed in more detail elsewhere herein, the methods may further include inserting the envelope into the volume using an introducer by placing the envelope in a collapsed state on a distal end of the introducer and inserted percutaneously through an opening in an annulus of the disc. Further, the opening may be the same opening via which the nucleotomy had been performed. The methods may also include charging the filler material into the interior of the envelope through the introducer. Further, the methods may include closing off the interior of the envelope by sealing a wall of the envelope. In certain exemplary embodiments, the methods may include closing off the interior of the envelope by the action of withdrawing the introducer from the envelope. In certain embodiments, the methods may use a minimally invasive technique or the percutaneously technique may be combined with the minimally invasive technique.

In certain exemplary embodiments the methods for implanting an intervertebral disc implant into an intervertebral disc may include percutaneously performing a nucleotomy on the disc to remove a nucleus pulposus of the disc to create a volume; inserting an introducer into an opening formed in an annulus of the disc; and introducing into the volume, via the introducer, at least one element which changes from a first configuration, in which the at least one element is able to be inserted into the introducer, to a second configuration in which the at least one element conforms substantially to the volume.

The methods may further include using a single element which, in its second configuration, conforms substantially or at least partially to the volume of the disc. Alternatively, the methods may include using a plurality of elements which together, when each such element is in its second configuration, conform substantially or at least partially to the volume of the disc. In the latter case, the methods may include, prior to insertion of the elements in the volume, introducing at least one envelope, in a collapsed state, into the volume and introducing the elements into the at least one envelope to cause the at least one envelope to expand to conform substantially or sufficiently to the volume of the disc. The methods may include, after introduction of the elements into the at least one envelope, closing off a filler opening of the at least one envelope. Preferably, the methods includes closing off the filler opening of the at least one envelope by withdrawal of the introducer from the filler opening of the envelope.

In certain exemplary embodiments, there is provided an introducer for introducing an intervertebral disc implant into a disc that has undergone a nucleotomy, the introducer including at least two sleeves arranged telescopically with respect to each other; and a displacement mechanism arranged on an operatively inner surface of an innermost one of the sleeves for assisting in displacing filler material along the sleeves into an interior of the disc, in use.

The displacement mechanism may comprise a ratchet arrangement for urging the filler material along the sleeve.

In certain exemplary embodiments, there may be provided methods of preparing a first assembly of a tissue prosthesis system for insertion into a patient's body, the method, or methods, comprising providing the first assembly which comprises a plurality of nested, or partially nested, tubes, one of the tubes being a carrier tube; mounting a component of the prosthesis on a distal end of the carrier tube, the component being of an elastically deformable material or a sufficiently elastically deformable material, inserting a stiffening member into the first assembly so that the stiffening member extends into an interior of the component and causing a proximal end of the stiffening member to sealingly engage a proximal end of the first assembly; attaching a withdrawing device to the first assembly so that the withdrawing device is in fluid communication with at least the interior of the component; and operating the withdrawing device to reduce the pressure in the interior of the component to cause the component to collapse about the stiffening member. The stiffening member may allow the retraction of the outer sleeve, which covers the component of the prosthesis, without the component buckling or prevent the total retraction into the carrier tube when the syringe is withdrawn to collapse the component.

The method, or methods, may include attaching the withdrawing device to a fluid port of the first assembly in a sealing manner. The withdrawing device may be a syringe which is attached by a Luer lock mechanism to the fluid port of the first assembly. Other withdrawing devices may be a vacuum pump, a pre-evacuated container (such as vacutainer), or a container with a preformed low pressure environment, or any apparatus (e.g., which has moveable walls allowing for the volume of the system to be alterable).

After the component has been collapsed, or sufficiently collapsed, about the stiffening member, the method, or methods, may include placing a protective sheath about the component. The method, or methods, may include placing the protective sheath about the component by sliding the protective sheath over the component, the protective sheath constituting one of the tubes of the nested tubes of the first assembly.

Further, the method, or methods, may include treating one of the protective sheath and the component with a lubricating medium to facilitate relative displacement between the protective sheath and the component.

Exemplary lubricants may include, but not limited to, media such as water for injections, 0.9% saline solution, albumin, fat, mineral oil, lipids, silicone oils, etc.

The method, or methods, may include using the withdrawing device to test the integrity of the combination of the first assembly and the component and the stiffening member attached to the first assembly. Testing the integrity may include determining whether the interior of the envelope is in fluid communication with fluid external to the walls of the envelope, and/or inspecting whether the system still remains a closed system or substantially closed system, or whether it is an open system. The feedback mechanism may have an associated pressure, force or volume monitor which is capable of indicating whether or not there is a breach of the seal. These monitors may indicate whether there is a loss in pressure, force, volume associated with the applied pressure, force or volume.

In certain exemplary embodiments, there may be provided methods of forming a tissue prosthesis at a site in a patient's body, the methods may comprise providing a first assembly comprising a plurality of nested tubes, one of the tubes being a carrier tube with a component of the prosthesis carried at a distal end of the carrier tube; inserting the first assembly into a cannula placed in the patient's body; magnetically attaching or engaging a second assembly to a proximal end of the first assembly; and charging a filler material from the second assembly into the component and allowing the filler material to set.

The methods may include, initially, preparing the first assembly as described elsewhere herein.

The methods may include, once the distal end of the first assembly is at the desired location at the site in the patient's body, withdrawing the protective sheath to expose the component, the component being an envelope of an elastically deformable material. The methods may also include activating the withdrawing device as the sheath is withdrawn to substantially collapse the envelope, minimizing the contact area between the envelope and the sheath, minimize the friction between the envelope and the sheath and hence facilitate sliding between the envelope and the sheath.

The methods may include removing a stiffening rod prior to magnetically attaching the second assembly to the first assembly. Further, the methods may include causing the second assembly to engage sealingly with the first assembly so that, together with the component and the withdrawing device, a closed system is formed.

After the second assembly has been attached to the first assembly, the methods may include operating the withdrawing device to create a low pressure in the component. Further, the methods may include using the withdrawing device to test the integrity of the system comprising the two assemblies and the component attached to the first assembly. This may be performed by either withdrawing or pushing forward on the piston of the withdrawing device and it should also be noted that the integrity of the system can be tested at the stage once the first assembly has been introduced to the desired location in the patient's body (as described above).

The methods may include dispensing the filler material from a dispenser of the second assembly. The methods may also include purging filler material from the dispenser prior to attaching the dispenser to a static mixer constituting a part of the second assembly. The methods may include, during filling of the component via a filler tube extending from the static mixer, operating the withdrawing device at least to maintain, or increase, the volume of the closed system. Mixing may also be performed dynamically. Also, the parts may be premixed and delivered rather than being mixed during the delivery (or charging) process. In certain aspects, the mixing may not be necessary if it is a single part filler material. The filler material may be a single part, or at least a 2 part mixture (i.e., may have 3 parts, etc.). For example, the $3^{rd}$ component of the mixture may be the initiating catalyst. Alternatively, these initiators for the curing reaction may be coated onto the inner surfaces of the lumen which the material comes into contact. For example, the lining of the static mixer, mixing elements, and the lumen of the filler tube may be treated with a platinum catalyst. Certain primers may contain the catalyst. Therefore the inner lining of the envelope may be coated/treated with the primer and when the 2 part filler material enters and fills the envelope, it comes into contact with the inner lining of the envelope, thereby initiating or accelerating the cure. Additionally, because it is also a primer, it may enhance the adhesion between the envelope and the filler material.

The methods may include, after filling the component, detaching the carrier tube from the tissue prosthesis formed by the combination of the component and the filler material contained in the component. The carrier tube may be detached prior to the filler material having cured or set or after the filler material has at least partially set. In some aspects, the carrier tube may be detached prior to the filler material having been partially or substantially cured. The methods may include detaching the carrier tube from the tissue prosthesis when the required pressure has been reached in the component. In the case of intervertebral disc nucleus prosthesis, the required pressure may be that which restores the height of the disc to that of pre-surgery, or that which substantially fills the volume of the disc. However in certain embodiments, pressure may not be a determinant. Another method may include the filling of the component being determined by the volume. The volume to be replaced can be determined by visual or mathematical calculation of the nuclear area from patients own images, amount of nuclear material removed, use of a sizing tool, progressive surgeon experience, use of a software or self learning algorithm that may determine the volume of nucleus that either exists or is removed or may be required to be replaced. The method of determining the nuclear volume could also use a disc mapping strategy. Additional methods may include the methods described in International Application No. PCT/AU03/001289, filed on Sep. 30, 2003 entitled "Mapping and Viewing Device for an Intervertebral Disc", which claimed priority from Australian Provisional Application No. 2002951762 filed on Oct. 1, 2002. The entire contents of which are herein incorporated by reference in its entirety In certain exemplary embodiments, the methods may include detaching the tissue prosthesis by relative axial motion between the carrier tube and a displacement device of the first assembly. The displacement device may be a further tube arranged about the carrier tube and the relative axial motion may be affected by withdrawing the carrier tube relative to the displacement device. In certain exemplary embodiments, the methods may include detaching the tissue prosthesis by filling the component with filler material to the extent that the component is released from the carrier tube. In a further exemplary embodiment, the methods may include detaching the tissue prosthesis by manipulating the carrier tube relative to the component to cause separation of a part of the component attached to the carrier tube from a remainder of the component, the separation occurring at a zone of weakness in the component. The manipulation may involve rotating the carrier tube with respect to the component.

The methods may further include, after formation of the tissue prosthesis, tamping a part of the tissue prosthesis into position.

In certain exemplary embodiments, the methods may also include, before placing the component in position at the site, preparing the site. The methods may include preparing the site by removing degenerative tissue from the site prior to placing the component at the site.

In certain exemplary embodiments, there may be provided methods of forming a tissue prosthesis in situ at a site in a patient's body, the methods may comprise accessing the site in the patient's body; if necessary, removing tissue from the site to form a cavity; inserting at least one envelope of a biologically inert, elastically deformable material into the cavity; charging a filler material, in a fluent state, into the envelope to cause the envelope to expand and conform to the shape of the cavity; and allowing the filler material to cure, the filler material being of the same class of material as the envelope so that, when the filler material has cured, a unified, or substantially unified, prosthesis is formed.

The methods may further include accessing the site by inserting an introducer through an aperture formed in tissue associated with the site and removing nuclear tissue, if required, from the site. The nuclear material may be removed by mechanical, ultrasonic, laser, Argon gas or radio frequency ablation, or the like, in combination with suction and irrigation. For example, mechanical removal may be effected by using a reaming-type tool. Additional methods may include the methods described in U.S. Provisional Application No. 60/971,633, filed on Sep. 12, 2007, entitled "Equipment for, and a method of, removing tissue from a site in a patient's body". The entire contents of which are herein incorporated by reference in its entirety.

Once the nuclear tissue has been removed, the methods may include checking dimensions of the cavity so formed. Thus, the methods may include using the at least one envelope, containing suitable markers, to check the dimensions and or position of the cavity. This may be effected by inflating the at least one envelope using a suitable fluid such as a water/saline solution. Instead of using the at least one envelope with markers, the method may include using a flexible wire fed down the introducer and checking the position of the wire using a fluoroscopic x-ray technique once the wire is in position. In a further way of checking the dimensions of the cavity, the methods may include deploying at least one jacket of similar dimensions to the at least one envelope in the cavity, inflating the jacket with the water/saline solution and, using a fluoroscope, detecting the periphery of the jacket by radio opaque markers on an outer surface of the jacket.

Once the at least one envelope has been placed in position, the methods may include checking the integrity, of the at least one envelope, i.e. to ensure that the at least one envelope does not have any leaks or other defects. This may be effected and affected by filling the at least one envelope with the water/saline or radiopaque solution.

The methods may include manipulating an interior of the envelope to inhibit the formation or entrapment of fluid bubbles in the filler material. Instead, the methods may include commencing filling of the envelope from a distal end of the envelope and progressively filling the envelope towards a proximal end of the envelope (by withdrawing a filler tube or allowing the material buoyancy to lift the filler tube) to inhibit the formation or entrapment of fluid bubbles in the filler material. In the latter case, either a delivery device by which the envelope is introduced into the cavity or the envelope may define a formation allowing the escape of air, or gas, or certain fluids, as the envelope is charged with the filler material. It may be desirable, in certain embodiments, to limit the formation or entrapment of bubbles, or to eliminate substantially the formation or entrapment of bubbles, in the filler material. An advantage of minimizing air or gas or certain fluid bubbles is that it maximizes the volume occupied by the biomaterial and the less voids (air bubbles) the implant has, it may maximize the mechanical performance and stability from a fatigue and creep resistance perspective. Any trapped air may be compressed inside the envelope.

The methods may include, once filling of the at least one envelope has been completed and a filler element withdrawn, occluding the aperture in the tissue of the site. Occluding the aperture may comprise closing it off by a non-return valve or by crimping closed a neck portion of the envelope. A removable tube may be nested over the delivery device and may be propelled distally to remove the at least one envelope and valve from the delivery device.

The methods may include attaching the at least one envelope to a distal end of a tubular delivery device and everting the at least one envelope on the distal end prior to insertion of the delivery device into the introducer for delivery of the envelope into the cavity of the site.

In certain exemplary embodiments, the method, or methods, may include accessing the site using an appropriate percutaneous surgical procedure. Hence, the method, or methods, may be used to perform less invasive (as compared with minimally invasive and/or other surgical procedures) intervertebral disc nucleus replacement and may comprise forming an aperture in an annulus fibrosis of the disc percutaneously; extracting a nucleus pulposus of the disc to form a disc cavity bounded by the annulus fibrosis of the disc and end plates of vertebrae between which the disc is located; inserting the at least one envelope, in a substantially relaxed state (or first state), into the cavity through the aperture; charging the filler material into the at least one envelope to cause (or resulting in) the at least one envelope to expand (or second state) and conform, or substantially conform, to the shape of the disc cavity; allowing the filler material to cure to form, together with the at least one envelope, the unified, or substantially unified, prosthesis; and occluding the aperture.

In certain exemplary embodiments, the method, may include accessing the site using a percutaneous surgical procedure. Hence, the method may be used to perform less invasive intervertebral disc nucleus replacement and may comprise forming an aperture in an annulus fibrosis of the disc percutaneously; extracting a nucleus pulposus of the disc to form a disc cavity bounded by the annulus fibrosis of the disc and end plates of vertebrae between which the disc is located; inserting the envelope, in a first state, into the cavity through the aperture; charging the filler material into the envelope to cause the envelope to expand and conform to the shape of the disc cavity; allowing the filler material to cure to form, together with the envelope, the unified prosthesis; and occluding the aperture.

In certain exemplary embodiments, the methods include expanding and stretching the walls of the envelope and retaining the envelope under tension after charging it with filler material. In other embodiments where the cavity is relatively small, it may not be necessary for the envelope to expand.

Figure 2:
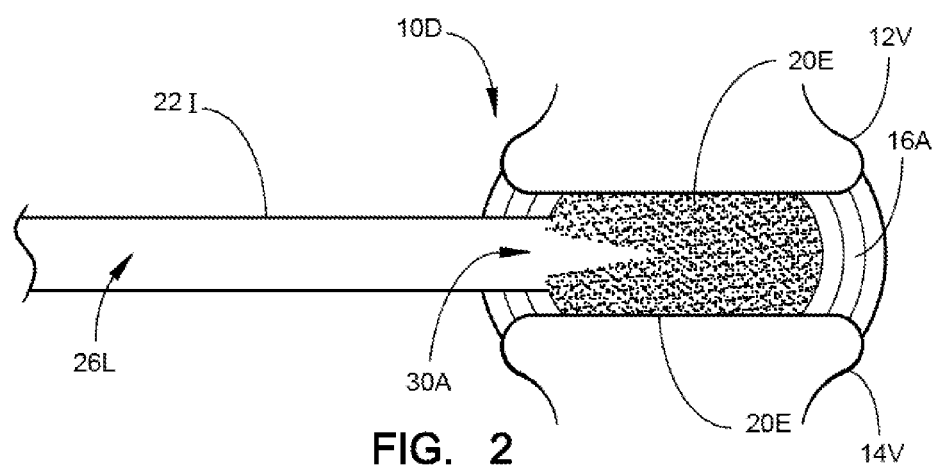

In an exemplary embodiment disclosed herein a method of forming tissue prosthesis, in situ is provided. In the exemplary method, a damaged nucleus pulposus 18N of the disc 10D is removed and is replaced by an artificial prosthesis. Thus, as shown in FIG. 1 of the drawings, an introducer 22I is inserted percutaneously into abutment with the disc 10D. An aperture forming element in the form of a trocar 24T is inserted into a lumen 26L of the introducer 22I. A point 28P of the trocar 24T pierces the annulus fibrosis 16A of the disc 10D forming an aperture 30A (FIG. 2) in the annulus fibrosis 16A of the disc 10D.

Figure 3:
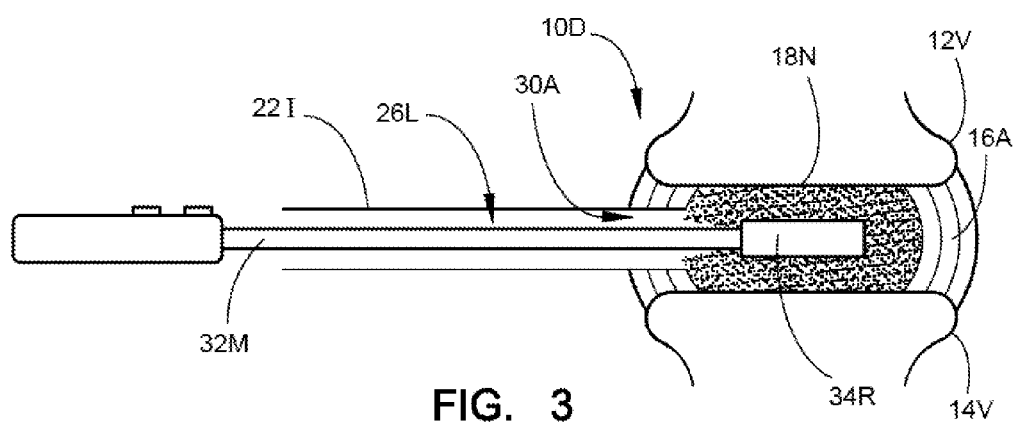
Figure 4:
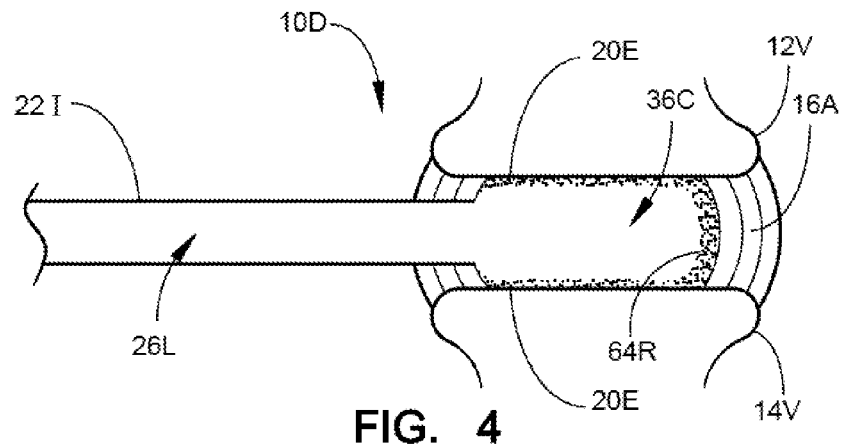

After the formation of the aperture 30A, the trocar 24T is removed from the introducer 22I. Once the trocar 24T has been removed, a nucleotomy is performed on the disc 10D. The nucleotomy involves the removal of sufficient nuclear tissue constituting the nucleus pulposus 18N. While various methods of removing the nucleus pulposus can be used (examples of which are discussed throughout the specification), the example herein shows the use of a mechanical device 32M. The mechanical device 32M comprises a reaming tool 34R. The mechanical device 32M is inserted through the lumen 26L of the introducer 22I and the aperture 30A in the annulus fibrosis 16A of the disc 10D into the nucleus pulposus 18N. The reaming tool 34R (FIG. 3) is operated to remove the nucleus pulposus 18N as shown in FIG. 4 of the drawings so that a cavity 36C remains. The cavity 36C is bounded by the annulus fibrosis 16A and the end plates 20E of the vertebrae 12V and 14V. Residue 64R of the nucleus pulposus 18N remains resulting in the cavity 36C having irregular walls.

Figure 5:
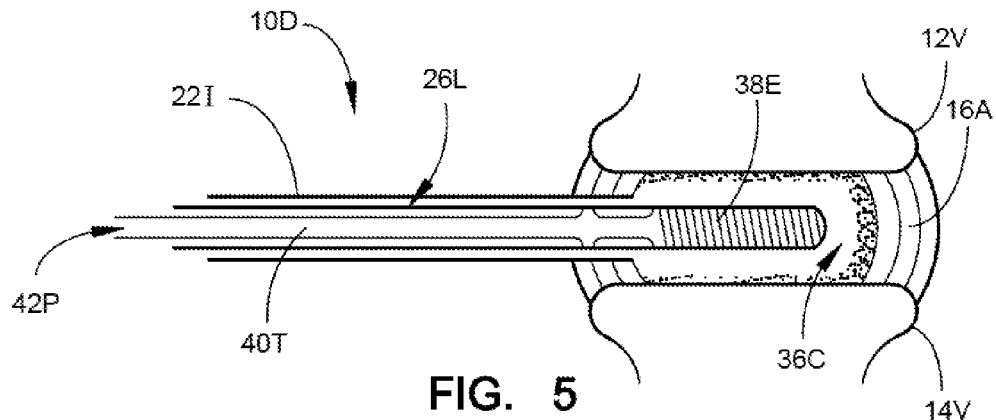

In certain embodiments, an envelope 38E of an elastomeric material, more particularly, a silicone rubber material is mounted on a distal end of a tubular delivery device 40T. The tubular delivery device 40T defines a passageway 42P (FIG. 5). The envelope 38E may be made from the silicone rubber material which is biologically inert and which can elastically deform up to for example 3, 5, 7, 10, 20, 30, 40, 50, 60, 80, 100, 120, 140, or 150 times the size of the envelope 38E in its relaxed state.

Figure 10:
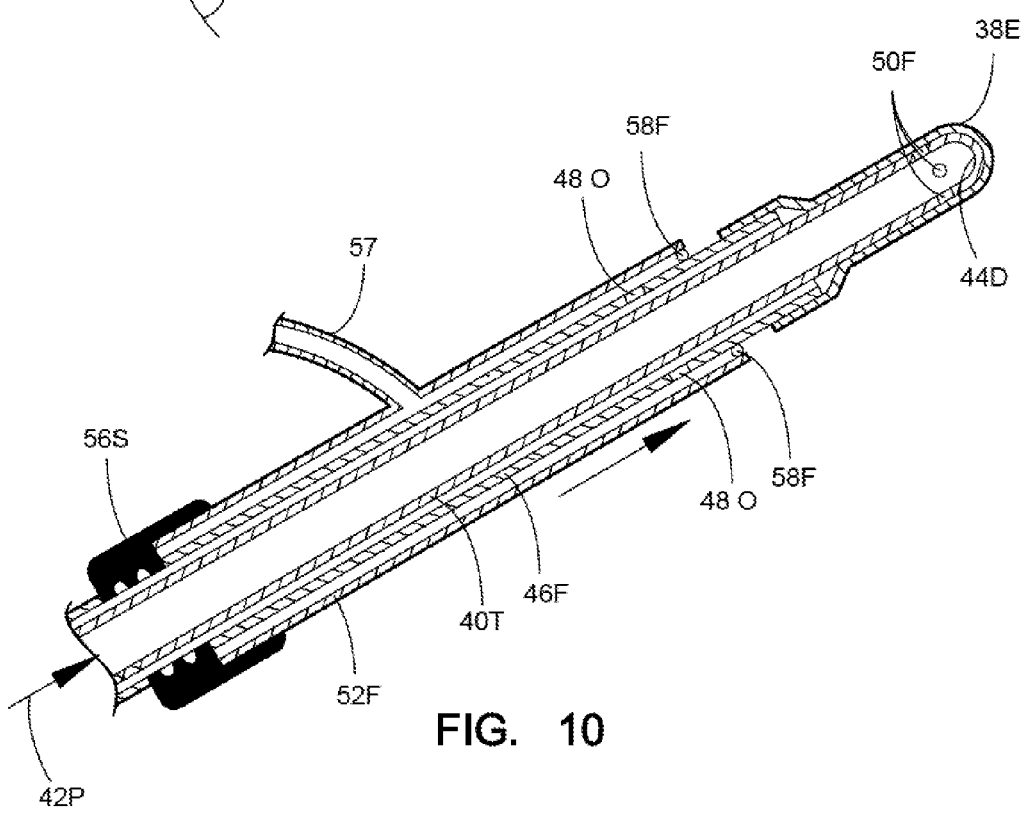
FIG. 10 shows a schematic, sectional side view of part of equipment, in accordance with certain exemplary embodiments disclosed herein, for forming a tissue prosthesis, in situ at a site in a patient's body.

In an exemplary embodiment, as shown in greater detail in FIG. 10, the envelope 38E, in its relaxed, or deflated, state, is a snug fit over a distal end 44D of the tubular delivery device 40T. A first sleeve 46F is arranged coaxially over the tubular delivery device 40T adjacent the distal end 44D of the tubular delivery device 40T. This sleeve 46F may have a plurality of openings 48O defined in it. These openings 48O cooperate with openings 50F at the distal end 44D of the tubular delivery device 40T. A further sleeve 52F is mounted coaxially about the sleeve 46F and communicates with a fluid manipulation device (not shown) via a fluid manipulation tube 57. Proximal ends of the sleeves 46F and 52F are sealed against an outer surface of the tubular delivery device 40T via seals 56S. A further seal 58F is arranged between a distal end of the sleeve 52F and the sleeve 46F.

When filler material, referenced generally by the reference numeral 60F (and discussed in more detail elsewhere herein), is injected into the envelope 38E, a low (e.g., lower than ambient) pressure may be, simultaneously, prior to injection, or a combination thereof imparted to the tubular delivery device 40T and or envelope 38E to manipulate (e.g., evacuate) fluid, more particularly, gases, from within the envelope 38E. This assists in substantially airless mixing and helps ensure that the formation of gas bubbles in the filler material 60F is substantially inhibited. Manipulation of gases also helps inhibit entrapment of gases within the envelope 38E by the incoming filler material 60F and facilitates the flow of the filler material 60F into the envelope 38E. As the filler material 60F is charged into the envelope 38E through the filling openings 50F, gas is drawn out of the envelope 38E by operation of the fluid manipulation device via the fluid manipulation tube 57. The gas is received between the outer surface of the tubular delivery device 40T and the sleeve 46F. This gas passes through the openings 48O in the sleeve 46F and through the evacuation fluid manipulation tube 57.

Figure 96:
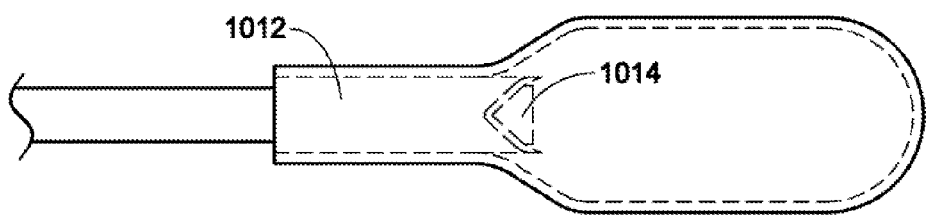
FIG. 96 illustrates a single lumen delivery means where the air vents around the space between the filler tube and the valve-like structure in accordance with certain exemplary embodiments disclosed herein.
Figure 97:
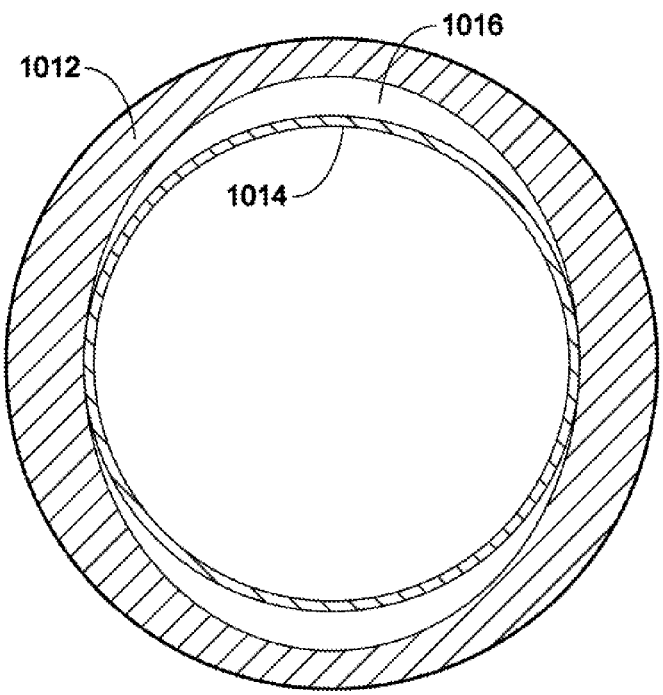
FIG. 97 illustrates an end on view of the space around the tube when it has been pushed into the valve in accordance with certain exemplary embodiments disclosed herein.

In alternative embodiments (e.g.; open and/or closed multi lumen systems), gas can be removed in other manners as well. For example, the filler tube could be primed before it is inserted it into the envelope (or carrier) tube and deliver the biomaterial into the envelope. Alternatively, the envelope could be maintained in a collapsed state so that the envelope does not need to be actively manipulated during any stages of the filling. In other embodiments, a first and second lumen may be used to deliver fluid (one of course delivers low pressure fluid). The term deliver is not specifically directional towards the envelope or away from the envelope. In a closed or open system scenario, the filling tube may extend (perhaps half way or all the way to the end) into the envelope and as the envelope is filled, the fluid in the envelope may be pushed out through a second lumen. In certain embodiments, the filling tube terminates at a point substantially in alignment with the proximal end of the envelope or just proximal to the envelope. The filling tube may terminate substantially in line with the distal end of the carrier tube, or just proximal to the distal end of the carrier tube. As the filler material is charged into the envelope, evacuation, or manipulation of fluid, or withdrawal of fluid, at least from within the envelope may no longer be active, as the annular space between the first and second lumen, which was in fluid communication with the interior of the envelope has been substantially occluded. In a single lumen filling system, the envelope may be carried by the filling tube (thereby the filling tube being both the filling tube and carrier tube) and the fluid in the envelope may be vented around the space 1016 between the filling tube 1014 and a valve 1012 on the envelope (see, e.g., FIGS. 96 and 97). In certain embodiments, a valve may not be necessary, so long as there is some clearance between the envelope and the outside of the filling tube, fluid will be able to be pushed out from the envelope as the envelope fills with a biomaterial.

Figure 6:
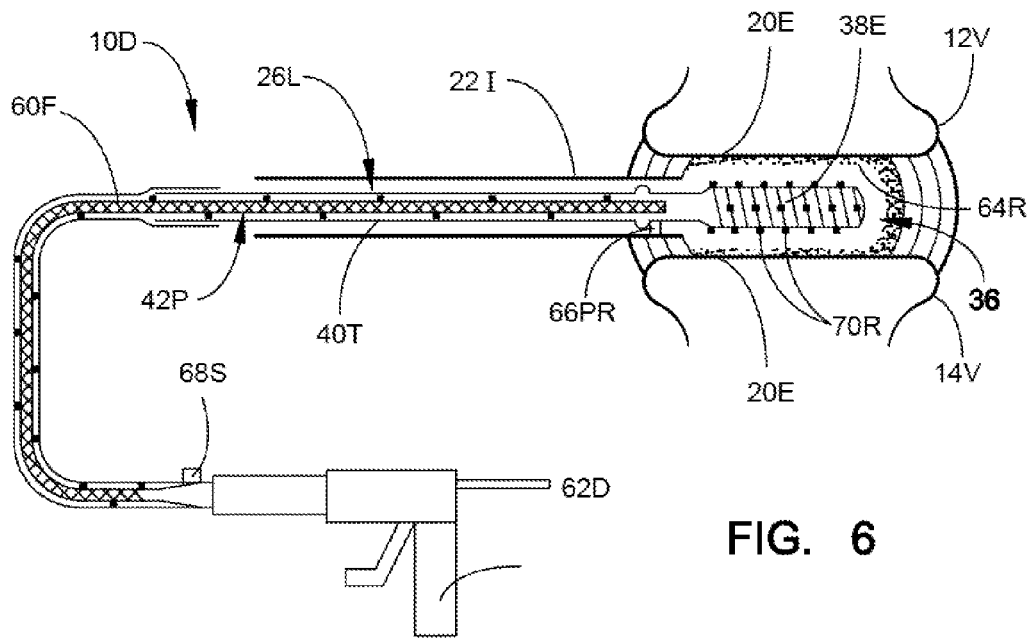

As shown in FIG. 6, it may also be useful to monitor the shape and size of the cavity 36C taking the residue 64R into account. This can be achieved in a number of ways. One of the ways in which this can be achieved is by having radio opaque markers 70R arranged on the envelope 38E. Prior to charging the envelope 38E with the filler material 60F, the envelope 38E can be expanded to conform to the shape of the cavity 36C by means of a water/saline solution or a radio opaque solution. The markers 70R, being radio opaque, are monitored under a fluoroscope to determine the shape and size of the cavity 36C.

Other methods of assessing the size of the cavity 36C include the use of a flexible wire inserted down the lumen 26L of the introducer 22I, the wire being monitored by a fluoroscope. Yet a further way of monitoring the shape and size of the cavity 36C is by use of a dedicated jacket, of similar dimensions to the cavity 36C, which is inserted into the cavity 36C and inflated using the water/saline solution or the radio opaque solution. The jacket carries radio opaque markers which are monitored by a fluoroscope.

FIGS. 77-79 illustrate an embodiment of equipment for preparing a site for implantation of tissue prosthesis. The equipment 10E comprises a conduit assembly 12C carrying a member 14M at a distal end of the conduit assembly 12C. The equipment 10E further may also include a plurality of fluid dispensers 16F connectable to a proximal end of the conduit assembly 12C to communicate with the member 14M. In certain aspects, the member may be sufficiently inflatable, resiliently flexible, able to be elastically deformed, or combinations thereof of these properties.

This equipment 10E may be used to determine, or approximate, the size of a cavity 18C formed in an intervertebral disc 20I. The disc 20I has an annulus 22 surrounding a nucleus 24. Degeneration of the disc 20I may result in herniation of nuclear material of the nucleus 24N through the annulus 22A. To repair a damaged disc 20I, the nucleus 24N may be replaced by an intervertebral disc prosthesis as described in the embodiments disclosed in this specification.

In addition, the equipment 10E may also measure the position of the cavity. The position of the cavity as well as the position of the prosthesis may be checked under the fluoroscope or other imaging means to check the cavity position laterally and in the anterior-posterior view (AP view). In other words, the sizing device can be viewed as a mock implant. An advantage of sizing the cavity and the position is that the remainder of the implant can actually be performed blind without the need of any imaging assistance. This is because the working cannula will position the implant and the sizing device has determined for the surgeon the volume required to fill the implant.

To prepare the site for implantation of the prosthesis, it may be desirable to conduct a nucleotomy to remove portions, or substantial portions, of the nuclear material from the disc 20I. However, in certain circumstances, the nuclear material 24N may have either degenerated or herniated through the annulus 22A to a sufficient extent that a cavity 18C is formed which can receive the tissue prosthesis to reconstruct the intervertebral disc 20I. The amount of nuclear material that needs to be removed may be expected to vary from situation to situation.

The member 14M may be made from a number of different materials. In certain preferred embodiments, it is desirable that the member be inflatable, resiliently flexible andfor able to be elastically deformed. In certain embodiments, the member 14M could be of a silicone material and may have similar or substantially the same characteristics of the envelope of the applicant's tissue prosthesis described herein.

In the exemplary embodiment illustrated, the equipment 10E comprises a pair of fluid dispensers 16F each in the form of a syringe 26S, 28S. The syringe 26S has a barrel 30B and a plunger 32P slidably displaceable in the barrel 30B. Similarly, the syringe 28S has a barrel 34B and a plunger 36P slidably displaceable in the barrel 34B. Further, in this embodiment, the conduit assembly 12C comprises a first, outer conduit, or tube, 38O. The member 14M is mounted on a distal end of the outer tube 38O. An inner, filler conduit, or tube, 40F is co-axially arranged within the outer tube 38O. The filler tube 40F projects from the syringe 26S through a branched connector 42B arranged at a proximal end of the tube 38O. The branched connector 42B may be a Y connector defining a primary lumen 44P through which the tube 40F extends and a secondary, branched lumen 44P. The syringe 28S is connected to a part 48P of the connector 42B defining the secondary lumen 46S.

In use, in this exemplary embodiment, the equipment 10E is inserted percutaneously via a working cannula (not shown in these figures but described elsewhere) so that the member 14M is received in the cavity 18C of the disc 20I. The equipment 10E is inserted percutaneously.

Initially, the equipment 10E may be primed. The priming of the equipment 10E is effected and affected by drawing on the plunger 36P of the syringe 28S in the direction of arrow 50A. This may result in the member 14M collapsing. Because the equipment 10E defines a closed system, or substantially closed system, it also results in the plunger 32P of the syringe 26S being drawn in the direction of arrow 52A. The syringe 26S contains a volume measuring fluid. In certain embodiments, the volume measuring fluid may comprise non-compressible fluid, and/or fluids, such as a liquid (e.g., but not limited to, a radioopaque dye (such as urografin), or water or a saline solution). In some aspects, the fluid may be substantially non-compressible fluid and/or fluids. The equipment 10E is regarded as being fully or substantially primed when the liquid from the syringe 26S begins to flow into the syringe 28S.

The position of the plunger 36P of the syringe 28S may be fixed in position as shown in FIG. 78. The plunger 32P of the syringe 26S is then further pushed in the direction of arrow 52A to inflate the inflatable member 14M fully. Instead of fixing the position of the plunger 36P in the syringe 28S, can be removed and a sealing cap (not shown) can be placed over the branch of the Y connector to maintain the closed or substantially closed system.

Referring to FIG. 79, the plunger 32P of the syringe 26S may be drawn in the direction of arrow 54A to deflate the member 14M. Inflation and deflation of the member 14M using the syringe 26S is then repeated for a number of cycles to condition the disc 20I. The cyclical inflation/deflation of the disc 20I increases the laxity of the disc 20I and is generally referred to as "mobilizing the joint". By cycling the member 14M a number of times, surrounding residual nuclear material 55R in the disc 20I may be compressed or compacted and is less likely to interfere with the subsequently implanted nuclear prosthesis.

Once the disc 20I has been cycled a number of times, the plunger 32P of the syringe 26S may be drawn to a start position in which the member 14M is, once again, substantially collapsed. It will be appreciated that, because the system is a closed system, and the plunger 36P of the syringe 28S is locke in position, the plunger 32P of the syringe 26S will only be able to be withdrawn to a certain fixed, start position in the barrel 30B of the syringe 26S. In this position, the member 14M is substantially collapsed and the conduits 38O and 40F are filled with gas and/or liquid, respectively, it being appreciated that there will also be some liquid in the conduit 38O. Depending on the degree of withdrawal of the piston 36P, conduit 38O may be composed completely or substantially of fluid (liquid) also. In this position, the equipment 10E is substantially primed.

The plunger 32P of the syringe 26S is urged in the direction of arrow 52A to displace the volume measuring liquid from the syringe 26S into the inflatable member 14M. This fully inflates the member 14M so that it conforms to the shape of the cavity 18C in the disc 20I. When the member 14M fully conforms to the cavity 18C, any attempt to further displace the plunger 32P in the direction of the arrow 52A will result in a substantial increase in pressure. This is therefore the end point indicating that the member 14M fully conforms to the cavity 18C of the disc 20I and the amount of liquid dispensed from the syringe 26S after priming of the equipment 10E is an accurate indication of the volume of the cavity 18C.

As will be described in the embodiments described below with reference to FIGS. 80-85, the plunger 32P may carry a transducer (not shown in this embodiment). The transducer may, for example, be a pressure transducer and, when the sudden increase in pressure occurs, an enunciator may be activated to indicate the end point.

Referring now to FIGS. 80-85, additional embodiments of equipment for preparing a site for implantation of tissue prosthesis is described. In these embodiments, the conduit assembly 12C comprises a single tube 38S to which the connector 42B is connected at a proximal end of the tube 38S. A distal end of the tube 38S carries the member 14M.

In this embodiment, the connector 42B may be a T-connector defining the primary lumen 44P and the secondary lumen 46S. It will, however, be appreciated that the connector 42B could, as in the previous embodiments, be a Y-connector.

The conduit assembly 12C further includes a fluid control arrangement in the form of a three way stopcock 56ST. The stopcock 56ST is operable to place either, or both, or neither lumen 44P and 46S of the connector 42B in fluid communication with an interior of the tube 38S or the lumen 46S of the connector 42B in communication with the interior of the tube 38S.

As in the case of the previous embodiments, the syringe 26S is connected to the connector 42B to be in communication with the lumen 44P of the connector 42B. The syringe 28S is connected to the connector 42B to be in communication with the lumen 46S of the connector 42B. In use, in these embodiments, the equipment 10E may be inserted percutaneously via a working cannula (not shown).

To prime the equipment 10E, the syringes 26S and 28S are operated. More particularly, the stopcock 56ST is positioned so that the lumen 46S is occluded while the lumen 44P of the connector 42B is open. The plunger 32P of the syringe 26S is urged in the direction of arrow 58A. This causes inflation of the member 14M. Some liquid from the syringe 26S will enter the member 14M and so will gas which was present in the equipment 10E. The fluid from the syringe 26S, being heavier than the gas, will sink to the distal end of the member 14M. The gas in the equipment 10E will be displaced to be arranged near the distal end of the tube 38S.

Withdrawal of the piston 32P of the syringe 26S in a direction of arrow 59 will draw out the gas from the tube 38S and, subsequently, fluid from the member 14M as well. These steps may be repeated a number of times to ensure that the equipment 10E is fully primed. The equipment 10E is regarded as being fully primed when the piston 32P of the syringe 26S is drawn to the position shown in FIG. 82 in which the member 14M is substantially collapsed.

It should be appreciated that the priming method described above is applicable when the inflating member is pointing down (i.e., as it would be the case if the device were positioned in the disc) and the filling tube/member stops at the proximal junction to the inflation member. For the case where the filling tube extends into the distal part of the inflating member, the priming should occur with the inflating member pointing up (i.e., or as the case may be, primed before being positioned into the disc). This is because when the fluid is ejected from the syringe to prime the system, the buoyancy of the gas may force the gas towards the distal part of the inflatable member where the lumen of the tube is.

Figures 81, 82:
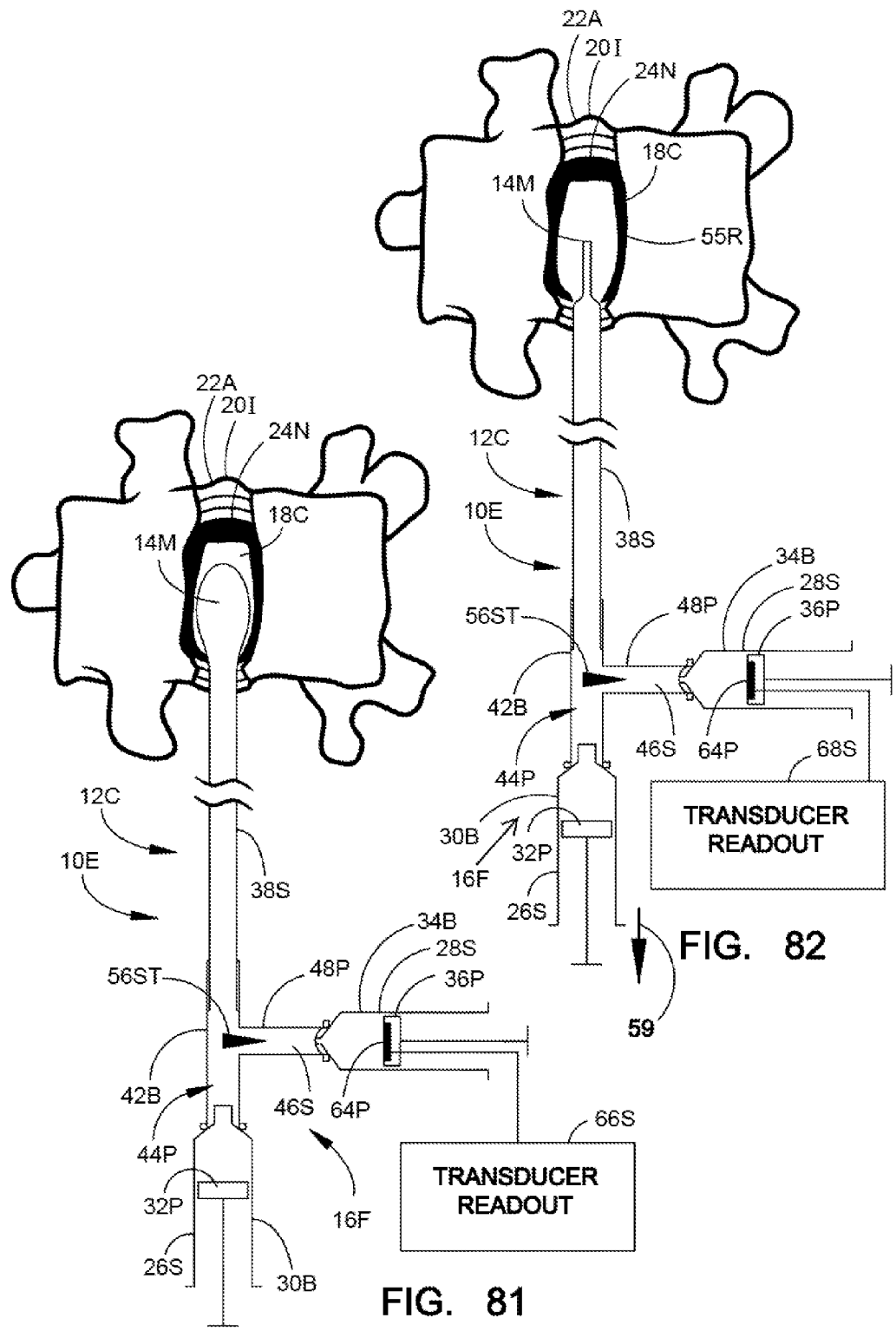
Figures 83, 84:
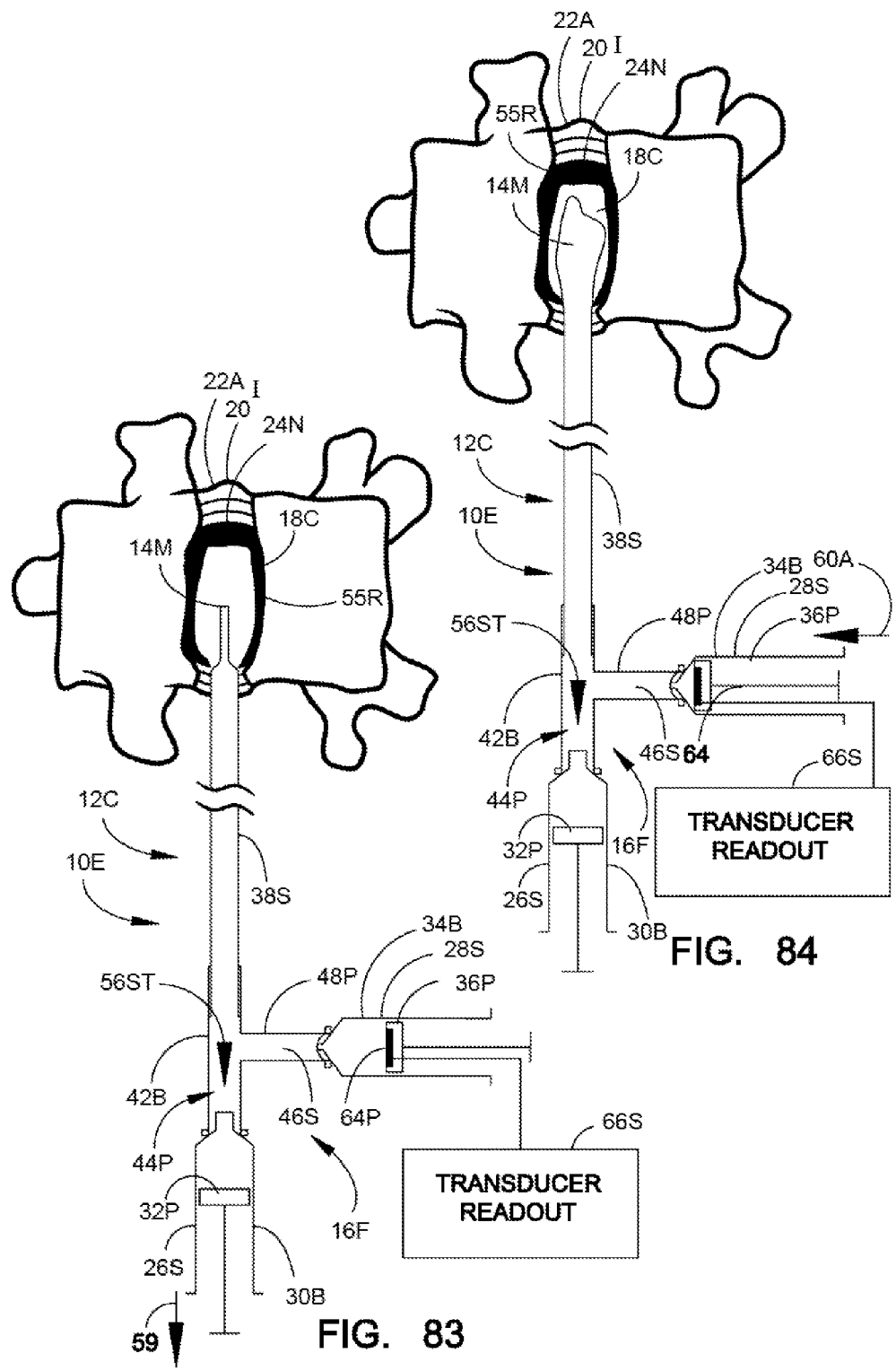
Figure 85:
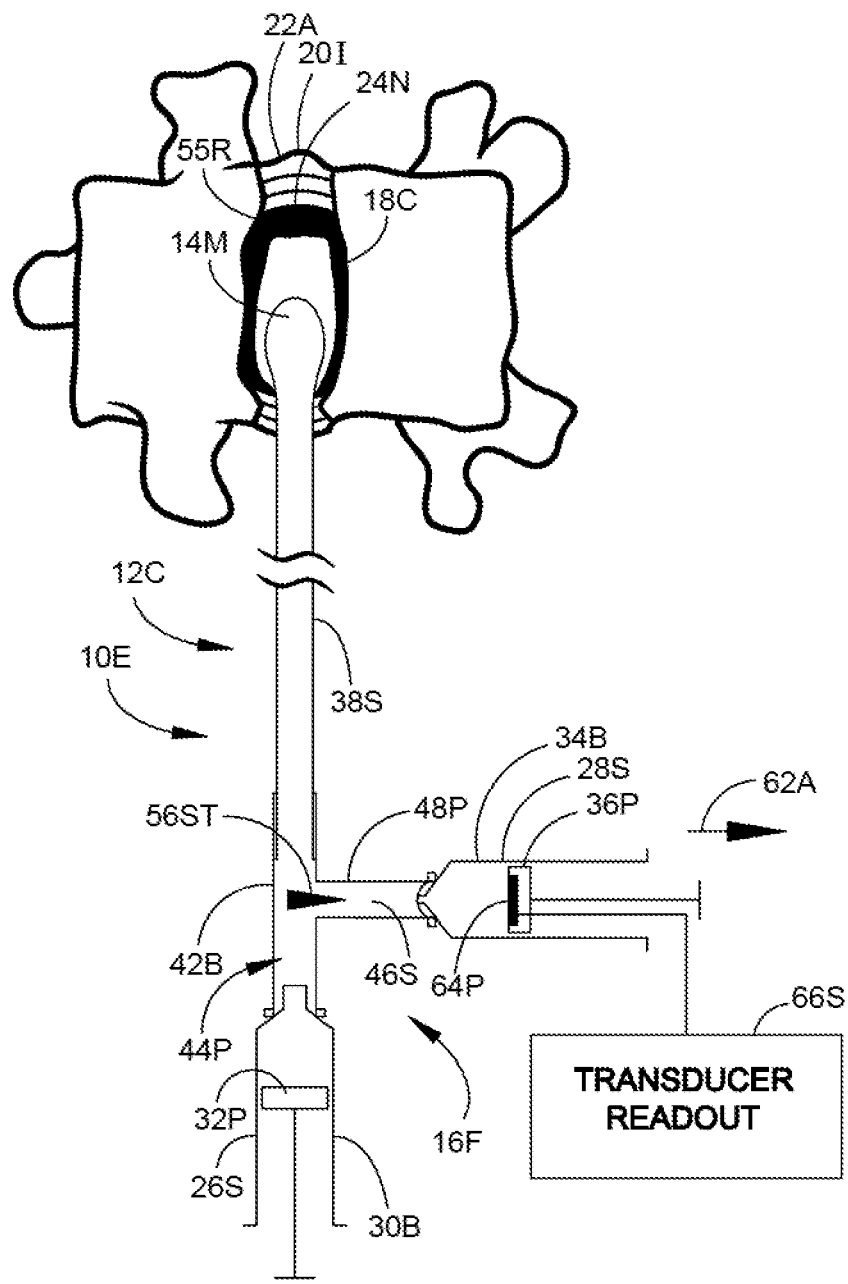

With the piston 32P of the syringe 26S in the position shown in FIG. 82, the stopcock 56ST is switched to occlude the lumen 44P of the connector 42B and to open the lumen 46S of the connector 42B (see FIG. 83). This places the syringe 28S in communication with the interior of the tube 38S and the interior of the member 14M. The syringe 28S contains a volume measuring liquid (e.g., water or a saline solution).

The plunger 36P of the syringe 28S is urged in the direction of arrow 60A (FIG. 84) to inflate the member 14M fully so that it substantially conforms, or at least partially conforms to the shape of the cavity 18C of the disc 20I. The plunger 36P of the syringe 28S is then drawn in the direction of arrow 62A (FIG. 85) to cause deflation of the member 14M. The plunger 36P is cycled a number of times to inflate and deflate the member 14M to condition the disc 20I as described in this specification.

After conditioning the disc 20I, the plunger 36P is drawn to a zeroing position in the syringe 28S. It will be appreciated that, because the equipment 10E defines a closed system, or substantially closed system, the plunger 36P can only be withdrawn to a certain, fixed position in the syringe 28S. This position occurs when the member 14M is sufficiently collapsed. In this zeroing position, the plunger 36P is, once again, urged in the direction of arrow 60A to inflate the member 14M fully so that it conforms, or substantially conforms to the cavity 18C of the disc 20I. It will be appreciate that, when the member 14M has been fully or appropriately inflated, further attempts to displace the plunger 36P in the direction of arrow 60A will typically result in a sudden or steep increase in pressure. The pressure is recorded by a pressure transducer 64P carried on the plunger 36P of the syringe 28S. The transducer 64P is connected to a transducer readout 66S which contains an enunciator. The enunciator may be an audible and/or visual enunciator to alert an operator that the end point has been reached and that the member 14M is fully, or appropriately, inflated. The volume of liquid displaced from the syringe 28S represents the volume of the cavity 18C of the disc 20I. Since the radioopaque dye being injected is significantly incompressible, there is a significant difference (steep pressure rise) in the resistance to further displacement of the syringe piston 36P when the member 14M has been inflated to capacity, thus the tactile feedback is a sensitive enough indication in being able to gauge the endpoint of filling. The feedback which the surgeon receives from the resistance of the syringe piston 36P is significantly sensitive for the surgeon to be able to gauge the endpoint of filling.

In certain embodiments disclosed herein, the conduit assembly 12C may act as a stiffening member for the member 14M. Thus, in certain embodiments, the filler tube 40F may extend to a distal end of the member 14M as indicated by dotted lines 68D in FIGS. 78 and 80 of the drawings. The extension 68D of the filler tube 40F has a slot 70 defined in it to place the interior of the member 14M in communication with the interior of the filler tube 40F to allow inflation and deflation of the member 14M. In these embodiments, when the member 14M is substantially collapsed, it is collapsed about the extension 68D of the filler tube 38S. Similarly, in the embodiments described with reference to FIGS. 80-85, the tube 38S of the conduit assembly 12C may have the extension 68D with the slots 70S defined in the extension 68E. In these embodiments, it may be desirable to prime the equipment 10E externally of the patient as gas needs to move to a top of the member 14M with the equipment 10E being held vertically so that the member 14M is at the top of the equipment 10E. In such cases, it is desirable to have the slot 70S substantially distal. In certain embodiments, the equipment 10, whether with the extension 68D of the filler tube 40F or not, can be primed when the equipment 10E is positioned within the patient. In general, the equipment 10E should be able to be primed so that an accurate measure of the volume of a cavity to receive tissue prosthesis can be determined. In addition, by cycling the inflatable member, the surrounding tissue can be conditioned for receiving the tissue prosthesis.

Figure 7:
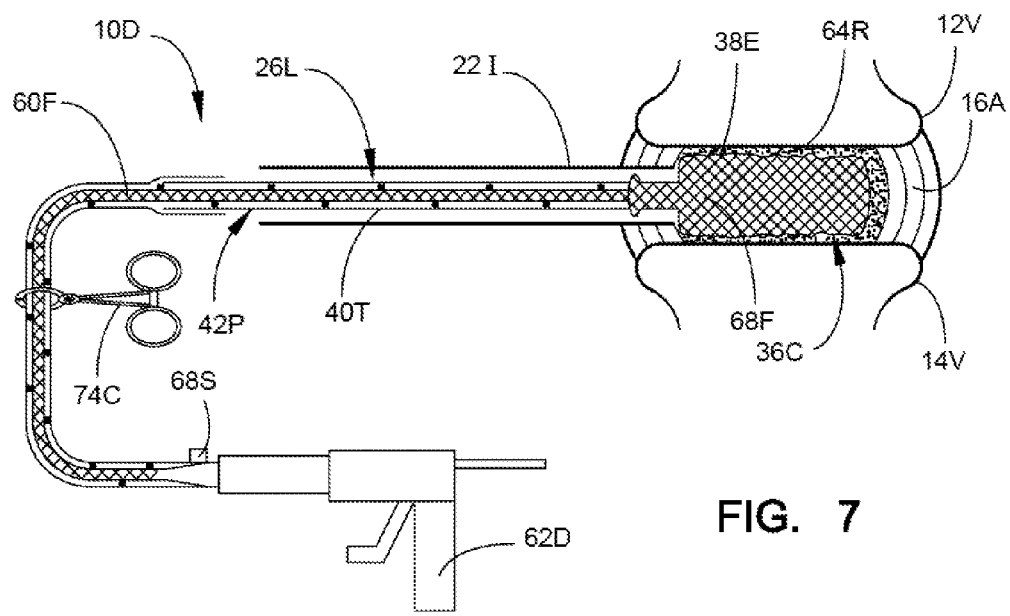

As shown in FIG. 6, after the shape and size of the cavity 36C have been determined, the filler material 60F is dispensed from the dispenser 62D and is monitored via the sensing arrangements 66S or 68S, as the case may be. As illustrated in FIG. 7 of the drawings, the filler material 60F causes elastic expansion or inflation of the envelope 38E so that the envelope 38E conforms to the shape of the cavity 36C and bears against the residue 64R of the nucleus pulposus remaining in the cavity 36C. The envelope 38E, having been elastically expanded by the filler material 60F, remains under tension around the filler material 60F while conforming to the shape of the cavity 36C.

Figure 13:
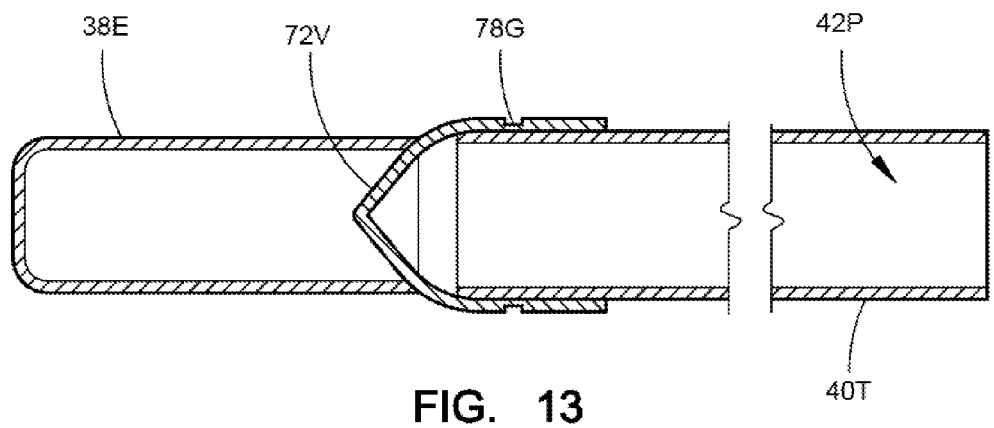
FIG. 13 shows a sectional side view of an envelope, attached to a delivery device, the envelope forming part of a tissue prosthesis, in accordance with certain exemplary embodiments disclosed herein.

Backflow filler material 60F from the interior of the envelope 38E may be controlled either by a valve 72V as shown in FIG. 13 of the drawings or by a clamping device 74C as shown in FIG. 7 of the drawings. The valve 72V is a duckbill valve and acts as a one way valve so that backflow of filler material 60F from the envelope 38E is substantially restricted or inhibited.

Figure 8:
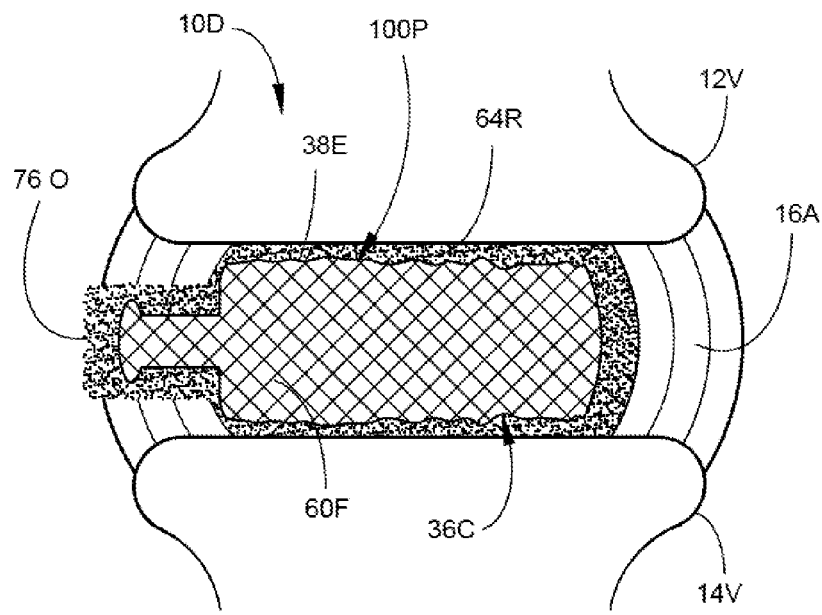

Once the envelope 38E has been filled and has expanded so that it conforms closely, sufficiently, and/or substantially to the shape of the cavity 36C and is received snugly in the cavity 36C, the filler material 60F is allowed to cure for a predetermined period of time of, for example, up to about 5, 10, 15, 20, 25 or 30 minutes. After substantial curing of the filler material 60F, the tubular delivery device 40T is removed (alternatively, as described elsewhere herein, the tubular delivery device 40T may be removed after delivery of the filler material 60F but before curing) leaving the aperture 30A occluded as shown at 76O in FIG. 8 of the drawings. The unified tissue prosthesis 100P so formed is preferably, substantially cured after about 10 minutes.

To facilitate removal of the tubular delivery device 40T from the envelope 38E, the envelope 38E may incorporate a zone of weakness in the form of a circumferential groove 78G (FIG. 14) formed at a proximal end. The zone or area of weakness may be achieved in a number of different manners as well, for example, but not limited to, being built in during the manufacturing process. As the tubular delivery device 40T is withdrawn, when its distal end comes into register with the groove 78G, the tubular delivery device 40T is twisted relative to the envelope to cause a break at the groove 78G to form the occlusion 76O in the aperture 30A of the annulus fibrosis 16A of the disc 10D. In certain embodiments, the occlusion 76O may be formed as a result of the annular fibers closing over the aperture after the delivery device has been removed.

Figure 9:
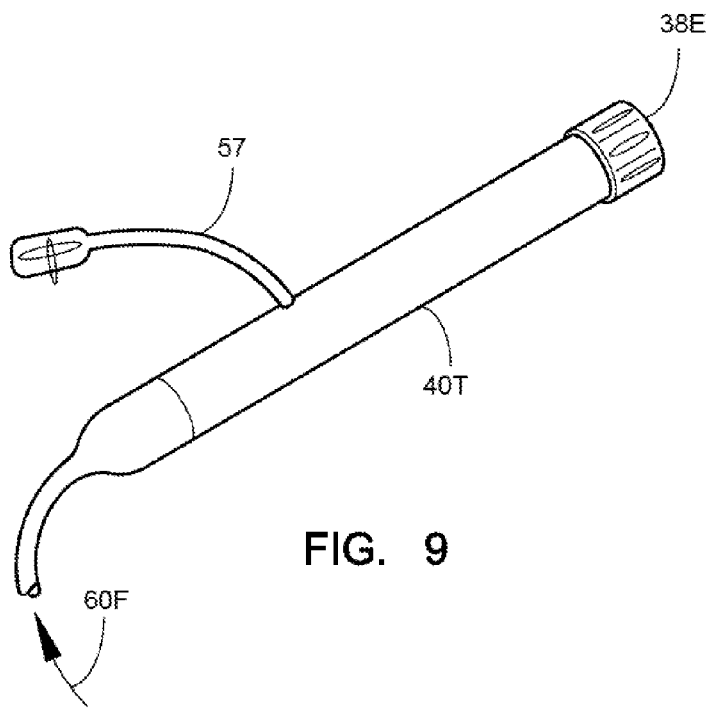
FIG. 9 shows a schematic illustration of a delivery device for use in accordance with certain exemplary embodiments disclosed herein.
Figure 12:
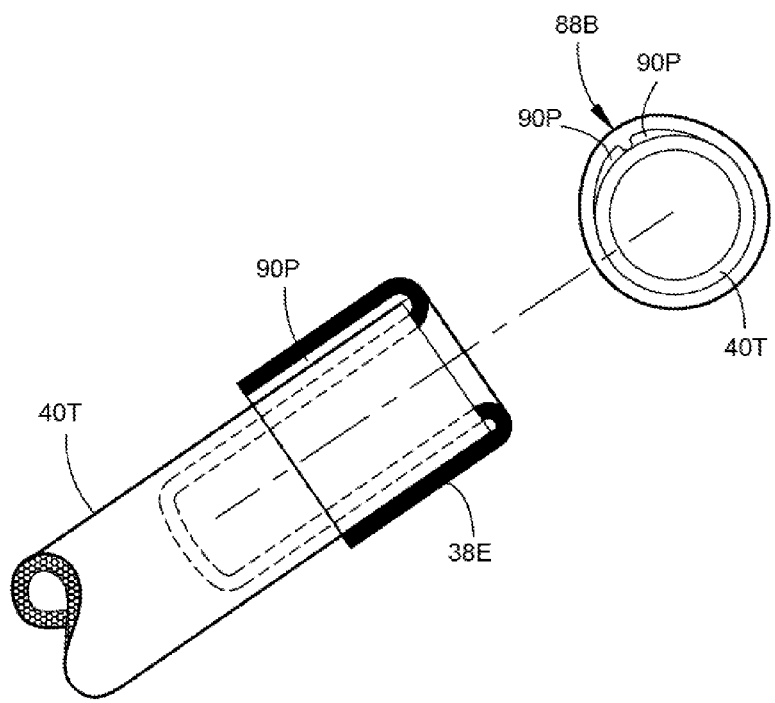
FIG. 12 shows a schematic, side view and end view of part of the equipment in accordance with certain exemplary embodiments disclosed herein.
Figure 14:
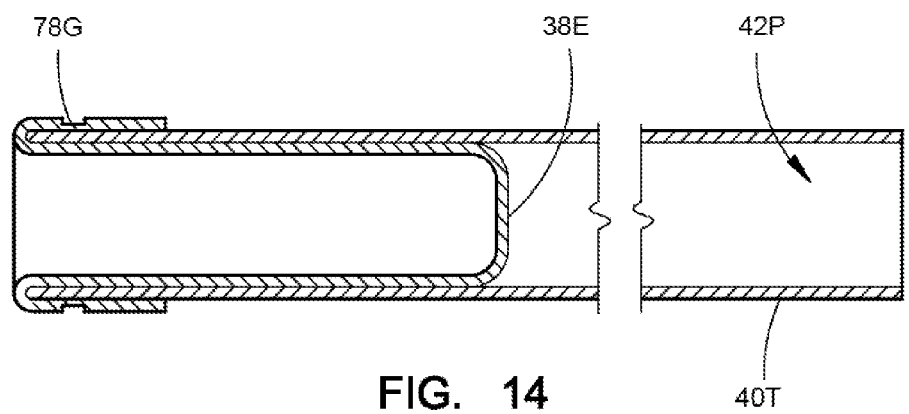
FIG. 14 shows a sectional side view of another mounting of the envelope on the delivery device in accordance with certain exemplary embodiments disclosed herein.

FIG. 12 shows another way of delivering the envelope 38E into the cavity 36C in accordance with certain embodiments. In. FIG. 12, the envelope 38E is everted to lie within the distal end of the delivery device 40T to facilitate its insertion into the cavity 36C. A similar arrangement is shown in FIG. 9 and FIG. 14.

Figure 11:
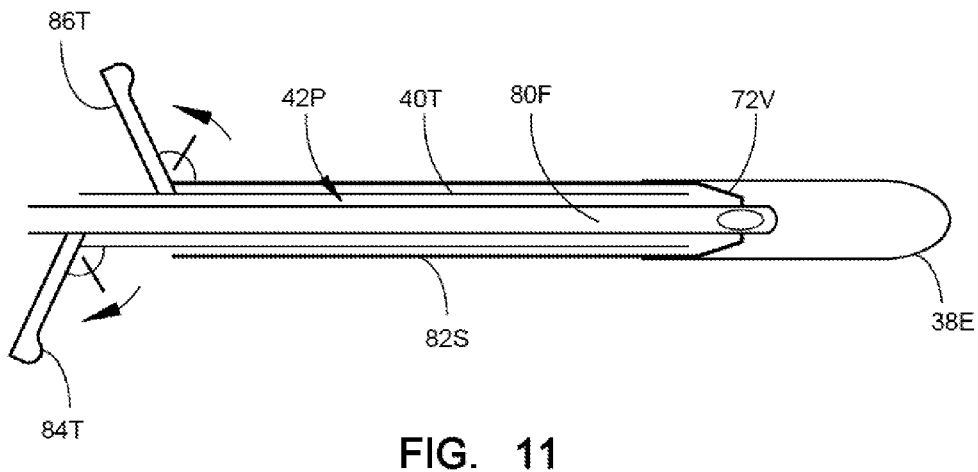
FIG. 11 shows a schematic, sectional side view of the equipment in accordance with certain exemplary embodiments disclosed herein.

In FIG. 11, another embodiment of equipment for forming the tissue prosthesis 100P is shown. In this embodiment, a filler tube 80F is used. The tube 80F is received in the passageway 42P of the delivery device 40T. A sleeve 82S is arranged coaxially about the delivery device 40T. A first displacement device, such as a trigger, MT is provided for controlling relative movement between the delivery device 40T and the tube 80F. A second displacement device, which may also be in the form of a trigger. 86T controls relative movement between the delivery device 40T and the sleeve 82S.

The equipment, as shown in FIG. 11, is for use where a fluid manipulating device is not used. Thus, to fill the envelope 38E, the tube 80F is urged towards the distal end of the envelope 38E and charging of the filler material 60F into the envelope 38E commences at the distal end of the envelope 38E. Filling of the envelope 38E progresses from its distal end towards its proximal end. Thus, as filler material 60F is charged into the envelope 38E, the tube 80F is slid proximally relative to the tube 40T by manipulating the trigger 84T or slides back through buoyancy of the filler material. Once the envelope 38E is in its fully inflated state, the envelope 38E is urged off the distal end of the tubular delivery device 40T by manipulating the trigger 86T. As the tube BOF is withdrawn from the valve 72V and the envelope 38E is removed from the distal end of the tubular delivery device 40T, the valve 72V closes to form the occlusion 76O. To facilitate expulsion of gas when a fluid manipulation system is not being used, the envelope 38E has a bead 88B (FIG. 12) formed along that portion which seats on the distal end of the tubular delivery device 40T to create passages 90P through which air or gas or certain fluids can be discharged as the envelope 38E is charged with the filler material 60F.

The envelope 38E may be constructed of a silicone rubber material which can be inflated up to about 5, 10, 15, 25, 50, 75, 100, or 150 times its relaxed size without rupturing. In certain embodiments, the envelope 38E may be made of less expansible material such as a biological or a synthetic polymeric material. A suitable synthetic polymeric material may, for example, be a polyester such as polyethylene terephthalate (PET). The envelope 38E may be constructed of a knitted PET material so that, when the filler material 60F is charged into the envelope 38E, the filler material fills foramens or interstices in the envelope 38E to form an integrated structure which resists relative movement between the filler material 60F and the envelope 38E. Alternatively, the knitted PET material may be coated with silicone allowing the filler material 60F to integrate with the coating.

Figure 15:
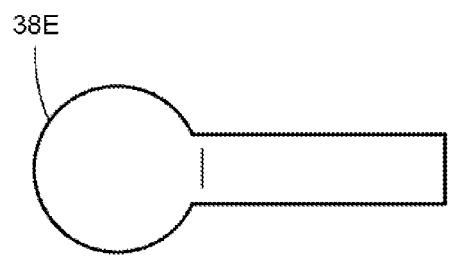
FIGS. 15-17 show different shapes of envelopes for use in the tissue prosthesis in accordance with certain exemplary embodiments disclosed herein.
Figure 16:
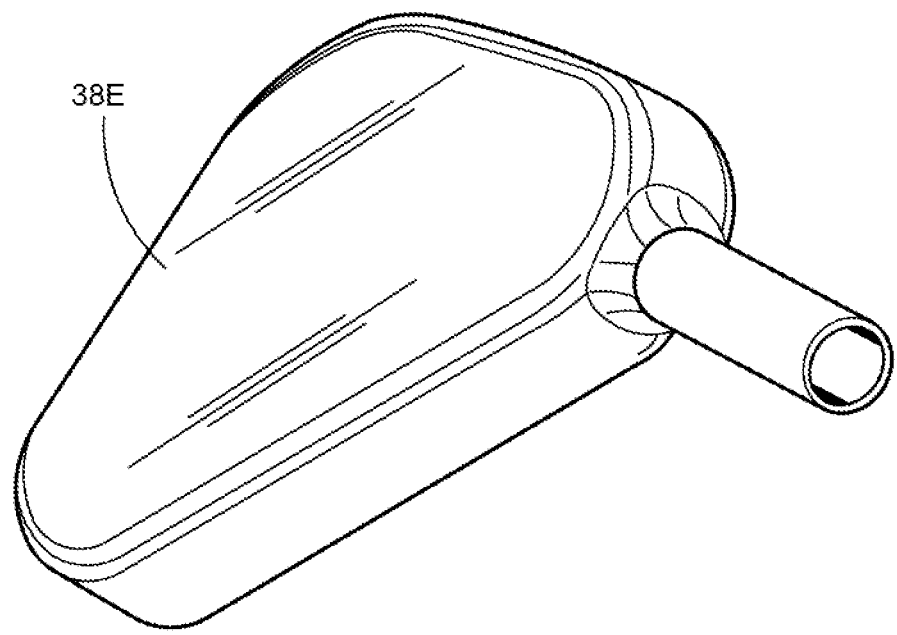
Figure 17:
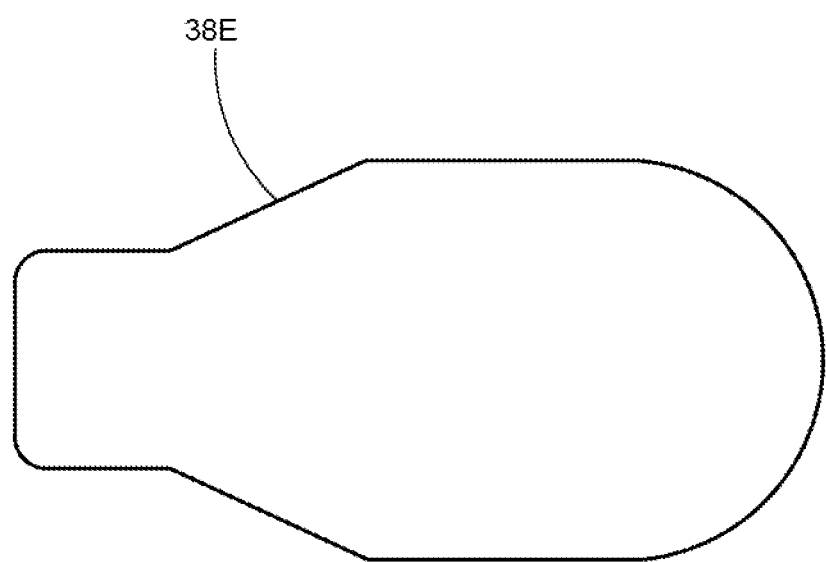

FIGS. 15 to 17 show different shapes of envelopes 38E which can be used depending on which intervertebral disc 10D is to have its nucleus pulposus 18N replaced. Additional detail regarding the envelopes is provided elsewhere herein.

FIGS. 18 to 21, show further embodiments of equipment for forming a tissue prosthesis, in situ, at a site in a patient's body is illustrated. In these embodiments, the equipment 110E comprises a delivery device in the form of an envelope tube 112E. The envelope tube 112E carries the envelope 38E at its distal end.

Figures 20, 21:
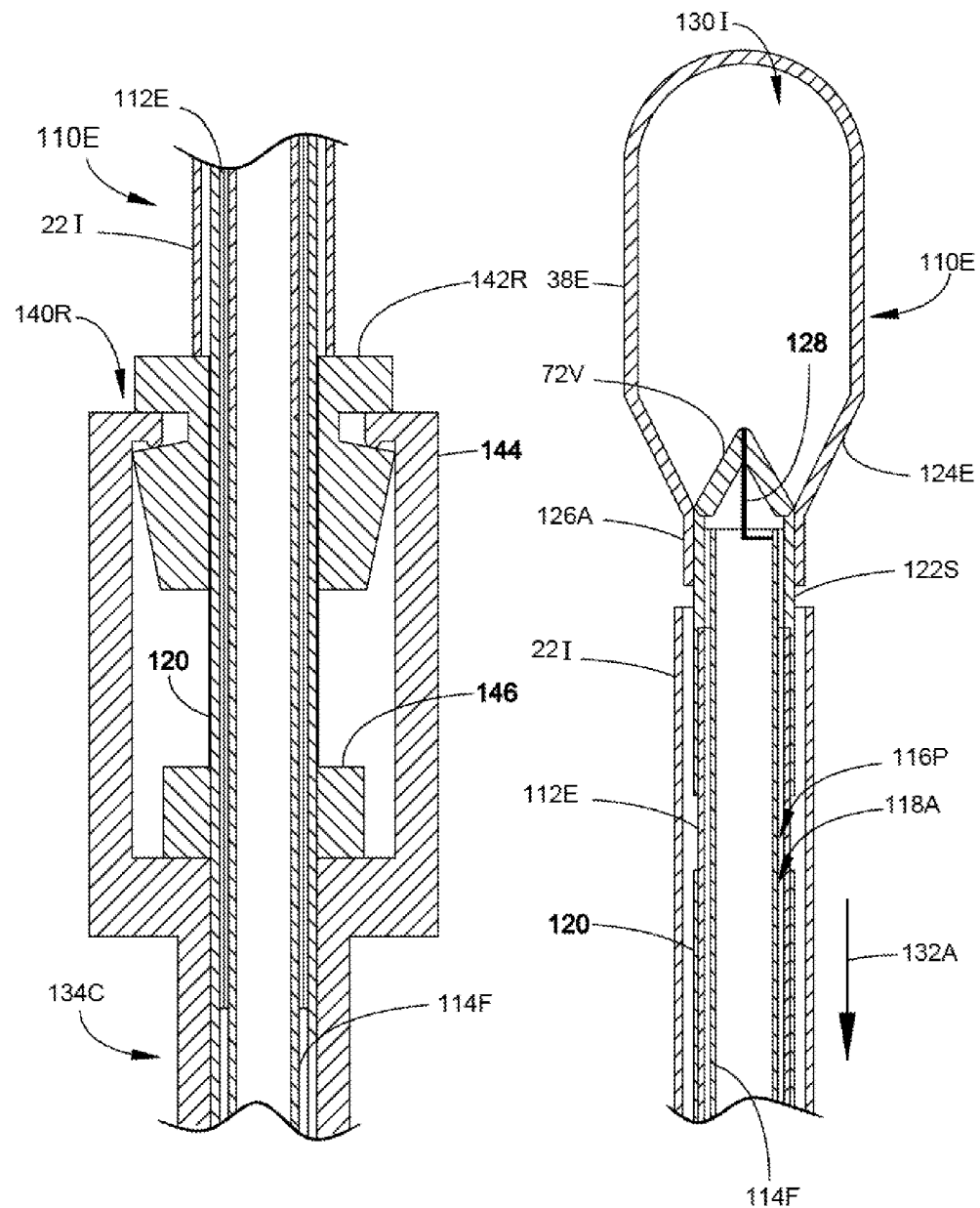
FIG. 20 shows, on an enlarged scale, a sectional side view of the part of the equipment encircled by circle "20" in FIG. 19 in accordance with certain exemplary embodiments disclosed herein.
FIG. 21 shows, on an enlarged scale, a sectional side view of the part of the equipment encircled by circle "21" in FIG. 19 in accordance with certain exemplary embodiments disclosed herein.

A filler member in the form of a filler tube 114F is slidably received within a passage 116P of the envelope tube 112E. As illustrated in FIG. 21, the filler tube 114F has a smaller outer diameter than an inner diameter of the envelope tube 112E to form an annular gap 118A between the filler tube 114F and the envelope tube 112E.

A removal mechanism in the form of a push-off tube 120 is a snug fit on the outer surface of the envelope tube 112E.

In certain embodiments, the envelope 38E is of a two part construction comprising a sleeve 122S (FIG. 21) to which an envelope defining member 124E is adhesively bonded as shown by an annular adhesive layer 126A. The sleeve 122S (and hence the valve) may be molded into the envelope defining member 124E via insert molding or alternatively, the molded envelope may include a valvular member. The sleeve 122S defines the valve 72V. For materials other than silicone, the sleeve 122S may be welded (hot or cold), insert molded (or overmolded), onto the envelope defining member 124E. Alternatively, the sleeve 122S and the envelope defining member 124E may be held together by a friction fit. Combinations of all of the above may also be applicable.

A distal end of the filler tube 114F carries an engaging member 128E which engages and opens the valve 72V so that the annular gap 118A is in flow communication with an interior 130I of the envelope 38E. A distal end of the push-off tube 120 terminates short of a proximal end of the sleeve 122S of the envelope 38E. However, it is also to be noted, that the envelope tube 112E is displaceable relative to the push-off tube 120 in the direction of arrow 132A. Instead of the engaging member 128E, the valve 72V could have a small opening (not shown) in it. The size of the opening in the valve 72V is selected to allow the passage of air, gas and certain other fluids through it in a particular direction or directions, but is sufficiently small that the viscosity of the filler material will substantially restrict or inhibit the passage of the filler material through it in a particular directions or directions.

Yet a further way of manipulating the interior 130I of the envelope 38E is to insert the filler tube 114F into the interior 130I of the envelope 38E and to have a slit (not shown) in the filler tube 114F upstream of the valve 72V. Thus, if the valve 72V seals about the filler tube 114F, air can still be drawn from the interior 130I of the envelope 38E into the gap 116P via the slit when the fluid manipulation device is operated.

A proximal end of the envelope tube 112E carries a connector 134C. The connector 134C is a Y-connector having a primary member 136P and a secondary member 138S projecting from the primary member 136P. The envelope tube 112E is fast with the primary member 136P of the connector 134C. The secondary member 138S of the connector 134C is in flow communication with the passage 116P of the envelope tube 112E and, hence, in use with the gap 118A between the envelope tube 112E and the filler tube 114F. The secondary member 138S is connectable to a fluid manipulation device (not shown) such as an evacuation pump for creating a low pressure in the gap 118A and, via the engaging member 128E opening the valve 72V, the interior 130I of the envelope 38E prior to filler material being charged into the interior 130I of the envelope 38E.

As shown in FIG. 20, the connector 134C includes a retaining mechanism 140R for retaining the envelope tube 112E in position relative to the introducer 22I. The retaining mechanism 140R comprises a receiving formation 142R carried at a proximal end of the introducer 22I. The retaining mechanism 140R further includes a clip portion 144 forming the distal end of the connector 134C which clips into the receiving formation 142R to retain the envelope tube 112E in position relative to the introducer 22I.

A proximal end of the push-off tube 120 carries a gripping formation 146 which is accessible externally of the retaining mechanism 140R for enabling the push-off tube 120 to be held while the envelope tube 112E is moved in the direction of the arrow 132A after charging of the envelope 38E with the filler material.

Figure 18:
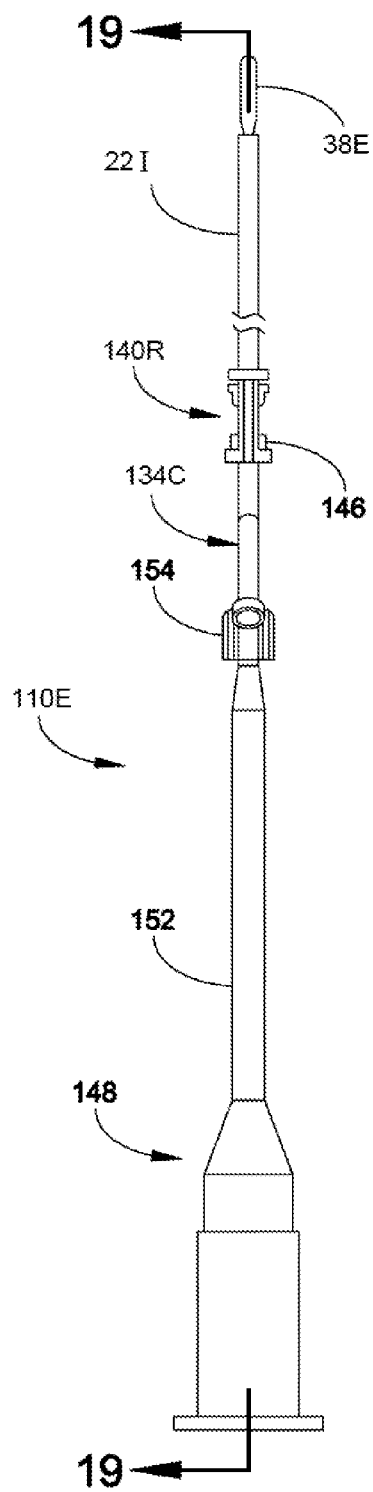
FIG. 18 shows a plan view of another embodiment of equipment for forming a tissue prosthesis, in situ, at a site in a patient's body in accordance with certain exemplary embodiments disclosed herein.
Figure 19:
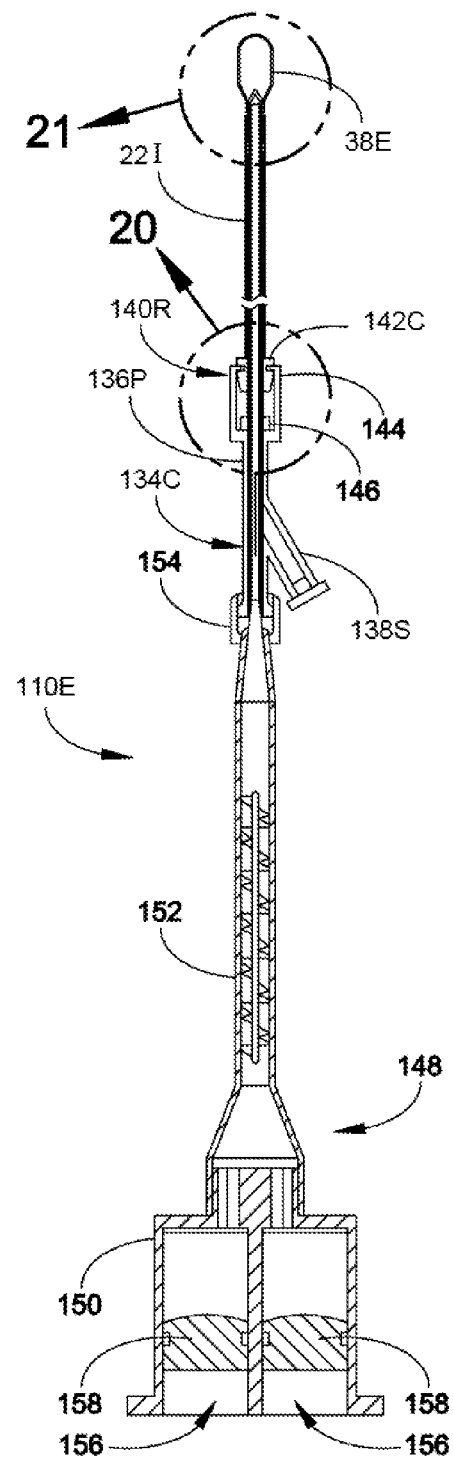
FIG. 19 shows a sectional side view taken along line 19-19 in FIG. 18 in accordance with certain exemplary embodiments disclosed herein.

As best seen in FIGS. 18 and 19, the equipment 110E may further include a dispensing device 148 for dispensing filler material. The dispensing device 148 includes a dispenser 150 feeding into a mixing device in the form of a static mixer 152. A distal end of the static mixer 152 carries the filler tube 114F. A Luer lock arrangement 154 is arranged at the distal end of the static mixer 152 and connects the dispensing arrangement 148 to the connector 134C.

In certain embodiments, the filler material is of a silicone rubber. To inhibit curing of the filler material prior to its being charged into the envelope 38E, the filler material is retained in two, separate parts. Thus, the dispenser 150 includes two reservoirs 156 in each of which a part of the filler material is initially received. Each reservoir 156 has a plunger 158 associated with it for dispensing the parts from the reservoirs 156 into the static mixer 152 where the parts are mixed prior to being charged into the envelope 38E. It is to be noted that the plungers 158 are displaceable together with each other via a suitable displacing device (not shown) such as a pneumatic gun.

Thus, in use, the filler material to be charged into the envelope 38E is provided in the dispensing arrangement 148. The dispensing arrangement 148 is connected to the connector 134C via the Luer lock 154. An envelope 38E, in a deflated condition, is mounted on the envelope tube 112E.

After the nucleotomy has been performed on the disc 10D, the envelope tube 112E with the envelope 38E on its distal end is inserted through the introducer 22I so that the envelope 38E, in its deflated condition, is received within the cavity 36C of the disc 10D. The filler tube 114F is inserted into the interior of the envelope tube 112E so that the engaging member 128E engages the valve 72V and opens the valve 72V. By opening the valve 72V, the interior 130I of the envelope 38E is placed in fluid communication with the gap 118A between the tube 112E and the filler tube 114F.

A fluid manipulation device (not shown) is attached to the secondary member 138S of the connector 134C and the pressure is reduced creating a lower pressure within the gap 118A and the interior 130I of the envelope 38E and inhibits the formation of gas bubbles in the prosthesis 100P as the filler material is charged into the envelope 38E.

The filler material is dispensed from the dispensing device 148 into the filler tube 114F and into the interior 130I of the envelope 38E. This causes the envelope 38E to expand elastically to conform to the shape of the cavity 36C of the disc 10D with the envelope 38E being retained under tension by the filler material.

After charging of the filler material into the interior 130 of the envelope 38E, the filler tube 114F is withdrawn. The withdrawal of the filler tube 114F, causes withdrawal of the engaging member 128E allowing the valve 72V to close to inhibit leakage of filler material from the interior 130I of the envelope 38E.

Either before, during or after curing, the envelope tube 112E is moved relative to the push off tube 120 in the direction of the arrow 132A by holding the push off tube 120 using the gripping device 146. This urges the sleeve 122S of the envelope 38E off the end of the envelope tube 112E as the envelope tube 112E is withdrawn relative to the push off tube 120. The valve 72V occludes the opening to the envelope 38E. The equipment 110E, including the introducer 22I, is then withdrawn from the patient's body, allowing the aperture 30A to occlude as the fibres of the annulus fibrosis 16A close over and the procedure is complete.

Figure 22:
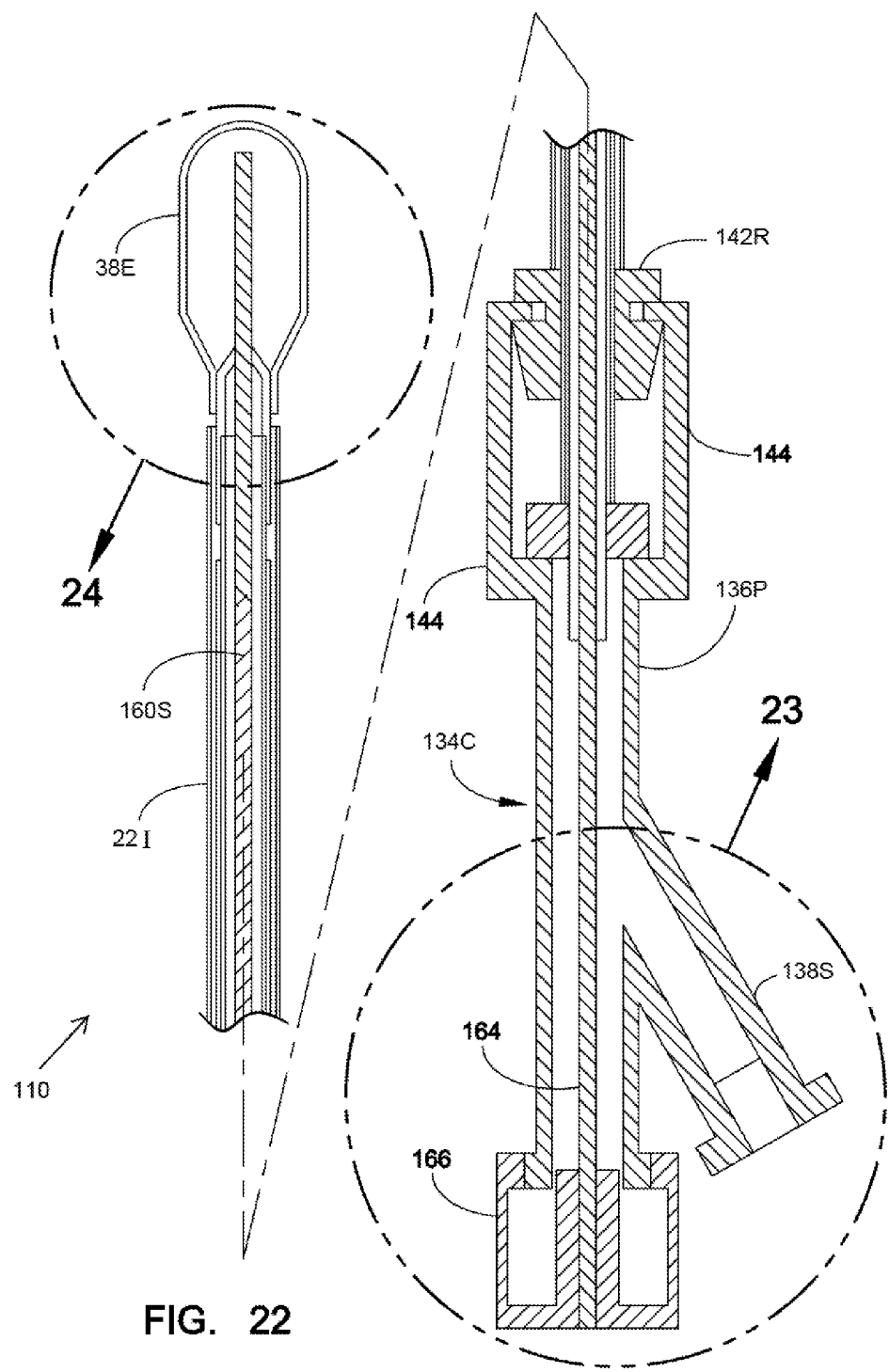
FIG. 22 shows a sectional side view of yet a further embodiment of equipment for forming a tissue prosthesis, in situ at a site in a patient's body in accordance with certain exemplary embodiments disclosed herein.
Figures 23, 24:
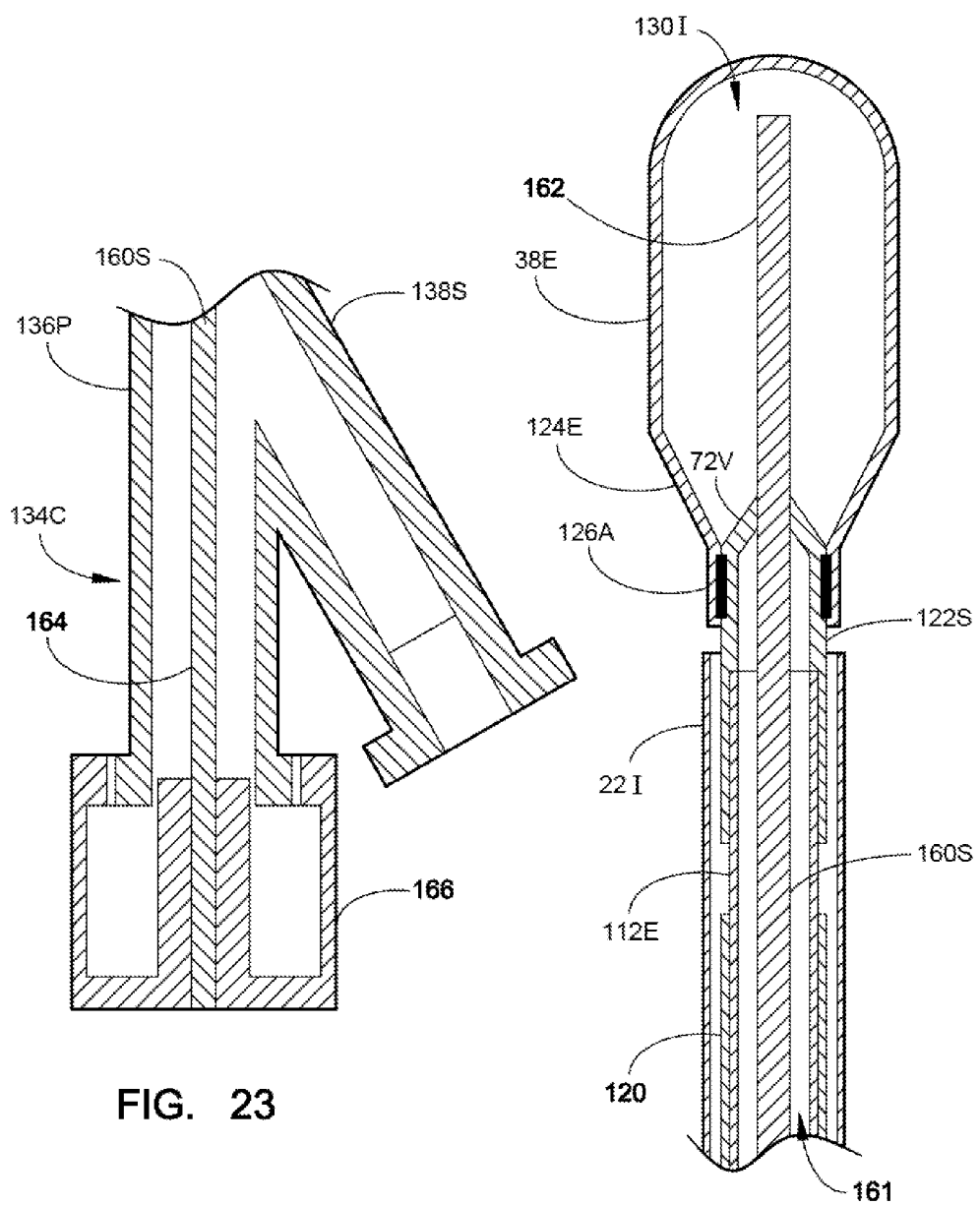
FIG. 23 shows on an enlarged scale, a sectional side view of the part of the equipment encircled by circle "23" in FIG. 22 in accordance with certain exemplary embodiments disclosed herein.
FIG. 24 shows on an enlarged scale, a sectional side view of the part of the equipment encircled by circle "24" in FIG. 22 in accordance with certain exemplary embodiments disclosed herein.
Figure 29:
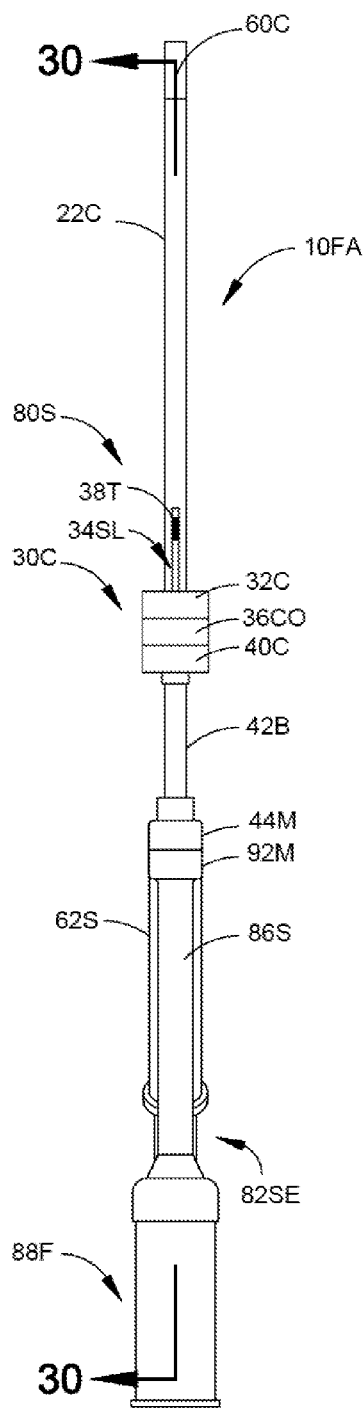
FIG. 29 shows a plan view of an assembly of the tissue prosthesis insertion system in accordance with certain exemplary embodiments disclosed herein.
Figure 30:
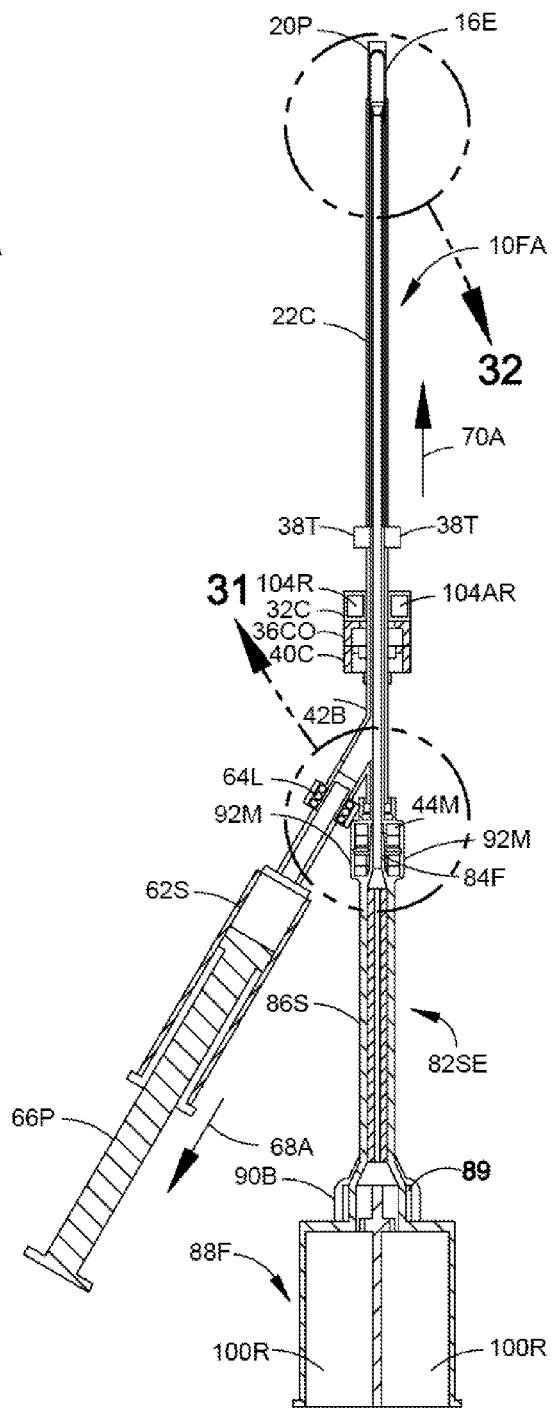
FIG. 30 shows a sectional side view of the assembly of the system taken along line 30-30 in FIG. 29 in accordance with certain exemplary embodiments disclosed herein.

FIGS. 22 to 24, illustrate further embodiments of equipment for forming a tissue prosthesis, in situ, at a site in a patient's body is illustrated. The equipment 110E includes a stiffening element in the form of a stiffening rod or tube 160S. Prior to insertion of the filler tube 114F into the envelope tube 112E, the stiffening rod 160S is inserted into the passage 116P of the envelope tube 112E. A distal end 162 of the stiffening rod 160S projects beyond a distal end of the envelope tube 112E and terminates at a distal wall in the interior 130I of the envelope 38E. A gap 161 is created between the envelope tube 112E and the stiffening rod 160S. The gap 161 and the interior 130I of the envelope 38E are manipulated by operation of the manipulation device to cause the envelope 38E to collapse on to the distal end 162 of the stiffening rod 160S. This facilitates insertion of the envelope 38E into the introducer 22I and into the cavity 36C of the disc 10D.

Once the envelope 38E has been located within the cavity 36C, the fluid manipulation device is turned off to release the envelope 38E from the distal end 162 of the stiffening rod 160S and this allows the stiffening rod 160S to be withdrawn. The filler t tube 114F can then be inserted into the envelope tube 112E, as described above, to enable filler material 60F to be charged into the envelope 38E.

In certain embodiments (not illustrated), the stiffening rod 160S is dimensioned to fit in the interior of the filler tube 114F. With this arrangement, the gap 118A between the envelope tube 112E and the filler tube 114F is manipulated, as described above, with the stiffening rod 160S projecting through the distal end of the envelope tube 112E and the envelope 38E being collapsed over the distal end 162 of the stiffening rod 160S.

A proximal end 164 of the stiffening rod carries a cap connector 166 which connects to the Y connector 134C to retain the stiffening rod 160S in position relative to the envelope tube 112E and/or the filler tube 114F, as the case may be. The cap connector 166 seals against a proximal end of the Y connector 134C to enable the fluid and or the fluid pressure in the gap 161 and the interior 130I of the envelope 38E to be manipulated through operation of the withdrawal device, connected to the Y connector 134C (the port, which does not have the cap connector 166 attached to it). Such a withdrawal device may be a syringe.

In additional exemplary embodiments, there may be provided a prosthesis delivery system which includes a plurality of nested tubes, an outermost tube of which functions as a cannula in which the remaining tubes are received, the remaining tubes forming part of a prosthesis delivery apparatus, a wall portion of at least one of the tubes having a change in diameter along its length to mate with a corresponding part of a dispensing arrangement for use with the prosthesis delivery apparatus.

The prosthesis delivery devices may include a carrier tube which carries a component of the prosthesis on its distal end and a filler tube received in the carrier tube for charging a filler material into the component when the component is located at the desired location at a site in a patient's body. The prosthesis delivery apparatus may include a connector for connection to a withdrawal device to enable gas to be withdrawn from the component during formation of the prosthesis in situ, the connector being arranged, in use, at a proximal end of the prosthesis delivery apparatus. Further, the prosthesis delivery apparatus may include a displacement device for displacing the component of the prosthesis after it has been charged with the filler material. The displacement device may be a further tube mounted about the carrier tube. In addition, the prosthesis delivery apparatus may include a cover tube to cover the component of the prosthesis, the cover tube fitting over the carrier tube. The cover tube may include a resiliently flexible distal portion to accommodate the component of the prosthesis. In certain embodiments, the prosthesis delivery apparatus may include a connector for connection to a withdrawal device to enable gas to be withdrawn, or manipulated from at least the component during formation of the prosthesis in situ. More specifically and preferably, the withdrawal device may manipulate the fluid and or fluid pressure at least within the delivery apparatus and or the envelope; when in use. Although the fluid and or the fluid pressure manipulation remains active whilst the filler material is being charged down the filler tube, once the material reaches the distal end of the filler tube (i.e., The proximal end of the component/envelope), the annular space/gap between the filler tube and the carrier tube is occluded by the filler material. Hence during the formation and filling of the envelope, the fluid and or fluid pressure manipulation of at least the interior of the envelope is no longer active.

In certain embodiments, a wall portion of each of the tubes may have a change in diameter along its length. The change in diameter along the length of each tube may be provided by a flared wall portion of each tube.

The disclosed systems may include a manipulating arrangement carried at a proximal end of at least the cannula for effecting manipulation of the nested tubes. The manipulating arrangement of the cannula may include a rupturing mechanism for rupturing the cannula for removal. The rupturing mechanism may include a plurality of circumferentially spaced, longitudinally extending zones of weakness in a wall of the tube of the cannula and a gripping device arranged at a proximal end of the tube of the cannula. The gripping device may comprise a plurality of circumferentially spaced radially outwardly extending tabs which are pulled outwardly to cause rupturing of the zones of weakness of the cannula to facilitate withdrawal of the cannula after placement and setting of the prosthesis.

The systems may include the dispensing mechanism, the dispensing mechanism including a tubuldar element having a distal end which corresponds with and mates with that part of the wall portion of the at least one tube having the change in diameter. The nested tubes may be configured to extend proximally of the distal end of the element to overlie the element. With this arrangement, the length of the unsupported ends of the tubes is considerably shortened thereby improving the rigidity of the tubes and the stability of the system. In addition, the balance of the system is improved rendering it easier for the clinician to control system.

The dispensing mechanism may include a dispenser to which the element is attachable. The element may be a static mixer.

In certain embodiments, there are provided systems which includes a plurality of tubes, wherein an outermost tube functions as a cannula in which the remaining tubes are received, the remaining tubes forming part of a prosthesis delivery apparatus, a wall portion of at least one of the tubes having a change in diameter along its length to mate with a corresponding part of a dispensing arrangement for use with the prosthesis delivery apparatus.

In certain embodiments, the prosthesis delivery devices may include at least one carrier tube which may carry at least one component of the prosthesis on its distal end and at least one filler tube received in the carrier tube for charging a filler material into the component when the component is located at the desired location. The prosthesis delivery apparatus may include a connector for connection to a withdrawal device to enable gas and or certain fluids to be withdrawn from the component during formation of the prosthesis in situ, the connector being arranged, in use, at a proximal end of the prosthesis delivery apparatus.

In certain embodiments, the prosthesis delivery apparatus may include a displacement device for displacing the component of the prosthesis after it has been charged with the filler material. The displacement device may be a further tube mounted about the carrier tube.

In certain embodiments, the prosthesis delivery apparatus may include at least one cover tube to cover the component of the prosthesis, the at least one cover tube fitting over the at least one carrier tube. The at least one cover tube may include a resiliently flexible distal portion to accommodate the component of the prosthesis.

In certain embodiments, a wall portion of each of the tubes has a change in diameter along its length. In some aspects, the change in diameter along the length of each tube may be provided by a flared wall portion of each tube.

In certain embodiments, the system may include a manipulating arrangement for effecting manipulation of the tubes located within the cannula. The manipulating arrangement may include a rupturing mechanism for rupturing the cannula for removal. The rupturing mechanism may include a plurality of spaced zones of weakness in a wall of the tube of the cannula and a gripping device arranged at a proximal end of the tube of the cannula. The gripping device may comprise a plurality of outwardly extending tabs which are pulled outwardly to cause rupturing of the zones of weakness of the cannula to facilitate withdrawal of the cannula after placement and setting of the prosthesis.

In certain embodiments, the system may include the dispensing mechanism, the dispensing mechanism including a tubular element having a distal end which corresponds with and mates with that part of the wall portion of the at least one tube having the change in diameter. The nested tubes may be configured to extend proximally of the distal end of the element to overlie the element. With this arrangement, the length of the unsupported ends of the tubes is shortened thereby improving the rigidity of the tubes and the stability of the system. In addition, the balance of the system is improved rendering it easier for the clinician to control system.

In certain embodiments, the dispensing mechanism may include a dispenser to which the element is attachable and/or the element may be a static mixer.

In certain exemplary embodiments, there may be provided a prosthesis delivery system which includes a plurality of nested tubes, one tube being a carrier tube which carries at least a component of a prosthesis at its distal end and another tube constituting a delivery tube for delivering the nested tubes to a site at a patient's body; and a cover tube forming part of the nested tubes, the cover tube being arranged outwardly of the carrier tube to cover the component when the carrier tube is inserted into the delivery tube to protect the component. The cover tube may have a length approximating a length of the delivery tube with the carrier tube being dimensioned so that the component protrudes beyond a distal end of the delivery tube in an uncovered condition.

In certain exemplary embodiments, the system may include a displacement device arranged outwardly of the carrier tube with the cover tube being arranged outwardly of the displacement device. The displacement device may be a further tube mounted about the carrier tube. The cover tube may have a resiliently flexible distal end to accommodate the component of the prosthesis. The resilient flexibility of the distal end of the cover tube may be affected and effected by slotting the distal end to provide a plurality of leaves able to flex radially outwardly.

The equipment may include at least one sensing arrangement configured to sense a parameter of the filler material charged into the at least one envelope. The at least one sensing arrangement may comprise a pressure sensor for sensing the pressure of filler material charged into the at least one envelope, a temperature sensor for sensing the temperature of the filler material charged into the at least one envelope, be configured to sense the quantity of filler material charged into the envelope and/or comprise a flow rate sensor for sensing the rate of flow of the filler material into the at least one envelope. Further, the at least one sensing arrangement may be configured to sense the presence of gas bubbles in the filler material charged into the at least one envelope. Further, the sensing arrangement may be configured to sense the displacement of the pistons of the dispenser mechanism. Further, the sensing arrangement may be configured to sense the force applied to the pistons to displace the pistons of the dispenser mechanism.

In certain embodiments, there may be provided equipment for forming a tissue prosthesis in situ at a site in a patient's body, the equipment comprising a tubular delivery device, the delivery device defining a passageway, and at least one envelope of the prosthesis being mountable to a distal end of the delivery device to be received in a cavity at the site; a stiffening element arranged to project from a distal end of the delivery device with the envelope, in use, being received over the stiffening element to be supported by the stiffening element; and a removal mechanism carried by the delivery device for enabling the at least one envelope to be removed from the delivery device after the at least one envelope has been charged with filler material via the filler member.

In certain embodiments, the stiffening element may be an elongate element, such as a rod or tube, receivable with clearance in the passageway of the delivery device to define a gap to enable at least some fluid to be withdrawn from the at least one envelope to collapse the envelope on to a distal end of the elongate element projecting from the distal end of the delivery device.

The equipment may include a filler member receivable in the passageway of the delivery device after removal of the stiffening element, the filler member being receivable, after removal of the stiffening element, with clearance in the passageway to define a gap to enable fluid to be manipulated at least from the at least one envelope.

In certain embodiments, the equipment may include a tubular filler member receivable in the passageway of the delivery device, the filler member being receivable with clearance in the passageway to define a gap to enable fluid to be manipulated at least from the envelope and the stiffening element being an elongate element receivable through the passage of the filler member.

In certain embodiments, there may be provided a tissue prosthesis insertion system which includes a first assembly comprising a plurality of nested tubes, one of the tubes being a carrier tube which, in use, receives a component of a tissue prosthesis at a distal end of the carrier tube; a magnetic mount carried at a proximal end of the first assembly; a second assembly removably attachable to the first assembly; and an attachment device carried at a distal end of the second assembly, the attachment device being responsive to the magnetic mount of the first assembly, the magnetic mount and the attachment device carrying complementary engaging formations to facilitate sealing between the magnetic mount and the attachment device.

The use of a plurality of nested tubes, as described herein, may have several advantages. For example, the device may be more compact than other devices which allow the device and all of its components to fit into a smaller confinement. This may, in certain embodiments, provide a means for conducting percutaneous and/or minimally invasive procedures. The nested tubes also reduce trauma to the tissue that can result from repeatedly moving instruments in and out of the body. The nested tubes also provide additional protection for the instruments inside of the outermost tube. Additionally, the device can be more easily maintained in its desired location and the system may operate with less frictional resistance. Since the working cannula is fixed and docked relative to the patient, and all the other nested tubes lock to the working cannula, the positioning and deployment of the envelope within the disc space is consistent and repeatable. Also, since all the tubes are fixed relative to each other, during any process of the implant procedure, the risk of damage to the envelope is minimised because movement (laterally and or axially) of the envelope is minimised. Excessive movement of the envelope during any part of the implant procedure increases its chances of being damaged by either the surrounding tissue or other tubes (in particular the working cannula).

The complementary engaging formations of the magnetic mount and the attachment device may comprise a Luer slip fitting (see, e.g., the luer slip fitting mechanism 1006 of FIG. 94). By "Luer slip fitting" is meant that one of the engaging formations comprises a tapered socket and the other of the engaging formations comprises a tapered fitting receivable in the tapered socket to form a sufficient or substantial seal between the fitting and the socket.

In certain embodiments, instead of a luer slip fit formation, sealing can be achieved through the use of an O-ring or a gasket between the surfaces of the mounts such that a substantial seal is formed.

Figure 92:
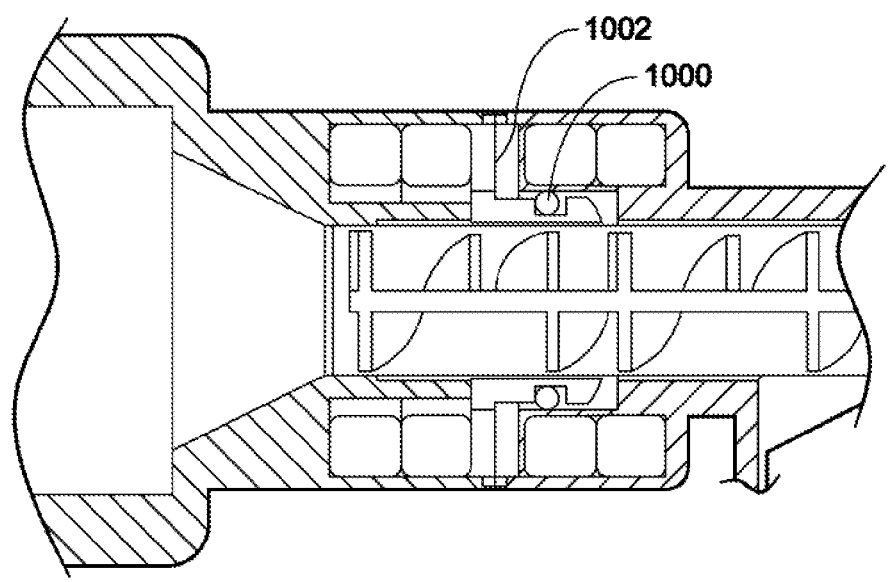
FIG. 92 illustrates a means of sealing through an O-ring (the cross section of the O-ring can be seen in the close up view) in accordance with certain exemplary embodiments disclosed herein.

Also, one engaging end can have a protruding member, in the form of a tapered fitting, and the receiving end may comprise an engaging formation (not necessarily tapered) which is substantially parallel, but of a softer material than the protruding member such that it deforms to accommodate the protruding member and form a seal. Two surfaces of dissimilar materials (dissimilar hardness) engaging with mechanical interference may provide a substantial seal. For two surfaces of similar materials engaging with mechanical interference, to improve the seal, a dissimilar material (e.g. Silicone) can be used between the two surfaces to provide a substantial seal. Also the applicant of a sealant between the two similar surfaces can provide the necessary seal. FIG. 92 illustrates the use of an O-ring 1000 between the two surfaces. Although not illustrated, the seal could also be formed at the interface 1002 of the two surfaces.

The magnetic mount of the first assembly may be a first magnetic mount and the attachment device may comprise a second magnetic mount which magnetically attaches to the first magnetic mount.

In certain embodiments, both mounts do not necessarily have to be magnetic, as long as one is magnetic, the other can be of a material which is attracted to a magnet.

Alternatively, another means of engaging two surfaces is through the application of an adhesive on one or more of the surfaces and using the tackiness of the surfaces as a means for engaging the two surfaces.

Other means of coupling can include a luer lock connection (see, e.g., the luer locking mechanism 1004 of FIG. 93), bayonet connection, ball seal connection and any other connection which allow the two engaging components to be reversibly attachable. To achieve the closed system status, any of the listed engaging means can be used in conjunction with any or all of the above mentioned sealing mechanisms either singly or in combination.

The second assembly may include a stiffening member received within the first assembly, the stiffening member, in use, projecting into an interior of the component of the prosthesis, the stiffening member having a securing formation at its proximal end which engages the engaging formation of the magnetic mount in a sealing manner.

Further, the system may include a withdrawing device attachable to the first assembly, the withdrawing device, in use, being in communication with the interior of the component of the prosthesis and, with the stiffening member in position, creating a closed system, contained system, or hermetically sealed system so that operating the withdrawing device causes an increase in the volume of the closed system with a corresponding reduction in the pressure in the interior of the component, resulting in the component collapsing about the stiffening member.

The withdrawing device may be operable to test the integrity of the first assembly with the component mounted on the first assembly.

The first assembly may include a protective sheath, constituting one of the tubes of the first assembly, received over the component after it has been collapsed on to the stiffening member. At least one of the protective sheath and the component may be treated to facilitate sliding displacement between the protective sheath and the component. The treating of the protective sheath and/or the component may occur prior to inserting the first assembly into a working cannula used for insertion of the tissue prosthesis into position at a site in a patient's body. The treating may involve immersing the distal end of the first assembly in a lubricating fluid such as water. Instead, the treating may involve coating an inner surface of the protective sheath with a hygroscopic material or a hydrophilic material such as, for example, a hydrogel. Alternatively, rather than treating the inner surface of the protective sheath, the protective sheath itself may be made from lubricious materials which include, but not limited to, polytetrafluoroethylene (Teflon), acetal, polypropylene, polyethylene. All of the above mentioned materials may also be a treatment option for the inner lining of the protective sheath. Further, should the protective sheath be made from the described polymers, they may also be treated to improve the lubricity.

The protective sheath may have a distal end configured to facilitate sliding displacement of the protective sheath relative to the component of the prosthesis. In some aspects, the distal end of the protective sheath may be configured by being bifurcated. The protective sheath may include an operating member arranged at its proximal end to facilitate manipulation of the protective sheath.

Figure 87:
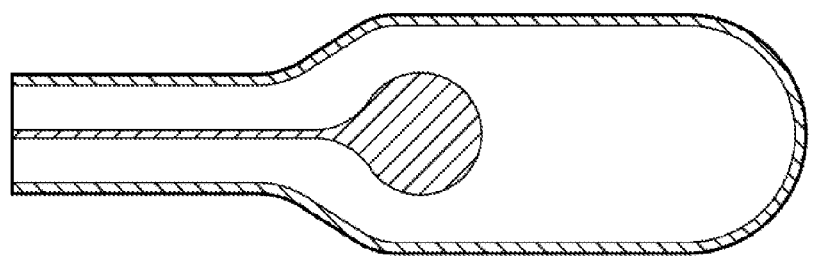
FIG. 87 illustrates a sectional view of a ball valve inside an envelope in an open position in accordance with certain exemplary embodiments disclosed herein.
Figure 88:
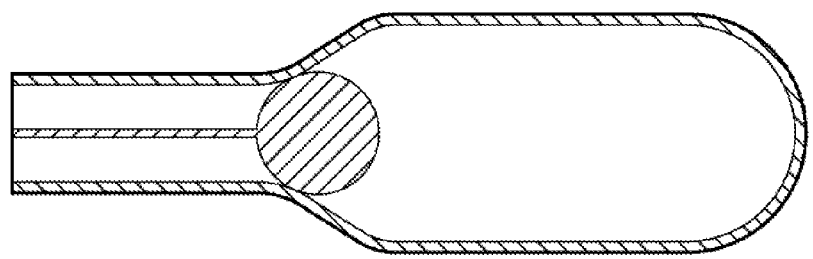
FIG. 88 illustrates a sectional view of a ball valve inside an envelope in a closed position in accordance with certain exemplary embodiments disclosed herein.
Figure 89:
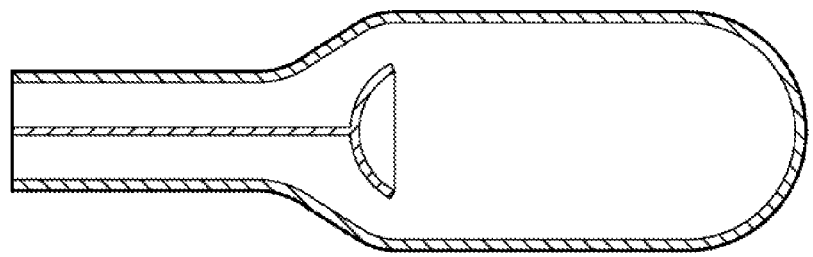
FIG. 89 illustrates a sectional view of a umbrella valve inside an envelope in an open position in accordance with certain exemplary embodiments disclosed herein.
Figure 90:
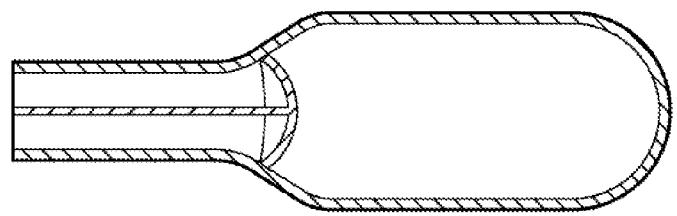
FIG. 90 illustrates a sectional view of a umbrella valve inside an envelope in a closed position in accordance with certain exemplary embodiments disclosed herein.

The systems may include the component, the component comprising at least one envelope of an elastically deformable material, the at least one envelope defining an access opening with a flow control member being arranged in the access opening, the flow control member being configured to permit withdrawal of fluid from an interior of the at least one envelope prior to filling the at least one envelope with a filler material. The flow control member may be a flow control valve which, in a rest condition, defines a withdrawal opening to allow withdrawal of the fluid from the interior of the at least one envelope. In certain aspects, the valve may be a duckbill valve having a pair of opposed operating flaps, the flaps being shaped so that, in their rest condition, they are spaced from each other to define the withdrawal opening The flaps may be skewed or staggered so that when the flaps come together, a small opening is defined. Other types of valves include umbrella valves, star valves, valves which have at least 1 flap (preferably 2), ball valve, dome shaped (e.g., umbrella shaped) valve with a slit(s) cut into the very tip of the dome. For example, FIGS. 87 and 88 illustrate an exemplary ball valve in an open and closed position, respectively and FIGS. 89 and 90 illustrate an exemplary umbrella valve in an open and closed position, respectively. The valve may be pressure sensitive whereby it prevents flow in a particular direction at a certain pressure. When that certain pressure is exceeded, it allows for fluid to flow in that particular direction.

Figure 91:
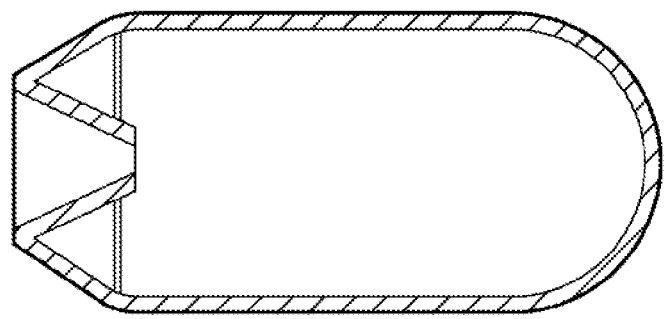
FIG. 91 illustrates an exemplary valve-like configuration where the diameter gradually decreases to limit backflow in accordance with certain exemplary embodiments disclosed herein.

In certain embodiments, the flow control member may not necessarily have to be a valve. If the neck of the envelope were inverted, once the envelope has been filled, the inverted neck would form a flap which seals to prevent the backflow of material. The inverted neck may be parallel (tubular), tapered or stepped (i.e., the diameter changes). Also, another alternative to a valve (which is built into the envelope) is a tubular section which has a gradual reduction in diameter (See, for example, FIG. 91). This functions like a valve but may not necessarily be referred to as a valve.

Various cross sections are possible for this form of flow restricting mechanism. It still has an opening in its relaxed state but once the envelope is filled, the significantly more viscous biomaterial cannot flow back out. All of the above mentioned design features can be applicable for a valve or a valve like structure which does not have an opening defined in its relaxed state. It could require an extending member (either an extension of the carrier tube or other) to open up the valvular member in order to define this opening, which may be necessary to operate the envelope (e.g., collapse). Alternate to a valve, the delivery apparatus can be twisted (or rotated) once the filling is completed and this twisting crimps and seals the neck of the implant.

In certain embodiments, the flow control member in its resting condition may be configured to define at least one withdrawal opening and in its non resting condition may be configured to allow less viscous fluids to flow in at least two directions and more viscous fluids to flow in at least one direction. Less viscous materials are those materials that require less energy to flow. Less viscous fluids include, but not limited to, air, water, certain oils. (The term "less viscous" can be seen as a relative term where it defines a material which is less viscous than the material being introduced into the envelope as the biomaterial, or less viscous than the material which is limited to flow in at least one direction by the flow control member.)

In certain embodiments, the flow control member in its first condition may be configured to define at least one withdrawal opening and in its second condition may be configured to allow less viscous fluids to flow in at least two directions and more viscous fluids to flow in one direction.

In some aspects, other flow control mechanisms or means for flow control may be used. For example star valves, multi cuspid valves, umbrella valves. In some aspects, other flow control mechanisms may be used as long as that mechanism controls the flow of certain fluids in at least one direction. In certain aspects, the flow control mechanism may be configured to allow less viscous fluids to flow in at least two directions and more viscous fluids to flow in at least one direction. For example, using certain flow control mechanisms fluids such as gas, water, solutions or combinations thereof, will be permitted to substantially flow in at least two directions through the flow control mechanism and viscous filler material will be permitted to substantially flow through the control mechanism into the envelope.

In certain aspects, the means for flow control may be configured to allow less viscous fluids to flow in either direction or more viscous fluids to flow in at least one direction.

In certain embodiments, the flow control member may be configured to allow less viscous filler material to flow into the envelope where the filler material becomes more viscous, thereby preventing it from flowing back through the flow control member.

One advantage of certain flow control members disclosed herein is that they may be configured to permit viscous materials to flow in one direction allowing the carrier tube to be detached after the viscous material has been delivered to the envelope. Thus permitting shorter surgery times and anaesthesia for the patient, resulting in a faster recovery and less chance of complications.

The second assembly may comprise a filler tube received through the first assembly to communicate with the interior of the envelope and a filler material dispenser mountable to a proximal end of the filler tube. The dispenser assembly may feed into a static mixer, a distal end of the static mixer carrying the attachment device, the arrangement being such that, when the second assembly is fast with the first assembly and the withdrawing device is attached to the first assembly, a second closed system is created which enables fluid to be withdrawn from the interior of the envelope by the withdrawing device to create a low pressure region in the envelope. A "low" pressure may be defined as a pressure below ambient pressure.

Whether the filler material is a single part, two part, etc, it can be premixed and delivered through the filler tube rather than having to go through a static mixer. Alternatively, the mixing can be through a dynamic mixer. Also, the in situ curing filler material usually relies on a catalyst and or cross-linker. That molecule required to initiate the chemical reaction can be added into the mixture by having it coated on the surfaces the filler material is in contact with. This includes but is not limited to, the static mixer, inner lining or filler tube, inner lining of envelope etc.

The dispenser may contain filler material, the filler material preferably being of the same class or type of material as the material of the envelope so that, when the envelope has been charged with the filler material and the filler material has been allowed to set, a tissue prosthesis is formed which is elastically deformable. The envelope is filled with the filler material initially up until the envelope reaches its relaxed configuration (i.e., its premolded form). Then, when the filling continues, it undergoes elastic deformation for up to 10 times its relaxed volume, or for up to 3, 4, 5, 6, 7, 8, or 9 times its relaxed volume or until it fills to conform substantially to the cavity of the nucleus where the substantiality of the fill is not limited by the limitations of the apparatus.

In certain embodiments, the envelope may be resilient and elastically deformable. The in situ curing material may also be resilient and elastically deformable. When the systems combine, they form a resilient and elastically deformable implant. When the envelope and in situ material combine, they take on the properties substantially similar to that of the envelope, or to that of the in situ curing material, or the combined system may take on completely different mechanical properties (possibly due to the fact that when they combine, they undergo a chemical reaction which changed the properties altogether). By "elastically deformable" it is meant that the prosthesis can be deformed by the application of a force and, upon removal of the force, the tissue prosthesis substantially returns to its undeformed state. In certain embodiments, the filler material may be of a different class or type than the material of the envelope. For example, but not limited to, a polyurethane envelope filled with a silicone filler material, a silicone envelope with a polyurethane filler material, a polyester envelope filled with a silicone filler, polyester envelope filled with polyurethane, or other combinations of acceptable filler material and acceptable envelope material. Further, the envelope may be a polyethylene envelope filled with either a polyurethane or a silicone filler. Combinations of the materials also apply. For example, the filler may be a combination of silicone and polyurethane.

The system may include an obturating device receivable in one of the tubes of the first assembly for tamping a part of the tissue prosthesis into position after formation of the tissue prosthesis. The obturating device may carry a locking member at its proximal end for locking to a working cannula of the system so that, after tamping of the part of the tissue prosthesis, the working cannula and the obturator can be removed simultaneously.

In certain embodiments, there may be provided a tissue prosthesis insertion system which includes an assembly comprising a plurality of nested tubes, one of which is a carrier tube for carrying a component of a tissue prosthesis at its distal end and another of which is a filler tube received with clearance in the carrier tube to define a passage between the filler tube and the carrier tube, the proximal end of the filler tube and the proximal end of the carrier tube being in sealing engagement; and a withdrawing device attachable to the assembly so that, when the withdrawing device is attached and the component of the tissue prosthesis is mounted on the distal end of the carrier tube, a closed system is formed which allows the withdrawing device to be used to increase the volume of the closed system to form a low pressure region at least in the component.

The assembly may comprise a stiffening member received in the carrier tube, a proximal end of the stiffening member and a proximal end of the assembly carrying complementary engaging formations for enabling the stiffening member to engage sealingly with at least one of the plurality of nested tubes to create an initial closed system, operation of the withdrawing device forming a low pressure region in the interior of the component, in use, to cause the component to collapse around the stiffening member. The system may include a filler tube insertable into the carrier tube after removal of the stiffening member to contribute to the formation of a further closed system which is then acted on by the withdrawing device to increase the volume of the closed system to reduce the pressure in the interior of the component.

The withdrawing device may be operable to test the integrity of the system to ensure that there are no leaks in the system.

In certain embodiments, there may be provided a tissue prosthesis insertion system which includes a working cannula for accessing a site in a patient's body percutaneously and/or minimally invasive manner for carrying out a tissue prosthesis insertion procedure at the site; and an obturating device receivable in the cannula for tamping a part of a tissue prosthesis into position after formation of the tissue prosthesis.

The obturating device may comprise a blunt-ended rod slidably receivable in the working cannula.

In certain embodiments, there may be provided a tissue prosthesis component which includes an envelope of an elastically deformable material, the envelope defining an access opening; and a flow control member arranged in the access opening, the flow control member being configured to permit withdrawal of fluid from an interior of the envelope prior to filling the envelope with a filler material.

The flow control member may be a flow control valve which, in a rest condition, defines a withdrawal opening to allow the passage of certain fluids in both directions. The envelope may have a neck portion, the neck portion defining the access opening and the flow control member being arranged within the neck portion.

In certain embodiments, there may be provided methods of preparing a first assembly of a tissue prosthesis system for insertion into a patient's body, the methods comprising providing the first assembly which comprises a plurality of nested tubes, one of the tubes being a carrier tube; mounting a component of the prosthesis on a distal end of the carrier tube, the component being of an elastically deformable material; inserting a stiffening member into the first assembly so that the stiffening member extends into an interior of the component and causing a proximal end of the stiffening member to sealingly engage a proximal end of the first assembly; attaching a withdrawing device to the first assembly so that the withdrawing device is in fluid communication with the interior of the component; and operating the withdrawing device to reduce the pressure in the interior of the component to cause the component to collapse about the stiffening member.

The methods may include attaching the withdrawing device to a fluid port of the first assembly in a sealing manner. The withdrawing device may be a syringe which is attached by a Luer lock mechanism to the fluid port of the first assembly.

After the component has been collapsed about the stiffening member, the methods may include placing a protective sheath about the component. More particularly, the methods may include placing the protective sheath about the component by sliding the protective sheath over the component, the protective sheath constituting one of the tubes of the nested tubes of the first assembly. Further, the methods may include treating one of the protective sheath and the component with a lubricating medium to facilitate relative displacement between the protective sheath and the component.

The methods may include using the withdrawing device to test the integrity of the combination of the first assembly and the component and the stiffening member attached to the first assembly.

In certain embodiments, there may be provided methods of forming a tissue prosthesis at a site in a patient's body, the methods including providing a first assembly comprising a plurality of nested tubes, one of the tubes being a carrier tube with a component of the prosthesis carried at a distal end of the carrier tube; inserting the first assembly into a cannula placed in the patient's body; magnetically attaching a second assembly to a proximal end of the first assembly; and charging a filler material from the second assembly into the component and allowing the filler material to set.

The methods may include, initially, preparing the first assembly as described above.

The methods may include, once the distal end of the first assembly is at the desired location at the site in the patient's body, withdrawing the protective sheath to expose the component, the component being an envelope of an elastically deformable material. Further, the methods may include using the withdrawing device to test the integrity of the first assembly either after or before withdrawing the protective sheath.

The methods may include removing the stiffening rod prior to magnetically attaching the second assembly to the first assembly. Further, the methods may include causing the second assembly to engage sealingly with the first assembly so that, together with the component and the withdrawing device, a closed system is formed.

After the second assembly has been attached to the first assembly, the methods may include operating the withdrawing device to create a low pressure in the component. Further, the methods may include using the withdrawing device to test the integrity of the system comprising the two assemblies and the component attached to the first assembly.

The methods may include dispensing the filler material from a dispenser of the second assembly. Preferably, the methods include purging filler material from the dispenser prior to attaching the dispenser to a static mixer constituting a part of the second assembly. The methods may include, during filling of the component via a filler tube extending from the static mixer, operating the withdrawing device at least to maintain, or increase, the volume of the closed system.

The methods may include after filling the component, detaching the carrier tube from the tissue prosthesis formed by the combination of the component and the filler material contained in the component. The carrier tube may be detached prior to the filler material having cured or set or after the filler material has at least partially set. The methods may include detaching the carrier tube from the tissue prosthesis when the required pressure has been reached in the component. In the case of intervertebral disc nucleus prosthesis, the required pressure may be that which inhibits distraction of the disc.

In certain embodiments, the methods may include detaching the tissue prosthesis by relative axial motion between the carrier tube and a displacement device of the first assembly. The displacement device may be a further tube arranged about the carrier tube and the relative axial motion may be effected and affected by withdrawing the carrier tube relative to the displacement device. In other embodiments, the methods may include detaching the tissue prosthesis by filling the component with filler material to the extent that the component is released from the carrier tube. In further embodiments, the methods may include detaching the tissue prosthesis by manipulating the carrier tube relative to the component to cause separation of a part of the component attached to the carrier tube from a remainder of the component, the separation occurring at a zone of weakness in the component. The manipulation may involve rotating the carrier tube with respect to the component.

The methods may include, after formation of the tissue prosthesis, tamping a part of the tissue prosthesis into position. If necessary or desirable, the methods may include, before placing the component in position at the site, preparing the site. The methods may include preparing the site by removing degenerative tissue from the site prior to placing the component at the site.

In certain embodiments, there may be provided equipment for forming a tissue prosthesis in situ at a site in a patient's body, the equipment comprising a delivery device displaceably receivable in a lumen of an introducer, the delivery device defining a passageway; an envelope carried at a distal end of the delivery device, the envelope being of a biologically inert, elastically deformable material capable of being expanded to conform to an interior surface of a cavity formed at the site; and a supply of a filler material chargeable in a fluent state into the envelope through the passageway of the delivery device, the filler material being of the same class of material as the envelope to form, when cured, together with the envelope, a unified prosthesis.

The equipment may include an aperture forming element to form an aperture into the site, the aperture forming element being receivable through the introducer for delivery to the site. The aperture forming element may, for example, be a trocar.

Further, the equipment may include a tissue removal mechanism insertable through the aperture for removing tissue, if required, to form the cavity. The tissue removal mechanism may comprise mechanical, ultrasonic, laser, Argon gas or radio frequency ablation mechanisms, or the like in combination with suction and irrigation. For example, the tissue removal mechanism may be a reaming-type tool.

The equipment may include a dispenser containing the supply of filler material. Further, the equipment may include a sensing arrangement configured to sense a parameter of the filler material charged into the envelope. The sensing arrangement may comprise a pressure sensor for sensing the pressure of filler material charged into the envelope, a temperature sensor for sensing the temperature of the filler material charged into the envelope, be configured to sense the quantity of filler material charged into the envelope and/or comprise a flow rate sensor for sensing the rate of flow of the filler material into the envelope. Further, the sensing arrangement may be configured to sense the presence of air bubbles in the filler material charged into the envelope.

In certain embodiments, there may be provided equipment for forming a tissue prosthesis in situ at a site in a patient's body, the equipment comprising a tubular delivery device, the delivery device defining a passageway, an envelope of the prosthesis being mountable to a distal end of the delivery device to be received in a cavity at the site; a filler member receivable in the passageway of the delivery device, the filler member being receivable with clearance in the passageway to define a gap to enable fluid to be manipulated at least from the envelope, at least prior to the filler material being charged into the envelope; and a removal mechanism carried by the delivery device for enabling the envelope to be removed from the delivery device after the envelope has been charged with filler material via the filler member.

The equipment may include a tubular introducer and an aperture forming element, such as a trocar, to form an aperture at the site, the aperture forming element being receivable through the introducer for delivery to the site.

Further, the equipment may include a tissue removal mechanism insertable through the aperture for removing tissue, if required, to form the cavity.

The introducer and the delivery device may include a retaining arrangement for retaining the delivery device with respect to the introducer.

In addition the equipment may include a supply of filler material attachable to a proximal end of the filler member. The filler material may be a mixture of a plurality of parts and the supply of filler material may comprise a dispenser defining a plurality of chambers in each of which one part of the filler material is received prior to use. The dispenser may further comprise a mixer arranged intermediate an outlet of the dispenser and the proximal end of the filler member for mixing the filler material prior to charging it into the envelope.

A proximal end of the delivery device may carry a connector for connection to a fluid manipulation mechanism such as an evacuation pump.

The equipment may include the envelope, the envelope being of an elastomeric material capable of expanding to up to about 3, 4, 5, 10, 40, 50, 100, or 150 times its relaxed state. Preferably, the envelope is expanded to be stretched and retained under tension after being charged with the filler material. The envelope may include a neck portion, the neck portion defining a zone of weakness for facilitating separation of the envelope from the delivery device.

FIGS. 25-32, illustrate an exemplary assembly of a tissue prosthesis insertion system designated generally by the reference numeral 10FA. The assembly 10FA comprises a plurality of nested tubes 12N. As shown in FIG. 28, the set of nested tubes 12N comprises an inner, carrier tube 14C on which a component, in the form of an envelope 16E of a tissue prosthesis is mounted, the envelope 16E being mounted on a distal end of the carrier tube 14C. The carrier tube 14C is received within a push-off tube 18P which is used for removing the envelope 16E, after filling, from the carrier tube 14C as will be described in greater detail below.

The nested tubes 12N further include a protective sheath 20P, arranged about the push-off tube 18P. As illustrated in FIGS. 26 and 28, the protective sheath 20P is of a length to cover the envelope 16E, the sheath 20P projecting beyond a distal end of the envelope 16E when in its operative, protective position. It is to be noted that the nested tubes 12N are shown, in use, mounted in a working cannula 22C used for inserting the first assembly 10FA percutaneously to deliver the envelope 16E into a site at a patient's body in which the prosthesis is to be formed. The nested tubes 12N may be of a metal material such as a steel material which is bio-compatible.

The first assembly 10FA further includes a stiffening member in the form of a stiffening rod 24S. The stiffening rod 24S is of a length to project from a proximal end of the first assembly 10FA through a lumen 26L (FIG. 28) of the carrier tube 14C to be received in an interior 28I of the envelope 16E.

A collar assembly 30C is arranged at a proximal end of the nested tubes 12N. The collar assembly 30C comprises a first collar 32C secured to a proximal end of the cannula 22C. The cannula 22C has a pair of diametrically opposed, longitudinally extending slits, one of which is shown at 34SL in FIG. 25 of the drawings, arranged distally of the collar 32C. The protective sheath 20P is slidably arranged relative to the cannula 22C and has a pair of opposed, radially outwardly extending tabs 38T arranged at its proximal end. The tabs 38T project through the slits 34SL in the cannula 22C to enable a clinician to manipulate the protective sheath 20P.

The push-off tube 18P has a collar 36CO arranged at its proximal end, the collar 36CO being connected to the collar 32C of the cannula 22C via a bayonet fitting. The carrier tube 14C carries a branch or Y-connector 42B at its proximal end, the Y-connector 42B extending from a collar 40C. The collar 40C attaches to the collar 36CO of the push-off tube 18. The Y-connector 42B carries a magnetic mount 44M at its proximal end. The magnetic mount 44M carries a plurality of annular magnets 46M. These magnets 46M are rare earth magnets and are covered by a cover member 48C.

The Y-connector 42B further includes a branch limb 50B defining a connection port 52C for a withdrawing device. The connection port 52C is in communication with a passage (not shown) defined between the carrier tube 14C and, initially, the stiffening rod 24S. The stiffening rod 24S carries a securing formation in the form of a mount 54M at its proximal end. A distal part 56D of the mount 54M is tapered and engages a tapered socket 58S defined by the magnetic mount 44M in a sealing or closing manner so that, once a withdrawing device has been attached to the port 52C, a closed system is formed.

More particularly, once the envelope 16E has been attached to the distal end of the carrier tube 14C, the stiffening rod 24S is inserted through the lumen 26L of the carrier tube 14C to be received in the interior 28I of the envelope 16E. When the distal end of the stiffening rod 24S is received in the envelope 16E, the distal part 56D of the mount 54M of the stiffening rod 24S sealingly engages with the socket 58S in the magnetic mount 44M of the Y-connector 42B to form a substantial seal, or a hermetic seal.

A withdrawing device in the form of a syringe 62S (FIG. 30) is connected via a Luer fitting 64L to the port 52C of the Y-connector 42B to form a closed system. A plunger 66P of the syringe 62S is drawn in the direction of arrow 68A. This increases the volume of the closed system, reducing the pressure in the interior 28I of the envelope 16E and causing the envelope 16E to collapse about the distal end of the stiffening rod 24S.

Prior to insertion into the cannula 22, the tabs of the protective sheath 20P are gripped by an operator assembling the first assembly 10FA and are urged in the direction of arrow 70A (FIG. 26) to cause the protective sheath 20P to slide over and protect the envelope 16E. To facilitate sliding movement between the protective sheath 20P and the envelope 16E, a distal end of the first assembly 10FA can be immersed in a suitable lubricating medium such as, for example, water. In this regard it should be noted that the envelope 16E is made of silicone material rendering it hydrophobic. Thus, the water acts as a lubricant and enables the protective sheath 20P to be slid over the envelope 16E. Instead of immersing the distal end of the first assembly 10FA in the lubricating medium, an internal surface of the protective sheath 20P could, optionally, be coated with a lubricating medium of a hygroscopic or hydrophilic material such as a hydrogel. Alternatively, rather than treating the inner surface of the protective sheath, the protective sheath itself may be made from lubricious materials which include, but not limited to, polytetrafluoroethylene (Teflon), acetal, polypropylene, polyethylene. All of the above mentioned materials may also be a treatment option for the inner lining of the protective sheath. Further, should the protective sheath be made from the described polymers, they may also be treated to improve the lubricity.

After retracting the sheath 20P in the direction opposite to that of arrow 70A, the integrity of the first assembly 10FA is tested for leaks by further withdrawing the plunger 66P of the syringe 62S in the direction of arrow 68A. If the plunger 66P does not return to its previous position, this is an indication that there is a leak in the first assembly 10FA and remedial action can be taken to locate the leak. Conversely, should the plunger 66P return to its previous position, this is an indication that the integrity of the first assembly 10FA is intact and the procedure can proceed.

Instead of pulling on the plunger 66P of the syringe 62S, testing of the integrity of the first assembly 10FA could involve pushing on the plunger 66P of the syringe 62S and then releasing the plunger 66P. If the plunger 66P does not return to its original position that is an indication that there is a leak in the system such as may occur if the envelope 16E is torn.

FIGS. 29-32, show a tissue prosthesis insertion system which is designated generally by the reference numeral 80S. The system 80S includes the first assembly 10FA and a second assembly 82SE. The second assembly 82SE comprises a filler tube 84F including a static mixer 86S at a proximal end of the filler tube 84F. The static mixer 86S is secured to a distal end of a filler material dispenser 88F. The filler material dispenser 88F has a screw-threaded attachment 89 for engaging a screw-threaded boss 90B at a proximal end of the static mixer 86S. A distal end of the static mixer 86S carries an attachment device in the form of a second magnetic mount 92M. As illustrated in FIG. 31 the magnetic mount 92M comprises a pair of annular rare earth magnets 94R closed off by a cover 96C. The mount 92M also includes a tapered fitting 98. The tapered fitting 98 of the mount 92M and the tapered socket 58S of the mount 44M define complementary engaging formations. Thus, the tapered fitting 98 is received within the socket 58S of the magnetic mount 44M of the Y-connector 42B in a hermetically sealing manner, the fitting 98 and the socket 58S constituting a Luer slip fitting. Thus, once again, once the syringe 62S has been attached to the port 52C of the Y-connector 42B, a closed system is formed.

The benefit of magnetically attaching the second assembly 82SE to the first assembly 10FA is that the requirement for relative rotation between the two assemblies 10FA and 82SE for attachment to each other is obviated, as would the case be otherwise if were for example a luer lock attachment. This also enables the cannula 22C of the first assembly 10FA more accurately to be retained in position, in use. It also maintains the engagement of the two assemblies 10FA and 82SE during filling of the envelope 16E. The filler material used for forming the tissue prosthesis is a silicone rubber material. To inhibit curing of the filler material prior to its being charged into the envelope 16E, the filler material is retained in two, separate parts. For this purpose, the dispenser 88F includes two separate reservoirs 100R, in each of which one part of the filler material is initially received. Each reservoir 100R has a plunger (not shown) associated with it for dispensing the parts of the filler material simultaneously from the reservoirs 100R into the static mixer 86S where the parts are mixed prior to being charged into the filler tube 84F to be injected into the interior 28I of the envelope 16E. The plungers are displaceable together with each other via a suitable displacing device (also not shown), for example, a pneumatic gun.

After removal of the stiffening rod 24S, the second assembly 82SE is attached to the first assembly 10FA via the magnetic mounts 44M and 92M. More particularly, the part of the second assembly 82SE comprising the static mixer 86S with the filler tube 84F projecting from the static mixer 86S is magnetically attached to the first assembly 10FA via the magnetic mounts 44M and 92M with the fitting 98 sealingly engaging in the socket 58S. Prior to attaching the dispenser 88F to the static mixer 86S, filler material is purged from the reservoirs 100R by urging the plungers towards the threaded end 89 of the dispenser 88F to expel a portion of filler material from the reservoirs 100R to ensure that the correct ratio of the two parts of the filler material is dispensed. The dispenser 88F is then attached to the static mixer 86S.

The pressure in the interior 28I of the envelope 16E is again lowered by withdrawing the plunger 66P of the syringe 62S in the direction of arrows 68A. This serves to collapse the envelope 16E prior to the filler material being charged via the filler tube 84F into the interior 28I of the envelope 16E. To enable the pressure in the interior 28I of the envelope 16E to be lowered, the filler tube 84F is a loose fit within the carrier tube 14C to create an annular passage 102P (FIG. 32) via which air, gas or certain other fluids can be withdrawn from the interior 28I of the envelope 16E by the syringe 62S.

After lowering the pressure in the interior of the envelope 16E, the integrity of the system 80S is again checked by further attempting to withdraw the plunger 66P from the syringe 62S in the direction of the arrows 68A. Should the plunger 66P remain in its withdrawn position, this is an indication that there is a leak in the system and remedial action can be taken to locate the leak. Conversely, should the plunger 66P return to its previous position, this is an indication that the integrity of the system 80S is intact and the clinician can proceed. Once again, instead of pulling the plunger 66P, testing could involve pushing the plunger 66P and determining whether or not it returns to its original position. If not, that is an indication that there is a leak in the system 80S and remedial action can be taken to locate the leak.

Referring generally to FIGS. 33-37, to insert the nucleus prosthesis into the disc, an incision in made in the patient's skin and an annulotomy is performed on the annulus 126AN of the disc 124D in a minimally invasive manner to form an opening 132AN. This enables access to be gained to the interior of the disc 124D. To perform the annulotomy, the cannula 22C is inserted through the incision until a distal ends abuts the annulus 126AN. An annulotomy performing tool, such as a trocar or a guide wire plus dilator (not shown), is inserted through the cannula 22C and pierces the annulus 126AN to enable access to be gained to the nuclear material of the disc 124D. If necessary, a nucleotomy is performed to remove the nuclear material. However, in certain circumstances, the degenerative process may have dehydrated, extruded or shrunken the nuclear material so that a cavity has already been formed and the necessity to perform the nucleotomy is obviated.

Whether or not a nucleotomy is performed, once the cavity in the disc 124D is present, the first assembly 10FA is inserted into the cannula 22C. As indicated above, the first assembly 10FA comprises the carrier tube 14C with the envelope 16E mounted on a distal end of the carrier tube 14C, the push-off tube 18P and the protective sheath 20P, with the protective sheath 20P extending over the envelope 16E.

Once the envelope 16E is in position within the disc 124D, the protective sheath 20P is withdrawn by urging the tabs 38T of the protective sheath 20P in the direction opposite to that of the arrow 70A, the tabs 38T being received within recesses 104R of the collar 32C of the cannula 22C.

The first assembly 10FA is locked in position relative to the working cannula 22C by the bayonet fitting of the collar 36CO of the push-off tube 18P engaging the collar 32C of the cannula 22C.

The stiffening rod 24S is removed and the second assembly 82SE is attached to the first assembly 10FA, as previously described. Some filler material is purged from the reservoirs 100R of the dispenser 88F and the dispenser 88F is then attached to the proximal end of the static mixer 86S. This re-forms the closed system enabling air to be removed from the envelope 16E by operating the syringe 62S and pulling its plunger 66P in the direction of arrows 68A.

The plungers of the dispenser 88F are then urged towards the distal end of the dispenser 88F to discharge material from the reservoirs 100R. The parts of the filler material discharged from the reservoir 100R are mixed together in the static mixer 86S before being fed into the filler tube 84F. The plunger 66P of the syringe 62S is continued to be withdrawn in the direction of arrow 68A during passage of the filler material along the filler tube 84F at least to maintain or to increase the volume of the closed system to remove air from the envelope 16E as the filler material is charged into the envelope 16E. The filler material is conveyed through the filler tube 84F into the interior 28I of the envelope 16E through a tissue prosthesis component in the form of a filler valve 106V. The filler valve 106V will be described in greater detail below.

As the filler material enters the interior 28I of the envelope 16E, it causes the envelope 16E to expand to conform to the shape of the cavity within the intervertebral disc. It will be appreciated that, due to the resilient flexibility of the envelope 16E, the envelope 16E will readily conform to the shape of the cavity and the envelope 16E need not be of any particular pre-configured dimensions.

FIGS. 33-35, illustrate the tissue prosthesis component in the form of the filler valve 106V of the envelope 16E that is described in greater detail. It is to be noted that the envelope 16E has a bulbous body portion 108 (FIG. 32) integrally formed with a neck portion 110N. The envelope 16E is attached to the distal end of the carrier tube 14C via the neck portion 110N. The valve 106V is received within the neck portion 110N of the envelope 16E. The valve 106V is a duck bill valve having a pair of opposed operating members or operating flaps 112O. The operating flaps 112O, when in their rest condition, as shown in FIGS. 33-35 or the drawings, do not close fully and a slit 114S is defined between the operating flaps 112O of the valve 106V. This is desirable so that, prior to filler material being charged into the interior 28I of the envelope 16E, air can be withdrawn from the interior 28I of the envelope 16E via the slit 114S using the syringe 62S.

Once the filler material has filled the interior 28I of the envelope 16E, it occludes the slit 114S or, instead, presses down on the operating flaps 112O to cause them to deform to close the slit 114S. Also, the filler material could have sufficient viscosity to inhibit extrusion of the filler material outwardly through the slit 114S. It will be appreciated that, once the filler material has set, it no longer matters whether or not the slit 114S is fully closed.

To inhibit overfilling of the envelope 16E, the envelope 16E is mounted on the carrier tube 14C such that as the envelope 16E fills with tiller material, any excess filler material will "extrude" between the neck portion 110N of the envelope 16E and the carrier tube 14C causing the envelope 16E to be released from the carrier tube 14C.

After the desired quantity of filler material has been charged into the envelope 16E, the second assembly 82SE is detached from the first assembly 10FA by breaking the magnetic bond between the magnetic mounts 44M and 92M. The filler tube 84F is withdrawn from the interior of the carrier tube 14C.

The envelope 16E is detached from the carrier tube 14C by relative displacement between the carrier tube 14C and the push-off tube 18P. More particularly, the carrier tube 14C is withdrawn from the push-off tube 18P by detaching the collar 40C of the Y-connector 42B from the collar 36CO of the push-off tube 18P and withdrawing the carrier tube 14C. This causes the proximal end of the neck portion 110N of the envelope 16E to come into abutment with the distal end of the push-off tube 18P causing detachment of the envelope 16E from the carrier tube 14C. The push-off tube 18P is then removed. The tissue prosthesis 134P (FIGS. 36 and 37), comprising the envelope 16E filled with the filler material, is retained in position within the intervertebral disc 124D of the patient. Additional methods for removing the envelope may include, for example, an external or internal cutting mechanism on the tubes which can sever the implant from the delivery apparatus, means of twisting and crimping the neck of the implant (in certain embodiments, this may both seal and detach the implant, and if the means in which the envelope is held onto the carrier tube is purely an interference fit or just tight fit, then pulling on the carrier tube 14C can result in detachment of the envelope (the tube can also be rotated to detach).

Figure 36:
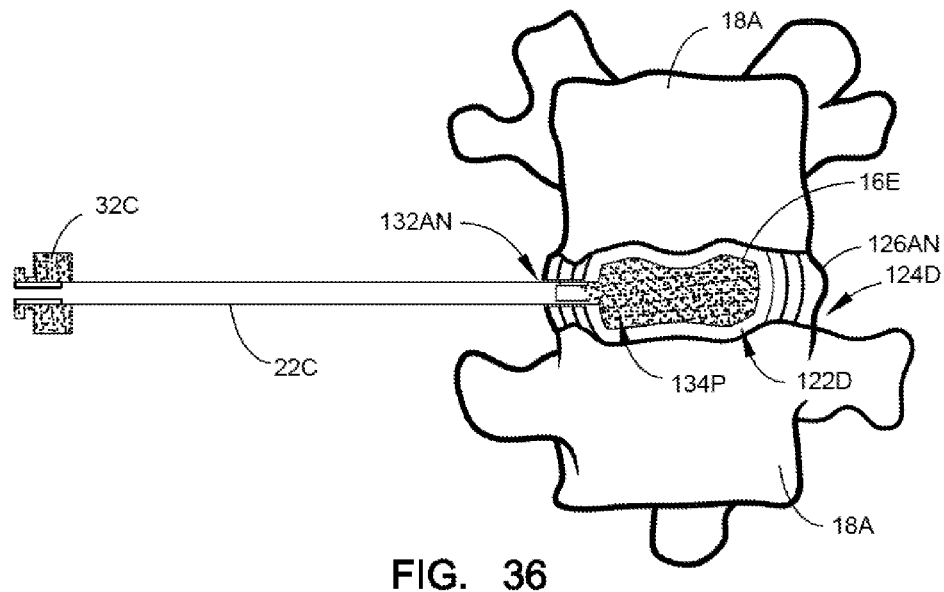
FIG. 36 shows a schematic side view of a working cannula of the assembly in position after formation of the tissue prosthesis in accordance with certain exemplary embodiments disclosed herein.
Figure 37:
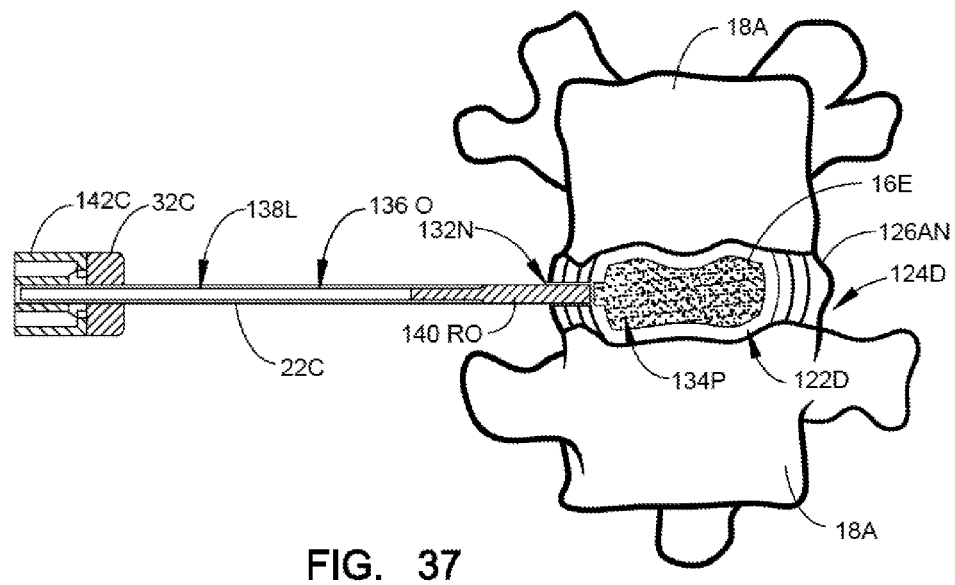
FIG. 37 shows a schematic side view of a further part of the system inserted into the cannula to complete formation of the tissue prosthesis in accordance with certain exemplary embodiments disclosed herein.

As shown in FIGS. 36 and 37, after removal of the carrier tube 14C, at least a part of the neck portion 110N of the envelope 16E may protrude through the annulus 126AN of the intervertebral disc 124D. In addition a residue of filler material may be present in the distal end of the working cannula 22C. Therefore, prior to removal of the working cannula 22C, an obturator 136O is inserted into a lumen 138L of the cannula 22C. The obturator 136O comprises a blunt-ended rod 140RO which is a tight fit within the lumen 138L of the cannula 22C.

The obturator 136O is used to urge any residue of filler material into the disc cavity 122D and/or to tamp the part of the neck portion 110N of the envelope 16E into the disc cavity 122D, as shown in FIG. 37. The prosthesis 134P is thus entirely contained within the disc cavity 122D with minimal, if any, protrusion into the annulus 126AN of the disc 124D.

The obturator 136O can, if desired, be locked to the working cannula 22C by an attachment collar 142C carried at a proximal end of the obturator 136O locking to the collar 32C of the working cannula 22C in a bayonet fitting manner. This allows the obturator 136O to be retained in position during setting of the filler material and inhibits extrusion of filler material from the envelope 16E and/or from the disc cavity 122D. After completion of the tamping and setting process, the working cannula 22C and the obturator 136O are removed.

Tamping the neck portion 110N of the envelope 16E into the disc cavity 122D inhibits prosthesis expulsion and excessive loading on the aperture 132AN in the annulus 126AN of the disc 124D. In addition, the fact that there is no remnant of the envelope 16E in the annulus 126AN enhances closure of the aperture 132AN in the annulus 126AN.

It is an advantage of this (and other embodiments) that a tissue prosthesis insertion system is provided which is simple to operate by a clinician. The assemblies are easily connected together using the magnetic connection which improves the stability of the device and obviates the need for relative rotation of the assemblies relative to one another to connect them together. In addition, the use of the protective sheath protects the envelope against damage while it is being inserted into and positioned in the patient's body. The sheath is relatively simple to operate by the clinician thereby improving the performance of the system as a whole. Further, the use of the syringe as a low pressure generating device simplifies the system and precludes the need for complicated pumps, etc. Also, due to the fact that the syringe provides a closed system, it is not necessary to continuously withdraw gas out of the envelope while it is being charged with filler material. This further simplifies operation of the system.

Figure 38A:
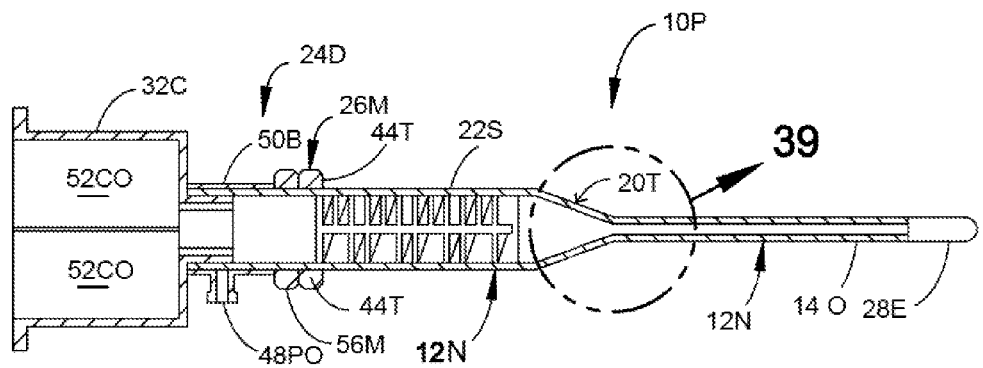
FIGS. 38A and B shows a sectional side view of a prosthesis delivery system in accordance with certain exemplary embodiments disclosed herein.
Figure 38B:
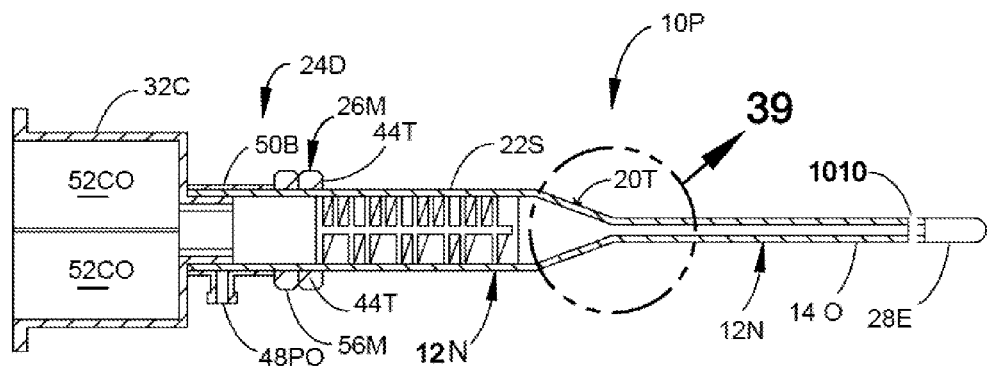
Figure 39:
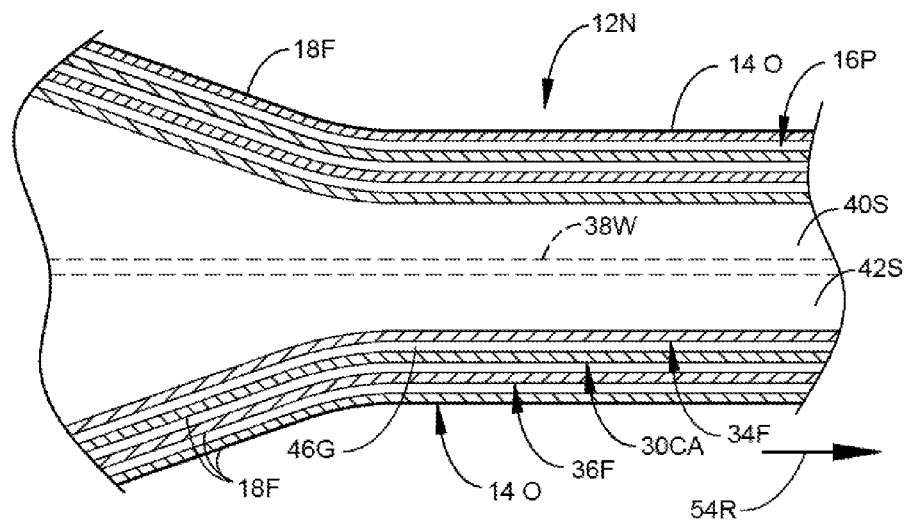
FIG. 39 shows, on an enlarged scale, a sectional side view of the encircled portion of the system marked "39" in FIGS. 38A and 38B of the drawings in accordance with certain exemplary embodiments disclosed herein.

Referring to FIGS. 38A, 38B and 39, reference numeral 10P generally designates another exemplary embodiment of a prosthesis delivery system. The prosthesis delivery system 10P includes a plurality of nested tubes 12N shown in FIG. 39. In some embodiments, the nested tube will be 3, 4, 5, or 6. A cannula or outermost tube 14O of the nested tubes 12N, functions as a cannula in which the remaining tubes are received. The remaining tubes form part of a prosthesis delivery apparatus 16P. The tubes of the nested tubes 12N have a flared wall portion 18F. The flared wall portion 18F of the nested tubes mates 12N with a tapered end 20T of a static mixer 22S of a dispensing arrangement 24D of the apparatus 16P of the system 10P The cannula 14O further includes a manipulating arrangement 26M, arranged at a proximal end of the cannula 14O, for connecting and effecting manipulation of the nested tubes 12N.

An outermost or first tube 14O of the nested tubes is the cannula which is used for insertion of the prosthesis delivery apparatus 16P percutaneously to a site in which a prosthesis is to be inserted.

The system 10FA is intended for use in the insertion of an intervertebral disc nucleus prosthesis in position in a disc after performance of a nucleotomy, if necessary, on a disc to remove the natural nucleus of the disc. The nucleus may have herniated through an annulus of the disc due to degeneration of the disc. In such circumstance, it may not be necessary to perform a nucleotomy on the disc.

The prosthesis includes an envelope 28E. The envelope 28E is carried on the end of a carrier tube 30CA. The envelope 28E is an expansible envelope of an elastically deformable material which is charged with a filler material to fill a cavity of the disc left by removal of the natural nucleus. Typically, the envelope is of a silicone material which is capable of expanding up to 100%, 200%, 300%, 400%, 500%, 6005, 700%, 800%, 900%, 1000% its relaxed state without plastically deforming. The filler material used with the envelope 28E is also of a silicone material and is dispensed from a dispenser 32C of the dispensing arrangement 24D. The filler material is charged into the envelope 28E, in use through a filler tube 34F. The filler tube 34F is nested within the carrier tube 30CA.

A further tube 36F is arranged outwardly of the carrier tube 30CA and is used to push off the envelope 28E from the carrier tube 30CA after being filled with the filler material and the filler material has at least partially set or cured.

It will be noted that, in this embodiment, each of the tubes 14O, 30CA, 34F and 36F has the flared portion 18F so that all the tubes mate with the tapered end 20T of the static mixer 22S of the dispensing arrangement 24D. Further, a proximal portion of the nested tubes 12N projects proximally of the tapered end 20T of the static mixer 22S to surround the static mixer 22S as shown in FIG. 38. The tubes 14O, 30CA, 34F and 36F are locked together once nested. Further, the tubes 30CA and 34F may seal hermetically once nested and locked together.

The manipulating arrangement 26M of the cannula 14O includes a rupturing mechanism for rupturing the cannula 14O after placement of a distal end of the prosthesis delivery apparatus 16P. The rupturing arrangement comprises at least a pair of opposed longitudinally extending lines of weakness, one of which is shown at 38W in FIG. 39. The other line of weakness is diametrically opposed to the shown line of weakness 38W. The lines of weakness 38W, divide the cannula into two shells 40S and 42S. The manipulating arrangement 26M comprises a pair of opposed tabs 44T. Each tab 44T is integrally formed with one of the shells 40S, 42S of the cannula 14O. The tabs 44T are used for connecting the nested tubes 12N to the cannula 14O. Also, by pulling radially on the tabs 44T, the cannula 14O ruptures along the lines of weakness 38W facilitating withdrawal of the cannula 14O from the prosthesis delivery apparatus 16P.

A gap 46G (FIG. 39) is defined between the carrier tube 30CA and the filler tube 34F. The gap 46G communicates with a port 48PO (FIG. 38) and with the interior of the envelope 28E. The port 48PO, in use, forms part of a boss 50BO and a fluid manipulation apparatus (not shown is connected to the port 48PO to enable the interior of the envelope 28E to be manipulated either prior to or as the filler material is charged into the envelope 28E.

The silicone used for expanding the envelope 28E is of the type which, prior to use, is maintained in two separate parts. Thus, the dispenser 32C has at least two compartments 52CO, in each of which one part of the silicone material is stored, prior to being fed through the static mixer 22S, where mixing of the parts takes place, and being charged into the envelope 28E.

In use, an incision is formed in the skin of the patient. The cannula 14O, with a trocar (not shown) contained in a lumen of the cannula 14O, is inserted through the incision to the disc on which the operation is to be performed. The trocar is used to perform an annulotorny on an annulus of the disc. Once that operation has been completed, the trocar is withdrawn. A device (not shown) is inserted through the cannula 14O to perform the nucleotomy, if necessary. The device could, for example, be a mechanical device such as a reamer to ream the degenerative nuclear material from the intervertebral disc.

After completion of the nucleotomy, the device is withdrawn. The prosthesis delivery apparatus 16P is then inserted into the lumen of the cannula 14O and the envelope 28E is inserted through the annulotomy aperture into the cavity of the disc formed as a result of the nucleotomy. The filler material is dispensed from the dispenser 32C, through the static mixer 22S and the filler tube 34F into the interior of the envelope 28E while, simultaneously, a lower pressure is maintained on the port 48PO and the gap 46G.

In an embodiment, the cannula 14O is then removed by rupturing it along the lines of weakness 38W by pulling radially outwardly on the tabs 44T.

Once this has occurred, the push off tube 36F is free to be manipulated relative to the carrier tube 30CA by being urged in a direction of arrow 54AR (FIG. 39) by means of a manipulating ring 56M carried at a proximal end of the push off tube 36F. Pushing off the envelope 28E from the carrier tube 30CA allows the prosthesis delivery apparatus 16P to be withdrawn from the patient's body.

In another embodiment, the cannula 14O remains in place. The envelope 28E is pushed off from the carrier tube 30CA by withdrawing the carrier tube 30CA relative to the push off tube 36F in a direction opposite to the arrow 54AR. The cannula 14O is the final item to be removed with the remaining nested tubes 12N still contained in and attached to the cannula 14O.

Figure 40:
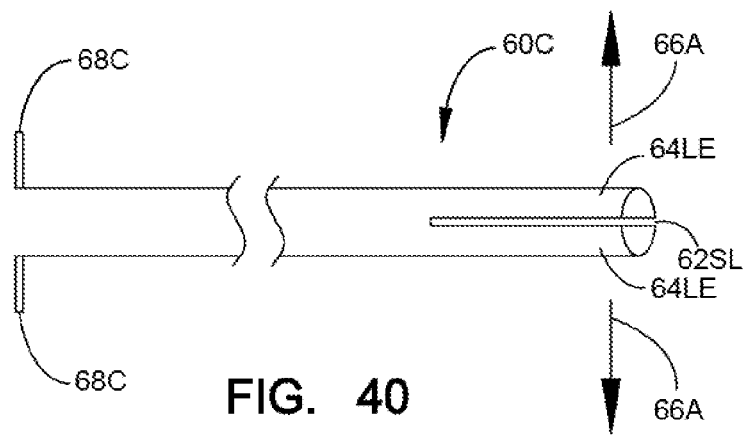
FIG. 40 shows a component of a prosthesis delivery system in accordance with certain exemplary embodiments disclosed herein.
Figure 41:
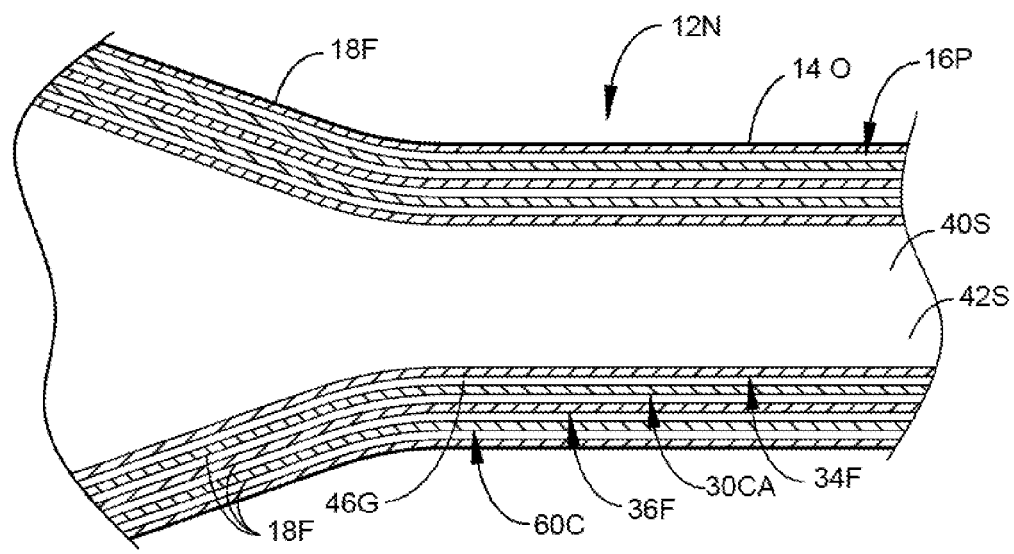
FIG. 41 shows a sectional side view of a part a prosthesis delivery system including the component of FIG. 40 in accordance with certain exemplary embodiments disclosed herein.
Figure 42:
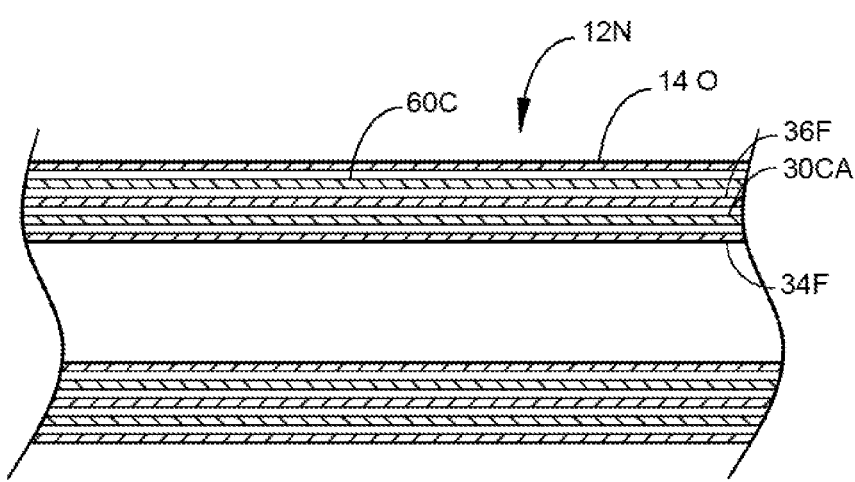
FIG. 42 shows a sectional side view of a part of a further embodiment of a prosthesis delivery system including the component of FIG. 40 in accordance with certain exemplary embodiments disclosed herein.

FIGS. 40-42, illustrates certain embodiments of a prosthesis delivery system 10P, in this embodiment, the system 10P includes a further component in the form of a cover tube 60C (FIG. 40). The cover tube 60C constitutes a sheath and, at least initially, protects the envelope 28E of the prosthesis when it is inserted into the cannula 14O.

For this purpose, a distal end of the cover tube 60C is slotted, as shown by slots 62SL. In these embodiments, two slots 62SL are provided to define a pair of opposed resiliently flexible leaves 64LE. The leaves 64LE are able to be displaced outwardly in the direction of arrows 66A. Thus, in use, the cover tube 60C, which has substantially the same length as the cannula 14O, is placed over the prosthesis delivery apparatus 16P so that the envelope 28E is received between the leaves 64LE at the distal end of the cover tube 60C. The entire prosthesis delivery apparatus 16P including the cover tube 60C, is then inserted into the cannula 14O and the distal end of the cover tube 60C protects the envelope 28E.

The cover tube 60C is arranged between the cannula 14O and the push-off tube 36F. It will, however, be appreciated that, if the cover tube 60C is appropriately dimensioned, it can, itself, act as the push-off tube, the push-off tube 36F then being omitted.

A proximal end of the cover tube 60C, carries connectors 68C. These connectors 68C engage with the tabs 44T of the cannula 14O so that the cover tube 60C engages with and connects to the cannula 14O to enable the remaining tubes of the nested tubes 12N to move towards a distal end of the nested tubes 12N so that the envelope 28E can protrude beyond the end of the cover tube 60C and the distal end of the cannula 14O as shown in FIG. 38 of the drawings. The tabs 44, in turn, engage with the manipulating ring 56M to retain the cannula 14O in position relative to the prosthesis delivery apparatus 16P.

In the embodiment shown in FIG. 41, the cover tube 60C has a flared portion 18F to nest with the remaining tubes 12N of the prosthesis delivery system 10P.

In FIG. 42 of the drawings, a set of nested tubes 12N is provided which does not have the flared portion 18F and is mountable to a distal end of the static mixer 22S.

It is an advantage of these embodiments that the cover tube 60C obviates the need for lubricants to enable the envelope 28E to be inserted into a lumen of the cannula 14O.

The cover tube 60C serves to protect the envelope 28E as the prosthesis delivery apparatus 16P is inserted into the cannula 14O.

It will be appreciated that this embodiment, in use, the incision is of such a size that at least part of the static mixer 22S can be inserted through the incision. Due to the flared portion 18F of the nested tubes 12N, the overall length of the prosthesis delivery apparatus 16P and the system 10P, itself is significantly shorter than would otherwise be the case. Because of this, the entire system 10P has improved stability and balance. The stability and balance improves because the lever arm of the system (with the pivot point of the system being at the docking point at the annulus) has now decreased. Since the length of the system has shortened, the length which the material must travel to the envelope decreases, therefore the pressure required to deliver the material also decreases. Due to the decreased delivery pressure, the surgeon requires less work (effort) to deliver the material. Less effort means that the surgeon's movements are more stable and less jerky. This stability allows the clinician a higher degree of control in maneuvering the system 10P both to the site at which the prosthesis is to be delivered as well as while forming the prosthesis at the site. This is enhanced due to the fact that the nesting of the tubes 12N about the static mixer 22S also improves the rigidity of the entire system 10P resulting in less free movement of a distal end of the prosthesis delivery apparatus 16P of the system 10P. This further enhances the clinician's control over the system 10P. Since the working cannula is fixed and docked relative to the patient, and all the other nested tubes lock to the working cannula, the positioning and deployment of the envelope within the disc space is consistent and repeatable. Also, since all the tubes are fixed relative to each other, during any process of the implant procedure, the risk of damage to the envelope is minimized because movement (laterally and or axially) of the envelope is minimized. Excessive movement of the envelope during any part of the implant procedure increases its chances of being damaged by either the surrounding tissue or other tubes (in particular the working cannula).

In certain embodiments, there is provided an intervertebral disc implant which includes an envelope constructed of at least one stretchable and/or elastically deformable elastomeric material, the envelope including an attaching formation for attachment to an introducer to enable the envelope, in a collapsed state, to be introduced into a volume of an intervertebral disc that has undergone a nucleotomy; and a filler material receivable in the envelope via the introducer to cause the envelope to expand elastically to conform substantially to the volume in which the envelope is received, in use.

In certain embodiments, there is provided an intervertebral disc implant which includes a first object constructed of at least one stretchable and/or elastically deformable elastomeric material, the first object being in communication with second object for attachment to a third object to enable the first object, in a first state, to be introduced into a volume of an intervertebral disc that has undergone a nucleotomy; and a material receivable in the first object via the second object which results in expansion, or partial expansion of the first object such that the first object substantially conforms to the volume in which the first object is received, in use.

In certain embodiments, there is provided an intervertebral disc implant which includes an envelope constructed of at least one stretchable and/or elastically deformable elastomeric material, the envelope including means for attaching an introducer to enable the envelope, in a collapsed state, to be introduced into a volume of an intervertebral disc that has undergone a nucleotomy; and means for introducing a filler material into the envelope via the introducer to cause the envelope to expand elastically to conform substantially to the volume in which the envelope is received, in use.

In some embodiments, the envelope is of a silicone material. In some aspects, the envelope is constructed with at least one silicone material.

In some embodiments, the attaching formation may comprise a filler tube mountable to the introducer, the attaching formation may include a closure device to inhibit back flow of filler material. In some embodiments, the attaching formation may comprise a filler tube in communication with the introducer, the attaching formation may include a closure device to inhibit back flow of filler material. In some aspects, the attaching formation may comprise a filler tube in communication with the introducer, the attaching formation may comprise a closure means for inhibiting back flow of filler material. Any suitable closure device may be employed such as, for example, but not limited to, a one-way, or non-return, valve, a filler tube extending outwardly from the remainder of the envelope to be closed off in a suitable manner or a filler tube extending into the interior of the envelope and which is crimped closed by the surrounding filler material upon withdrawal of the introducer.

In certain embodiments, the filler material may comprise a plurality of discrete, biocompatible, or substantially biocompatible elements. The elements may include, singly or in combination, beads, pellets, elongate elements, irregular shaped elements, collapsible elements, expansible elements, preformed elements, shape memory elements, partially cured elements, uncured elements, cured elements. The elements may be biocompatible elastomers, biocompatible plastics (e.g. silicone), biocompatible metals, biocompatible ceramics, organic or biological elements, or a combination of the foregoing. Further, the elements may be provided in a mixture of sizes.

The elongate elements may be selected from the group consisting of fibres, lengths of filamentary elements such as lengths of string, bristle carrying elements such as bottle brush-like elements, and helical elements such as lengths of coiled wires, or combinations thereof.

The discrete elements may be arranged in suspension in a filler within the volume. In certain aspects, the filler is an elastomeric, curable filler.

In certain aspects, each expansible element may be configured to change from a first configuration for insertion into the envelope to a second configuration which causes the envelope to conform substantially to the volume. In certain aspects, the at least one expansible element may be configured to change from a first configuration for insertion into the envelope to a second configuration. In certain aspects, at least one expansible element may be configured to change from a first configuration into a second configuration wherein the second configuration causes the envelope to partially conform to the volume. Further, each expansible element may be configured to be received, in its first configuration, in the introducer for introduction into the envelope.

In certain embodiments, each expansible element may, in its rest condition, adopt its second configuration. Further, each expansible element may include a biocompatible, shape memory alloy, such as, but not limited to nitinol, which causes the element to adopt its second configuration in the envelope after ejection from the introducer.

In certain embodiments, the filler material may be a foamed material which is introduced in a compressed state via the introducer into the interior of the envelope where it expands to its relaxed state to cause the envelope to conform to the volume. In certain embodiments, the filler material may be contain at least one foamed material which is introduced in a first state via the introducer into the interior of the envelope where it expands to a second state to cause the envelope to conform, or substantially conform, to the volume. The foamed material may be a polymeric material such as a polyethylene.

In certain embodiments, the filler material may comprise a plurality of discrete bands of a resiliently flexible material. In certain embodiments, the filler material may comprise at least in part a plurality of discrete bands of a resiliently flexible material. The bands may be configured to be arranged concentrically within the envelope. The bands may have a height approximating that of the volume.

In certain embodiments, the envelope may carry at least one layer of a tissue ingrowth material. In certain embodiments, the envelope may also including, tissue ingrowth materials. In some aspects, where a layer is used, the layer may be a polyester material such as Dacron (Registered Trade Mark).

In certain embodiments, there is provided an intervertebral disc implant which includes an envelope, the envelope including an attaching formation for attachment to an introducer to enable the envelope, in a collapsed state, to be introduced into a volume of an intervertebral disc that has undergone a nucleotomy; and a filler material receivable in the envelope after placement of the envelope in the volume of the disc, in use, to cause expansion of the envelope to conform to the volume, the filler material comprising a plurality of discrete, elongate elements introducible, via the introducer, into an interior of the envelope.

The envelope may be of an expansible material such as an elastomeric material having an elongation of at least 100% and, in some aspects, up to about 1000%, for example, silicone. Elastomeric materials such as silicone can have an elongation up to 250%, 500%, 750%.

In certain embodiments, there is provided an intervertebral disc implant which includes an envelope, the envelope including means for attachment to an introducer to enable the envelope, in a collapsed state, to be introduced into a volume of an intervertebral disc that has undergone a nucleotomy; and a filler material receivable in the envelope and means for placement of the envelope in the volume of the disc, in use, to cause expansion of the envelope to conform to the volume, the filler material comprising a plurality of discrete, elongate elements introducible, the introducer means, into an interior of the envelope.

The envelope may carry at least one layer of a tissue ingrowth material. Further, the envelope, in certain embodiments, may define a filler opening and may include a closure element for closing the opening after introduction of the filler material. In certain aspects the envelope may have a filler opening means and may include a closure means for closing the opening after introduction of the filler material.

In certain embodiments the elongate element may be selected from the group consisting of fibres, lengths of filamentary elements, bristle carrying elements and helical elements, or combinations thereof.

The elongate elements may be arranged in suspension in the filler within the volume. In some embodiments, the filler may be an elastomeric, curable filler.

In certain embodiments, the elongate elements may comprise a plurality of discrete bands of a resiliently flexible material. The bands may be configured to be arranged concentrically within the envelope.

In certain embodiments, the elongate elements may be expansible elements. Each expansible element may be configured to change from a first configuration for insertion into the envelope to a second configuration which causes the envelope to conform substantially to the volume. Each expansible element may be configured to be received, in its first configuration, in the introducer for introduction into the envelope. Further, each expansible element may, in its rest condition, adopt its second configuration.

In certain embodiments, there is provided an intervertebral disc implant which includes an envelope of a stretchable and elastically deformable elastomeric material the envelope including an attaching formation for attachment to an introducer to enable the envelope, in a collapsed state, to be introduced into a volume of an intervertebral disc that has undergone a nucleotomy; and a filler material receivable in the envelope via the introducer to cause the envelope to expand elastically to conform substantially to the volume in which the envelope is received, in use, the filler material being a foamed material which is introduced in a compressed state via the introducer into the interior of the envelope where it expands to its relaxed state to cause the envelope to conform to the volume.

The foamed material may be a polymeric material. The envelope may carry at least one layer of a tissue ingrowth material. The envelope may define a filler opening and may include a closure element for closing the opening after introduction of the packing material.

In certain embodiments, there is provided an intervertebral disc implant which includes an envelope, the envelope including an attaching formation for attachment to an introducer to enable the envelope, in a collapsed state, to be introduced, in a minimally invasive manner, into a volume of an intervertebral disc that has undergone a nucleotomy; and a filler material receivable in the envelope after placement of the envelope in the volume of the disc, in use, to cause expansion of the envelope to conform to the volume, the filler material comprising, in combination, a curable filler material and a plurality of discrete, biocompatible elements contained, in use, in the filler material within the envelope.

The elements may include, singly or in combination, beads, elongate elements and expansible elements. The elongate elements may be selected from the group consisting of fibres, lengths of filamentary elements, bristle carrying elements and helical elements.

Each expansible element may be configured to change from a first configuration for insertion into the envelope to a second configuration which causes the envelope to conform substantially to the volume. Further, each expansible element may be configured to be received, in its first configuration, in the introducer for introduction into the envelope. Each expansible element may, in its rest condition, adopt its second configuration.

The filler may be an elastomeric, curable filler.

In certain embodiments, there is provided an intervertebral disc implant which includes an envelope of a stretchable and elastically deformable elastomeric material, the envelope including an attaching formation for attachment to an introducer to enable the envelope, in a collapsed state, to be introduced into a volume of an intervertebral disc that has undergone a nucleotomy; and a filler material receivable in the envelope via the introducer to cause the envelope to expand elastically to conform substantially to the volume in which the envelope is received, in use, the filler material being an elastomeric material having a viscosity of at least 500 cP. In certain aspects, the filler material may have a viscosity of at least 1000 cP, of at least 5000 cP, of at least 10000 cP, of at least 50000 cP, of at least 100000 cP, of at least 500000 cP.

In certain embodiments, there is provided an intervertebral disc implant which includes an envelope receivable in a volume of an intervertebral disc that has undergone a nucleotomy, the envelope defining a plurality of chambers, the chambers being configured so that, when at least certain of the chambers contain a filler material, the envelope conforms substantially to the volume of the disc; a filler material receivable in the at least certain of the chambers; and at least one of the chambers having a filler mechanism associated with it.

The chambers may be defined by wall portions of the envelope, wall portions of some of the chambers being of a different wall thickness than wall portions of other chambers. In addition, wall portions of some of the chambers may be of a different material than wall portions of other chambers. Still further, the filler material receivable in at least one of the chambers may differ from the filler material that is receivable in at least one other of the chambers.

The envelope may include an attaching formation for attachment to a tubular introducer to enable the envelope, in a collapsed state, to be introduced, in a minimally invasive manner, into the volume of the disc.

Each chamber in which filler material is receivable may have a filler mechanism associated with it. The filler mechanism may be a one-way device that, upon closure, inhibits back flow of filler material. Preferably, the filler mechanism of an outer chamber of the envelope may be implemented as the attaching formation.

In certain embodiments, the system for implanting an intervertebral disc implant, comprises:

an implant as disclosed herein; and an introducer, the introducer comprising a plurality of filler tubes, each tube communicating independently of any other tube with its associated chamber of the envelope for charging filler material into the associated chamber.

In certain embodiments, there is provided an intervertebral disc implant which includes at least one element which changes from a first configuration for insertion into a volume of an intervertebral disc that has undergone a micleotomy to a second configuration in which the at least one element conforms substantially to the volume, the at least one element being configured to be received, in its first configuration, in an introducer to be inserted into the volume of the disc.

The at least one element, in its first configuration, may be elongate and, in its second configuration, may adopt a shape conforming substantially to the volume. The at least one element may include a biocompatible, shape memory alloy which causes the element to adopt its second configuration in the volume after ejection from the introducer.

Further, in certain embodiments, the at least one element, in its relaxed state, may be in the first configuration, the at least one element including a retention device for retaining the at least one element in the second configuration after ejection from the introducer.

In certain embodiments, the implant may include an envelope receivable in a collapsed state in the volume; and a plurality of the elements receivable in the envelope, the plurality of elements causing the envelope to expand substantially to conform to the volume.

In certain embodiments, there is provided a system for implanting an intervertebral disc implant as disclosed herein the systems including an introducer having a proximal and a distal end, a mount for the envelope of the implant being arranged at or adjacent the distal end of the introducer; a source of filler material connectable to the proximal end of the introducer, and a displacement mechanism for displacing the filler material along the introducer to be ejected from the introducer into the envelope, in use.

The introducer may comprise at least one tubular member. Instead, the introducer may comprise at least two tubular members arranged in a telescopic fashion, the tubular members being reciprocally displaceable relative to one another.

An innermost one of the tubular members may carry the displacement mechanism. The displacement mechanism may comprise a ratchet arrangement for urging the filler material along the introducer into the envelope.

Further, the envelope may include a flow control device arranged at an inlet opening to the envelope for inhibiting back flow of the filler material from the envelope. The equipment may include a flow control defining member, the flow control defining member being separate from the envelope and being arranged at the inlet opening to the envelope.

A distal end of the filler member may carry an engaging member which engages the flow control device to at least partially open the flow control device and to allow the interior of the envelope to be manipulated prior to being charged with the filler material. The envelope may carry a marker arrangement on an exterior surface for enabling the envelope to be used to assess dimensions and a shape of the cavity and positioning of the envelope in the cavity.

The filler material may be of an elastomeric material capable of absorbing shock and withstanding compressive, tensile, bending and torsional forces. The envelope and the filler material may be of an elastomeric material having a Shore Hardness in the range of about 5 to 90 A. The shore hardness may be between 5 and 15 A, 15 and 25 A, 25 and 35 A, 35 and 45 A, 45 and 55 A, 55 and 65 A, 65 and 90 A. Preferably, the envelope and the filler material are of a silicone rubber material.

The envelope may be of an elastomeric material capable of expanding to up to 3, 4, 5, 10, 25, 50, 75 or 100 times its relaxed state. The envelope is preferably expanded to be stretched and retained under tension after being charged with the filler material.

The envelope may include a neck portion, the neck portion defining a zone of weakness for facilitating separation of the envelope from the delivery device. Further, the envelope may include a flow control device arranged at an inlet opening to the envelope for inhibiting back flow of the filler material from the envelope. The equipment may include a flow control defining member, the flow control defining member being separate from the envelope and being arranged at the inlet opening to the envelope.

The envelope may carry a marker arrangement on an exterior surface for enabling the envelope to be used to assess dimensions and a shape of the cavity and positioning of the envelope in the cavity.

The filler material may be of an elastomeric material capable of absorbing shock and withstanding compressive, tensile, bending and torsional forces. More particularly, the envelope and the filler material may be of an elastomeric material having a Shore Hardness in the range of about 5 to 90 A. The shore hardness may be between 5 and 15 A, 15 and 25 A, 25 and 35 A, 35 and 45 A, 45 and 55 A, 55 and 65 A, 65 and 90 A. The envelope and the filler material may be of a silicone rubber material.

In certain embodiments, there is provided a tissue prosthesis which comprises an envelope of a biologically inert, elastically deformable material capable of being expanded to conform to an interior surface of a cavity formed at a site in a patient's body; and a filler material received in a fluent state in the envelope, the filler material being of the same class of material as the envelope to form, when cured, together with the envelope, a unified structure.

The envelope may be of an elastomeric material capable of expanding to up to 3, 4, 5, 10, 25, 50, 75 or 100 times its relaxed state. Further, the filler material may be of an elastomeric material capable of absorbing shock and withstanding compressive, tensile, bending and torsional forces. The envelope may be expanded to be stretched and retained under tension after being charged with the filler material.

Both the envelope and the filler material may be of an elastomeric material having a Shore Hardness in the range of between about 5 to 90 A. The shore hardness may be between 5 and 15 A, 15 and 25 A, 25 and 35 A, 35 and 45 A, 45 and 55 A, 55 and 65 A, 65 and 90 A The envelope and the filler material may be of a silicone rubber material. Preferably, the envelope and the filler material are of a silicone rubber material. However, to promote bonding between the envelope and the filler material, the envelope and the filler material may be of different grades of silicone rubber material and may be pre-treated in different ways prior to use.

The envelope may include a neck portion, the neck portion defining a zone of weakness for facilitating separation of the envelope from a delivery device. Further, the envelope may include a flow control device arranged at an inlet opening to the envelope for inhibiting back flow of the filler material from the envelope. In an embodiment, the prosthesis may include a flow control defining member, the flow control defining member being separate from the envelope and being arranged at the inlet opening to the envelope.

The envelope may carry a marker arrangement on an exterior surface for enabling the envelope to be used to assess dimensions and a shape of the cavity and positioning of the envelope in the cavity.

In certain embodiments, there may be provided a tissue prosthesis which comprises an envelope of a foraminous, chemically inert material shaped to conform, or substantially conform, to an interior surface of a cavity formed at a site in a patient's body in which the envelope is to be placed; and a filler material received in a fluent state in the envelope, the filler material being of an elastomeric material which, prior to being cured, is urged into foramens of the envelope to form an integrated structure which inhibits relative movement between the envelope and the filler material, in use, and once the filler material has cured.

The envelope may be of a knitted biological or synthetic polymeric material. More particularly, the envelope may be of a knitted polyester material, such as polyethylene terephthalate (PET). Further, the envelope may be coated with a material of the same class as the filler material.

The filler material 60F (see, e.g., FIG. 7) may also be constructed of a silicone rubber material which is able to absorb shocks and withstand compressive, tensile, bending and torsional forces imparted to it by movement of the vertebrae 12V and 14V. In addition, due to the fact that the filler material 60F is the same class or type as the material of the envelope 38E, once the filler material has cured in the envelope 38E, a unified or single, integrated structure is formed which is resistant to delamination and relative movement between the envelope 38E and the filler material 60F.

One component of certain embodiments is the use of at least one envelope to confine the filler material. Depending on the particular embodiment, the envelope may function to partially contain, substantially contain, or contain the at least one tiller material. The function of the envelope to contain the filler material may vary from fully containing the filler material to something less than fully containing the filler material. In certain embodiments, the envelope may be a balloon type structure, mesh-like structure, a band-like structure, may be comprised of a multi cavity like structure, may be a foldable structure and/or a foldable structure that has a shape memory or combinations thereof. In some aspects, the envelope may be expandable and/or stretchable up to 50%, 100%, 200%, 300%, 400%, 500%, 600%, 700% or up to 1000%, or greater than 1000% of its relaxed volume. In other embodiments, the envelope may be inelastic, or substantially inelastic. In some aspects of the disclosed embodiments, means for confining the filler material are provided. For example, but not limited to, the structures disclosed in this application. In some embodiments, the envelope may be configured to sufficiently contain the filler material at the desired location before the implant, during the method of implant and/or after the implant.

In certain embodiments, the biomaterial may be in the form of a biocompatible or substantially biocompatible polymer composition comprising a plurality of parts capable of being aseptically processed or sterilized, stably stored, and mixed at the time of use in order to provide a flowable composition. In some embodiments, the polymer composition may contain optionally, other ingredients such as antioxidants, and dyes. In some aspects, upon mixing, the composition is sufficiently flowable to permit it to be delivered to the desired site and there fully cured under physiologically conditions. In some aspects, the component parts are themselves flowable, or can be rendered sufficiently flowable, in order to facilitate their mixing and use.

Additionally, the devices disclosed herein are considered novel in their own right, and can be used with any suitable biomaterial. In certain embodiments, the devices may be used in combination with a curable silicone based polymer composition comprising a plurality of parts capable of being aseptically processed or sterilized, stably stored, and mixed at the time of use in order to provide a flowable composition and initiate cure. Those skilled in the art will, in turn, appreciate the manner in which such polymer compositions can be manipulated to produce cured and curing polymers with desired combination of properties within the scope of certain embodiments. The silicone can be chemically cross-linked, e.g., by the addition of multifunctional or branched OH-terminated crosslinking agents or chain extenders. The optimal level of chemical cross-linking improves the compression set of the material, reduces the amount of the extractable components, and improves the biodurability of the silicone polymer. This can be particularly useful in relatively soft silicone polymers, such as those suitable for the repair of damaged cartilage. Additional fillers may be added to the polymer composition such as silica, to alter the hardness, compression set, tensile strength, tear strength, viscosity, other physical or chemical properties, or combinations thereof. In this manner a balancing of the physical and/or chemical properties with respect to the overall characteristics of the polymer, can be achieved.

Additionally, certain polymer systems may contain at least one or more, biocompatible or non biocompatible catalysts that can assist in controlling the curing process, including the following periods: (1) the scorch time (2) the setting period, and finally, (3) the final cure of the biomaterial. Together these three periods, including their absolute and relative lengths, and the rate of acceleration or cure within each period, determines the cure kinetics or profile for the composition. Suitable examples of the catalyst for the formed polymer will depend upon the polymer material selected. In certain aspects where the polymer is a silicone based polymer the catalyst may be selected from, but not limited to the following: tin, platinum, peroxide.

As applied to intervertebral disc repair, the inclusion of an "additive" in the prepolymer, previously described and presently preferred by applicants in formulations for joints other than the disc, is not presently preferred (though remains optional) for use in the disc. When present, such an additive can provide several desirable features, both in the formulation and use of the prepolymer itself, as well as in the mixed composition. These features include an improved combination of such properties as moisture cure characteristics, cross-linking, viscosity, compression fatigue, and stability.

Certain preferred compositions provide certain desirable properties, including, but not limited to, compression set, hardness, strength, cure characteristics and combinations thereof.

When cured, suitable materials can be homogeneous, providing the same physico-chemical properties throughout, or they can be heterogeneous and exhibit varying features or properties. An example of a heterogeneous composition, e.g., for use as an intervertebral disc replacement, is a composition that mimics the natural disc by providing a more rigid outer envelope (akin to the annulus) and a more liquid interior core (akin to the nucleus). Such heterogeneous compositions can be prepared by the use of a single composition. e.g., by employing varying states of cure and/or by the use of a plurality of compositions, including varying compositions and/or ratios of the same ingredients used to form the composition.

Suitable compositions for use certain embodiments are those polymeric materials that provide an optimal combination of properties relating to their manufacture, application, and in situ use. In the uncured state, such properties include component miscibility or compatibility, process ability, and the ability to be adequately sterilized or aseptically processed and stored. In the course of applying such compositions, suitable materials exhibit an optimal combination of such properties as flow ability, mold ability, and in situ curability. In the cured state, suitable compositions exhibit a desired combination of such properties as strength (e.g., tensile and compressive), hardness, modulus, biocompatibility and biostability.

When cured, certain of the disclosed compositions demonstrate a desirable combination of properties, in terms of their conformational stability and retention of physical shape, resilience during load and unload conditions in situ, dissolution stability, biocompatibility, and physical performance, as well as physical properties such as density and surface roughness, and mechanical properties such as load-bearing strength, tensile strength, shear strength, shear fatigue resistance, impact absorption, wear resistance, and surface abrasion resistance. Such performance can be evaluated using procedures commonly accepted for the evaluation of natural tissue and joints, as well as the evaluation of materials and polymers in general. In particular, a preferred composition, in its cured form, exhibits mechanical properties that approximate or exceed those of the natural tissue it is intended to provide or replace. In some aspects, certain compositions may be capable of deforming and recovering resiliently in situ without plastic deformation, or substantial plastic deformation. In some aspects, certain compositions may be capable of deforming and recovering resiliently in situ with an acceptable level of plastic deformation. In some aspects, certain compositions may be capable of deforming and recovering resiliently in situ without compression set, or substantial compression set.

It should be appreciated that certain compositions may be produced that have a desired combination of the physical and chemical properties discussed in this application.

With respect to those polymer compositions that are uncured, components of such compositions, and the compositions themselves, should be miscible, compatible and stable under conditions used for sterilization and during storage and in the course of delivery. They are also capable of flowing to an in situ location, and being cured in situ, using a suitable catalyst, thereafter the cured composition is suitably amenable to conforming, shaping and/or contouring, by the use of the device embodiments disclosed herein. Over the course of its use in the body the cured, contoured composition exhibits physiological, physical-chemical and mechanical properties suitable for use in extended in situ applications.

To achieve these desirable uncured and delivery properties, a "polymer system", as used herein refers to the component or components used to prepare a polymeric composition. In an embodiment, a polymer system comprises the components necessary to form two parts (as discussed elsewhere herein, together with other ingredients (e.g., catalysts, stabilizers, plasticizers, antioxidants, dyes and the like). Such adjuvants or ingredients can be added to or combined with any other component thereof either prior to or at the time of or after mixing, delivery, and/or curing.

In choosing an optimal volume ratio for a given formulation, the following may be taken into consideration. The viscosity of the reactive parts in this temperature range of less than about 10° C., less than about 20° C., less than about 30° C., less than about 40° C., less than about 50° C., less than about 70° C., must be such to provide an acceptable degree of mixing and injection flow rate without mechanical failure of any component of the delivery system including cartridge, static mixer, gun and other components. Preferably, the biomaterial is sufficiently flowable to permit it to be delivered (e.g., injected) into the balloon). While such a material can be as thick as the bone cement paste, the preferred viscosity is less than 1000 Pa·s, 100 Pa·s, 80 Pa·s, 60 Pa·s, 40 Pa·s, 20 Pa·s, 15 Pa·s, 10 Pa·s, 8 Pa·s, or 6 Pa·s. In some aspects, one preferred viscosity is less than 100 Pa·s. The composition of both reactive parts must be such that these parts are homogeneous and phase stable in the temperature range of the application. The max temperature of the reaction exotherm is proportional to the concentration of the reactive groups in the mixed polymer. A high concentration of the reactive groups might evolve too high reaction exothermal energy and therefore may cause thermal damage to the surrounding tissues. The preferable implant-tissue interface temperature is below 70° C., 50° C., or more preferable below 40° C. It is desirable in some embodiments that the reactive parts stay liquid, or substantially liquid, during mixing. The complete or partial solidification of the reactive part when it comes into contact with another reactive part or any component of the delivery system or during mixing may be unacceptable. The certain volume ratio of the components can be achieved by different ways such as use of the dual-compartment cartridges with constant volume ratio or by using the injectors with delivery rates independently variable for each component.

Many mixing devices and methods have been used for multiple part biomaterials, such as bone cement and tissue sealant, used in operating rooms. Static mixers and manual dispenser guns are commonly used for tissue sealant and other multi-component biomaterial mixing and delivery.

It is important that the two parts of polyurethane prepolymer are mixed quickly and completely in the operating room in a sterile fashion. The number of mixing elements may vary and depends on the composition of the selected polymer. For example, with certain silicone based polymers, it is possible to use between 6 and 20 mixing elements, between 8 and 15 mixing elements, or between 10 and 12 mixing elements.

In certain embodiments, in situ curability may be dependent on the reaction rate, which can be measured by induction time and cure time. In general, fast cure (short induction time) will improve in situ curability and result in less leachable components. However, induction time should also be balanced with adequate working time needed for polymer injection.

A cured biomaterial of that may be used with certain embodiments preferably exhibits a compression modulus of between about 0.1 MPa and about 50 MPa, and more preferably between about 1 MPa and about 25 MPa, when measured using ASTM method D575 A at a physiological strain range between 3 and 20%. In certain embodiments, compositions having a compression modulus considerably below these levels will tend to either bulge or extrude from annular defects that may exist or appear, while those having a modulus considerably above these levels will tend to be too hard and cause stress shielding and abnormal high contact stress on the endplate.

In certain embodiments, the envelope 38E is made from a silicone rubber material having the following characteristics:

a Shore hardness (A scale) in the range from about 20-50;
a tensile strength in the range from about 2700 kPa to 11000 kPa;
an elongation of between about 400% and 800%; and
a tear strength of between about 1700 kg/m and 4500 kg/m.

The filler material 60F is also of a silicone rubber material which, prior to use, is stored in two separate parts. The filler material 60F, comprising the combined parts, when mixed in a ratio of 1:1 and cured, has the following characteristics:

a Shore hardness (A scale) in the range from about 20 to 40, more particularly, about 25 to 30 and, optimally, about 28;
a tensile strength in the range form about 7000 kPa to about 9500 kPa, more particularly, about 8000 kPa to about 9000 kPa and, optimally, about 8500 kPa;
an elongation in the range from about 550% to 700%, more particularly, about 600% to 650% and optimally, about 640%; and
a tear strength in the range from about 1000 to 2000 kg/m, more particularly, about 1250 kg/m to 1750 kg/m and, optimally, about 1500 kg/m.

One example of a suitable material for the filler material has the following characteristics after mixing the parts in a 1:1 ratio and after curing:

a Shore hardness (A scale) of 28;
a tensile strength of 8439 kPa;
an elongation of 639%; and
a tear strength of 1500 kg/m.

The filler material 60F may be treated to contain 5%, by volume, barium sulphate to appear radio-opaque under X-ray, CT, fluoroscopy and MRI. In addition, the filler material 60F contains a catalyst and has a scorch time of between about 1.5 to 2.5 minutes with a curing time of about 5 minutes. When the filler material 60F is charged into the envelope 38E it causes inflation or expansion of the envelope 38E in an elastically deformable manner. Expansion of the envelope 38E can occur to such an extent that, where necessary, the expanded envelope 38E distracts the vertebrae 12V and 14V to restore the original spacing between the vertebrae 12V and 14V. By using radio-opacity in the filler material 60F, distraction of the vertebrae 12V and 14V can be monitored in real time using a fluoroscope or similar equipment.

Further, the envelope 38E conforms to the shape of the cavity 36C. Because the envelope 38E expands within the cavity 36C and conforms closely to the shape of the cavity 36C, the envelope 38E self anchors within the cavity 36C and "extrusion" of a unified prosthesis 100P, comprising the envelope 38E and the filler material 60F, formed through the aperture 30A previously formed in the annulus 16A of the disc is inhibited.

The material for the envelope may, depending on the grade or class of material used, be post cured for a period of time. This is effected by placing the moulded envelope 38E into an oven, for example, for a period of about 1 to 4 hours at a temperature of about 150° C. to 180° C.

By having the material of the envelope 38E and the filler material 60F of the same type, but different grades or classes, chemical bonding between the materials is enhanced which encourages the formation of the prosthesis 100P.

An embodiment of the biomaterial was studied to characterize the mechanical and wear behavior of the implant.

Fatigue testing was performed to evaluate the mechanical and wear performance of the implant over its intended life. Fatigue testing in compression, flexion/extension, lateral bending and axial rotation were conducted to mimic in vivo physiological ranges. Specimens were loaded to 10 million cycles in compression as suggested by ASTM 2346-05 and 5 million cycles in flexion/extension, lateral bending and axial rotation.

The test implant was an annulus model (Silicone Shore Hardness 60 A) with a complete implant (filler material—CSM-2186-14 (Nusil Technologies) and jacket material—MED-4830 (Nusil Technologies) and Calf Serum 30 g/L solution (as per ISO/DIS 18192-1)) injected according to expected surgical procedure. Six implants were created.

The annulus model was placed between two Perspex constraining plates which prevent the model from bulging superiorly and inferiorly. Through the annulotomy, the implant was delivered using the equipment described herein until the implant had completely filled the cavity of the annulus model. The annulus model and the implant was placed inside a water bath set to 37° C. and let to cure for at least 1 hour.

6 specimens were glued to the test platens and left to dry for 24 hours. The specimens and test platens were then connected to the spinesimulator. The test stain was filled with calf senrum and maintained at 37±3° C.

The test execution was as follows:

1) A compression load of 100N and 600N was applied and the heights of the specimens at these loads were measured. This height was taken as the reference heights 2) Specimens were cyclically loaded under the following conditions:
Compression
Load range:
100N to 2000N for 10 000 cycles
600N to 1500N for 990 000 cycles
Load frequency: 2 Hz Flexion/Extension
Bending range: +6/−3.degree.
Range frequency: 1 Hz
Lateral Bending
Bending Range: .+−0.2.degree.
Range frequency: 1 Hz
Axial Rotation
Bending Range: .+−0.2.degree.
Range frequency: 1 Hz 3) After the completion of the 1 million compression cycles a 100N and 600N load was reapplied to measure the height change.

4) This process was repeated another 9 times such that the specimens underwent 10 million compression cycles.

5) At the completion of the cycling loading the specimens were left to recover for 24 hours a then 100N and 600N load was reapplied to measure the height change.

After each million compression cycles the calf serum test medium was collected and analyzed.

Since literature publications have suggested the standing load results in approximately 0.5 MPa of pressure in the lumbar discs while disc pressures whilst lifting is suggested to be between 1.0 to 2.3 MPa, it was believed that choosing a loading regime between 600N to 1500N and 600N to 2000N would represent a worse case scenario. The flexion/extension, lateral bending and axial rotations ranges are comparable to human in vivo conditions as suggested ISO/DIS18192-1. The frequency of 2 Hz was chosen so as to not overheat the samples.

In the fatigue test, one of the six specimens was destroyed due to it slipping from the stainless steel platen at about the 5.8 million cycle mark. Tears in the annulus were noticed in all test stations at the 3 million cycle mark.

Observations of a nucleus replacement device or CDD implant graded to the scale below.

Grade 1=Jacket peeling observed
Grade 2=Minor cracks observed
Grade 3=Progression of minor cracks observed
Grade 4=Major crack Wear particles collected in the test medium were subjected to SEM (Scanning Electron Microscope). The results characterized the size with respect to shape factor, roundness and equivalent circle diameter. The test medium was collected every million cycles and wear particles extracted. The number of particles found per million cycles was collated. The number of particles found per sample per million cycles ranged from 137 to 797 particles. The average number of particles per million cycles was approximately 500 particles. Most particles had a shape factor of between 0.9 and 1 indicating that most of the particles collated were round. The equivalent circle diameter for most particles was between 0.1 and 0.3 µm.

EDX (Energy dispersive X-ray spectroscopy) analysis of the wear particles showed no trace of barium, while silicon, gold and palladium were detected. The detection of gold and palladium was due to contamination via the SEM analysis. A sample of an untested nucleus specimen was also analyzed under EDX to determine the detectability of barium. The analysis showed barium was detected but the wear particles collected from the fatigue testing did not show any signs of barium. According to supplier of the composition, the barium sulfate particles contained within the filler material is approximately 1 µm. Hence the EDX analysis is sensitive enough to detect the presence of barium sulfate particles, but the lack of traces detected by the EDX for the implant indicated that the implant had not worn, or the wear had not been significant enough.

All 5 specimens passed the acceptance criteria which required the specimens to not split up into more than 3 distinct pieces which are smaller than the size of the annulotomy. This criterion was chosen as the mechanical function of the implant will remain even if it has broken up so long as the implant is adequately constrained within the annulus. So long as the implant is able to maintain its total volume it will still function as required. The 5 specimens all remained intact in one piece when the annulus remains essentially intact. In the tests involving Specimens 2 and 4 it was noted that the simulated annulus failed leading to a grading of higher than 1 for these tests at some point beyond 5 million cycles. It is noted that a protocol involving the replacement of the annulus after a set number of cycles, e.g., 2 million, may more closely represent the natural regeneration of the annulus that occurs in the body and provide a better measure of the performance of the implant. In spite of these shortcomings in the simulated annulus, the structural integrity of the 5 specimens remained intact after the fatigue testing and hence the acceptance criteria were met. The EDX analysis on the wear particles generated from the testing procedure showed no signs of barium or platinum and hence not from the nucleus filler material. The acceptance criteria also required no more than 10% of the volume lost. From visual observation of the 5 specimens, there were no sites where significant parts of the implants were worn away. Specimens tested where the annulus model did not fail remained fully intact with no cracks. The remaining two specimens where the annulus failed had cracks present in them but nonetheless remained intact as one functional body. Accordingly, the implant is capable of withstanding in vivo conditions for 10 years equivalent with supra-physiological loading.

Supra physiological loads in the lumbar spine may be encountered during accidents, thus evaluation of the impact performance of the implant is required.

The test set up for shock testing was as follows:

1) Specimens were loaded in compression to 100N to measure the reference height.

2) A shock load of 3000N at a rate of 200 kN/min was then applied.

3) Specimens were then unloaded to 100N at a rate of 200 kN/min and hold for 20 seconds to measure the reference height.

This particular test was performed because a shock load rate of 250 mm/min or greater has been suggested by ASTM draft standard WK4863.

| Specimen | Permanent deformation (mm) |
| --- | --- |
| 2.1 | 0.5 |
| 2.2 | 0.5 |
| 2.3 | 0.4 |
| 2.4 | 0.3 |
| 2.5 | 0.3 |
| 2.6 | 0.4 |
| Mean | 0.45 |
| Std. dev. | 0.09 |

The mean permanent height loss for the specimens was 0.45 mm or 3.2%. The permanent deformation of the implant constrained within an annulus model is less than 4%.

In vivo, the lumbar discs encounter both static and dynamic loading. Conducting static testing is essential in understanding the creep and recovery behavior of the implant under a constant load.

1) Specimens were loaded compression to 100N to measure the reference height and then unload.

2) Specimens were loaded in compression to 600N and held continuously for 16 hours.

3) A load of 100N was applied to measure the height following static creep

4) Specimen was unloaded for 8 hours for recovery.

5) 100N load was reapplied to measure the recovery and permanent deformation from that measured in step 1.

6) Steps 1 to 5 was repeated.

This test was performed because a 600N load over 16 hours is approximately equivalent to a person standing continuously for 16 hours.

The loading regime of the specimens aimed to simulate a person standing continuously for two 16 hour periods followed by 8 hours of rest over 48 hour period. At the first 600N compression load all specimens crept less than 0.2 mm over the 16 hour period which is equivalent to less than 1.5% height loss. At the second 600N load all test specimens crept less that 0.2 mm, again equivalent to less than 1.5% height loss.

The specimens were also subjected to a 100N reference height before the commencement of testing. The 100N load was also applied before and after the 8 hour no load (rest periods). In average height loss at 100N load at the end of testing was 0.2 mm when compared to the reference height. The maximum height loss at 100N load occurred after the second 600N loading period and it showed the height loss at this load was approximately 0.3 mm when comparing to the reference height.

This indicates the implant looses minimal height after constant static loading. The static creep of the implant constrained within an artificial annulus model creeps less than 2% over a 16 hour period.

Other nucleus replacement prostheses, mainly hydrogels require fluid absorption to form the required dimensional characteristics and thus swelling tests are essential in the mechanical characterization process. The implant is not made from a hydro-expanding material. It allows water molecules to pass through, therefore this test was not considered necessary. It was included in this protocol for completeness and to verify the above claim.

Specimens were dried in an oven at temperatures above 100 degrees for a minimum of 4 hours.

1) Specimens were placed within a swell test jig with a plastic plate placed on top.

2) The jig was then filled with Ringer's solution.

3) A LVDT transducer was used to measure the height change over a 48 hour period.

| Specimen | Max. sensor deflection (mm) | Min. sensor deflection (mm) | Fluctuation Range (mm) | Height Change after 48 hours (mm) |
|---|---|---|---|---|
| 1 | 0.02 | −0.02 | 0.04 | −0.01 |
| 2 | 0.01 | −0.01 | 0.02 | 0.01 |
| 3 | 0.01 | 0.00 | 0.01 | 0.01 |
| 4 | 0.00 | −0.02 | 0.02 | −0.01 |
| 5 | 0.00 | −0.03 | 0.03 | −0.02 |
| 6 | 0.00 | −0.02 | 0.02 | −0.01 |
| Mean | 0.01 | −0.02 | 0.02 | −0.01 |
| Std. dev. | 0.01 | 0.01 | 0.01 | 0.01 |

The results the mean height change after 48 hours soaking in Ringer's Solution was 0 mm. The maximum change in height occurred on specimen 5 with a 0.03 mm. The results indicate that the implant is not affected by swelling through fluid absorption as opposed to hydrogels.

Previous clinical studies of other prostheses have raised concern with extrusion of the device. Therefore, it is important to evaluate the risk of extrusion with the implant. The proposed surgical procedure used to implant the implant is through the creation of an annulotomy. Therefore this extrusion test will be done on a similar sized annulotomy in an artificial annulus model (this being the worst case opening in the annulus). Because of the characteristics of the implant, it is doesn't really lend itself to extrusion. This test was performed for completeness and no extrusion of any kind or severity was expected.

The implant was partially filled to a volume between 1.5 to 2 ml inside the annulus cavity to represent a worse case scenario since it was believed that partially filled implant specimens have a greater chance of extrusion due to their relative size to the annulotomy opening.

1) Specimens were fatigue loaded for 200,000 compression cycles under the following conditions:
Compression
Load range: 600N to 2000N
Frequency: 2 Hz
Flexion/Extension
+6/−3.degree. Frequency: 1 Hz
Frequency: 1 Hz Partially filled implants (30 to 50% fill) were subjected to fatigue testing in compression and flexion/extension. The position of the annulotomy was positioned such that the annulotomy underwent tension during the flexion cycle. During this cycle the implant and the encompassing annulus model are flexed to 6 degrees. This accompanied with the compression cycles subjected the implant to conditions that would induce expulsion. After 200,000 cycles no expulsions or protrusions were observed in any of the test specimens. Detachment between the superior section of the annulus and the stainless steel test platen occurred in specimens 3 and 4 after the 200,000 cycles.

A partially filled implant (30 to 50% fill) was chosen as a smaller sample would more likely extrude than a fully filled implant as the size of the annulotomy remained the same. Also the implant was inflated through the annulotomy and hence the proximal end of the implant sits at the inner edge of the annulotomy. In addition to this test, no expulsions were observed during the fatigue test in which the implant was subjected to multi directional testing to 10 years equivalent with an annulotomy present. From the literature expulsion studies have been conducted using cadaveric models. This test was performed in an artificial annulus model as it would allow testing to be conducted to 200,000 cycles which would otherwise not be possible in a cadaveric test model due to tissue degeneration.

No expulsions or protrusions were observed for all 6 test articles after 200,000 cycles hence the acceptance criteria were met. In addition no expulsions were observed during any point of the fatigue test.

Due to the viscoelastic nature of the implant, it is expected to creep under an applied load. This test aims to evaluate this. An implant specimen was filled into a 25.4 mm diameter cylindrical mould to approximately 10.5 mm in height.

1) The specimen was placed between test platens.

2) The specimen was then subjected to a 253N (0.5 MPa) compression load for 16 hours.

3) Specimen was then unloaded (no load applied) for 8 hours to recovery.

4) Steps 2 and 3 were repeated a further three times such that the specimen was subjected to four 16 hour loading regimes over a four day per period.

| Time Point | Height Loss (%) |
|---|---|
| End of first session | −3.47 |
| Start of 2$^{nd}$ session | −0.71 |
| End of 2$^{nd}$ session | −4.18 |
| Start of 3$^{rd}$ session | −1.10 |
| End of 3$^{rd}$ session | −4.44 |
| Start of 4$^{th}$ session | −1.69 |
| End of 4$^{th}$ session | −4.53 |

The results show a gradual decrease in height during the loading periods (approximately 3.5% per 16 hour period). During the 8 hour rest periods the specimen recovered approximately 80% of the height loss. During loading on the fourth day aspects of recovery was observed. The implant showed signs of permanent deformation and recovery after loading due to its viscoelastic properties.

Conducting mechanical tests on aged samples is critical in ensuring the mechanical performance of the implant is not compromised over time. Samples were aged using heat as proposed by the literature. The implants were aged using a 10 degree temperature acceleration method suggested by the literature. All specimens were subjected to 11 hours in a dry oven at 177° C. and then placed in a saline water bath for 46 days at 87° C. This subjected the specimens to 24 years equivalent worth of aging. It has been suggested that an increase of 10 degrees C. doubles the aging process. Therefore placing the samples to the above heating conditions will be equivalent to at least 24 years worth of aging.

Specimens were glued to the test platens and left to dry for 24 hours. The specimens and test platens were then connected to the spinesimulator. The test stain was filled with calf serum and maintained at 37±3° C.

The test execution was as follows: —

1) A compression load of 100N and 600N was applied and the heights of the specimens at these loads were measured. This height was taken as the reference heights 2) Specimens were cyclically loaded under the following conditions:—

Compression

Load range:

600N to 2000N for 10 000 cycles 600N to 1500N for 990 000 cycles

Load frequency: 2 Hz

Flexion/Extension

Bending range: +6/−3°

Range frequency: 1 Hz

Lateral Bending

Bending Range: ±2°

Range frequency: 1 Hz

Axial Rotation

Bending Range: ±2°

Range frequency: 1 Hz

3) After the completion of the 1 million compression cycles a 100N and 600N load was reapplied to measure the height change.

All specimens were loaded to 100N and 600N and the heights measured at this load. After the specimens were subjected to cyclic load the 100N and 600N load was reapplied to measure the heights. These values were compared to the reference heights.

| Specimen | Height loss at 100N reference load | Height loss at 600N reference load |
|---|---|---|
| 3.1 | 0.53 | 1.4 |
| 3.2 | 0.49 | 1.3 |
| 3.3 | 0.44 | 1.3 |
| 3.4 | 0.45 | 1.1 |
| 3.5 | 0.55 | 1.3 |
| 3.6 | 0.46 | 1.2 |
| Mean | 0.49 | 1.3 |
| Std. dev. | 0.1 | 0.1 |

The average height loss at the 100N and 600N reference loads was 0.49 mm and 1.3 mm, respectively. The height measurements after 1 million cycles showed the aged specimens performed better than the fatigue specimens in terms of height loss.

No cracks were observed on any of the specimens and aging does not have any serious adverse mechanical effects on the implant.

Height maintenance is an important mechanical function in a nucleus replacement device. This test aims to evaluate the dynamic fatigue properties of the implant constrained within an artificial annulus model.

The filler material (CSM-2186-14) was injected into the annulus cavity via a 4 mm annulotomy and left to cure for 24 hours.

Specimen was placed between the two test platens.

2) Specimens were subjected to a 509N compressive load to reduce the creep affects.

3) The specimen was then subjected to a cyclic compression loading between 509N and 1730N at 2 Hz for 100,000 cycles.

The change in peak height during the cyclic loading and the change in height during the cyclic loading was measured.

The maximum and minimum height (at 509N and 1730N load respectively) of the samples was recorded for the predetermined cycles. A reduction in height during the 1 million cycles (dynamic creep) was evident in both samples where the greatest observable difference was recorded between cycles 1 and 5,000. The rate of height loss (dynamic creep) plateaus out between cycles 5,000 to 100,000.

Cycling the specimens between 509N (0.5 MPa) and 1730N (1.7 MPa) is approximately equivalent to a person standing in a relaxed position and lifting a 20 kg. Cycling the implant in this fashion is thus a gross over-exaggeration of what a person would encounter in everyday life however the aim was to test the lifecycle of the device in a worst case scenario at accelerated loading conditions and thus justified.

The dynamic creep of the implant constrained within an annulus model over 100,000 cycles was, less than 5%.

A finite element analysis of the implant was also performed, and the following items were observed from the model.

The implant is believed to restore the nucleotomy model to near-physiological axial displacement when the implant completely fills the nucleotomy volume. Data indicates that the implant axial displacement approaches the result provided by the intact model. In contrast to this, the untreated nucleotomy results in an abnormally low axial stiffness.

Figure 86:
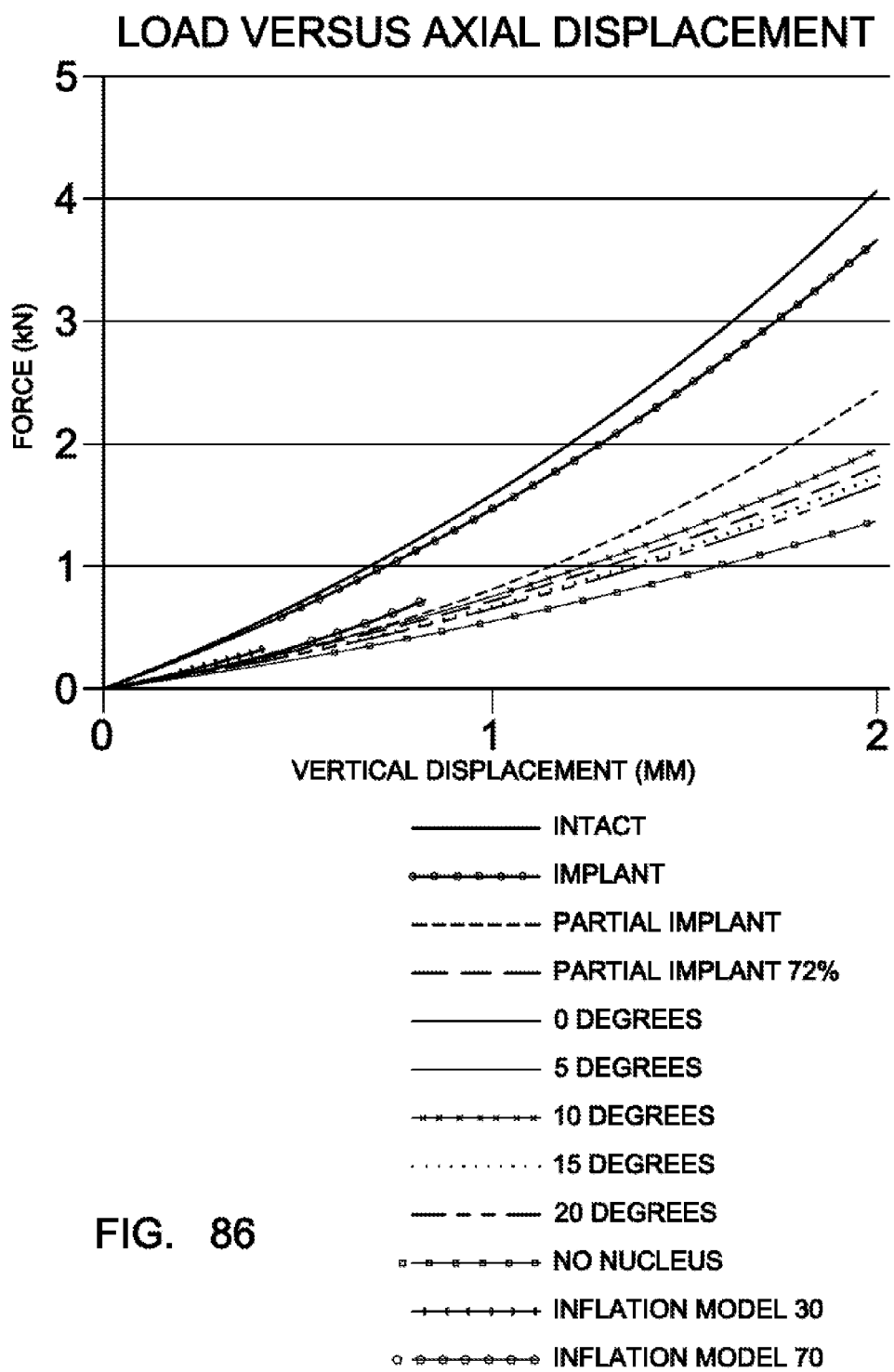
FIG. 86 illustrates spinal disk load vs. displacement as determined in accordance with a finite element analysis of an exemplary implant.

The extent of the nucleotomy relative to the nucleus volume does not have as pronounced effect on the axial stiffness when compared to the extent the implant fills the nucleotomy. This is apparent when the implant model (based on a finite element analysis) (100% filling of nucleotomy) is compared with the partial implant (see, FIG. 86). The partial implants and new inflation models (30%, 70%) do not show significant difference between each other. This phenomenon relies on the assumption that a void remains between the implant and the nucleotomy in the partial-fill implant.

In reference to FIGS. 3-7, when the nucleus pulposus 18N has been removed, a residue 64R remains about the inner surface of the annulus fibrosis and on the end plates 20E of the vertebrae 12V and 14V. This residue 64R is of an irregular shape. Therefore, in charging the envelope 38E with the filler material 60F, it is necessary to monitor the charging of the filler material 60F into the envelope 38E. This is done by a sensing arrangement. In one embodiment, the sensing arrangement comprises a pressure sensor 66PR at an inlet to the envelope 38E. In another embodiment, the sensing arrangement comprises a volume sensor 68S arranged at an outlet of the dispenser 62D for monitoring the volume of filler material 60F dispensed. The sensing arrangement could, in addition or instead, be a flow rate sensor which monitors the rate of flow of the filler material 60F.

Yet a further method of monitoring filling of the envelope 38E is monitoring back flow of filler material 60F from between the envelope 38E and the distal end of the tubular delivery device 40T. As the filler material 60F oozes out it may loosen the envelope 38E allowing the tubular delivery device 40T to be removed.

In FIGS. 43-76, reference numeral 10I generally designates an intervertebral disc implant in accordance with various embodiments. The implant 10I comprises an envelope 12E in which a filler material 14FM is received. The implant 10I is intended for use in replacing a nucleus pulposus of an intervertebral disc 16I arranged between adjacent vertebrae 18A, 20A. Generally, the procedure is formed in a minimally invasive manner as will be described in greater detail below. It will also be appreciated that the procedure may be conducted in a percutaneous manner as described herein and in greater detail below.

It will be appreciated that the disc 16I comprises an annulus 22A circumscribing a nucleus pulposus. The intervertebral disc implant 10I is intended to replace a degenerate nucleus pulposus of the disc 16I. Thus, the implant 10I is implanted after the disc 16I has undergone a nucleotomy to remove the nucleus pulposus.

In the embodiments illustrated in FIGS. 43 to 53, the envelope 12E of the implant 10I is of a stretchable and elastically deformable elastomeric material such as a silicone material. Various filler materials 14FM can be used with the envelope 12E in order to mimic as closely as possible the biomechanical actions of a natural, healthy nucleus pulposus.

Figures 43A, 43B:
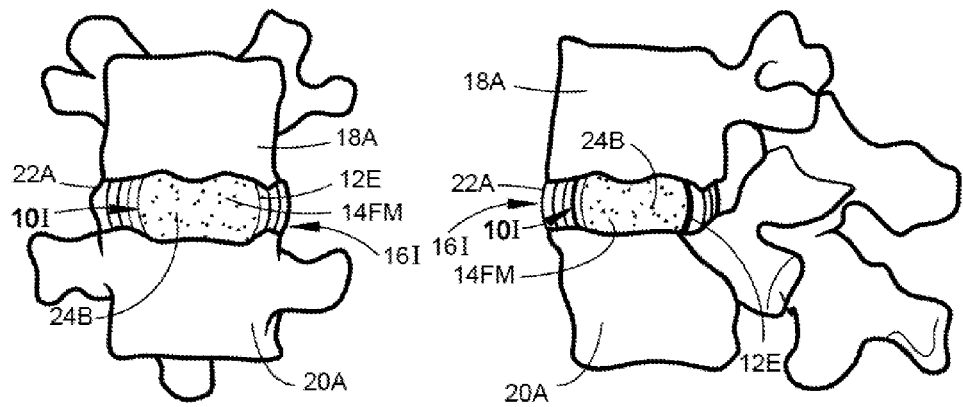
FIGS. 43a, 43b and 43c show, respectively, front, side and plan views of an intervertebral disc implant, in accordance with certain exemplary embodiments disclosed herein.
Figure 43C:
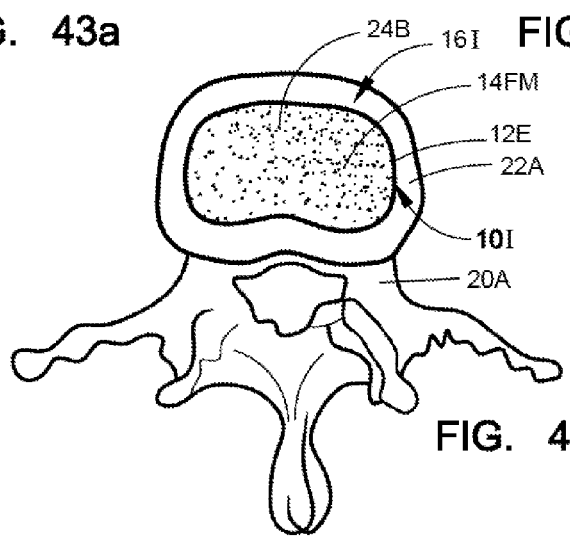

In the embodiment shown in FIGS. 43a, 43b and 43c, the filler material 14FM comprises beads 24B held in suspension in a curable elastomeric material. The elastomeric material is, once again, preferably a silicone material.

The beads 24B are of a biocompatible material. Thus, for example, the beads 24B could be of a suitable biocompatible plastics material, a biocompatible elastomeric material, a biocompatible metal material, a biocompatible ceramic material or suitable biological material such as proteoglycans. The beads 24B may be homogenous in the sense that all the beads are of the same size and same material. Instead, the beads 24B may be of different sizes and different materials in order to obtain particular biomechanical characteristics for the implant 10I.

In certain embodiments, the beads need not be spherical in shape. They could, instead, be any one of bullet shaped, polygonal, triangular, heart shaped, kidney shaped, ovoid, oblong, crescent shaped, cubic, elongated, conical, trapezoidal, prismatic irregular, or combinations thereof. In some aspects, a preferred shape is one which allows for convenient and unobstructed insertion. Thus, preferably, the beads 24B have radius-like corners and/or edges to minimize the risk of damaging the envelope 12E.

The beads 24B may range in size from 0.01 mm to 5 mm and, optimally, any size in order that the beads 24B can be introduced into the interior of the envelope 12E by an introducer.

Figures 44A, 44B:
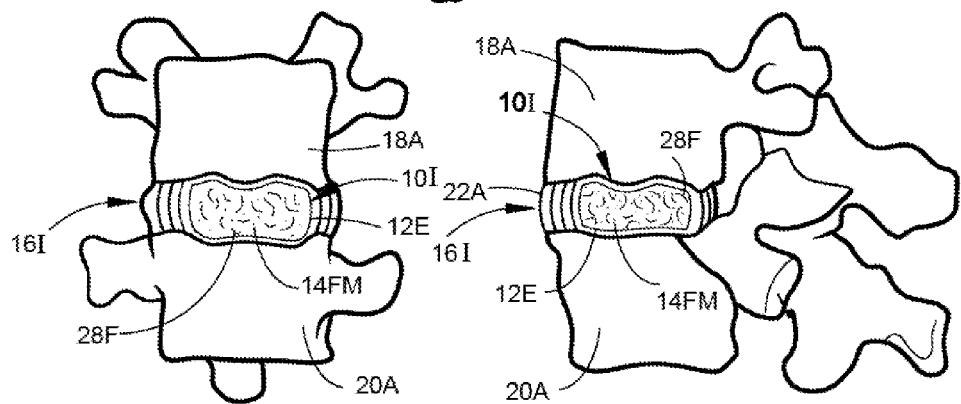
FIGS. 44a, 44b and 44c show, respectively, front, side and plan views of an intervertebral disc implant, in accordance with certain exemplary embodiments disclosed herein.
Figure 44C:
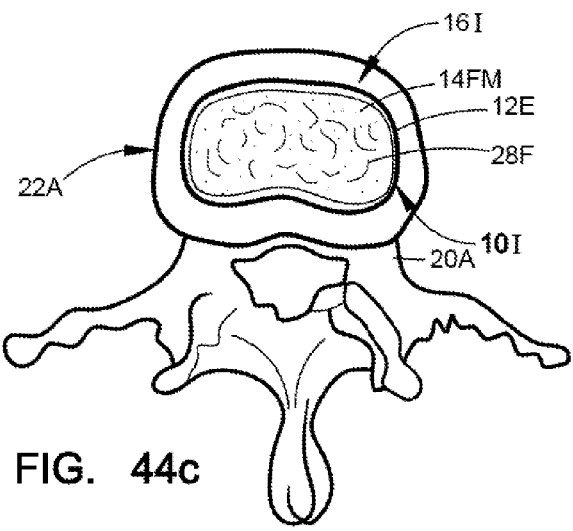

In the embodiment shown in FIGS. 44a, 44b and 44c, the filler material 14FM comprises elongate, filamentary elements 28F carried in suspension in the silicone. The filamentary elements 28F are "string-like" elements which are, once again, of suitable biocompatible materials. The elements 28F typically have lengths not exceeding 1 cm. Once again, the lengths of the filamentary elements 28F may all be the same or they may differ to obtain the desired biomechanical characteristics for the implant 10I.

Figures 45A, 45B:
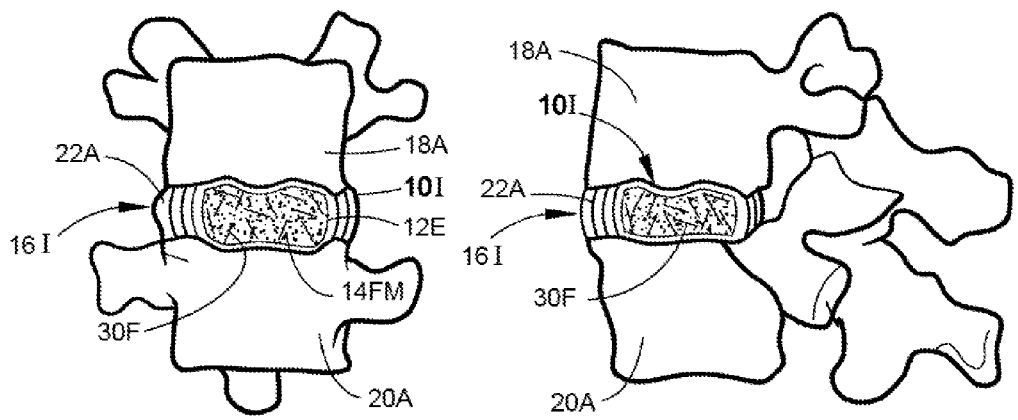
FIGS. 45a, 45b and 45c show, respectively, front, side and plan views of an intervertebral disc implant, in accordance with certain exemplary embodiments disclosed herein.
Figure 45C:
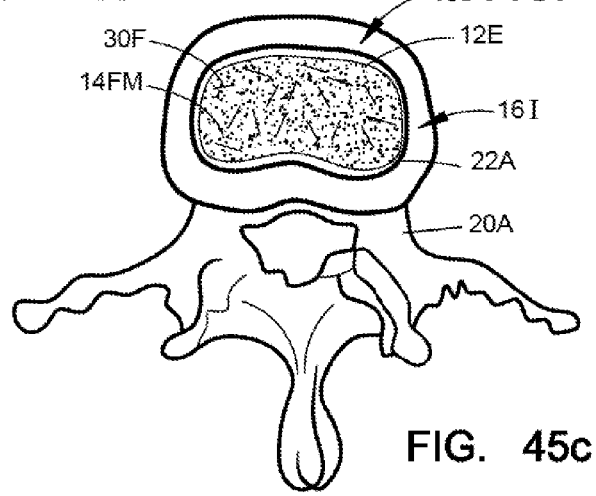

In FIGS. 45a, 45b and 45c, the filler material 14FM comprises fibres 30F in suspension in the silicone. The fibres 30F are, typically, of lengths less than 3 mm. As in the case of other disclosed embodiments, the fibres 30F are made up of suitable biocompatible materials. The fibres 30F are selected either to all be of substantially the same material and lengths or they may be of different materials and of different lengths to obtain the desired biomechanical characteristics for the implant 10I.

Figure 46A:
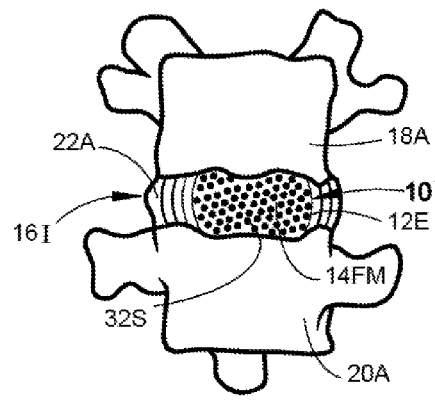
FIGS. 46a, 46b and 46c show, respectively, front, side and plan views of an intervertebral disc implant, in accordance with certain exemplary embodiments disclosed herein.
Figure 46B:
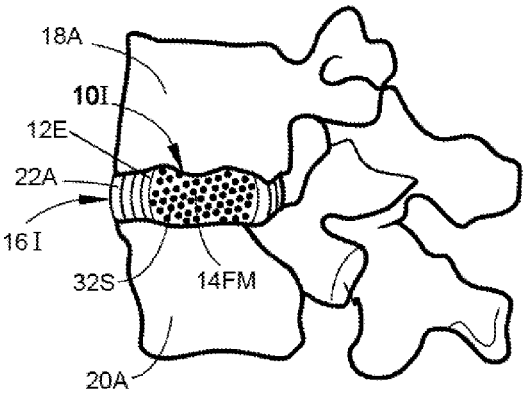
Figure 46C:
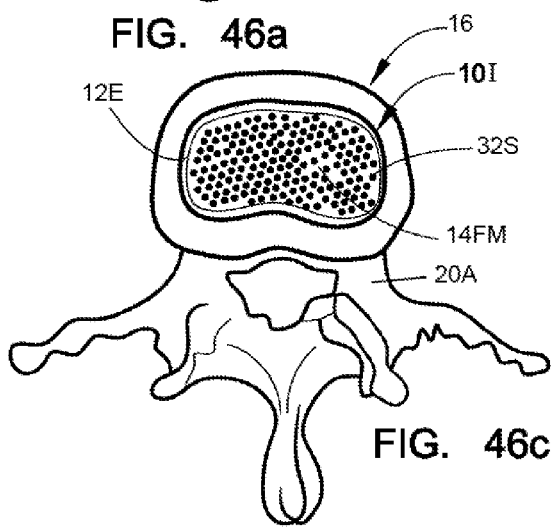

FIGS. 46a, 46b and 46c illustrate certain embodiments in which the filler material 14FM comprises spherical elements contained in the envelope 12E. The spherical elements 32S are of suitable biocompatible materials such as biocompatible plastics, biocompatible elastomers, biocompatible metals, biocompatible ceramics or biological material. The spherical objects may be in a range of sizes not exceeding 3 mm to 4.5 mm (e.g., not exceeding 3, 3.25, 3.5, 3.75, 4, 4.25, 4.5, etc.) in order to be able to be introduced into the interior of the envelope 12E via an introducer as will be described in greater detail below.

The spherical elements 32S are typically provided in a range of sizes to provide compacted packing of the filler material 14FM within the interior of the envelope 12E but still allowing compressive stresses on the disc 16I to be transmitted to the annulus 22A of the disc.

Figure 47A:
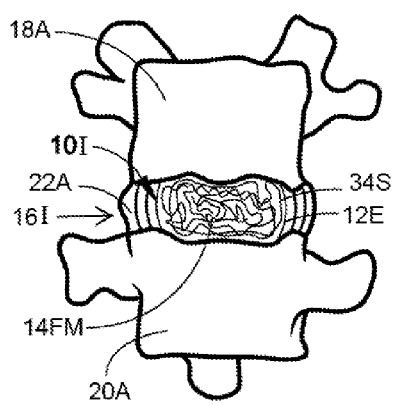
FIGS. 47a, 47b and 47c show, respectively, front, side and plan views of an intervertebral disc implant, in accordance with certain exemplary embodiments disclosed herein.
Figure 47B:
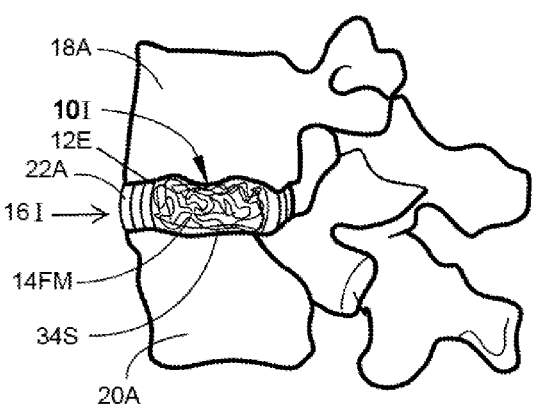
Figure 47C:
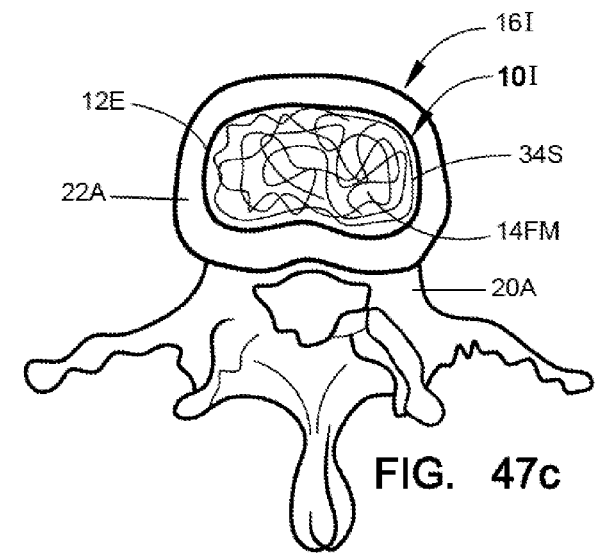

In FIGS. 47a, 47b and 47c, the filler material 14FM comprises one or more lengths of string-like elements 34S. Each element 34S may typically have a length less than 10 cm and a diameter less than 3.5 mm to 4 mm. Sufficient lengths of elements 34S are provided to pack the interior of the envelope 12E to provide the necessary weight bearing functions of the implant 10I. These elements 34S are, once again, of biocompatible material.

Figures 48A, 48B:
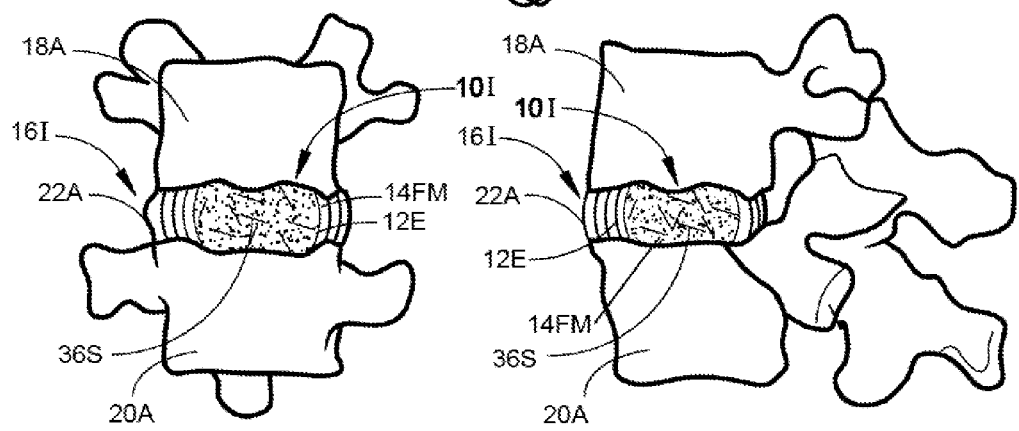
FIGS. 48a, 48b and 48c show, respectively, front, side and plan views of an intervertebral disc implant, in accordance with certain exemplary embodiments disclosed herein.
Figure 48C:
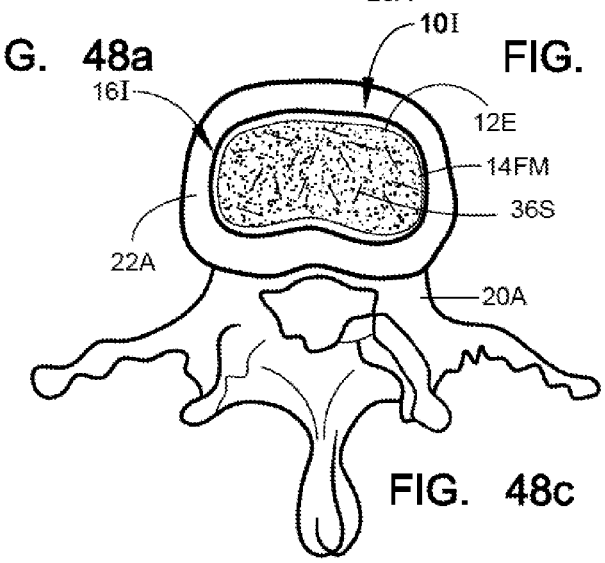

Referring now to FIGS. 48a, 48b and 48c, the filler material 14FM comprises a plurality of short lengths of fibre 36S. The fibres 36S are, typically, about 2 to 3 mm long and are of biocompatible materials. The fibres 36S are packed into the interior of the envelope in a compacted state in order to impart the required biomechanical characteristics to the implant 10I. Once again, the fibres 36S may be of different materials and different lengths.

Figure 49A:
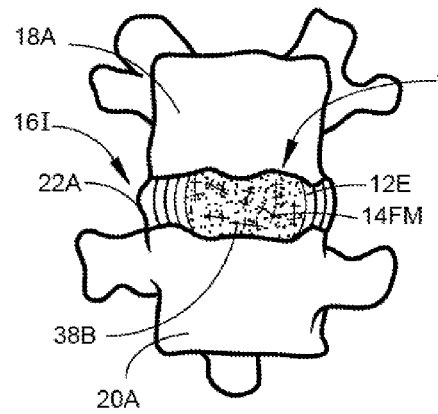
FIGS. 49a, 49b and 49c show, respectively, front, side and plan views of an intervertebral disc implant, in accordance with certain exemplary embodiments disclosed herein.
Figure 49B:
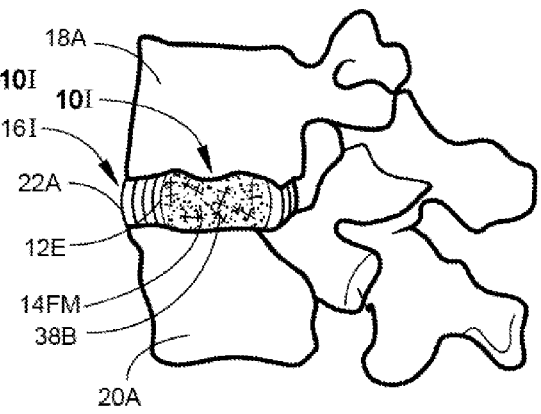
Figure 49C:
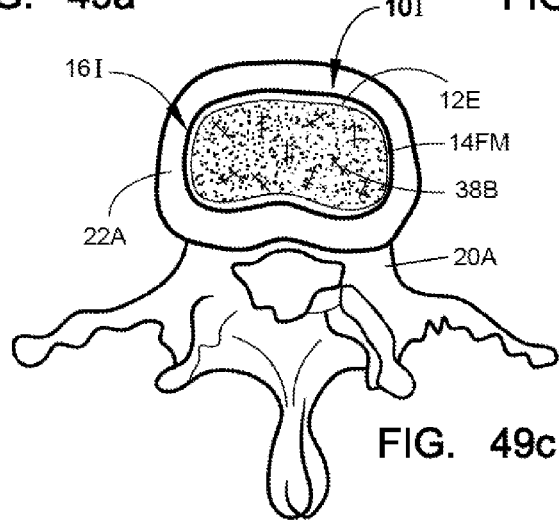

In FIGS. 49a, 49b and 49c, the filler material 14FM comprises a plurality of bottlebrush-like elements 38B. The bottlebrush elements 38B are of the form having a central spine with bristles projecting radially outwardly from the spine. The bristles are folded on to the spine for introduction into the envelope 12E via an introducer.

Once again, the bottlebrush elements 38B are packed, in a compacted state, within an interior of the envelope 12E to impart the necessary biomechanical characteristics to the implant 10I. The bottlebrush elements 38B may be of biocompatible plastics materials. In addition, the bottlebrush elements 38B may be in the form of biocompatible metals/biocompatible plastics combinations. An example of this would be a bottlebrush elements 38B having a metal spine with plastics bristles. Still further, the bottlebrush elements 38B could be of all metal construction. The elements 38B typically have a length of less than about 1 cm, preferably about 5 mm. When the bristles are folded on to the spine for insertion into the introducer, the elements 38B may have a diameter not greater than about 3.5 mm to 4 mm.

Once again, if desired, bottlebrush elements of mixed sizes and materials may be used together to mpart the desired biomechanical characteristics to the implant 10I.

Figure 50A:
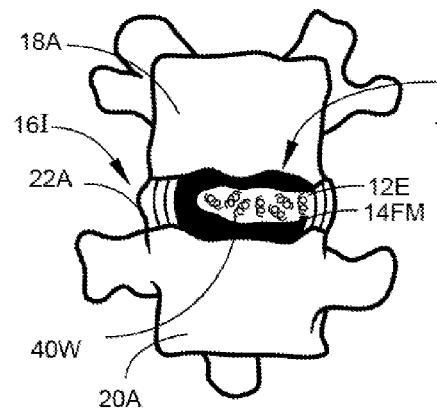
Figure 50B:
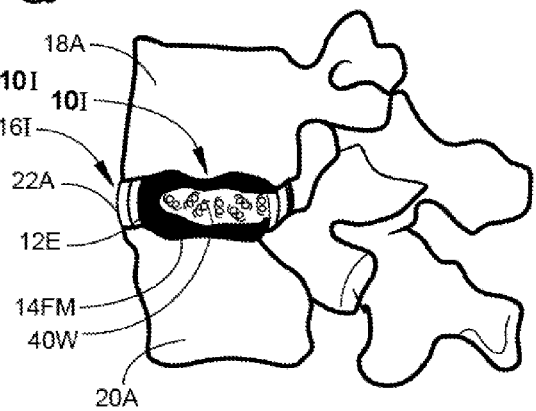

Referring now to FIGS. 50a, 50b and 50c, the filler material 14FM comprises lengths of helical or coiled wires 40W. The coiled wires 40W are packed, to be in a compacted state, in the interior of the envelope 12E in order to provide the necessary biomechanical characteristics. The coiled wires, in their relaxed state, may typically be less than about 1 cm in length, preferably, about 5 mm in length. The wires 40W may be of biocompatible plastics, biocompatible elastomers, or biocompatible metals. As in the previous embodiments, wires 40W of different lengths and different materials may be used together, if desired, in the implant 10I.

In the embodiment shown in FIGS. 51a, 51b and 51c, the filler material 14FM comprises a plurality of discrete bands 42D of a resiliently flexible, biocompatible material arranged concentrically within the envelope 12E to form the implant 10I. The bands 42D have a thickness not exceeding about 1 mm and a height not exceeding of about 9 mm.

Figure 52A:
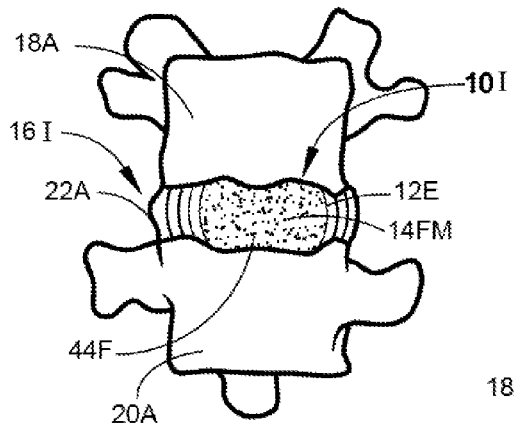
FIGS. 52a, 52b and 52c show, respectively, front, side and plan views of an intervertebral disc implant, in accordance with certain exemplary embodiments disclosed herein.
Figure 52B:
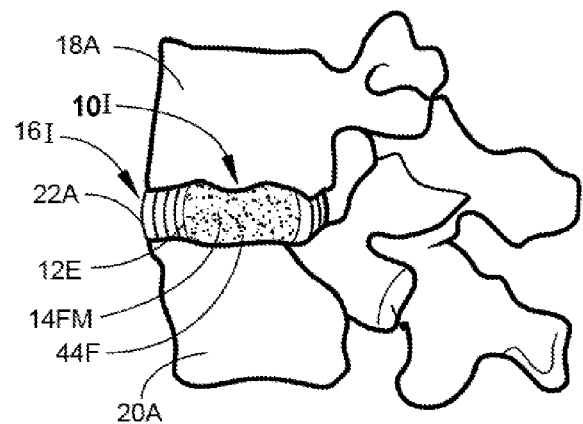
Figure 52C:
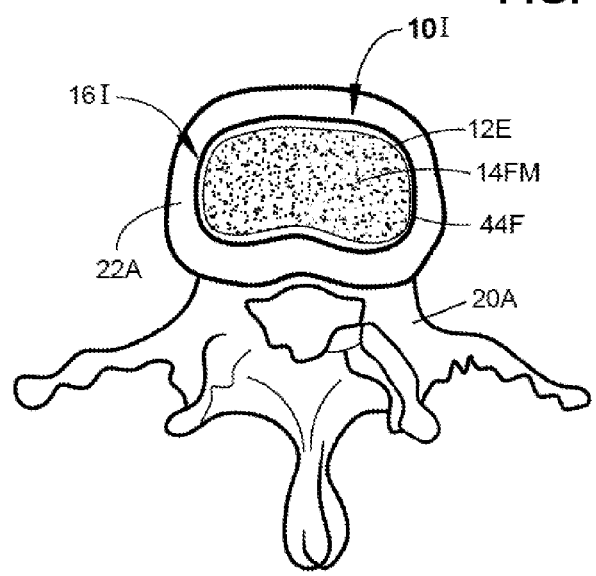

The filler material 14FM in the embodiments illustrated in FIGS. 52a, 52b and 52c are made from a foamed material 44F. The foamed material 44F is introduced, in a compressed state, via the introducer into the interior of the envelope 12E. Once the introducer is withdrawn, the foamed material 44F expands to a relaxed state to cause the envelope 12E to conform to the volume in which it is placed. Typically, the foamed material 44F is a polymeric material such as a polyethylene.

Figure 53A:
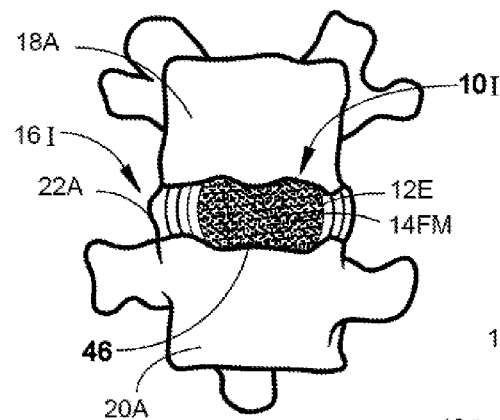
FIGS. 53a, 53b and 53c show, respectively, front, side and plan views of an intervertebral disc implant, in accordance with certain exemplary embodiments disclosed herein.
Figure 53B:
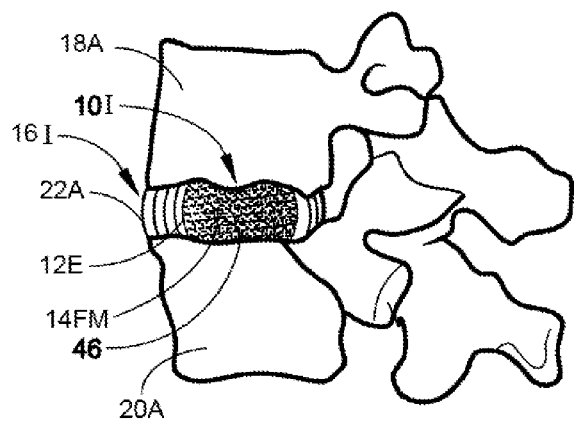
Figure 53C:
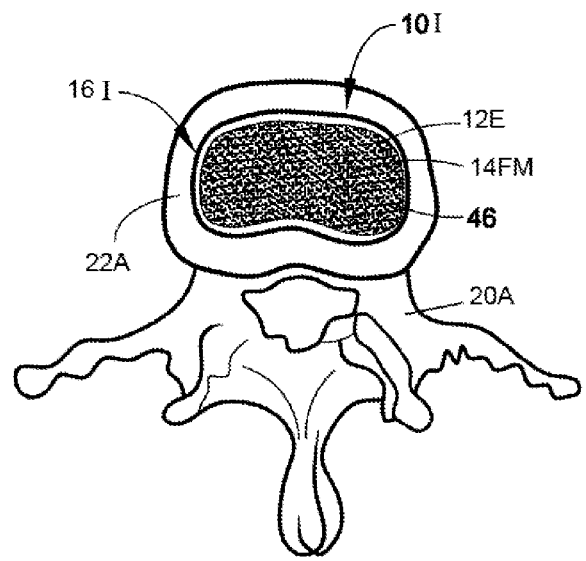
Figure 55:
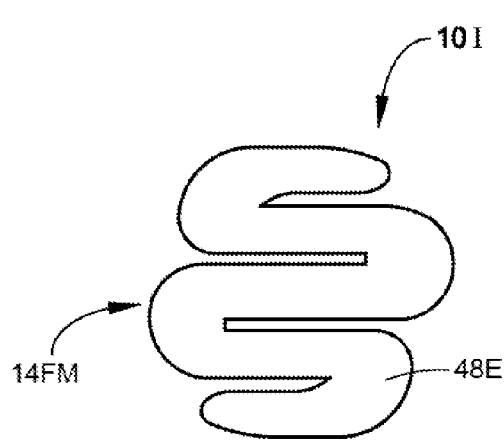
FIG. 55 shows a schematic plan view of the implant of FIG. 54 in a second configuration in accordance with certain exemplary embodiments disclosed herein.

In FIGS. 53a, 53b and 53c, the filler material 14FM is silicone oil 46SI, having a viscosity of at least 500 cP. This material exhibits surprisingly good biomechanical characteristics and mimics closely a natural, healthy nucleus pulposus of an intervertebral disc.

In the embodiments described above, as previously described, the envelope 12E is generally of a silicone material which has an elongation of up to 1000%. where it can expand elastically without plastically deforming. In certain circumstances, it may not be necessary to have the envelope have such extensive elongation and, if desired, the envelope could be made of other materials in appropriate circumstances, such as, for example, woven metal fibres such as stainless steel, nitinol, chrome cobalt, titanium, or the like; or combinations thereof. Instead, the envelope may be of a plastics material such as a polymeric material like polytetrafluoroethylene.

Figure 54:
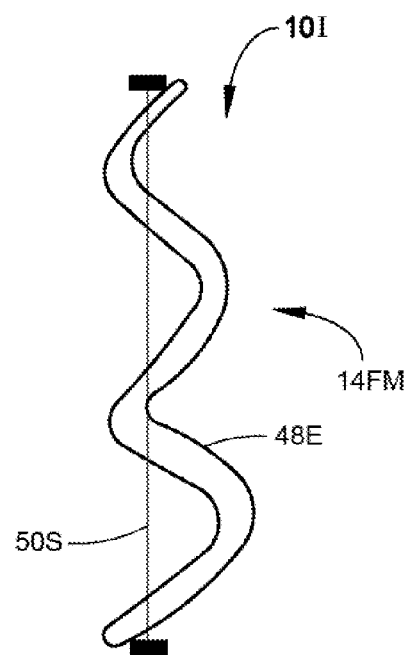
FIG. 54 shows a schematic side view of an intervertebral disc implant in a first configuration, in accordance with certain exemplary embodiments disclosed herein.

Further, in the embodiments described above, the implant 10I makes use of an envelope. In certain circumstances, the implant 10I may not require an envelope 12E. In the embodiments illustrated in FIGS. 54 and 55, the implant 10I comprises an elongate element 48E of a suitable resiliently flexible material, such as a silicone material. In this embodiment, the element 48E is inserted into the volume resulting after the nucleotomy has been performed on the disc 16I in an elongated state as shown in FIG. 54 of the drawings. Use of a stylet 50S maintains the elongate element in its extended state. When the elongate element 48E is inserted into the volume, the stylet 50S is withdrawn causing the elongate element 48E to adopt the configuration shown in FIG. 55 in which the element 48E substantially fills the volume. In a similar embodiment to this, a plurality of such elements 48E are used, either side by side or one on top of the other in layers, to conform to the volume. In the latter case, the elements 48E may, if desired, be inserted into an envelope (not shown).

Figure 56:
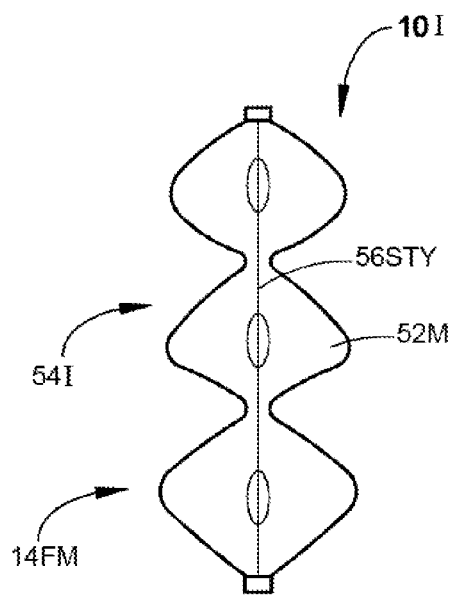
FIG. 56 shows a schematic side view of an intervertebral disc implant in a first configuration, in accordance with certain exemplary embodiments disclosed herein.
Figure 57:
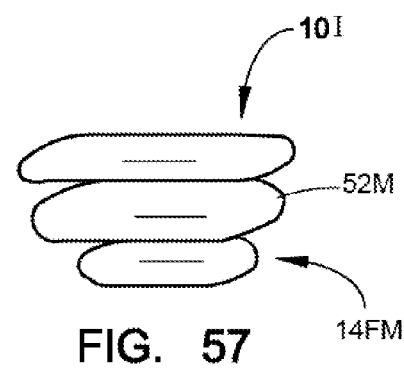
FIG. 57 shows a schematic plan view of the implant of FIG. 56 in a second configuration in accordance with certain exemplary embodiments disclosed herein.

FIGS. 56 and 57 show a similar embodiment of implant 10I in which the implant 10I comprises a plurality of doughnut-like members 52M interconnected serially to form an implantable element 54I. Once again, the implantable element 54I has a stylet 56STY associated with it to aid implantation.

In a relaxed state, the implantable element 54I adopts the configuration shown in FIG. 57. The implantable element 54I is implanted, in its first configuration, as shown in FIG. 56, into the volume of the disc 16I. Withdrawal of the stylet 56STY causes the implantable element 54I to be compressed, as shown in FIG. 57, into a second configuration in which it conforms substantially to the volume of the disc 16I.

Once again, in a similar manner to the embodiment described above with reference to FIGS. 54 and 55, a plurality of the implantable elements 54I may be used, either side by side or in layers to conform to the volume of the disc 16I. In this case, the implantable elements 54I may be received in an envelope (not shown).

Figure 59:
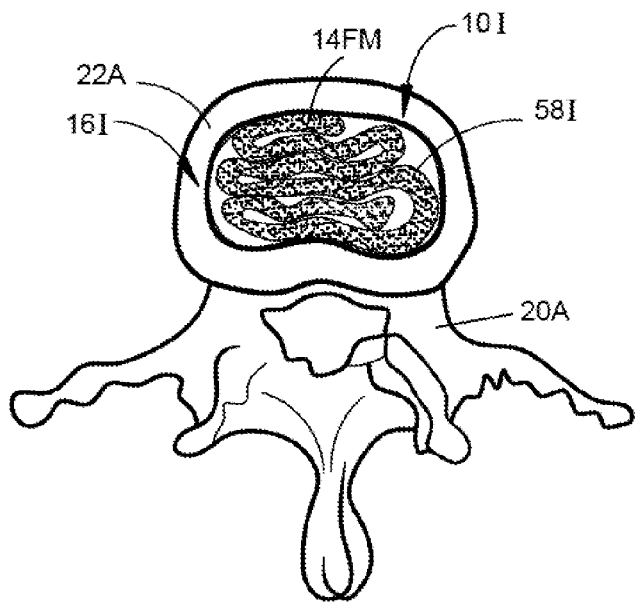
FIG. 59 shows a schematic plan view of the implant of FIG. 58, in use, in a second configuration in accordance with certain exemplary embodiments disclosed herein.
Figure 58:
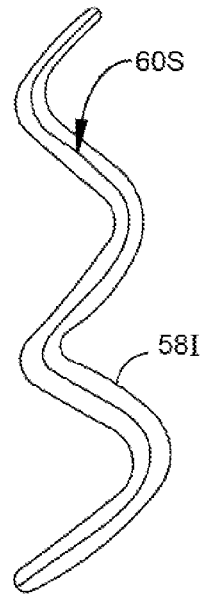
FIG. 58 shows a schematic side view of an intervertebral disc implant in a first configuration, in accordance with certain exemplary embodiments disclosed herein.

Referring now to FIGS. 58 and 59, yet a further embodiment of an implant 10I is illustrated.

In this embodiment, the implant 10I for an intervertebral disc 20I generally comprises an elongate implantable element 58I which, optionally, has a stiffening spine 60S. The implantable element 58I is, typically, an elastomeric material such as, for example, silicone. The spine 60S is of a shape forming material or shape memory alloy such as nitinol.

The implantable element 58I is inserted via an introducer into the volume of the disc 16I. One or more lengths of the implantable element 58I may be used to cause the implantable element 58I to conform to the shape of the volume in order to function as a replacement nucleus pulposus of the disc 16I.

Figure 60:
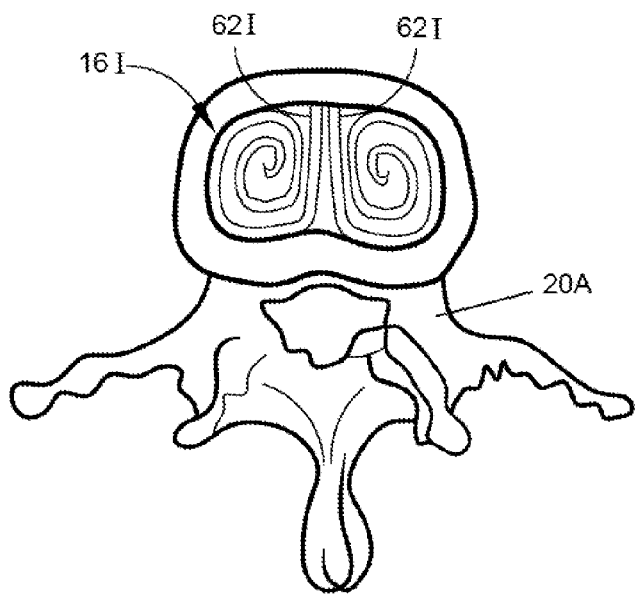
FIG. 60 shows a schematic plan view of an intervertebral disc implant, in accordance with certain exemplary embodiments disclosed herein.

In FIG. 60, an embodiment similar to that described above with reference to FIGS. 58 and 59 is illustrated. In this embodiment, the implant 10I for an intervertebral disc 20I generally comprises two, coiled implantable elements. Each implantable element 62I has a coiled shaped in its relaxed state. This coiled shape may be imparted by a stiffening spine of shape forming alloy such as nitinol (not shown). Instead, the implantable elements 62I may be formed in such a manner that, in their relaxed state, they adopt a coiled configuration.

In this embodiment, the implantable elements 62I are straightened for introduction into the volume of the disc 16I. Once in the volume, the implantable elements 62I coil in oppositely directed orientations substantially to fill the volume resulting from removal of the original nucleus pulposus of the disc 16I.

Figure 61:
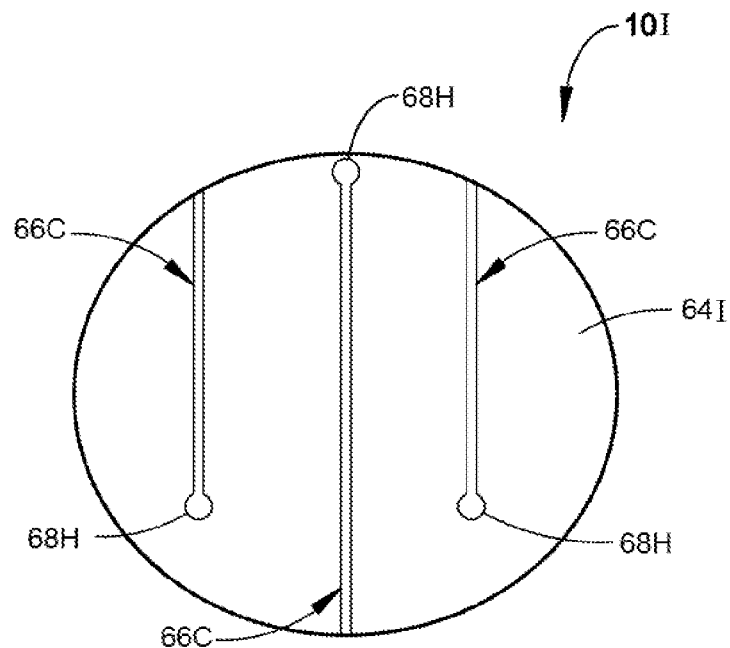
FIG. 61 shows a schematic plan view of an intervertebral disc implant, in accordance with certain exemplary embodiments of the inventions disclosed herein.
Figure 62:
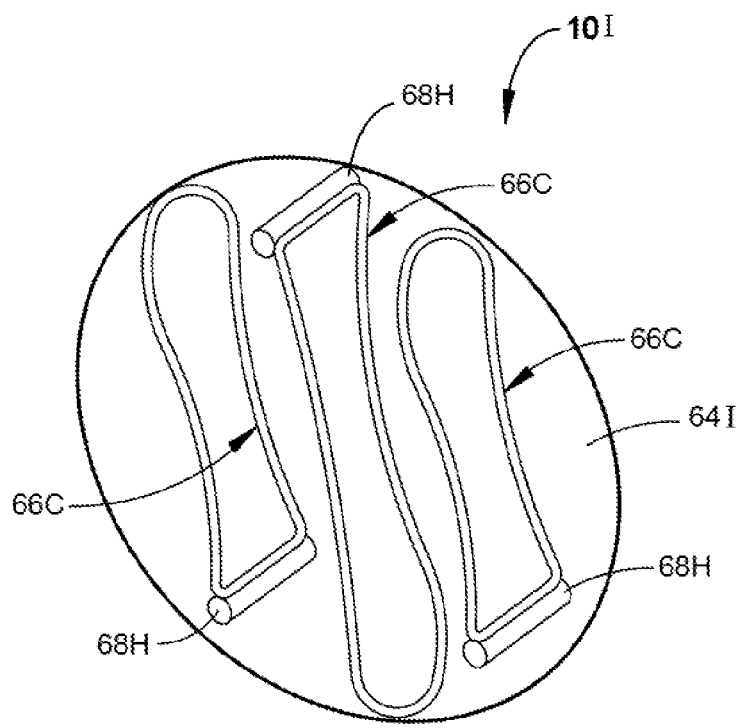
FIG. 62 shows a schematic three dimensional view of the implant of FIG. 61 in accordance with certain exemplary embodiments disclosed herein.

In FIGS. 61 and 62, the implant 10I comprises a single, implantable element 64I. The implantable element 64I is of an elastomeric material, such as silicone, and, in its relaxed states, is in a shape which will substantially conform to the volume of the disc into which the element 64I is to be imparted.

To aid in implantation of the element 64I, a plurality of cuts 66C are made in the element. These cuts 66C cause "hinges" 68H to be formed about which the parts of the element on either side of the cut 66C can hinge to straighten the element 64I to be implanted via an introducer into the vacated volume of the disc 16I.

Figure 63:
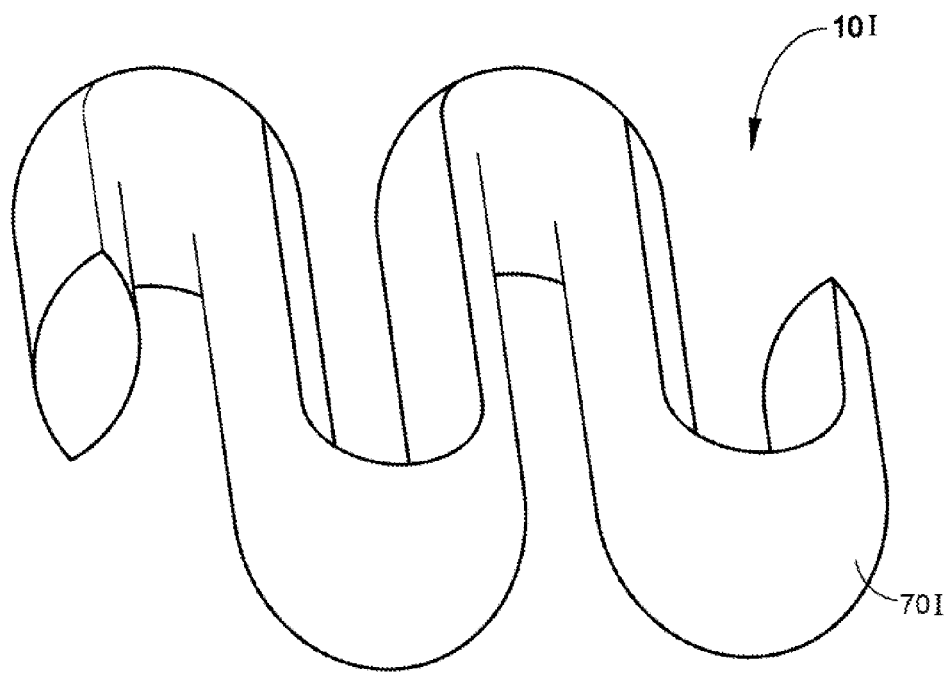
FIG. 63 shows a schematic three dimensional view of an intervertebral disc implant, in accordance with certain exemplary embodiments disclosed herein.
Figure 64:
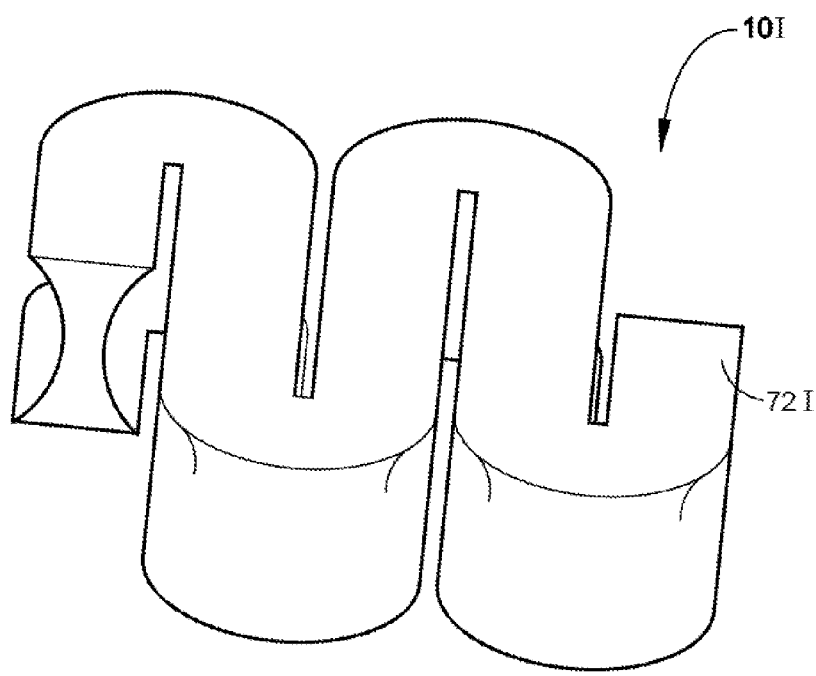
FIG. 64 shows a schematic three dimensional view of an intervertebral disc implant, in accordance with certain exemplary embodiments disclosed herein.

The embodiments of the implants shown in FIGS. 63 and 64 are similar to those shown in FIGS. 61 and 62. In the embodiment shown in FIG. 63 of the drawings, the implant 10I comprises a single implantable element 70I formed into a snake-like configuration, in its relaxed state. The implantable element 70I has a convex profile. The embodiment shown in FIG. 64 of the drawings is of a similar form with the distinction that an implantable element 72I of the implant 10I of the embodiment shown in FIG. 64 has a concave profile. Once again, in both embodiments, the implantable element 70I, 72I is extended into a straight configuration for implantation via an introducer. Once in the volume of the disc 16I, the implantable element 70I, 72I adopts its relaxed, illustrated configuration substantially to conform to the volume of the disc 16I.

Figure 65:
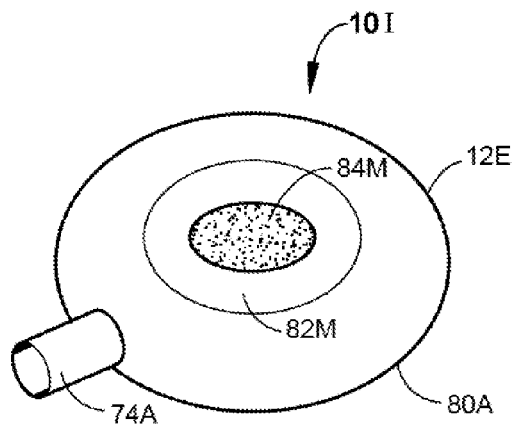
FIG. 65 shows a three dimensional view of an intervertebral disc implant, in accordance with certain exemplary embodiments disclosed herein.
Figure 66:
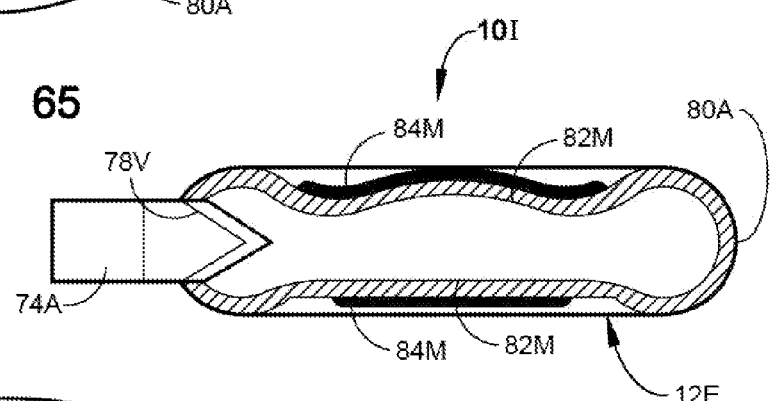
FIG. 66 shows a sectional side view of the implant of FIG. 65 in accordance with certain exemplary embodiments disclosed herein.
Figure 67:
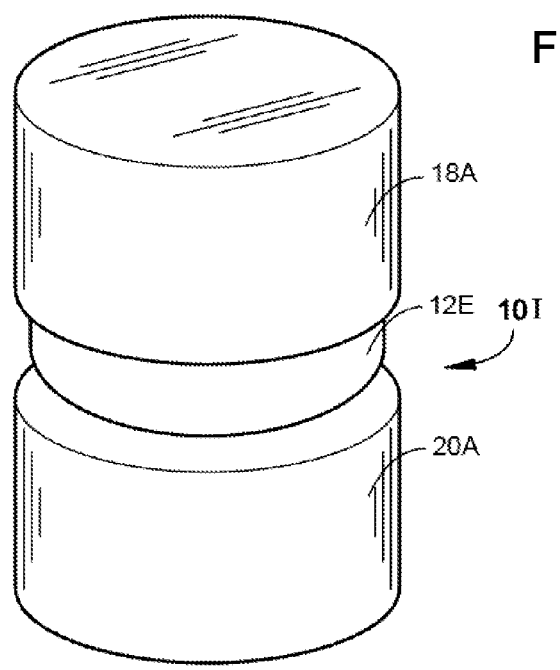
FIG. 67 shows a three dimensional view of the implant of FIG. 65, in accordance with certain exemplary embodiments disclosed herein.

Yet a further embodiment of an implant 10I is shown in FIGS. 65-67. Once again, with reference to the previous embodiments, like reference numerals refer to like parts, unless otherwise specified.

Figure 74:
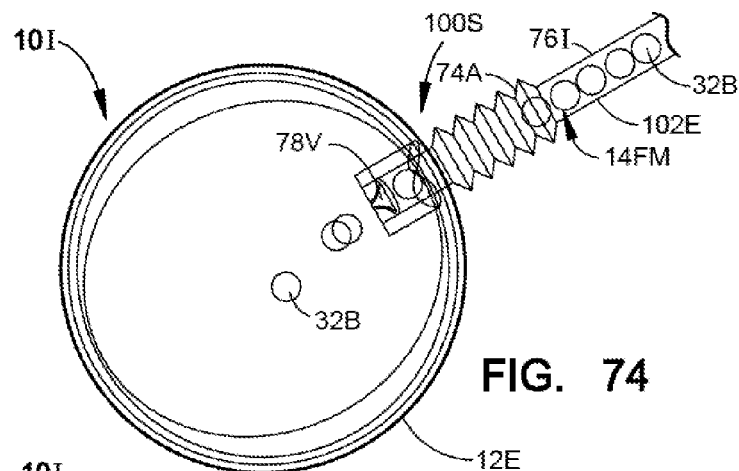
FIG. 74 shows a three dimensional view of a system, in accordance with certain exemplary embodiments disclosed herein, for implanting an intervertebral disc implant.

In this embodiment, an attaching formation 74A of the envelope 12E is shown. It is to be understood that the envelope 12E of each of the embodiments described above also includes such an attaching formation. The attaching formation 74A is used for attaching the envelope to an introducer 76I (FIG. 74). The attaching formation 74A is in the form of a filler tube. The filler tube 74A, in this embodiment, extends radially outwardly from the body of the envelope 12E. A closure device in the form of a duck-billed valve 78V is arranged at a distal end of the filler tube 74A. When the introducer 76I is inserted into the filler tube 74A, it causes the valve 78V to open. Withdrawal of the introducer 76I from the filler tube 74A causes the valve 78V to close.

In this embodiment, the envelope 12E has an annular region 80A of a reasonably rigid material. The material of the annular region 80A is more rigid than material forming upper member 86M and lower member 82M of a central part of the envelope 12E. The annular region 80A of the envelope 12E, bears against the annulus 22A of the disc 16I, in use. When the filler material 14FM is charged into the interior of the envelope 12E, the members 82M and 86M expand outwardly as shown by the upper member 86M in FIG. 66 of the drawings to bear against the vertebrae 18A, 20A and so cause the envelope 12E to conform substantially to the volume of the disc 16I.

It is to be noted that both members 82M and 86M carry, on their outer surfaces, a layer of tissue ingrowth material 84M. The material 84M is, typically, a polyester material such as that sold under the registered trade mark Dacron.

The annular region 80A is of a substantially non-stretchable material while the members 82M and 84M are made to stretch and expand in volume. The material of the annular region 80A is still sufficiently flexible to enable the envelope 12E to be collapsed to be inserted via an introducer into the vacated volume of the disc 16I.

FIGS. 68-73 show various embodiments of a multi-chambered envelope 12E. As shown in FIG. 69, the envelope 12E has a plurality of chambers 86C, each of which is fed by a collapsible delivery tube 88D. Each delivery tube 88D has a valve (not shown) at its distal end. Filler material is introduced into each of the chambers 86C of the envelope 12E via the associated delivery tube 88D. Thus, filling of each of the chambers 86C can occur independently. In addition, the filler material received in each chamber 86C may differ from the filler material received in any other chamber 86C. Still further, certain of the chambers 86C may, in certain circumstances, not have any filler material at all.

A sample of the construction of the envelope 12E is shown in FIGS. 71-73. The envelope 12E has an upper member 90U and a lower member 92L interconnected by a sidewall 94S. A plurality of partitions 96P extend in the interior of the envelope 12E between the upper member 90U and the lower member 92L. The partitions 96P are configured to have strong compressive load bearing capabilities but to collapse in shear as shown in FIG. 73 of the drawings. Thus, for introduction of the envelope into the vacated volume of the disc 16I, the partitions 96P are collapsed, as shown in FIG. 73 by moving the members 90U and 92L laterally relative to each other.

It will be appreciated that various other configurations of multi-chambered envelopes 12E can be formed by using different materials for different chambers of the envelope and/or filling the various chambers with different filler materials 14FM, as described above.

Figure 75:
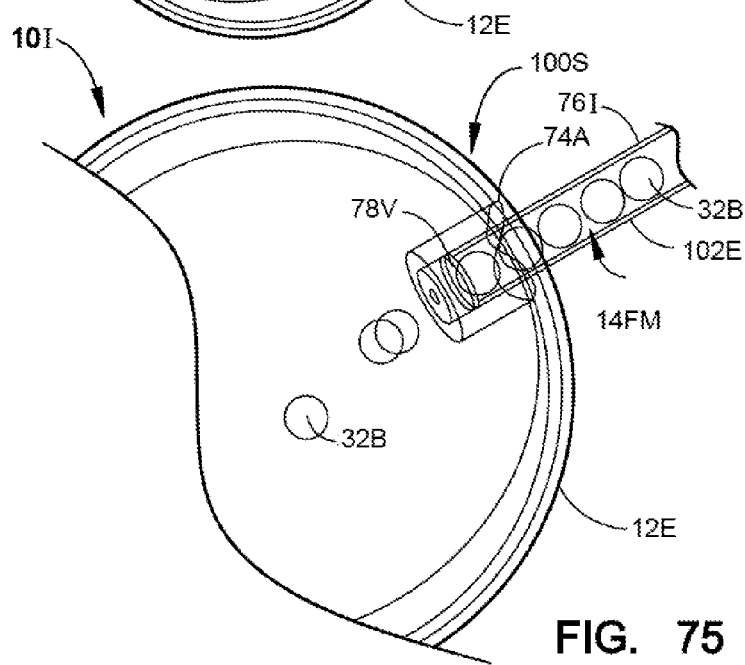
FIG. 75 shows, on an enlarged scale, a three dimensional view of the system of FIG. 74 in accordance with certain exemplary embodiments disclosed herein.

In FIGS. 74 and 75, a system, in accordance with another embodiment, for implanting an intervertebral disc implant is shown and is illustrated generally by the reference numeral 100S. The system 100S comprises the implant 10I and an introducer 76I. The introducer 76I has an elongate tubular element 102E on a distal end of which is received the attaching formation 74A of the envelope 12E. A non-return valve 78V is arranged at a distal end of the attaching formation 74A. In the embodiment illustrated in FIGS. 74 and 75, the filler material comprises the balls 32B of the embodiment described above with reference to FIGS. 46a, 46b and 46c.

The annulus 22A of the disc 16I is accessed percutaneously in a patient and an opening is made through the annulus 22A. The degenerate nucleus pulposus is removed using ablation, lasers or mechanical means to create a vacated volume. The introducer 76I with the envelope 12E in a collapsed configuration on the distal end of the tubular member 102E is inserted through the incision so that the envelope 12E is within the volume of the disc 16I.

Filler material 14FM is fed through the tubular member 102E of the introducer 76I into the interior of the envelope 12E to cause the envelope 12E to expand to conform to the volume of the disc 16I. In the embodiment shown in FIGS. 74 and 75, the filler material is fed through the introducer 76I via an appropriate displacement mechanism, such as a pump (not shown). Once the envelope 12E has expanded to conform to the volume, charging of filler material 14FM into the interior of the envelope 12E ceases. The tubular member 102E of the introducer 76I is withdrawn from the attaching formation 74A of the envelope 12E. Withdrawal of the tubular member 102E causes the value 78V to close inhibiting leakage of the filler material 14FM from within the envelope 12E.

It will be appreciated that the balls 32B have been shown merely as one example of the type of material 14FM used with the introducer 76I. Other filler materials having discrete elements are also able to be injected into the envelope 12E of the implant 10I using the introducer 76I.

Figure 76:
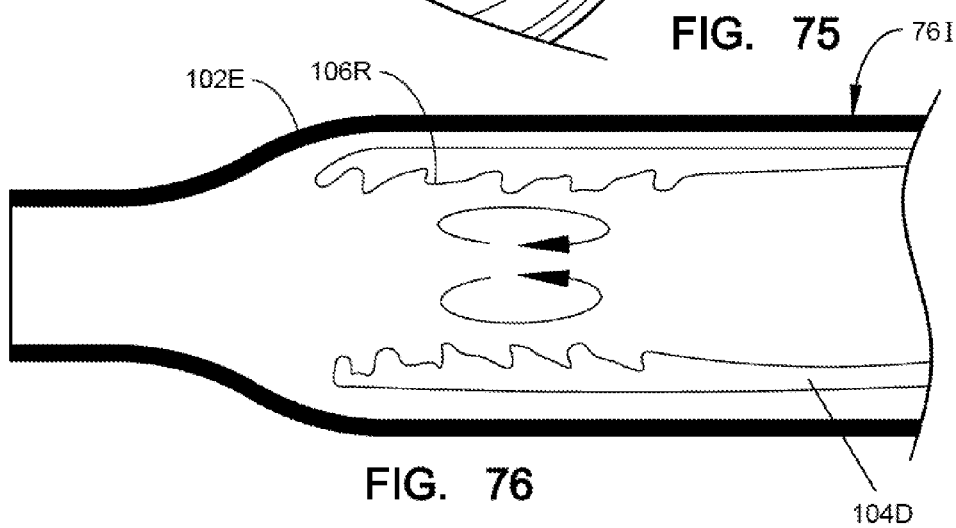
FIG. 76 shows a schematic, sectional side view of an introducer for a system, in accordance with certain exemplary embodiments disclosed herein, for implanting an intervertebral disc implant.

In FIG. 76, part of another embodiment of an introducer is illustrated. In this embodiment, the displacement mechanism for charging filler material 14FM into the interior of the envelope 12E comprises a displaceable element 104D. The displaceable element 104D is a sleeve received within the tubular member 102E of the introducer 76I and which is able to reciprocate relative to the tubular member 102E. An inner surface of the sleeve 104D carries a ratchet arrangement 106R. By reciprocating the sleeve 104D relative to the tubular member 102E filler material 14FM can be fed along the introducer 76I into the interior of the envelope 12E by means of the ratchet arrangement. The introducer 76I of the embodiment shown in FIG. 76 of the drawings is useful for introducing elongate elements into the interior of the envelope or, in certain circumstances, such as the embodiments shown in FIGS. 54-64 directly into the volume where no envelope is used. An example of an implant 10I which would use the introducer 76I of the embodiment of FIG. 76 is that shown in FIGS. 47a, 47b and 47c as well as the embodiment shown in FIGS. 51a, 51b and 51c.

It is to be noted that the implant 10I may be used to deliver bioactive substances to the annulus 22A of the intervertebral disc 16I. The bioactive substances may be substances which induce cell growth and/or cell reproduction. Further, the implant 10I may be used as a drug delivery means for active and/or prophylactic treatment at the site of implantation. Substances to be delivered may include may include gene telomerase, proteins, cells, autologous chondrocytes and autologous bone marrow derived mesenchymal stem cells.

Hence, it is an advantage of certain embodiments, that an intervertebral disc implant is provided which can mimic the biomechanical characteristics of a natural, healthy nucleus fibrosis of an intervertebral disc. It is a particular advantage of certain embodiments that an implant and system are provided which enables the implant to be inserted in a minimally invasive manner thereby obviating the need for drastic surgery. By use of discrete elements for the filler material 14FM, the biomechanical properties of the implant 10I can be tailored to particular requirements as desired by a clinician.

The disc is a highly viscoelastic structure and this makes it a very efficient and effective shock absorbing unit. In a healthy disc, the NP is well hydrated with a very gel like consistency and under the various modes of loading, the NP is pressurised and deformed, directing the incident load radially onto the AF and end plates. This creates an intradiscal pressure and load transfer between adjacent vertebrae is facilitated as the AF fibers are maintained in tension from the hoop stresses which result from the intradiscal pressure. This cooperative mechanism between the NP and AF provides the disc with the ability to sustain compressive loads retain the separation required between the adjacent vertebrae and provides controlled movement. With the onset of disc degeneration, brought upon by age or injury, there is a disruption in the balance between the NP and AF resulting in a destabilization of the motion segment. Common parameters which are used to evaluate the mobility and stability of the motion segment are neutral zone (NZ) and range of motion (ROM). In disc degeneration, the NZ (or joint laxity) increases along with its ROM. As the disc degenerates and becomes dehydrated, the NP shrinks and the ability to act as a shock absorbing, energy dissipating mechanism is compromised. A shrinkage in the NP results in a loss in the intradiscal pressure which then alters the stress distribution through the disc and since the intradiscal pressure is lost, the hoop stresses are lost also. Without the hoop stresses, the annulus is not able to be maintained in a taught orientation, eventually leading to delamination and shearing of the annular layers. The loss in intradiscal pressure also creates an increased laxity in the joint and an increase in the joint laxity means that there is a greater range of motion from the neutral position that is unsupported and unresisted, indicating an increased level of instability in the segment, adding more stress on the posterior articulating elements and adjacent segments to sustain the loads.

As it can be shown in the kangaroo motion segment study, by implanting a nucleus prosthesis, more specifically, one of the prostheses disclosed herein into a degenerate disc or at least a nucleotomised disc, the NZ and ROM of the motion segment is capable of being restored to that of an intact disc.

Specifically, the objectives of this study were to evaluate the biomechanical properties of the device using a cadaveric kangaroo lumbar spine model. The specific research question was whether kinematic variables differ when treating a motion segment with nucleotomy or nucleotomy then implantation with the exemplary device?

Ten kangaroo spine lumbar motion segments (L3/L4 and L5/L6) with all musculature, ligamentous tissue and posterior elements removed were separated into two equal groups. All specimens were tested in an intact state (pretreatment) prior to undergoing either a nucleotomy (nucleotomy) or undergoing a nucleotomy with implantation of a conformable elastomeric NR device (such as the devices disclosed herein) and then retested. All samples where tested in lateral bending and flexion-extension on a custom built jig attached and tested at 3.4 deg/sec with loads of −1.4 Nm to 1.4 Nm. Kinematic data were collated from the load displacement curve included; Neutral Zone (NZ), Range of motion (ROM), and Hysteresis. NZ is defined as the range which the specimen displaces with zero loads; ROM is defined as range from the start position to the point of maximal displacement in a given direction; and Hysteresis is defined as the energy difference between loading and unloading cycles on a stress-strain curve.

Before and after treatment analysis was performed using the Student Paired t-test with alpha set at 0.05. Results were presented as median percentage change compared with control with 95% confidence intervals for difference of means.

In flexion-extension the ROM of the nucleotomy and implant group increased by 24% (CI 5% to 65%) and 12% (CI −6% to 30%) respectively when compared to pretreatment. The NZ in the nucleotomy and implant group increased by 124% (CI 20% to 202%) and 0.5% (CI 7% to 31%) respectively when compared to pretreatment. In lateral bending, the ROM of the nucleotomy and implant group increased by 35% (CI 6% to 72%) and 5% (CI −22% to 42%) respectively when compared to pretreatment. The NZ in the nucleotomy and implant group increased by 69.8% (25% to 256%) and 0.5% (CI −28% to 33%) respectively when compared to pretreatment.

Accordingly, in this study, there was an increase in motion segment laxity after nucleotomy during sagital and coronal movements of flexion-extension and lateral bending, which is reversed with implantation of the exemplary device. The data suggests that the exemplary device can restore the biomechanical changes in a de-nucleated motion segment.

Additionally, an embodiment of the implant disclosed herein was implanted into a 41 year old male who presented with lower back pain for 4.5 years following a work related injury in 2003. He subsequently underwent a posterior decompression surgery in 2005 which resulted in relief of pain for a brief time but then continued to complain of back pain which he rates at 9 out of 10 and bilateral leg pain. He had significant restriction of all activities of daily living and was taking high doses of narcotic analgesics to control his pain. He has no other medical co-morbidities nor does he have any ongoing legal issues related to his work injury. A physical examination revealed a cooperative, pleasant gentleman who overall has good balance and station. The movements of the thoracolumbar spine were painful and grossly restricted in the sagittal plane. Lower limb neurology was nearly normal. The straight leg raising test was positive on the right side.

An MRI scan of the LS spine showed degeneration of the L4-L5 disc. The adjacent discs appeared to be well hydrated. Radiographs of the lumbo-sacral spine showed normal alignment. The patient had no relief of symptoms following a whole range of non-operative treatment modalities, including physiotherapy and spinal injections. He was eventually considered for the procedure disclosed herein.

He underwent a partial nucleus replacement procedure on 27 Dec. 2007 and the immediate post-operative period was uneventful. At the six week mark after surgery, the patient had about an 80% reductionin his back pain and about a 90% reduction in his leg pain. He is presently undergoing physiotherapy to increase his activity levels and the narcotic analgesics are being tapered. The short term results have been very encouraging.

In one of the embodiments, a polymeric material, more specifically an elastomer, and preferably a silicone, of a particular hardness is used for a nucleus prosthesis. The hardness of the material may be in the range of 1-20 A or 21-40 A or 41-60 A or 61-80 A or greater than 81 A Shore Hardness, but preferably about 25 A. Materials like silicones are well suited for a nucleus prosthesis application because it is a viscoelastic material which means it is capable of providing the shock absorbing requirements of the motion segment. Under a given load, the prosthesis deforms and is capable of distributing the applied load radially to evenly distribute the load across the endplate and to the annulus. This reduces the risk of the implant subsiding into the endplates and restores the intradiscal pressure which restores the hoop stresses to the annulus. More importantly, the nucleus prosthesis is elastically deformable. Thus, the application of force will cause the nucleus prosthesis to deform elastically so that, once the force has been removed, the prosthesis will return to its relaxed, undeformed state.

Therefore, some beneficial characteristics of the implant disclosed herein may include, for example, shock absorption, restore hoop stresses, provide required range of motion, restore biomechanics, within the required range of hardness (shore hardness) (less chance of implant subsidence), using same class of materials results in homogeneity, fast curing, substantially biocompatible, in mild to moderate disc degeneration the implant is not only load distributing but also load bearing, substantially silicone, silicone composites, polyurethane, cellulose, collagen based, elastin based.

It will be appreciated by persons skilled in the art that numerous variations and/or modifications may be made to the inventions as shown in the embodiments without departing from the spirit or scope of the inventions as broadly described. The present embodiments are, therefore, to be considered in all respects as illustrative and not restrictive.

We claim:

1. A self-contained closed implant system for the formation of a prosthesis device percutaneously within a nucleus cavity formed in an intervertebral disc at an in situ implant site, comprising:
   a single lumen working cannula, said single lumen working cannula configured to be docked against an outer surface area of an annulus surrounding the nucleus cavity, wherein said single lumen working cannula has arranged at about its proximal end a collar assembly to facilitate matingly engaging the single lumen working cannula with said closed insertion assembly;
   a closed sizing assembly configured to be partially received within said single lumen working cannula for carrying at a distal end thereof an elastically deformable mock implant member to the in situ implant site to facilitate determining, without fluid evacuation from the closed implant system, a known volume of filler material to substantially fill the volume of the nucleus cavity;
   a closed insertion assembly configured to be partially received within said single lumen working cannula in place and stead of said closed sizing assembly for protectively carrying an elastically deformable implant member to the in situ implant site to facilitate its filling with said known volume of filler material;
   a closed dispensing assembly configured to be partially received within said single lumen working cannula and removably coupled to said closed insertion assembly without relative rotational motion therebetween to facilitate the filling of the elastically deformable implant member with said known volume of filler material without fluid evacuation from the closed implant system; and
   wherein the closed dispensing assembly includes a distal end magnetic mount for removably coupling the closed dispensing assembly to the single lumen working cannula and a proximal end magnetic mount for removably coupling the closed dispensing assembly to the closed sizing assembly to facilitate determining, without fluid evacuation from the closed implant stem the known volume of filler material to substantially fill the volume of the nucleus cavity and for removably coupling the dispensing assembly to the closed insertion assembly in place and stead of the closed sizing assembly to facilitate the filling of the elastically deformable implant member with the known volume of filler material without fluid evacuation from the closed implant system to help reduce tissue trauma to a patient by obviating relative rotational coupling motions.

2. The self-contained closed implant system according to claim 1, wherein said closed sizing assembly includes:
   a tube having a single lumen for carrying the mock implant member at a distal end thereof;
   a connector coupled at a proximal end of said tube, said connector defining a primary lumen for fluid communication with said tube and a secondary lumen for fluid communication with said tube;
   at least one pressure transducer coupled fluid dispenser arrangement including a primary syringe connectable to the primary lumen for fluid communication with said single tube and a secondary syringe connectable to the secondary lumen for fluid communication with said single tube;
   a fluid control arrangement disposed at a proximal end area of said single tube operable to place either the primary lumen of the connector in fluid communication with the tube or secondary lumen of the connector in fluid communication with the tube;
   wherein said primary syringe is connectable to said connector to be in fluid communication with said primary lumen, said primary syringe having a barrel and a plunger slidably displaceable in the barrel to facilitate the delivery and removal of a non-compressible liquid to the mock implant member;
      wherein said secondary syringe is connectable to said connector to be in fluid communication with said secondary lumen, said secondary syringe having another barrel and another plunger slidably displaceable in said another barrel to facilitate the delivery and removal of a compressible liquid to the mock implant member;

wherein said fluid control arrangement is operable in a priming step to occlude, the fluid communication path between said primary lumen and the tube and to open the fluid communication path between said secondary lumen and the tube to facilitate inflating said mock implant member with compressible liquid dispensed from said secondary syringe and compressible liquid contained within the closed delivery system; and wherein said fluid control arrangement is operable in another priming step to occlude the fluid communication path between said secondary lumen and the tube and open the communication path between said primary lumen and the tube to facilitate placing said primary syringe in fluid communication with said tube for inflating the mock implant member with non-compressible liquid dispensed from said primary syringe, said primary syringe containing a sufficient volume of the non-compressible liquid to inflate said mock implant member to a fully expanded state conforming to the shape of the nucleus cavity to provide an indication of said known volume of filler material to substantially fill the volume of the nucleus cavity.

3. The self-contained closed implant system according to claim 2, wherein the non-compressible fluid dispensed from said primary syringe is heavier that the compressible fluid dispensed from said secondary syringe;

wherein said heavier non-compressible fluid sinks to a distal end portion of the mock implant member; and wherein the compressible fluid contained within the closed implant system collects at about a distal end of the tube.

4. The self-contained closed implant system according to claim 3, wherein said mock implant member, in its fully collapsed primed state, points upwardly since the buoyancy of the compressible fluid within the closed sizing assembly causes the compressible fluid therein to disperse toward a distal portion of said mock implant member in close proximity to the single lumen of said tube; and wherein said mock implant member, in its fully inflated state, points downwardly during said priming step to facilitate an accurate measurement of the nucleus cavity.

5. The self-contained closed implant system according to claim 4, wherein withdrawal displacement of said another plunger within said another barrel is prevented in the closed sizing assembly from extending beyond a zeroing position when said mock implant member is in said fully collapsed state and is extendable in an opposite displacement until a sudden increase in pressure resulting from the mock implant member becoming fully inflated with a sufficient volume of non-compressible liquid so the mock implant member substantially conforms to the shape of the nucleus cavity.

6. The self-contained closed implant system according to claim 5, wherein said sudden increase in pressure causes a transducer coupled to the plunger of said primary syringe to emit an enunciation.

7. The self-contained closed implant system according to claim 6, wherein said enunciation is an audible enunciation indicative of an end point in filling the mock implant member with the non-compressible fluid.

8. The self-contained closed implant system according to claim 6, wherein said enunciation is a visible enunciation indicative of n end point in filling the mock implant member with the non-compressible fluid.

9. The self-contained closed implant system according to claim 1, wherein said closed dispensing assembly includes:
a connector in fluid communication with the elastically deformable implant member;
a withdrawing device in fluid communication with said connector for increasing the volume of the closed implant system to facilitate collapsing the elastically deformable implant member and removing substantially all fluids therefrom so said elastically deformable implant member may be filed with said know volume of filler material without fluid evacuation from the closed implant system; and
a dispensing device in fluid communication with said connector for dispensing to collapsed elastically deformable implant member said known volume of filler material without fluid evacuation from the closed implant system.

10. The self-contained closed implant system according to claim 9, wherein said closed dispensing assembly further includes a sensing arrangement for providing an indication that the elastically deformable implant member has been inflated with a sufficient volume of filler material corresponding to said known volume of filler material;
wherein upon said sensing arrangement providing said indication, said dispensing assembly may be immediately removed from the working cannula without waiting for the filler material in the elastically deformable implant member to cure.

11. The self-contained closed implant system according to claim 10, wherein said dispensing assembly still further includes an occluding arrangement for occluding access to the inflated elastically deformable implant member concurrently with the immediate removal of said dispensing assembly.

12. The self-contained closed implant system according to claim 1, said collar assembly including:
a cannula collar secured at a proximal end of said single lumen working, cannula; said cannula collar having a set of recesses to help facilitate the removal of a protective sheath surrounding the implant member once it is placed within nucleus cavity;
a push-off collar removably secured to a proximal end of said cannula collar to help facilitate separating the implant member from the closed implant system;
a connector collar removably secured to a proximal end of said push-off collar for coupling said closed insertion assembly to said closed dispensing assembly without relative rotational motion therebetween to facilitate the filling of the implant member with said known volume of filler material without fluid evacuation from the closed implant system; and
wherein said single lumen working cannula is configured with a pair of oppositely disposed longitudinally extending slits dimensioned for slidably receiving therein a set of tabs extending outwardly from said protective sheath, said tabs being dimensioned to be received within the set of recesses disposed in said cannula collar to further help facilitate the removal of the protective sheath from the implant member once the implant member is placed within the nucleus cavity.

13. The self-contained closed implant system according to claim 1, wherein said closed insertion assembly includes:
a single lumen carrier tube for carrying at a distal end thereof the elastically deformable implant member;

a protective sheath extending over the elastically deformable implant member for protecting it while being carried and placed within the nucleus cavity by said single lumen carrier tube;

a stiffening rod dimensioned to be slidably received within said single lumen carrier tube and having a sufficient length extending between a distance beyond the distal end of the single lumen carrier tube to be received within the interior of the elastically deformable implant member and another distance beyond a proximal end of said single lumen working cannula to facilitate collapsing the elastically deformable implant member onto a distal end of said stiffening rod; and a push off tube to facilitate the removal of the elastically deformable implant member from said single lumen carrier tube once filled with said known volume of filler material, said push off tube dimensioned to be slidably received within said single lumen working cannula and for slidably receiving therein said single lumen carrier tube;

said push off tube having arranged about its distal end the protective sheath, said sheath extending beyond a distal end of the elastically deformable implant member during its placement within the nucleus cavity;

said push off tube having disposed at about its proximal end a bayonet fitted collar dimensioned to be received within said cannula collar to facilitate locking engagement between the single lumen working cannula and the closed insertion assembly; and the proximal end magnetic mount being coupled to a tube connector in fluid communication with said carrier tube to facilitate coupling said closed insertion system to said closed dispensing system without relative rotational motion therebetween for filling of the elastically deformable implant member with said known volume of filler material without fluid evacuation from the closed implant system.

14. An apparatus for use with a working cannula, said cannula being configured to be fixedly docked percutaneously to an in situ implant site, the apparatus comprising:

a closed dispensing assembly which includes a distal end magnetic mount for removably coupling said closed dispensing assembly to a working cannula and a proximal end magnetic mount for removably coupling said closed dispensing assembly to a closed suing assembly during an implant site size determination procedure and for removably coupling said closed dispensing assembly to a closed insertion assembly in place and stead of said closed sizing assembly during an implant placement and filling procedure;

said closed sizing assembly is configured to be partially received within the working cannula for carrying at a distal end thereof an elastically deformable mock implant member to an in situ implant site to facilitate determining, without fluid evacuation from a closed implant system, a known volume of filler material to substantially fill a prosthesis implant to be formed at the implant site;

wherein the closed insertion assembly is configured to be partially received within said working cannula in place and stead of the closed sizing assembly for protectively carrying an elastically deformable implant member to the in situ implant site to facilitate its filling with the known volume of filler material;

wherein the closed dispensing assembly is configured to be partially received within the working cannula and removably coupled to the closed insertion assembly to facilitate the filling of the elastically deformable implant member with the known volume of filler material without fluid evacuation from the closed implant system;

wherein said distal end magnetic mount facilitates connecting and disconnecting said dispensing assembly from said working cannula without relative rotational motion therebetween to help reduce tissue trauma to the patient; and wherein said proximal end magnetic mount facilitates connecting and disconnecting said dispensing assembly from said closed sizing assembly without relative rotational motion therebetween to further help reduce tissue trauma to the patient and to further facilitate connecting and disconnecting said dispensing assembly from said insertion assembly without relative rotational motion therebetween to still further help reduce tissue trauma to the patient.

15. A self-contained closed implant system for the formation of a prosthesis device percutaneously at an in situ implant site, comprising:

a single lumen working cannula, said single lumen working cannula configured to be docked against an outer surface area of the in situ implant site for the implanting of a prosthesis device percutaneously at an in situ implant site;

a closed sizing assembly configured to be partially received within the single lumen working cannula, said closed sizing assembly for carrying at a distal end thereof an elastically deformable mock implant member to the in situ implant site to facilitate determining, without fluid evacuation from the closed implant system, a known volume of filler material to substantially fill the volume of an implant receiving cavity;

a closed insertion assembly configured to be partially received within said single lumen working cannula in place and stead of said closed sizing assembly for protectively carrying an elastically deformable implant member to the in situ implant site to facilitate its filling with said known volume of filler material;

a closed dispensing assembly configured to be partially received within said single lumen working cannula and removably coupled to said closed insertion assembly without relative rotational motion therebetween to facilitate the filling of the elastically deformable implant member with said known volume of filler material without fluid evacuation from the closed implant system; and wherein the closed dispensing assembly includes a distal end magnetic mount for removably coupling the closed dispensing assembly to the single lumen working cannula and a proximal end magnetic mount for removably coupling the closed dispensing assembly to the closed sizing assembly to facilitate determining, without fluid evacuation from the closed implant system, the known volume of filler material to substantially fill the volume of the implant receiving cavity and for removably coupling the dispensing assembly to the closed insertion assembly in place and stead of the closed sizing assembly to facilitate the filling of the elastically deformable implant member with the known volume of filler material without fluid evacuation from the closed implant system to help reduce tissue trauma to a patient by obviating relative rotational coupling motions.

* * * * *